(12) United States Patent
Fu et al.

(10) Patent No.: US 11,873,499 B2
(45) Date of Patent: Jan. 16, 2024

(54) METHODS OF INCREASING NUTRIENT USE EFFICIENCY

(71) Applicant: Institute of Genetics and Developmental Biology Chinese Academy of Sciences, Beijing (CN)

(72) Inventors: Xiangdong Fu, Beijing (CN); Shan Li, Beijing (CN); Kun Wu, Beijing (CN); Yonghang Tian, Beijing (CN); Qian Liu, Beijing (CN)

(73) Assignee: INSTITUTE OF GENETICS AND DEVELOPMENTAL BIOLOGY CHINESE ACADEMY OF SCIENCES, Beijing (CN)

( * ) Notice: Subject to any disclaimer, the term of this patent is extended or adjusted under 35 U.S.C. 154(b) by 0 days.

(21) Appl. No.: 16/969,656

(22) PCT Filed: Feb. 13, 2019

(86) PCT No.: PCT/GB2019/050376
§ 371 (c)(1),
(2) Date: Aug. 13, 2020

(87) PCT Pub. No.: WO2019/158911
PCT Pub. Date: Aug. 22, 2019

(65) Prior Publication Data
US 2021/0071191 A1  Mar. 11, 2021

(30) Foreign Application Priority Data

Feb. 14, 2018 (WO) ................ PCT/CN2018/076831
May 22, 2018 (WO) ................ PCT/CN2018/087850

(51) Int. Cl.
*C12N 15/82* (2006.01)
*C07K 14/415* (2006.01)

(52) U.S. Cl.
CPC ........ *C12N 15/8261* (2013.01); *C07K 14/415* (2013.01)

(58) Field of Classification Search
None
See application file for complete search history.

(56) References Cited

U.S. PATENT DOCUMENTS

| 5,565,350 | A | 10/1996 | Kmiec |
| 8,440,431 | B2 | 5/2013 | Voytas et al. |
| 8,440,432 | B2 | 5/2013 | Voytas et al. |
| 8,450,471 | B2 | 5/2013 | Voytas et al. |
| 8,697,359 | B1 | 4/2014 | Zhang |

| 2006/0123505 | A1* | 6/2006 | Kikuchi et al. | C07K 14/415 800/278 |
| 2008/0148432 | A1* | 6/2008 | Abad | C12N 15/8279 435/468 |
| 2010/0199382 | A1* | 8/2010 | Frankard et al. | C12N 15/8261 800/278 |
| 2012/0278929 | A1* | 11/2012 | Baum et al. | C12N 15/8285 800/265 |

FOREIGN PATENT DOCUMENTS

| CN | 104710521 A1 | 6/2015 |
| CN | 105646684 A | 6/2016 |
| CN | 106554397 A | 4/2017 |
| WO | WO0015815 A1 | 3/2000 |
| WO | WO2015143972 A1 | 1/2015 |

OTHER PUBLICATIONS

Clynen et al. (2004) Gen Comp Endocrinol 139:173-78.*
Whisstock & Lesk (2003) Q Rev Biophys. 36(3):307-40.*
Guo et al. (2004) Proc Natl Acad Sci USA 101:9205-10.*
Zhang (2003) Curr Opin Plant Biol 6:430-40.*
Kim & Kende (2004) Proc Natl Acad Sci (USA) 101(36):13374-79.*
Fourgoux-Nicol et al. (1999) Plant Mol Biol 40:857-72.*
Donald & Cashmore (1990) EMBO J 9:1717-26.*
Dolferus et al. (1994) Plant Physiol 105:1075-87.*
Kim et al. (1994) Plant Mol Biol 24:105-17.*
Sasaki et al. (2001) GenBank AP003994 (only first page provided).*
Kikuchi et al. (2008) GenBank AK063983 (only first page provided).*
Sun et al. (2016) J Integr Plant Biol 58(10):836-47.*
Potenza et al. (2004) In Vitro Cell. Dev. Biol Plant 40:1-22.*
NCBI Blast Seq ID No. 51 (2023).*
NCBI Blast Seq ID No. 172 (2023).*
Sun et al., "OsGRF4 controls grain shape, panicle length and seed shattering in rice", Journal of Integrative Plant Biology, Oct. 2016 (Oct. 2016), p. 836-847, vol. 58, No. 10.
Duan et al., "Regulation of OsGRF4 by OsmiR396 controls grain size and yield in rice.", Nature Plants, Dec. 2015 (Dec. 21, 2015), p. 1-5, vol. 2, 21.
Hu et al., "A Rare Allele of GS2 Enhances Grain Size and Grain Yield in Rice", Molecular Plant, Oct. 2015 (Oct. 2015), p. 1455-1465, vol. 8, No. 10.
Li et al., "The OsmiR396c-OsGRF4-OsGIF1 regulatory module determines grain size and yield in rice", Plant Biotechnology Journal, Nov. 2016 (Nov. 2016), p. 2134-2146, vol. 14, No. 11.

* cited by examiner

*Primary Examiner* — Russell T Boggs
(74) *Attorney, Agent, or Firm* — Greer, Burns & Crain, Ltd.

(57) ABSTRACT

The invention relates to methods for increasing nitrogen uptake, nitrogen assimilation, nitrogen use efficiency as well as yield in a plant, without affecting plant height, the method comprising increasing the expression or levels of a growth regulatory factor (GRF). Also described are genetically altered plants characterised by the above phenotype as well as methods of producing such plants.

16 Claims, 21 Drawing Sheets
Specification includes a Sequence Listing.

METHODS OF INCREASING NUTRIENT USE EFFICIENCY

CROSS-REFERENCE TO RELATED APPLICATIONS

This application is the U.S. National phase application corresponding to PCT/GB2019/050376 which was assigned an international filing date of Feb. 13, 2019 and associated with publication WO 2019/158911 A1 and which claims priority to PCT/CN2018/087850, filed on May 22, 2018 and PCT/CN2018/076831, filed on Feb. 14, 2018, the disclosures of which are expressly incorporated herein by reference.

FIELD OF THE INVENTION

The invention relates to methods for increasing nitrogen uptake, nitrogen assimilation, nitrogen use efficiency as well as yield in a plant, without affecting plant height, the method comprising increasing the expression or levels of a growth regulatory factor (GRF). Also described are genetically altered plants characterised by the above phenotype as well as methods of producing such plants.

BACKGROUND OF THE INVENTION

The agricultural 'green revolution' of the 1960's boosted cereal yields, fed an expanding world population, and was driven by rapid adoption of semi-dwarf green revolution varieties (GRVs)[1-3]. Most modern elite varieties of wheat and rice retain the semi-dwarfing genes characteristic of GRVs[4-6]. However, semi-dwarf GRV soil nitrogen (N) use is inefficient[7], and high yields are heavily dependent upon N fertilizer inputs that are not only a major input cost but also unsustainably damage the environment. Developing new varieties that are high-yielding with reduced N fertilization is thus a strategic sustainable agriculture goal of urgent global importance[1,8].

There therefore exists a need to increase nitrogen uptake as well as yield in commercially important cereal crops, such as rice and wheat, but more importantly, in the semi-dwarf green revolution varieties without loss of the yield benefits of semi-dwarfism. The present invention addresses this need.

SUMMARY OF THE INVENTION

To achieve an increase in nutrient use-efficiency of GRVs it is necessary to understand the regulatory relationship between growth and metabolism. To date, the molecular mechanisms underlying this relationship remain largely unknown. Here we show that rice GROWTH-REGULATING FACTOR4 (OsGRF4) interacts directly with the DELLA growth-inhibitor, and that this interaction confers homeostatic co-regulation of carbon (C)-nitrogen (N) balance. Whilst OsGRF4 promotes and integrates C fixation, N assimilation and cell proliferation, DELLA inhibits them. The DELLA accumulation of GRV tips the balance to favour semi-dwarfism with reduced N assimilation. In contrast, we show that increased GRV OsGRF4 abundance alters the OsGRF4-DELLA balance to favour increased C (carbon) and N (nitrogen) assimilation without loss of yield-enhancing dwarfism. Modulating coordination of plant growth and metabolism thus elevates N use-efficiency and yield, enabling strategic breeding for sustainably increased global food security.

In a first aspect of the invention, there is provided a method of increasing nitrogen uptake and/or nitrogen assimilation and/or nitrogen use efficiency in a plant, the method comprising increasing the expression or levels of a growth regulatory factor (GRF) or increasing the activity of a growth regulatory factor.

In a further embodiment, the method further comprises increasing grain yield in the plant. Preferably, an increase in grain yield is selected from an increase in grain numbers per panicle or per plant and/or an increase in 1000-grain weight.

In another embodiment, the method further comprises increasing C assimilation, as described below.

In another aspect of the invention, there is provided a method of producing a plant with increased nitrogen uptake and/or nitrogen assimilation and/or nitrogen use efficiency, the method comprising increasing the expression or levels of a growth regulatory factor (GRF) or increasing the activity of a growth regulatory factor. Preferably, the plant also has an increased yield and/or increased C assimilation.

In one embodiment, the method further comprises measuring an increase in at least one of nitrogen uptake and/or nitrogen assimilation and/or nitrogen use efficiency and grain yield.

In another embodiment, the method further comprises regenerating a plant and screening for an increase in nitrogen uptake and/or nitrogen assimilation and/or nitrogen use efficiency and grain yield.

In one embodiment, the method comprises introducing at least one mutation into a least one nucleic acid encoding a GRF and/or the promoter of a GRF. Preferably, the mutation is a substitution. In one embodiment, the mutation is in a micro RNA (miRNA) binding site, preferably a miRNA396 binding site. In an alternative embodiment, the mutation is in the GRF promoter.

Preferably, the GRF is GRF4 or a functional variant or homologue thereof. In one embodiment, the nucleic acid encodes a GRF polypeptide wherein the GRF polypeptide comprises or consists of SEQ ID NO: 3 or a functional variant or homologue thereof. Preferably, the nucleic acid comprises or consists of SEQ ID NO: 1 or 2 or a functional variant or homologue thereof. In a further embodiment, the nucleic acid encoding a GRF promoter comprises or consists of SEQ ID NO: 7 or 8 or a functional variant or homologue thereof.

In one embodiment, the mutation is introduced using targeted genome modification, preferably ZFNs, TALENs or CRISPR/Cas9.

In an alternative embodiment, the method comprises introducing and expressing in the plant a nucleic acid construct comprising a GRF nucleic acid. Preferably, the GRF nucleic acid construct is operably linked to a regulatory sequence. More preferably, the regulatory sequence is a constitutive promoter. Even more preferably, the regulatory sequence is the GRF promoter as defined in SEQ ID NO: 9 or a functional variant or homologue thereof. Preferably, the GRF nucleic acid encodes a GRF polypeptide wherein the GRF polypeptide comprises or consists of SEQ ID NO: 3 or 6 or a functional variant or homologue thereof. More preferably, the nucleic acid comprises or consists of SEQ ID NO: 1, 2, 4 or 5.

In one embodiment, said increase in nitrogen uptake and/or nitrogen assimilation and/or nitrogen use efficiency and/or yield and/or C metabolism is relative to a wild-type or control plant. Preferably, nitrogen uptake and/or nitrogen assimilation and/or nitrogen use efficiency is increased in the shoots and/or roots of the plant. More preferably, nitrogen uptake and/or nitrogen assimilation and/or nitrogen use efficiency is increased under low or high nitrogen conditions, preferably under low nitrogen conditions.

In a preferred embodiment, plant height is not affected.

In another aspect of the invention, there is provided a genetically altered plant, part thereof or plant cell, wherein the expression or level of a growth regulatory factor (GRF) or activity of a GRF is increased compared to a wild-type or control plant, and wherein the plant is characterised by an increase in at least one of nitrogen uptake and/or nitrogen assimilation and/or nitrogen use efficiency compared to a wild-type or control plant. Preferably, the plant also has an increased yield and/or increased C assimilation.

In one embodiment, the plant expresses a nucleic acid construct comprising a GRF nucleic acid. Preferably, the nucleic acid construct comprises a regulatory sequence. More preferably, the regulatory sequence is a constitutive promoter. In one embodiment, the regulatory sequence is the GRF promoter as defined in SEQ ID NO: 9 or a functional variant or homologue thereof.

In an alternative embodiment, the plant comprises at least one mutation in at least one nucleic acid encoding a GRF polypeptide and/or a GRF promoter. Preferably, the mutation is a substitution. More preferably, the mutation is introduced using targeted genome modification, preferably ZFNs, TALENs or CRISPR/Cas9. In one embodiment, the mutation is in a micro RNA (miRNA) binding site, preferably a miRNA396 binding site. In another embodiment, the mutation is in the GRF promoter.

In one embodiment, the plant part is a grain or a seed.

In another aspect of the invention, there is provided a method for identifying and/or selecting a plant that will have increased nitrogen uptake and/or nitrogen assimilation and/or nitrogen use efficiency, preferably compared to a wild-type or control plant, the method comprising detecting in the plant or plant germplasm at least one polymorphism in at least one GRF gene or GRF promoter and selecting said plant or progeny thereof. Preferably, the polymorphism is substitution. More preferably, the method further comprises introgressing the chromosomal region comprising at least one polymorphism in the GRF gene or promoter into a second plant or plant germplasm to produce an introgressed plant or plant germplasm.

In a further aspect of the invention, there is provided a nucleic acid construct comprising a GRF nucleic acid, wherein the GRF nucleic acid encodes a GRF polypeptide wherein the GRF polypeptide comprises or consists of SEQ ID NO: 3 or 6 or a functional variant or homologue thereof, and preferably a regulatory sequence. Preferably, the regulatory sequence is a constitutive promoter. In one embodiment, the regulatory sequence is the GRF promoter as defined in SEQ ID NO: 9 or a functional variant or homologue thereof. More preferably, the nucleic acid comprises or consists of SEQ ID NO: 1, 2, 4 or 5.

In another aspect of the invention, there is provided a vector comprising the nucleic acid construct as described herein.

In a further aspect of the invention, there is provided a host cell comprising the nucleic acid construct described herein. Preferably, the cell is a bacterial or plant cell.

In another aspect of the invention, there is provided a transgenic plant expressing the nucleic acid construct or vector as described herein.

In another aspect of the invention, there is provided the use of a nucleic acid construct as defined herein to increase nitrogen uptake and/or nitrogen assimilation and/or nitrogen use efficiency in a plant.

In a further aspect of the invention, there is provided a method of increasing nitrogen uptake and/or nitrogen assimilation and/or nitrogen use efficiency and/or yield and/or C assimilation in a plant, the method comprising modulating the expression and/or activity of GRF, wherein the method comprises introducing at least one mutation into a GRF gene, wherein the GRF gene comprises or consists of
a. a nucleic acid sequence encoding a polypeptide as defined in SEQ ID NO: 3; or
b. a nucleic acid sequence as defined in SEQ ID NO: 1 or 2; or
c. a nucleic acid sequence with at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% overall sequence identity to either (a) or (b); or
d. a nucleic acid sequence encoding a GRF polypeptide that is capable of hybridising under stringent conditions as defined herein to the nucleic acid sequence of any of (a) to (c).

In yet a further aspect of the invention there is provided a nucleic acid construct comprising a nucleic acid sequence encoding at least one DNA-binding domain that can bind to at least one GRF gene.

In one embodiment, the nucleic acid sequence encodes at least one protospacer element, and wherein the sequence of the protospacer element is selected from SEQ ID NOs: 50, 53, 58, 61, 66, 69, 74, 77, 82, 86, 91, 94, 99, 102, 107, 110, 115, 118, 123, 126, 131, 134, 139, 142, 147, 150, 155, 158, 163, 166, 171, 174, 179, 182, 187 and 190 or a sequence that is at least 90% identical to SEQ ID NOs: 50, 53, 58, 61, 66, 69, 74, 77, 82, 86, 91, 94, 99, 102, 107, 110, 115, 118, 123, 126, 131, 134, 139, 142, 147, 150, 155, 158, 163, 166, 171, 174, 179, 182, 187 and 190.

In a further embodiment, the construct further comprises a nucleic acid sequence encoding a CRISPR RNA (crRNA) sequence, wherein said crRNA sequence comprises the protospacer element sequence and additional nucleotides.

In a further embodiment, the construct further comprises a nucleic acid sequence encoding a transactivating RNA (tracrRNA), wherein preferably the tracrRNA is defined in SEQ ID NO.46 or a functional variant thereof.

In another embodiment, the construct encodes at least one single-guide RNA (sgRNA), wherein said sgRNA comprises the tracrRNA sequence and the crRNA sequence, wherein the sgRNA comprises or consists of a sequence selected from SEQ ID NOs 51, 54, 59, 62, 67, 70, 75, 78, 83, 87, 92, 95, 100, 103, 108, 111, 116, 119, 124, 127, 132, 135, 140, 143, 148, 151, 156, 159, 164, 167, 172, 175, 180, 183, 188 and 191 or a variant thereof.

Preferably, the construct is operably linked to a promoter. More preferably, the promoter is a constitutive promoter.

In one embodiment, the nucleic acid construct further comprises a nucleic acid sequence encoding a CRISPR enzyme. Preferably, the CRISPR enzyme is a Cas protein. More preferably, the Cas protein is Cas9 or a functional variant thereof.

In an alternative embodiment, the nucleic acid construct encodes a TAL effector. Preferably, the nucleic acid construct further comprises a sequence encoding an endonuclease or DNA-cleavage domain thereof. More preferably, the endonuclease is FokI.

In another aspect of the invention there is provided a single guide (sg) RNA molecule wherein said sgRNA comprises a crRNA sequence and a tracrRNA sequence, wherein the crRNA sequence can bind to at least one sequence selected from SEQ ID NOs: 49, 52, 57, 60, 65, 68, 73, 76, 81, 85, 90, 93, 98, 101, 106, 109, 114, 117, 122, 125, 130, 133, 138, 141, 146, 149, 154, 157, 162, 165, 170, 173, 178, 181, 186 and 189 or a variant thereof.

In another aspect of the invention, there is provided a nucleic acid construct comprising a DNA donor nucleic acid selected from SEQ ID NOs: 48, 56, 64, 72, 80, 84, 89, 97, 105, 113, 121, 129, 137, 145, 153, 161, 169, 177 and 185 ora variant thereof, wherein said DNA donor nucleic acid is operably linked to a regulatory sequence. Preferably, the construct further comprises at least one sgRNA selected from SEQ ID NOs: 51, 54, 59, 62, 67, 70, 75, 78, 83, 87, 92, 95, 100, 103, 108, 111, 116, 119, 124, 127, 132, 135, 140, 143, 148, 151, 156, 159, 164, 167, 172, 175, 180, 183, 188 and 191 preferably operably linked to a regulatory sequence. More preferably, the construct further comprises a nucleic acid encoding a CRISPR enzyme preferably operably linked to a regulatory sequence.

In another aspect, there is provided an isolated plant cell transfected with at least one nucleic acid construct as described herein or at least one sgRNA as described herein.

In a further aspect of the invention, there is provided an isolated plant cell transfected with at least one nucleic acid construct as described herein and a second nucleic acid construct, wherein said second nucleic acid construct comprises a nucleic acid sequence encoding a Cas protein, preferably a Cas9 protein or a functional variant thereof. In one embodiment, the second nucleic acid construct is transfected before, after or concurrently with the nucleic acid construct described herein, preferably comprising only the sgRNA nucleic acid.

In another aspect of the invention there is provided a genetically modified plant, wherein said plant comprises the transfected cell described herein.

In a further aspect of the invention, there is provided a genetically modified plant as described herein, wherein the nucleic acid encoding the sgRNA and/or the nucleic acid encoding a Cas protein is integrated in a stable form.

In another aspect of the invention, there is provided a method of increasing nitrogen uptake and/or nitrogen assimilation and/or nitrogen use efficiency and/or yield and/or C assimilation in a plant, the method comprising introducing and expressing in a plant the nucleic acid construct described herein or the sgRNA described herein, wherein preferably said increase is relative to a control or wild-type plant.

In another embodiment, there is provided the use of a nucleic acid construct as defined herein or the sgRNA as described herein to increase nitrogen uptake and/or nitrogen assimilation and/or nitrogen use efficiency in a plant. Preferably, the nucleic acid construct or sgRNA increases the expression and/or activity of GRF in a plant.

In another aspect of the invention, there is provided a method for obtaining the genetically modified plant as described herein, the method comprising:
a. selecting a part of the plant;
b. transfecting at least one cell of the part of the plant of paragraph (a) with the nucleic acid construct as described herein;
c. regenerating at least one plant derived from the transfected cell or cells; by selecting one or more plants obtained according to paragraph (b) that show increased expression of at least one GRF nucleic acid in said plant.

In a final aspect of the invention, there is provided a method of increasing carbon metabolism and/or cell proliferation in plants (as well, as optionally, as described above, nitrogen metabolism), the method comprising increasing the expression or increasing the levels of GRF4. In one embodiment, carbon metabolism is selected from at least one of photosynthesis, carbon signalling, sugar signalling, and sucrose or phloem loading. In another embodiment, cell proliferation comprises cell division. In particular, the method may comprise increasing the expression of genes involved in carbon metabolism and/or cell signalling (e.g. cyclin dependent kinases). In one embodiment, the increase in cell proliferation increases leaf and stem width, but preferably not stem height.

In one embodiment of any above described aspect, the GRF nucleic acid encodes a GRF polypeptide wherein the GRF polypeptide comprises or consists of SEQ ID NO: 3 or 6 or a functional variant or homologue thereof. Preferably, the nucleic acid comprises or consists of SEQ ID NO: 1, 2, 4 or 5. In another embodiment, the nucleic acid encoding a GRF promoter comprises or consists of SEQ ID NO: 7 or 8 a functional variant or homologue thereof.

In one embodiment, GRF is GRF4 or a homologue or orthologue thereof.

In one embodiment, of any above described aspect, the nitrogen is nitrate or ammonium.

In another aspect of the invention, there is provided a plant obtained or obtainable by any of the methods described herein.

In one embodiment, of any above described aspect, the plant is a monocot or dicot.

Preferably, the plant is selected from rice, maize, wheat, barley, sorghum, potato, tomato, soybean and *B. napus*. More preferably, the plant is rice. Even more preferably, rice is the indica or *japonica* variety.

DESCRIPTION OF THE FIGURES

The invention is further described in the following non-limiting figures.

DETAILED DESCRIPTION OF THE INVENTION

Figure 1:
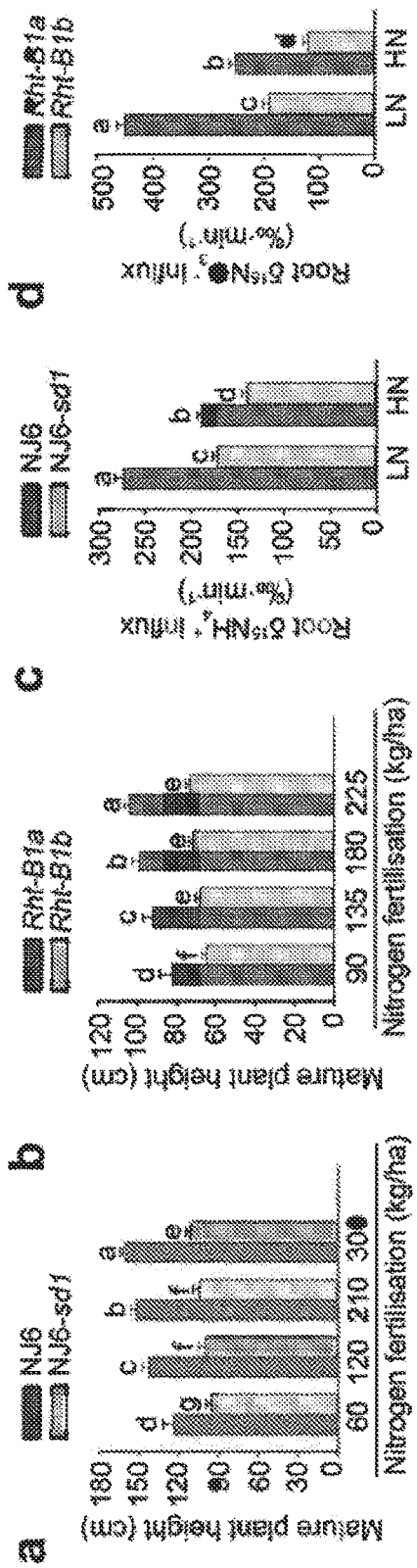
FIG. 1 shows DELLA accumulation inhibits growth N-response and N-uptake of rice and wheat GRVs. a, Heights of rice plants grown in differing N-supply regimes. b, Heights of wheat plants grown in differing N-supply regimes. Data (a, b) shown as mean±s.e.m. (n=30). c, Rice root $^{15}NH_4^+$ uptake rates in low (0.375 mM $NH_4NO_3$; LN) and high (1.25 mM $NH_4NO_3$; HN) N supply. d, Wheat root $^{15}NO_3^-$ uptake rates in low (0.375 mM $Ca(NO_3)_2$; LN) and high (1.25 mM $Ca(NO_3)_2$; HN) N supply. Data (c, d) shown as mean±s.e.m. (n=9). Statistical analyses were performed using Duncan's multiple range tests, the same lowercase letter denotes a non-significant difference between means (P>0.05).

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The practice of the present invention will employ, unless otherwise indicated, conventional techniques of botany, microbiology, tissue culture, molecular biology, chemistry, biochemistry and recombinant DNA technology, bioinformatics which are within the skill of the art. Such techniques are explained fully in the literature.

As used herein, the words "nucleic acid", "nucleic acid sequence", "nucleotide", "nucleic acid molecule" or "polynucleotide" are intended to include DNA molecules (e.g., cDNA or genomic DNA), RNA molecules (e.g., mRNA), natural occurring, mutated, synthetic DNA or RNA molecules, and analogs of the DNA or RNA generated using nucleotide analogs. It can be single-stranded or double-stranded. Such nucleic acids or polynucleotides include, but are not limited to, coding sequences of structural genes, anti-sense sequences, and non-coding regulatory sequences that do not encode mRNAs or protein products. These terms also encompass a gene. The term "gene" or "gene sequence" is used broadly to refer to a DNA nucleic acid associated with a biological function. Thus, genes may include introns and exons as in the genomic sequence, or may comprise only a coding sequence as in cDNAs, and/or may include cDNAs in combination with regulatory sequences.

The terms "polypeptide" and "protein" are used interchangeably herein and refer to amino acids in a polymeric form of any length, linked together by peptide bonds.

The term "promoter" typically refers to a nucleic acid control sequence located upstream from the transcriptional start of a gene and which is involved in the binding of RNA polymerase and other proteins, thereby directing transcription of an operably linked nucleic acid. Encompassed by the aforementioned terms are transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression in response to developmental and/or external stimuli, or in a tissue-specific manner. Also included within the term is a transcriptional regulatory sequence of a classical prokaryotic gene, in which case it may include a −35 box sequence and/or −10 box transcriptional regulatory sequences.

The aspects of the invention involve recombination DNA technology and exclude embodiments that are solely based on generating plants by traditional breeding methods.

The term "GRF" refers to Growth Regulatory Factor, a plant-specific transcription factor. Preferably GRF is GRF4. In one example, GRF is rice GRF4 (also termed OsGRF4) or an orthologue thereof.

The term "nitrogen" as used herein may include nitrate (NO$_{3-}$) and/or ammonium (NH$_{4+}$).

For the purposes of the invention, a "genetically altered plant" or "mutant plant" is a plant that has been genetically altered compared to the naturally occurring wild type (WT) plant. In one embodiment, a mutant plant is a plant that has been altered compared to the naturally occurring wild type (WT) plant using a mutagenesis method, such as any of the mutagenesis methods described herein. In one embodiment, the mutagenesis method is targeted genome modification or genome editing. In one embodiment, the plant genome has been altered compared to wild type sequences using a mutagenesis method. Such plants have an altered phenotype as described herein, such as an increased nitrogen metabolism. Therefore, in this example, increased nitrogen metabolism is conferred by the presence of an altered plant genome, for example, a mutated endogenous GRF gene or promoter. In one embodiment, the endogenous promoter or gene sequence is specifically targeted using targeted genome modification and the presence of a mutated gene or promoter sequence is not conferred by the presence of transgenes expressed in the plant. In other words, the genetically altered plant can be described as transgene-free.

Nonetheless, in an alternative embodiment, the genetically altered plant is a transgenic plant. For the purposes of the invention, "transgenic", "transgene" or "recombinant" means with regard to, for example, a nucleic acid sequence, an expression cassette, gene construct or a vector comprising the nucleic acid sequence or an organism transformed with the nucleic acid sequences, expression cassettes or vectors according to the invention, all those constructions brought about by recombinant methods in which either (a) the nucleic acid sequences encoding proteins useful in the methods of the invention, or (b) genetic control sequence(s) which is operably linked with the nucleic acid sequence according to the invention, for example a promoter, or (c) a) and b) are not located in their natural genetic environment or have been modified by recombinant methods, it being possible for the modification to take the form of, for example, a substitution, addition, deletion, inversion or insertion of one or more nucleotide residues.

The natural genetic environment is understood as meaning the natural genomic or chromosomal locus in the original plant or the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp. A naturally occurring expression cassette—for example the naturally occurring combination of the natural promoter of the nucleic acid sequences with the corresponding nucleic acid sequence encoding a polypeptide useful in the methods of the present invention, as defined above—becomes a transgenic expression cassette when this expression cassette is modified by non-natural, synthetic ("artificial") methods such as, for example, mutagenic treatment. Suitable methods are described, for example, in U.S. Pat. No. 5,565,350 or WO 00/15815.

A plant according to all aspects of the invention described herein may be a monocot or a dicot plant. Preferably, the plant is a crop plant. By crop plant is meant any plant which is grown on a commercial scale for human or animal consumption or use. In a preferred embodiment, the plant is a cereal. In another embodiment the plant is *Arabidopsis*.

In a most preferred embodiment, the plant is selected from rice, maize, wheat, barley, sorghum, *brassica*, soybean, potato and tomato. In one embodiment, the plant is a GRV (semi-dwarf green revolution variety). In a most preferred embodiment the plant is rice, preferably from the *japonica* or indica varieties. In this example, the indica variety preferably carries a mutant sd1 allele which causes stabilisation of growth repressing DELLA proteins (DELLAs), and more preferably the indicia variety is selected from TQ, NJ11, ZF802, MH63, CY1, HHZ, GC2, HJX74, ZS97B, MH86, GLA4, WXQ, GF3, SKZ, SH527, XAZ9, FAZ, TZZL1, 78130, 93-11, SH881, LTZ, LTP, QXJZ, HY33, 8B, EJQ, QGH, XAZ4, H410, EJL1, YFZ, EJF and SG1. In another example, the *japonica* variety carries a variant (dep1) Gγ subunit, for example, WJY7-dep1. In another embodiment the plant is wheat and preferably the plant carries a mutant Rht allele which causes stabilisation of DELLAs, for example Chinese wheat GRV KN199.

The term "plant" as used herein encompasses whole plants, ancestors and progeny of the plants and plant parts, including seeds, fruit, shoots, stems, leaves, roots (including tubers), flowers, tissues and organs, wherein each of the aforementioned comprise the nucleic acid construct as described herein or carry the herein described mutations. The term "plant" also encompasses plant cells, suspension cultures, callus tissue, embryos, meristematic regions, gametophytes, sporophytes, pollen and microspores, again wherein each of the aforementioned comprises the nucleic acid construct or mutations as described herein.

The invention also extends to harvestable parts of a plant of the invention as described herein, but not limited to seeds, leaves, fruits, flowers, stems, roots, rhizomes, tubers and bulbs. The aspects of the invention also extend to products derived, preferably directly derived, from a harvestable part of such a plant, such as dry pellets or powders, oil, fat and fatty acids, starch or proteins. Another product that may be derived from the harvestable parts of the plant of the invention is biodiesel. The invention also relates to food products and food supplements comprising the plant of the invention or parts thereof. In one embodiment, the food products may be animal feed. In another aspect of the invention, there is provided a product derived from a plant as described herein or from a part thereof.

In a most preferred embodiment, the plant part or harvestable product is a seed or grain. Therefore, in a further aspect of the invention, there is provided a seed produced from a genetically altered plant as described herein.

In an alternative embodiment, the plant part is pollen, a propagule or progeny of the genetically altered plant described herein. Accordingly, in a further aspect of the invention there is provided pollen, a propagule or progeny produced from a genetically altered plant as described herein.

A control plant as used herein according to all of the aspects of the invention is a plant which has not been modified according to the methods of the invention. Accordingly, in one embodiment, the control plant does not have increased expression of a GRF nucleic acid and/or altered activity of a GRF polypeptide, as described above. In an alternative embodiment, the plant has not been genetically modified, as described above. In one embodiment, the control plant is a wild type plant. The control plant is typically of the same plant species, preferably having the same genetic background as the modified plant.

Methods of Increasing Nitrogen Uptake

In a first aspect of the invention there is provided a method of increasing nitrogen uptake and/or nitrogen assimilation and/or nitrogen use efficiency in a plant, the method comprising increasing the expression or levels of a growth regulatory factor (GRF) or increasing the activity of a growth regulatory factor.

An "increase" as used herein, may refer to an increase of at least 1%, 2%, 3%, 4%, 5%, 6%, 7%, 8%, 9%, 10%, 20%, 30%, 40%, 50%, 60%, 70%, 80%, 90 or 95% or more compared to a control plant. Said increase may be in the roots and/or shoots of the plant.

The term "nitrogen use efficiency" or NUE can be defined as being yield of crop (e.g. yield of grain). Alternatively, NUE can be defined as agricultural NUE that means grain yield/N. The overall N use efficiency of plants comprises both uptake and utilization efficiencies and can be calculated as UpE. In one embodiment, NUE is increased by 5%-50% or more compared to a control plant.

The term "nitrogen assimilation" can be defined as the formation of organic nitrogen compounds from inorganic nitrogen.

An increase in at least one of nitrogen uptake, nitrogen assimilation and nitrogen use efficiency may be referred to herein as an increase in nitrogen metabolism.

In a further embodiment, the method further comprises increasing yield, preferably grain yield in a plant. That is, the method comprises increasing at least one of nitrogen uptake, nitrogen assimilation and NUE in a plant, and increasing yield.

The term "yield" in general means a measurable produce of economic value, typically related to a specified crop, to an area, and to a period of time. Individual plant parts directly contribute to yield based on their number, size and/or weight. The actual yield is the yield per square meter for a crop per year, which is determined by dividing total production per year (includes both harvested and appraised production) by planted square metres.

The term "increased yield" as defined herein can be taken to comprise any or at least one of the following and can be measured by assessing one or more of (a) increased biomass (weight) of one or more parts of a plant, aboveground (harvestable parts), or increased root biomass, increased root volume, increased root length, increased root diameter or increased root length or increased biomass of any other harvestable part. Increased biomass may be expressed as g/plant or kg/hectare, (b) increased seed yield per plant, which may comprise one or more of an increase in seed biomass (weight) per plant or on an individual basis, (c) increased seed filling rate, (d) increased number of filled seeds, (e) increased harvest index, which may be expressed as a ratio of the yield of harvestable parts such as seeds over the total biomass, (f) increased viability/germination efficiency, (g) increased number or size or weight of seeds or pods or beans or grain (h) increased seed volume (which may be a result of a change in the composition (i.e. lipid (also referred to herein as oil)), protein, and carbohydrate total content and composition, (i) increased (individual or average) seed area, (j) increased (individual or average) seed length, (k) increased (individual or average) seed perimeter, (l) increased growth or increased branching, for example inflorescences on more branches, (m) increased fresh weight or grain fill (n) increased ear weight (o) increased thousand kernel weight (TKW), which may be taken from the number of filled seeds counted and their total weight and may be as a result of an increase in seed size and/or seed weight (p) decreased number of barren tillers per plant and (q) sturdier or stronger culms or stems. All parameters are relative to a wild-type or control plant.

In a preferred embodiment, said increased yield comprises an increase in at least one of grain numbers per panicle or per plant and/or an increase in 1000-grain weight. Yield is increased relative to a control or wild-type plant. For example, the yield is increased by 2%, 3%, 4%, 5%, 6%, 7%, 8%, 9%, 10%, 11%, 12%, 13%, 14%, 15%, 16%, 17%, 18%, 19% or 20%, 25%, 30%, 35%, 40%, 45% or 50% compared to a control or wild-type plant. Accordingly, an increase in grain yield can be measured by assessing one or more of grain numbers per panicle or per plant and thousand kernel weight. The skilled person would be able to measure any of the above yield parameters using known techniques in the art.

The terms "seed" and "grain" as used herein can be used interchangeably. The terms "increase", "improve" or "enhance" as used herein are also interchangeable.

In a further embodiment, the method further comprises increasing C assimilation in a plant. An increase is as defined above.

In a preferred embodiment, GRF is GRF4 (growth regulatory factor 4) or a homologue or orthologue thereof. In one embodiment, GRF4 is rice GRF4 or OsGRF4.

As used herein, the terms "increasing the expression" means an increase in the nucleotide levels and "increasing the levels" as used herein means an increase in the protein levels of GRF.

As also used herein "increasing the activity" of GRF means increasing the biological activity of GRF, for example, increasing the transcriptional activity of GRF (i.e. the ability of GRF to bind and increase transcription of its target genes). In one embodiment GRF is GRF4, and GRF4 acts in a transcriptional complex with GIF1, which binds to and promotes transcription of target genes, such as genes involved in N, C metabolism and in cell proliferation. This complex is inhibited by SLR1. SLR1 also reduces GRF4 accumulation by inhibition of GRF4 transcription. Accordingly, in one embodiment, increasing the activity of GRF, particularly GRF4 may comprise increasing the expression or activity of GIF1 or an orthologue thereof and/or decreasing or abolishing the expression or activity of SLR1 or an orthologue thereof. Thus, in an alternative aspect, the method may comprise introducing at least one mutation into a SLR1 and/or GIF1 gene or a homologue thereof or introducing a further copy of the GIF gene or a homologue thereof and/or decreasing or increasing the activity of SLR1 and GIF1 respectively. Alternatively, the method may comprise introducing and expressing in a nucleic acid comprising a nucleic acid sequence encoding GIF1. We have also shown here that GA (Gibberellic acid) promotes the proteasome-mediated destruction of SLR1. Accordingly, in one embodiment, the activity of SLR1 may be mediated using GA.

In one embodiment, the expression or levels or activity of GRF are increased by up to or more than 5%, 10%, 20%, 30%, 40%, 50%, 60%, 70%, 80% or 90% when compared to the level in a wild-type or control plant.

Methods for determining the level of GRF expression and/or activity would be well known to the skilled person. In particular increases can be measured by any standard technique known to the skilled person. For example, an increase in the expression and/or content levels of GRF may comprise a measure of protein and/or nucleic acid levels and can be measured by any technique known to the skilled person, such as, but not limited to, any form of gel electrophoresis or chromatography (e.g. HPLC).

As GRF encodes a transcription factor, in one embodiment, the method may comprise measuring the transcriptional profile of GRF (versus wild-type or a control) using techniques standard in the art, such as, but not limited to, RNA-seq and CHIP-seq.

In a preferred embodiment, the method does not affect plant height. That is, the method increases at least one of nitrogen uptake, nitrogen assimilation and NUE and optionally yield and/or C assimilation, but has no effect on plant height. As a result, the method does not affect the benefits of semi-dwarfism that is a characteristic of the GRVs.

In one embodiment, the method may comprise introducing at least one mutation into a least one nucleic acid encoding a GRF and/or the promoter of a GRF. In one embodiment, the method comprises introducing at least one mutation into at least one endogenous gene encoding a GRF, preferably GRF4 or the GRF4 promoter.

Alternatively, the method may comprise the insertion of at least one or more additional copy of a nucleic acid encoding a GRF polypeptide or a homolog or variant thereof such that said sequence is operably linked to a regulatory sequence.

In one embodiment, the nucleic acid encodes a GRF4 as defined in SEQ ID NO: 3 or a functional variant or homologue thereof. In a further embodiment, the nucleic acid comprises or consists of a nucleic acid sequence as defined in SEQ ID NOs 1 or 2 or a functional variant or homologue thereof.

By "GRF promoter" or "GRF4 promoter" is meant a region extending for at least 5 kbp, preferably at least 2.5 kbp, more preferably at least 1 kbp upstream of the ATG codon of the GRF, preferably GRF4 ORF (open reading frame). In one embodiment, the sequence of the GRF4 promoter comprises or consists of a nucleic acid sequence as defined in SEQ ID No: 7 (haplotype A) or 8 (haplotype C) a functional variant or homologue thereof.

In the above embodiments an 'endogenous' nucleic acid may refer to the native or natural sequence in the plant genome. In one embodiment, the endogenous sequence of the GRF4 gene comprises or consists of SEQ ID NO: 1 or 2 and encodes an amino acid sequence as defined in SEQ ID NO: 3 or homologs thereof. Also included in the scope of this invention are functional variants (as defined herein) and homologs of the above identified sequences. Examples of GRF4 homologs are shown in SEQ ID NOs 4 to 39 and 192 to 201. Accordingly, in one embodiment, the homolog encodes a polypeptide selected from SEQ ID NOs 12, 15, 18, 21, 24, 27, 30, 33, 36 and 39 or the homolog comprises or consists of a nucleic acid sequence selected from SEQ ID NOs 11, 14, 17, 20, 23, 26, 29, 32, 35 and 38. In another embodiment, the GRF promoter homolog comprises or consists of a nucleic acid sequence selected from SEQ ID NOs 192 to 201.

The term "variant" or "functional variant" as used herein with reference to any of SEQ ID NOs: 1 to 201 refers to a variant gene sequence or part of the gene sequence which retains the biological function of the full non-variant sequence. A functional variant also comprises a variant of the gene of interest, which has sequence alterations that do not affect function, for example in non-conserved residues. Also encompassed is a variant that is substantially identical, i.e. has only some sequence variations, for example in non-conserved residues, compared to the wild type sequences as shown herein and is biologically active. Alterations in a nucleic acid sequence that results in the production of a different amino acid at a given site that does not affect the functional properties of the encoded polypeptide are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

As used in any aspect of the invention described herein a "variant" or a "functional variant" has at least 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% overall sequence identity to the non-variant nucleic acid or amino acid sequence.

The term homolog, as used herein, also designates a GRF promoter or GRF gene orthologue from other plant species. A homolog may have, in increasing order of preference, at least 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% overall sequence identity to the amino acid represented by SEQ ID NO: 3 or to the nucleic acid sequences shown in SEQ ID NOs: 1 or 2. In one embodiment, overall sequence identity is at least 37%. In one embodiment, overall sequence identity is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, most preferably 90%, 91%, 92%, 93%, 94%, 95%, 96%, 97%, 98%, or at least 99%.

Functional variants of GRF homologs as defined above are also within the scope of the invention.

The GRF polypeptide encodes a transcription factor that is characterised by at least a conserved QLQ domain (glutamine, leucine, glutamine) and a WRC domain (tryptophan, arginine and cysteine). In one embodiment, a homolog or variant may also have at least one of a WRC and QLQ domain. Accordingly, in one embodiment, the homolog or variant encodes a GRF4 polypeptide with at least 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% overall sequence identity to the amino acid represented by SEQ ID NO: 3 and has at least one of a WRC and QLQ domain.

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognised that residue positions that are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Non-limiting examples of algorithms that are suitable for determining percent sequence identity and sequence similarity are the BLAST and BLAST 2.0 algorithms.

Suitable homologues can be identified by sequence comparisons and identifications of conserved domains. There are predictors in the art that can be used to identify such sequences. The function of the homologue can be identified as described herein and a skilled person would thus be able to confirm the function, for example when overexpressed in a plant.

Thus, the nucleotide sequences of the invention and described herein can also be used to isolate corresponding sequences from other organisms, particularly other plants, for example crop plants. In this manner, methods such as PCR, hybridization, and the like can be used to identify such sequences based on their sequence homology to the sequences described herein. Topology of the sequences and the characteristic domains structure can also be considered when identifying and isolating homologs.

Sequences may be isolated based on their sequence identity to the entire sequence or to fragments thereof. In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen plant. The hybridization probes may be genomic DNA fragments, cDNA fragments, RNA fragments, or other oligonucleotides, and may be labelled with a detectable group, or any other detectable marker. Methods for preparation of probes for hybridization and for construction of cDNA and genomic libraries are generally known in the art and are disclosed in Sambrook, et al., (1989) Molecular Cloning: A Library Manual (2d ed., Cold Spring Harbor Laboratory Press, Plainview, New York).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence dependent and will be different in different circumstances. By controlling the stringency of the hybridization and/or washing conditions, target sequences that are 100% complementary to the probe can be identified (homologous probing).

Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Duration of hybridization is generally less than about 24 hours, usually about 4 to 12 hours. Stringent conditions may also be achieved with the addition of destabilizing agents such as formamide.

In a further embodiment, a variant as used herein can comprise a nucleic acid sequence encoding a GRF polypeptide as defined herein that is capable of hybridising under stringent conditions as defined herein to a nucleic acid sequence as defined in SEQ ID NO: 1 or 2.

In one embodiment, there is provided a method of increasing nitrogen uptake and/or nitrogen assimilation and/or nitrogen use efficiency in a plant, as described herein, the method comprising increasing the expression and/or activity of a GRF, as described herein, wherein the method comprises introducing at least one mutation into a GRF gene and/or promoter, wherein the GRF gene comprises or consists of
  a. a nucleic acid sequence encoding a polypeptide as defined in one of SEQ ID NO:3, 12, 15, 18, 21, 24, 27, 30, 33, 36 and 39; or
  b. a nucleic acid sequence as defined in one of SEQ ID NO: 1, 2, 11, 14, 17, 20, 23, 26, 29, 32, 35, 38 and 192 to 201; or
  c. a nucleic acid sequence with at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% overall sequence identity to either (a) or (b); or
  d. a nucleic acid sequence encoding a GRF polypeptide as defined herein that is capable of hybridising under stringent conditions as defined herein to the nucleic acid sequence of any of (a) to (c).

and wherein the GRF promoter comprises or consists of
  e. a nucleic acid sequence as defined in one of SEQ ID NOs 7, 8, 9 and 192 to 201;
  f. a nucleic acid sequence with at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% overall sequence identity to (e); or
  g. a nucleic acid sequence capable of hybridising under stringent conditions as defined herein to the nucleic acid sequence of any of (e) to (f).

In one embodiment, the mutation that is introduced into the endogenous GRF gene or promoter thereof to increase the biological activity and/or expression levels of the GRF gene or protein may be selected from the following mutation types
  1. a "missense mutation", which is a change in the nucleic acid sequence that results in the substitution of an amino acid for another amino acid;
  2. a "nonsense mutation" or "STOP codon mutation", which is a change in the nucleic acid sequence that results in the introduction of a premature STOP codon and, thus, the termination of translation (resulting in a truncated protein); plant genes contain the translation stop codons "TGA" (UGA in RNA), "TAA" (UAA in RNA) and "TAG" (UAG in RNA); thus any nucleotide substitution, insertion, deletion which results in one of these codons to be in the mature mRNA being translated (in the reading frame) will terminate translation.
  3. an "insertion mutation" of one or more amino acids, due to one or more codons having been added in the coding sequence of the nucleic acid;
  4. a "deletion mutation" of one or more amino acids, due to one or more codons having been deleted in the coding sequence of the nucleic acid;
  5. a "frameshift mutation", resulting in the nucleic acid sequence being translated in a different frame downstream of the mutation. A frameshift mutation can have various causes, such as the insertion, deletion or duplication of one or more nucleotides.
  6. a "splice site" mutation, which is a mutation that results in the insertion, deletion or substitution of a nucleotide at the site of splicing.
  7. an "inversion" mutation, which is a one hundred and eighty rotation of a sequence of nucleic acid.

Most preferably however, the mutation is a substitution. That is, the substitution of one base for another, different base.

Such an altered GRF polypeptide may result in a dominant or semi-dominant gain of function allele as defined herein.

The mutation in the endogenous gene can comprise at least one mutation in any one of the following sites: the coding region of the GRF gene, preferably exon 3; a micro RNA (miRNA) binding site, preferably at the miR396 binding site; an intronic sequence, preferably intron 2 and/or intron 3; and/or at a splice site, in the 5'UTR, the 3'UTR, the termination signal, the splice acceptor site or the ribosome binding site.

In one example the miR396 binding or recognition site comprises or consists of the following sequence or a variant thereof, as defined herein:

SEQ ID NO: 45
CCGTTCAAGAAAGCCTGTGGAA:

Preferably the mutation is any mutation that prevents the cleavage of the sequence by microRNA and thus its subsequent degradation. This results in an increase in the levels of both GRF mRNA and protein. In one embodiment, the mutation is a substitution.

In a specific embodiment, the mutation is one or both of the following:
  a T to A at position 4 of SEQ ID NO: 45 or a homologous position thereof;
  a C to A at position 5 of SEQ ID NO: 45 or a homologous position thereof.

In an additional or alternative embodiment, the mutation is in intron 2 and/or intron 3 at least one of the following:
  an A to G at position 724 or 725 of SEQ ID NO: 1 or a homologous position thereof;
  a T to C at position 1672 of SEQ ID NO: 1 or a homologous position thereof.

Alternatively or in addition to at least one of the above described mutations in the endogenous gene, the mutation is in the GRF promoter. Preferably said mutation is any mutation that increases the expression of GRF. In one example, the mutation is at least one of or any combination thereof of the following mutations. The former positions are positions in the haplotype A promoter (for example, a promoter that comprises or consists of SEQ ID NO: 7 or a variant thereof). The latter positions are positions in the haplotype C promoter (for example, a promoter that comprises or consists of SEQ ID NO: 8 or a variant thereof).
  a C to T substitution at position −941 or −935 from the GRF start codon or at position 60 of SEQ ID NO: 7 or position 66 of SEQ ID NO: 8; or a homologous position thereof;
  a T to A substitution at position −884 or position −878 from the GRF start codon or at position 118 of SEQ ID NO: 7 or position 124 of SEQ ID NO: 8; or a homologous position thereof;
  a C to T substitution at position −855 or −849 from the GRF start codon or at position 148 of SEQ ID NO: 7 or position 154 of SEQ ID NO: 8; or a homologous position thereof;
  a C to T substitution at position −847 or −841 from the GRF start codon or at position 157 of SEQ ID NO: 7 or position 163 of SEQ ID NO: 8; or a homologous position thereof;
  a C to T substitution at position −801 or −795 from the GRF start codon or at position 204 of SEQ ID NO: 7 or position 210 of SEQ ID NO: 8; or a homologous position thereof;
  a C to T substitution at position −522 or −516 from the GRF start codon or at position 484 of SEQ ID NO: 7 or position 489 of SEQ ID NO: 8; or a homologous position thereof;
  a G to C substitution at position −157 from the GRF start codon or at position 850 of SEQ ID NO: 7 or position 516 of SEQ ID NO: 8; or a homologous position thereof;

In one embodiment, the mutation is
  a T to A substitution at position −884 or position −878 from the GRF start codon or at position 118 of SEQ ID NO: 7 or position 124 of SEQ ID NO: 8; or a homologous position thereof; and
  a C to T substitution at position −847 or −841 from the GRF start codon or at position 157 of SEQ ID NO: 7 or position 163 of SEQ ID NO: 8; or a homologous position thereof;
  a C to T substitution at position −801 or −795 from the GRF start codon or at position 204 of SEQ ID NO: 7 or position 210 of SEQ ID NO: 8; or a homologous position thereof.

A GRF promoter comprising all three of the above polymorphisms may be known as haplotype B.

In one embodiment, the GRF promoter comprises at least one of the following sequences, and the method comprises introducing at least one mutation, preferably at least one substitution, into at least one of these sequences:

CAAACT

TTCTAA

CTAATT

ATACAA

TTACAG

ACATAC

ACTTAC

TAATTT

In one example, the GRF promoter comprises or consists of SEQ ID NO: 192 and the mutation is at least one mutation, preferably at least one substitution, in at least one of the following sequences present in SEQ ID NO: 192:

CAAACT

TTCTAA

CTAATT

In another example, the GRF promoter comprises or consists of SEQ ID NO: 193 and the mutation is at least one mutation, preferably at least one substitution, in at least one of the following sequences present in SEQ ID NO: 193:

ATACAA

TTCTAA

In another example, the GRF promoter comprises or consists of SEQ ID NO: 194 and the mutation is at least one mutation, preferably at least one substitution, in at least one of the following sequences present in SEQ ID NO: 194:

CTAATT

ATACAA

TTCTAA

In another example, the GRF promoter comprises or consists of SEQ ID NO: 195 and the mutation is at least one mutation, preferably at least one substitution, in the following sequence present in SEQ ID NO: 195:

TTCTAA

In another example, the GRF promoter comprises or consists of SEQ ID NO: 196 and the mutation is at least one mutation, preferably at least one substitution, in the following sequence present in SEQ ID NO: 196:

ATACAA

In another example, the GRF promoter comprises or consists of SEQ ID NO: 197 and the mutation is at least one mutation, preferably at least one substitution, in the following sequence present in SEQ ID NO: 197:

TTCATAA

In another example, the GRF promoter comprises or consists of SEQ ID NO: 198 and the mutation is at least one mutation, preferably at least one substitution, in at least one of the following sequences present in SEQ ID NO: 198:

CTAATT

ATACAA

TTACAG

TTCTAA

CAAACT

ACATAC

In another example, the GRF promoter comprises or consists of SEQ ID NO: 199 and the mutation is at least one mutation, preferably at least one substitution, in at least one of the following sequences present in SEQ ID NO: 199:

ACATAC

TTCTAA

ACTTAC

ATACAA

CAAACT

In another example, the GRF promoter comprises or consists of SEQ ID NO: 200 and the mutation is at least one mutation, preferably at least one substitution, in at least one of the following sequences present in SEQ ID NO: 200:

TTCTAA

CTAATT

ACTTAC

TTACAG

TAATTT

In another example, the GRF promoter comprises or consists of SEQ ID NO: 201 and the mutation is at least one mutation, preferably at least one substitution, in at least one of the following sequences present in SEQ ID NO: 201:

ACATAC

CAAACT

ATACAA

TTCTAA

CTAATT

By "at least one mutation" is meant that where the GRF gene is present as more than one copy or homologue (with the same or slightly different sequence) there is at least one mutation in at least one gene. Preferably all genes are mutated.

In one embodiment, the mutation is introduced using targeted genome editing. That is, in one embodiment, the invention relates to a method and plant that has been generated by genetic engineering methods as described above, and does not encompass naturally occurring varieties or generating plants by traditional breeding methods.

Targeted genome modification or targeted genome editing is a genome engineering technique that uses targeted DNA double-strand breaks (DSBs) to stimulate genome editing through homologous recombination (HR)-mediated recombination events. To achieve effective genome editing via introduction of site-specific DNA DSBs, four major classes of customisable DNA binding proteins can be used: meganucleases derived from microbial mobile genetic elements, ZF nucleases based on eukaryotic transcription factors, transcription activator-like effectors (TALEs) from *Xanthomonas* bacteria, and the RNA-guided DNA endonuclease Cas9 from the type II bacterial adaptive immune system CRISPR (clustered regularly interspaced short palindromic repeats). Meganuclease, ZF, and TALE proteins all recognize specific DNA sequences through protein-DNA interactions. Although meganucleases integrate nuclease and DNA-binding domains, ZF and TALE proteins consist of individual modules targeting 3 or 1 nucleotides (nt) of DNA, respectively. ZFs and TALEs can be assembled in desired combinations and attached to the nuclease domain of FokI to direct nucleolytic activity toward specific genomic loci.

Upon delivery into host cells via the bacterial type III secretion system, TAL effectors enter the nucleus, bind to effector-specific sequences in host gene promoters and activate transcription. Their targeting specificity is determined by a central domain of tandem, 33-35 amino acid repeats. This is followed by a single truncated repeat of 20 amino acids. The majority of naturally occurring TAL effectors examined have between 12 and 27 full repeats.

These repeats only differ from each other by two adjacent amino acids, their repeat-variable di-residue (RVD). The RVD that determines which single nucleotide the TAL effector will recognize: one RVD corresponds to one nucleotide, with the four most common RVDs each preferentially associating with one of the four bases. Naturally occurring recognition sites are uniformly preceded by a T that is required for TAL effector activity. TAL effectors can be fused to the catalytic domain of the FokI nuclease to create a TAL effector nuclease (TALEN) which makes targeted DNA double-strand breaks (DSBs) in vivo for genome editing. The use of this technology in genome editing is well described in the art, for example in U.S. Pat. Nos. 8,440,431, 8,440,432 and 8,450,471. Cermak T et al. describes a set of customized plasmids that can be used with the Golden Gate cloning method to assemble multiple DNA fragments. As described therein, the Golden Gate method uses Type IIS restriction endonucleases, which cleave outside their recognition sites to create unique 4 bp overhangs. Cloning is expedited by digesting and ligating in the same reaction mixture because correct assembly eliminates the enzyme recognition site. Assembly of a custom TALEN or TAL effector construct and involves two steps: (i) assembly of repeat modules into intermediary arrays of 1-10 repeats and (ii) joining of the intermediary arrays into a backbone to make the final construct. Accordingly, using techniques known in the art it is possible to design a TAL effector that targets a GRF gene or promoter sequence as described herein.

Another genome editing method that can be used according to the various aspects of the invention is CRISPR. The use of this technology in genome editing is well described in the art, for example in U.S. Pat. No. 8,697,359 and references cited herein. In short, CRISPR is a microbial nuclease system involved in defense against invading phages and plasmids. CRISPR loci in microbial hosts contain a combination of CRISPR-associated (Cas) genes as well as non-coding RNA elements capable of programming the specificity of the CRISPR-mediated nucleic acid cleavage (sgRNA). Three types (I-III) of CRISPR systems have been identified across a wide range of bacterial hosts. One key feature of each CRISPR locus is the presence of an array of repetitive sequences (direct repeats) interspaced by short stretches of non-repetitive sequences (spacers). The non-coding CRISPR array is transcribed and cleaved within direct repeats into short crRNAs containing individual spacer sequences, which direct Cas nucleases to the target site (protospacer). Type II CRISPR is one of the most well characterized systems and carries out targeted DNA double-strand breaks in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer.

One major advantage of the CRISPR-Cas9 system, as compared to conventional gene targeting and other programmable endonucleases is the ease of multiplexing, where multiple genes can be mutated simultaneously simply by using multiple sgRNAs each targeting a different gene. In addition, where two sgRNAs are used flanking a genomic region, the intervening section can be deleted or inverted (Wiles et al., 2015).

Cas9 is thus the hallmark protein of the type II CRISPR-Cas system, and is a large monomeric DNA nuclease guided to a DNA target sequence adjacent to the PAM (protospacer adjacent motif) sequence motif by a complex of two non-coding RNAs: CRISPR RNA (crRNA) and trans-activating crRNA (tracrRNA). The Cas9 protein contains two nuclease domains homologous to RuvC and HNH nucleases. The HNH nuclease domain cleaves the complementary DNA strand whereas the RuvC-like domain cleaves the non-complementary strand and, as a result, a blunt cut is introduced in the target DNA. Heterologous expression of Cas9 together with an sgRNA can introduce site-specific double strand breaks (DSBs) into genomic DNA of live cells from various organisms. For applications in eukaryotic organisms, codon optimized versions of Cas9, which is originally from the bacterium *Streptococcus pyogenes*, have been used.

The single guide RNA (sgRNA) is the second component of the CRISPR/Cas system that forms a complex with the Cas9 nuclease. sgRNA is a synthetic RNA chimera created by fusing crRNA with tracrRNA. The sgRNA guide sequence located at its 5' end confers DNA target specificity. Therefore, by modifying the guide sequence, it is possible to create sgRNAs with different target specificities. The canonical length of the guide sequence is 20 bp. In plants, sgRNAs have been expressed using plant RNA polymerase III promoters, such as U6 and U3. Accordingly, using techniques known in the art it is possible to design sgRNA molecules that targets a GRF gene or promoter sequence as described herein.

In one embodiment, the method uses the sgRNA (and template or donor DNA) constructs defined in detail below to introduce a targeted SNP or mutation, in particular one of the substitutions described herein into a GRF gene and/or promoter. As explained below, the introduction of a template DNA strand, following a sgRNA-mediated snip in the double-stranded DNA, can be used to produce a specific targeted mutation (i.e. a SNP) in the gene using homology directed repair. In an alternative embodiment, at least one mutation may be introduced into the GRF gene and/or promoter, particularly at the positions described above, using any CRISPR technique known to the skilled person. In another example, sgRNA (for example, as described herein) can be used with a modified Cas9 protein, such as nickase Cas9 or nCas9 or a "dead" Cas9 (dCas9) fused to a "Base Editor"—such as an enzyme, for example a deaminase such as cytidine deaminase, or TadA (tRNA adenosine deaminase) or ADAR or APOBEC. These enzymes are able to substitute one base for another. As a result no DNA is deleted, but a single substitution is made (Kim et al., 2017; Gaudelli et al. 2017).

In one example, a mutation is introduced into a miRNA396 binding site using the following sgRNA sequences and donor DNA nucleic acid sequences, as described herein:

TABLE 1

CRISPR constructs to introduce a TC to AA mutation in the miRNA396 recognition site.

| Crop | sgRNA nucleic acid (SEQ ID NOs) | Donor DNA sequence (SEQ ID NOs) |
|---|---|---|
| Rice | 51 and/or 54 | 48 |
| Maize | 116 and/or 119 | 113 |
| Maize | 124 and/or 127 | 121 |
| Wheat | 132 and/or 135 | 129 |
| Wheat | 140 and/or 143 | 137 |
| Wheat | 148 and/or 151 | 145 |
| Barley | 156 and/or 159 | 153 |
| *Sorghum* | 164 and/or 167 | 161 |

TABLE 1-continued

CRISPR constructs to introduce a TC to AA
mutation in the miRNA396 recognition site.

| Crop | sgRNA nucleic acid (SEQ ID NOs) | Donor DNA sequence (SEQ ID NOs) |
| --- | --- | --- |
| Soybean | 172 and/or 175 | 169 |
| B. Napus | 180 and/or 183 | 177 |
| Tomato | 188 and/or 191 | 185 |

In another example, at least one mutation is introduced into at least one position in the GRF promoter using the following sgRNA sequences and donor DNA nucleic acid sequences, as described herein:

TABLE 2

CRISPR constructs to introduce promoter mutations into OsGRF4

| SNP position (relative to ATG start codon of GRF4) | sgRNA nucleic acid (SEQ ID NOs) | Donor DNA sequence (SEQ ID NOs) |
| --- | --- | --- |
| −884 (T to A) | 59 and/or 62 | 56 |
| −847 (C to T) | 67 and/or 70 | 64 |
| −801 (C to T) | 75 and/or 78 | 72 |
| −884 and −847 (TC to AT) | 83 and/or 87 | 80 |
| −884 and −801 (TC to AT) | 92 and/or 95 | 89 |
| −884, −847 and −801(TCC to ATT) | 100 and/or 103 | 97 |
| −847 and −801 (CC to TT) | 108 and/or 111 | 105 |

Cas9 expression plasmids for use in the methods of the invention can be constructed as described in the art.

Once targeted genome editing has been performed, rapid high-throughput screening procedures can be used to analyse amplification products for the presence of a mutation in the GRF gene and/or promoter, and specifically at the positions described above. Once a mutation is identified in a gene of interest, the seeds of the M2 plant carrying that mutation are grown into adult M3 plants and screened for the phenotypic characteristics associated with the target gene GRF4. Mutants with increased GRF expression or levels, and as a result, increased nitrogen metabolism compared to a control can thus be identified.

Plants obtained or obtainable by such method which carry a functional mutation in the endogenous GRF gene or promoter locus are also within the scope of the invention.

In an alternative aspect of the invention, the method comprises introducing and expressing in the plant a nucleic acid construct comprising a GRF nucleic acid. Preferably, the GRF nucleic acid is operably linked to a regulatory sequence.

According to all aspects of the invention, including the method above and including the plants, methods and uses as described below, the term "regulatory sequence" is used interchangeably herein with "promoter" and all terms are to be taken in a broad context to refer to regulatory nucleic acid sequences capable of effecting expression of the sequences to which they are ligated. The term "regulatory sequence" also encompasses a synthetic fusion molecule or derivative that confers, activates or enhances expression of a nucleic acid molecule in a cell, tissue or organ.

In one embodiment, the promoter may be a constitutive or a strong promoter.

A "constitutive promoter" refers to a promoter that is transcriptionally active during most, but not necessarily all, phases of growth and development and under most environmental conditions, in at least one cell, tissue or organ. Examples of constitutive promoters include the cauliflower mosaic virus promoter (CaMV35S or 19S), rice actin promoter, maize ubiquitin promoter, rubisco small subunit, maize or alfalfa H3 histone, OCS, SAD1 or 2, GOS2 or any promoter that gives enhanced expression.

A "strong promoter" refers to a promoter that leads to increased or overexpression of the gene. Examples of strong promoters include, but are not limited to, CaMV-35S, CaMV-35Somega, *Arabidopsis* ubiquitin UBQ1, rice ubiquitin, actin, or Maize alcohol dehydrogenase 1 promoter (Adh-1).

Alternatively, the promoter may be a GRF4 promoter, preferably the haplotype B promoter. In one embodiment the haplotype B promoter comprises or consists of the sequence as defined in SEQ ID NO: 9 or a functional variant thereof.

The term "operably linked" as used herein refers to a functional linkage between the promoter sequence and the gene of interest, such that the promoter sequence is able to initiate transcription of the gene of interest.

In one embodiment, the GRF nucleic acid encodes a GRF polypeptide wherein the GRF polypeptide comprises or consists of SEQ ID NO: 3 or 6 or a functional variant or homologue thereof, as defined above. More preferably, the nucleic acid comprises or consists of SEQ ID NO: 1, 2, 4 or 5 or a functional variant or homologue thereof, as defined above.

In one embodiment, the progeny plant is stably transformed with the nucleic acid construct described herein and comprises the exogenous polynucleotide which is heritably maintained in the plant cell. The method may include steps to verify that the construct is stably integrated. The method may also comprise the additional step of collecting seeds from the selected progeny plant.

In a further embodiment, the method may further comprise at least one or more of the steps of assessing the phenotype of the transgenically or genetically altered plant, specifically, measuring or assessing an increase in nitrogen uptake and/or nitrogen assimilation and/or nitrogen use efficiency and/or yield, wherein preferably said increase is relative to a control or wild-type plant.

In one embodiment, the nucleic acid and regulatory sequence are from the same plant family. In another embodiment, the nucleic acid and regulatory sequence are from a different plant family, genus or species.

In a further embodiment of the above described methods, the method increases nitrogen uptake and/or nitrogen assimilation and/or nitrogen use efficiency and/or yield under low N conditions (e.g. 180 kg N/ha or lower, preferably between 180 and 120 kg N/ha, and even more preferably 120 kg N/ha or lower). Accordingly, in one embodiment, the method increases nitrogen uptake and/or nitrogen assimilation and/or nitrogen use efficiency and/or yield under nitrogen stress conditions. In another embodiment, the method increases nitrogen uptake and/or nitrogen assimilation and/or nitrogen use efficiency and/or yield under normal (e.g. 210 kg/Nha) or high N (above 300 kg/Nha) conditions.

Genetically Altered or Modified Plants and Methods of Producing Such Plants

In another aspect of the invention there is provided a genetically altered plant, part thereof or plant cell characterised in that the plant has increased expression or activity of the GRF nucleic acid or polypeptide compared to a wild-type or control plant. More preferably, the plant is also characterised by an increase in at least one of nitrogen uptake, nitrogen assimilation and NUE in a plant. Even more preferably, the plant is further characterised by an increase in yield. The plant may additionally or alternatively be characterised by an increase in C assimilation.

In one embodiment, the plant comprises at least one mutation in the GRF gene and/or its promoter. Preferably, the mutation is a substitution, and even more preferably, the mutation is one of the mutations described above. In a further embodiment, the mutation has been introduced using targeted genome editing, again as described above.

In another embodiment, the plant expresses a polynucleotide "exogenous" to an individual plant that is a polynucleotide, which is introduced into the plant by any means other than by a sexual cross. Examples of means by which this can be accomplished are described below. In one embodiment of the method, an exogenous nucleic acid is expressed in the plant which is a nucleic acid construct comprising a nucleic acid encoding a polypeptide sequence as defined in SEQ ID NO: 3 or a homolog or functional variant thereof and that is not endogenous to said plant but is from another plant species. For example, the OsGRF4 construct can be expressed in another plant that is not rice. Alternatively, an endogenous nucleic acid construct is expressed in the transgenic plant. For example, the OsGRF4 construct can be expressed in rice.

Accordingly, in one embodiment, the plant expresses a nucleic acid comprising a nucleic acid encoding a polypeptide sequence as defined in SEQ ID NO: 3 or a homolog or functional variant thereof. In either of these embodiments, the plant is a transgenic plant.

In another aspect of the invention, there is provided a method of making a transgenic plant, characterised in that the plant shows an increase in nitrogen uptake and/or nitrogen assimilation and/or nitrogen use efficiency, and optionally, additionally an increase in yield and/or C assimilation, as described herein. Preferably, the method comprises introducing and expressing a nucleic acid construct comprising a nucleic acid encoding a polypeptide as defined in SEQ ID NO: 3 or a homolog or functional variant thereof in a plant or plant cell. In one embodiment, the nucleic acid construct comprises or consists of a nucleic acid sequence as defined in SEQ ID NO: 1 or 2 or a homolog or functional variant thereof.

Transformation methods for generating a transgenic plant of the invention are known in the art. Thus, according to the various aspects of the invention, a nucleic acid construct as defined herein is introduced into a plant and expressed as a transgene. The nucleic acid construct is introduced into said plant through a process called transformation. The terms "introduction" or "transformation" as referred to herein encompass the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

Transformation of plants is now a routine technique in many species. Advantageously, any of several transformation methods may be used to introduce the gene of interest into a suitable ancestor cell. The methods described for the transformation and regeneration of plants from plant tissues or plant cells may be utilized for transient or for stable transformation. Transformation methods include the use of liposomes, electroporation, chemicals that increase free DNA uptake, injection of the DNA directly into the plant, particle gun bombardment, transformation using viruses or pollen and microinjection. Methods may be selected from the calcium/polyethylene glycol method for protoplasts, electroporation of protoplasts, microinjection into plant material, DNA or RNA-coated particle bombardment, infection with (non-integrative) viruses and the like. Transgenic plants, including transgenic crop plants, are preferably produced via *Agrobacterium tumefaciens* mediated transformation.

To select transformed plants, the plant material obtained in the transformation is subjected to selective conditions so that transformed plants can be distinguished from untransformed plants. For example, the seeds obtained in the above-described manner can be planted and, after an initial growing period, subjected to a suitable selection by spraying. A further possibility is growing the seeds, if appropriate after sterilization, on agar plates using a suitable selection agent so that only the transformed seeds can grow into plants. Alternatively, the transformed plants are screened for the presence of a selectable marker. Following DNA transfer and regeneration, putatively transformed plants may also be evaluated, for instance using Southern blot analysis, for the presence of the gene of interest, copy number and/or genomic organisation. Alternatively or additionally, expression levels of the newly introduced DNA may be monitored using Northern and/or Western blot analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The method may further comprise regenerating a transgenic plant from the plant or plant cell wherein the transgenic plant comprises in its genome a nucleic acid sequence selected from SEQ ID NO: 1 or 2 or a nucleic acid that encodes a GRF protein as defined in SEQ ID NO: 3 and obtaining a progeny plant derived from the transgenic plant, wherein said progeny exhibits at least one of an increase in nitrogen uptake and/or nitrogen assimilation and/or nitrogen use efficiency, and optionally, additionally an increase in yield and/or C assimilation.

In another aspect of the invention there is provided a method for producing a genetically altered plant as described herein. In one embodiment, the method comprises introducing at least one mutation into the GRF gene and/or GRF promoter of preferably at least one plant cell using any mutagenesis technique described herein. Preferably said method further comprises regenerating a plant from the mutated plant cell.

The method may further comprise selecting one or more mutated plants, preferably for further propagation. Preferably said selected plants comprise at least one mutation in the GRF gene and/or promoter sequence. In one embodiment, said plants are characterised by increased levels of GRF expression and/or increased levels of GRF polypeptide activity. Expression and/or activity levels of GRF can be measured by any standard technique known to the skilled person. An increase is as described herein.

The selected plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

In a further embodiment of any of the methods described herein, the method may further comprise at least one or more of the steps of assessing the phenotype of the transgenic or genetically altered plant, measuring at least one of an increase in nitrogen uptake and/or nitrogen assimilation and/or nitrogen use efficiency, and optionally additionally yield and/or C assimilation and comparing said phenotype to determine an increase in at least one of nitrogen uptake and/or nitrogen assimilation and/or nitrogen use efficiency, and optionally additionally yield and/or C assimilation in a wild-type or control plant. In other words, the method may involve the step of screening the plants for the desired phenotype.

In a further aspect of the invention there is provided a plant obtained or obtainable by the above described methods.

Genome Editing Constructs for Use with the Methods of Targeted Genome Modification By "crRNA" or CRISPR RNA is meant the sequence of RNA that contains the protospacer element and additional nucleotides that are complementary to the tracrRNA.

By "tracrRNA" (transactivating RNA) is meant the sequence of RNA that hybridises to the crRNA and binds a CRISPR enzyme, such as Cas9 thereby activating the nuclease complex to introduce double-stranded breaks at specific sites within the genomic sequence of at least one GRF1 nucleic acid or promoter sequence.

By "protospacer element" is meant the portion of crRNA (or sgRNA) that is complementary to the genomic DNA target sequence, usually around 20 nucleotides in length. This may also be known as a spacer or targeting sequence.

By "donor sequence" is a nucleic acid sequence that contains all the necessary elements to introduce the specific substitution into a target sequence, preferably using homology-directed repair or HDR. In one embodiment, the donor sequence comprises a repair template sequence for introduction of at least one SNP. Preferably the repair template sequence is flanked by at least one, preferably a left and right arm, more preferably around 100 bp each that are identical to the target sequence. More preferably the arm or arms are further flanked by two gRNA target sequences that comprise PAM motifs so that the donor sequence can be released by Cas9/gRNAs.

By "sgRNA" (single-guide RNA) is meant the combination of tracrRNA and crRNA in a single RNA molecule, preferably also including a linker loop (that links the tracrRNA and crRNA into a single molecule). "sgRNA" may also be referred to as "gRNA" and in the present context, the terms are interchangeable. The sgRNA or gRNA provide both targeting specificity and scaffolding/binding ability for a Cas nuclease. A gRNA may refer to a dual RNA molecule comprising a crRNA molecule and a tracrRNA molecule.

By "TAL effector" (transcription activator-like (TAL) effector) or TALE is meant a protein sequence that can bind the genomic DNA target sequence (a sequence within the GRF1 gene or promoter sequence) and that can be fused to the cleavage domain of an endonuclease such as FokI to create TAL effector nucleases or TALENS or meganucleases to create megaTALs. A TALE protein is composed of a central domain that is responsible for DNA binding, a nuclear-localisation signal and a domain that activates target gene transcription. The DNA-binding domain consists of monomers and each monomer can bind one nucleotide in the target nucleotide sequence. Monomers are tandem repeats of 33-35 amino acids, of which the two amino acids located at positions 12 and 13 are highly variable (repeat variable diresidue, RVD). It is the RVDs that are responsible for the recognition of a single specific nucleotide. HD targets cytosine; NI targets adenine, NG targets thymine and NN targets guanine (although NN can also bind to adenine with lower specificity).

In another aspect of the invention there is provided a nucleic acid construct wherein the nucleic acid construct encodes at least one DNA-binding domain, wherein the DNA-binding domain can bind to a sequence in the GRF gene, wherein said sequence is selected from SEQ ID Nos 49, 52, 57, 60, 65, 68, 73, 76, 81, 85, 90, 93, 98, 101, 106, 109, 114, 117, 122, 125, 130, 133, 138, 141, 146, 149, 154, 157, 162, 165, 170, 173, 178, 181, 186 and 189. In one embodiment, said construct further comprises a nucleic acid encoding a (SSN) sequence-specific nuclease, such as FokI or a Cas protein.

In one embodiment, the nucleic acid construct encodes at least one protospacer element wherein the sequence of the protospacer element is selected from SEQ ID No 50, 53, 58, 61, 66, 69, 74, 77, 82, 86, 91, 94, 99, 102, 107, 110, 115, 118, 123, 126, 131, 134, 139, 142, 147, 150, 155, 158, 163, 166, 171, 174, 179, 182, 187 and 190 or a variant thereof.

In a further embodiment, the nucleic acid construct comprises a crRNA-encoding sequence. As defined above, a crRNA sequence may comprise the protospacer elements as defined above and preferably additional nucleotides that are complementary to the tracrRNA. An appropriate sequence for the additional nucleotides will be known to the skilled person as these are defined by the choice of Cas protein.

In another embodiment, the nucleic acid construct further comprises a tracrRNA sequence. Again, an appropriate tracrRNA sequence would be known to the skilled person as this sequence is defined by the choice of Cas protein. Nonetheless, in one embodiment said sequence comprises or consists of a sequence as defined in SEQ ID NO: 46 or a variant thereof.

In a further embodiment, the nucleic acid construct comprises at least one nucleic acid sequence that encodes a sgRNA (or gRNA). Again, as already discussed, sgRNA typically comprises a crRNA sequence, a tracrRNA sequence and preferably a sequence for a linker loop. In a preferred embodiment, the nucleic acid construct comprises at least one nucleic acid sequence that encodes a sgRNA sequence as defined in any of SEQ ID Nos 51, 54, 59, 62, 67, 70, 75, 78, 83, 87, 92, 95, 100, 103, 108, 111, 116, 119, 124, 127, 132, 135, 140, 143, 148, 151, 156, 159, 164, 167, 172, 175, 180, 183, 188 and 191 or variant thereof.

In a further embodiment, the nucleic acid construct may further comprise at least one nucleic acid sequence encoding an endoribonuclease cleavage site. Preferably the endoribonuclease is Csy4 (also known as Cas6f). Where the nucleic acid construct comprises multiple sgRNA nucleic acid sequences the construct may comprise the same number of endoribonuclease cleavage sites. In another embodiment, the cleavage site is 5' of the sgRNA nucleic acid sequence. Accordingly, each sgRNA nucleic acid sequence is flanked by an endoribonuclease cleavage site.

The term 'variant' refers to a nucleotide sequence where the nucleotides are substantially identical to one of the above sequences. The variant may be achieved by modifications such as insertion, substitution or deletion of one or more nucleotides. In a preferred embodiment, the variant has at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% identity to any one of the above described sequences. In one embodiment, sequence identity is at least 90%. In another embodiment, sequence identity is 100%. Sequence identity can be determined by any one known sequence alignment program in the art.

The invention also relates to a nucleic acid construct comprising a nucleic acid sequence operably linked to a suitable plant promoter. A suitable plant promoter may be a constitutive or strong promoter or may be a tissues-specific promoter. In one embodiment, suitable plant promoters are selected from, but not limited to, cestrum yellow leaf curling virus (CmYLCV) promoter or switchgrass ubiquitin 1 promoter (PvUbi1) wheat U6 RNA polymerase III (TaU6) CaMV35S, wheat U6 or maize ubiquitin (e.g. Ubi1) promoters. In one embodiment, the promoter is p35S (SEQ ID NO: 40) or pUbi (SEQ ID NO: 41)

The nucleic acid construct of the present invention may also further comprise a nucleic acid sequence that encodes a CRISPR enzyme. By "CRISPR enzyme" is meant an RNA-guided DNA endonuclease that can associate with the CRISPR system. Specifically, such an enzyme binds to the tracrRNA sequence. In one embodiment, the CRIPSR enzyme is a Cas protein ("CRISPR associated protein), preferably Cas 9 or Cpf1, more preferably Cas9. In a specific embodiment Cas9 is codon-optimised Cas9, and more preferably, has the sequence described in SEQ ID NO: 42 or a functional variant or homolog thereof. In another embodiment, the CRISPR enzyme is a protein from the family of Class 2 candidate xproteins, such as C2c1, C2C2 and/or C2c3. In one embodiment, the Cas protein is from *Streptococcus pyogenes*. In an alternative embodiment, the Cas protein may be from any one of *Staphylococcus aureus, Neisseria meningitides, Streptococcus thermophiles* or *Treponema denticola*.

The term "functional variant" as used herein with reference to Cas9 refers to a variant Cas9 gene sequence or part of the gene sequence which retains the biological function of the full non-variant sequence, for example, acts as a DNA endonuclease, or recognition or/and binding to DNA. A functional variant also comprises a variant of the gene of interest which has sequence alterations that do not affect function, for example non-conserved residues. Also encompassed is a variant that is substantially identical, i.e. has only some sequence variations, for example in non-conserved residues, compared to the wild type sequences as shown herein and is biologically active. In one embodiment, a functional variant of SEQ ID NO.42 has at least 90%, 91%, 92%, 93%, 94%, 95%, 96%, 97%, 98%, or 99% overall sequence identity to the amino acid represented by SEQ ID NO: 42. In a further embodiment, the Cas9 protein has been modified to improve activity.

Suitable homologs or orthologs can be identified by sequence comparisons and identifications of conserved domains. The function of the homolog or ortholog can be identified as described herein and a skilled person would thus be able to confirm the function when expressed in a plant.

In a further embodiment, the Cas9 protein has been modified to improve activity. For example, in one embodiment, the Cas9 protein may comprise the D10A amino acid substitution, this nickase cleaves only the DNA strand that is complementary to and recognized by the gRNA. In an alternative embodiment, the Cas9 protein may alternatively or additionally comprise the H840A amino acid substitution, this nickase cleaves only the DNA strand that does not interact with the sRNA. In this embodiment, Cas9 may be used with a pair (i.e. two) sgRNA molecules (or a construct expressing such a pair) and as a result can cleave the target region on the opposite DNA strand, with the possibility of improving specificity by 100-1500 fold. In a further embodiment, the Cas9 protein may comprise a D1135E substitution. The Cas 9 protein may also be the VQR variant. Alternatively, the Cas protein may comprise a mutation in both nuclease domains, HNH and RuvC-like and therefore is catalytically inactive. Rather than cleaving the target strand, this catalytically inactive Cas protein can be used to prevent the transcription elongation process, leading to a loss of function of incompletely translated proteins when co-expressed with a sgRNA molecule. An example of a catalytically inactive protein is dead Cas9 (dCas9) caused by a point mutation in RuvC and/or the HNH nuclease domains (Komor et al., 2016 and Nishida et al., 2016).

In a further embodiment, a Cas protein, such as Cas9 may be further fused with a repression effector, such as a histone-modifying/DNA methylation enzyme or a Base Editor, such as cytidine deaminase (Komor et al. 2016) to effect site-directed mutagenesis, as described above. In the latter, the cytidine deaminase enzyme does not induce dsDNA breaks, but mediates the conversion of cytidine to uridine, thereby effecting a C to T (or G to A) substitution. This approach may be particularly valuable to produce the polymorphisms at positions −855, −847, −801 and −522 described above.

In a further embodiment, the nucleic acid construct comprises an endoribonuclease. Preferably the endoribonuclease is Csy4 (also known as Cas6f) and more preferably a codon optimised csy4, for example as defined in SEQ ID NO: 43. In one embodiment, where the nucleic acid construct comprises a cas protein, the nucleic acid construct may comprise sequences for the expression of an endoribonuclease, such as Csy4 expressed as a 5' terminal P2A fusion (used as a self-cleaving peptide) to a cas protein, such as Cas9.

In one embodiment, the cas protein, the endoribonuclease and/or the endoribonuclease-cas fusion sequence may be operably linked to a suitable plant promoter. Suitable plant promoters are already described above, but in one embodiment, may be the *Zea Mays* Ubiquitin 1 promoter.

Suitable methods for producing the CRISPR nucleic acids and vectors system are known, and for example are published in Molecular Plant (Ma et al., 2015, Molecular Plant, DOI:10.1016/j.molp.2015.04.007), which is incorporated herein by reference.

In an alternative aspect of the invention, the nucleic acid construct comprises at least one nucleic acid sequence that encodes a TAL effector, wherein said effector targets a GRF sequence selected from SEQ ID NO 40, 49, 52, 57, 60, 65, 68, 73, 76, 81, 85, 90, 93, 98, 101, 106, 109, 114, 117, 122, 125, 130, 133, 138, 141, 146, 149, 154, 157, 162, 165, 170, 173, 178, 181, 186 and 189. Methods for designing a TAL effector would be well known to the skilled person, given the target sequence. Examples of suitable methods are given in Sanjana et al., and Cermak T et al, both incorporated herein by reference. Preferably, said nucleic acid construct comprises two nucleic acid sequences encoding a TAL effector, to produce a TALEN pair. In a further embodiment, the nucleic acid construct further comprises a sequence-specific nuclease (SSN). Preferably such SSN is an endonuclease such as FokI. In a further embodiment, the TALENs are assembled by the Golden Gate cloning method in a single plasmid or nucleic acid construct.

In another aspect of the invention, there is provided a sgRNA molecule, wherein the sgRNA molecule comprises a crRNA sequence and a tracrRNA sequence and wherein the crRNA sequence can bind to at least one sequence selected from SEQ ID Nos 49, 52, 57, 60, 65, 68, 73, 76, 81, 85, 90, 93, 98, 101, 106, 109, 114, 117, 122, 125, 130, 133, 138, 141, 146, 149, 154, 157, 162, 165, 170, 173, 178, 181, 186 and 189 or a variant thereof. A "variant" is as defined herein. In one embodiment, the sgRNA molecule may comprise at least one chemical modification, for example that enhances its stability and/or binding affinity to the target sequence or the crRNA sequence to the tracrRNA sequence. Such modifications would be well known to the skilled person, and include for example, but not limited to, the modifications described in Randar et al., 2015, incorporated herein by reference. In this example the crRNA may comprise a phosphorothioate backbone modification, such as 2'-fluoro (2'-F), 2'-O-methyl (2'-O-Me) and S-constrained ethyl (cET) substitutions.

In another aspect of the invention, there is provided an isolated nucleic acid sequence that encodes for a protospacer element (as defined in any of SEQ ID Nos 41, 50, 53, 58, 61, 66, 69, 74, 77, 82, 86, 91, 94, 99, 102, 107, 110, 115, 118, 123, 126, 131, 134, 139, 142, 147, 150, 155, 158, 163, 166, 171, 174, 179, 182, 187 and 190) or a variant thereof, or a sgRNA (as described in any of SEQ ID NO: 51, 54, 59, 62, 67, 70, 75, 78, 83, 87, 92, 95, 100, 103, 108, 111, 116, 119, 124, 127, 132, 135, 140, 143, 148, 151, 156, 159, 164, 167, 172, 175, 180, 183, 188 and 191 or a variant thereof).

In another aspect of the invention, there is provided a nucleic acid construct comprising a repair template sequence operably linked to a regulatory sequence, as defined herein. In one embodiment the repair template sequence comprises a nucleic acid sequence selected from SEQ ID NOs 47, 53, 63, 71, 79, 88, 96, 104, 112, 120, 128, 136, 144, 152, 160, 168, 176 and 184 or a variant thereof. A regulatory sequence is as defined herein.

In a yet another aspect of the invention, there is provided another nucleic acid construct, wherein the nucleic acid construct comprises a donor DNA sequence. In one embodiment, the donor DNA sequence comprises a nucleic acid sequence selected from SEQ ID NOs 48, 56, 64, 72, 80, 84, 89, 97, 105, 113, 121, 129, 137, 145, 153, 161, 169, 177 and 185 or a variant thereof. In a further preferred embodiment, the nucleic acid sequence comprises at least one, preferably two, sgRNA nucleic acid sequences, as defined herein and more preferably a Cas nucleic acid sequence, as defined herein. In one embodiment, the at least one sgRNA nucleic acid, Cas nucleic acid and donor DNA sequence are operably linked to the same regulatory sequence. In an alternative embodiment, the at least one sgRNA nucleic acid, Cas nucleic acid and donor DNA sequence are operably linked to different regulatory sequences. For example, the at least one sgRNA nucleic acid may be operably linked to the U3 promoter and Cas to the Ubi promoter. In this embodiment, the sgRNA nucleic acids expressed from the construct are used to produce a double strand break in the target sequence, which is then repaired using HDR and the donor DNA sequence as described in Sun et al. (2016). This method can be used to insert at least one, but preferably at least two substitutions in a target sequence.

In another aspect of the invention, there is provided a plant or part thereof or at least one isolated plant cell transfected with at least one nucleic acid construct as described herein. Cas9 and sgRNA may be combined or in separate expression vectors (or nucleic acid constructs, such terms are used interchangeably). Similarly, Cas9, sgRNA and the donor DNA sequence may be combined or in separate expression vectors. In other words, in one embodiment, an isolated plant cell is transfected with a single nucleic acid construct comprising both sgRNA and Cas9 or sgRNA, Cas9 and the donor DNA sequence as described in detail above. In an alternative embodiment, an isolated plant cell is transfected with two or three nucleic acid constructs, a first nucleic acid construct comprising at least one sgRNA as defined above, a second nucleic acid construct comprising Cas9 or a functional variant or homolog thereof and optionally a third nucleic acid construct comprising the donor DNA sequence as defined above. The second and/or third nucleic acid construct may be transfected before, after or concurrently with the first and/or second nucleic acid construct. The advantage of a separate, second construct comprising a Cas protein is that the nucleic acid construct encoding at least one sgRNA can be paired with any type of Cas protein, as described herein, and therefore is not limited to a single Cas function (as would be the case when both Cas and sgRNA are encoded on the same nucleic acid construct).

In one embodiment, the nucleic acid construct comprising a Cas protein is transfected first and is stably incorporated into the genome, before the second transfection with a nucleic acid construct comprising at least one sgRNA nucleic acid. In an alternative embodiment, a plant or part thereof or at least one isolated plant cell is transfected with mRNA encoding a Cas protein and co-transfected with at least one nucleic acid construct as defined herein.

Cas9 expression vectors for use in the present invention can be constructed as described in the art. In one example, the expression vector comprises a nucleic acid sequence as defined in SEQ ID NO: 42 or a functional variant or homolog thereof, wherein said nucleic acid sequence is operably linked to a suitable promoter. Examples of suitable promoters include the Actin, CaMV35S, wheat U6 or maize ubiquitin (e.g. Ubi1) promoter.

Also included in the scope of the invention, is the use of the nucleic acid constructs (CRISPR constructs) described above or the sgRNA molecules in any of the above described methods. For example, there is provided the use of the above CRISPR constructs or sgRNA molecules to increase GRF expression or activity as described herein.

Therefore, in a further aspect of the invention, there is provided a method of increasing GRF expression and/or activity, the method comprising introducing and expressing any one of the above described constructs or introducing a sgRNA molecule as also described above into a plant. In other words, there is also provided a method of increasing GRF expression and/or activity, as described herein, wherein the method comprises introducing at least one mutation into the endogenous GRF gene and/or promoter using CRISPR/Cas9, and specifically, the CRISPR (nucleic acid) constructs described herein.

Accordingly, in a further aspect of the invention, there is provided a method of producing a plant with a $GRF^{ngr2}$ allele, the method comprising introducing and expressing any nucleic acid construct as defined above or introducing a sgRNA molecule, as also defined above, in a plant.

In an alternative aspect of the present invention, there is provided an isolated plant cell transfected with at least one sgRNA molecule as described herein.

In a further aspect of the invention, there is provided a genetically modified or edited plant comprising the transfected cell described herein. In one embodiment, the nucleic acid construct or constructs may be integrated in a stable form. In an alternative embodiment, the nucleic acid construct or constructs are not integrated (i.e. are transiently expressed). Accordingly, in a preferred embodiment, the genetically modified plant is free of any sgRNA and/or Cas protein nucleic acid. In other words, the plant is transgene free.

The terms "introduction", "transfection" or "transformation" as referred to herein encompass the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The resulting transformed plant cell may then be used to regenerate a transformed plant in a manner known to persons skilled in the art. The transfer of foreign genes into the genome of a plant is called transformation. Transformation of plants is now a routine technique in many species. Any of several transformation methods known to the skilled person may be used to introduce the nucleic acid construct or sgRNA molecule of interest into a suitable ancestor cell. The methods described for the transformation and regeneration of plants from plant tissues or plant cells may be utilized for transient or for stable transformation.

Transformation methods include the use of liposomes, electroporation, chemicals that increase free DNA uptake, injection of the DNA directly into the plant (microinjection), gene guns (or biolistic particle delivery systems (biolistics)) as described in the examples, lipofection, transformation using viruses or pollen and microprojection. Methods may be selected from the calcium/polyethylene glycol method for protoplasts, ultrasound-mediated gene transfection, optical or laser transfection, transfection using silicon carbide fibers, electroporation of protoplasts, microinjection into plant material, DNA or RNA-coated particle bombardment, infection with (non-integrative) viruses and the like. Transgenic plants can also be produced via *Agrobacterium tumefaciens* mediated transformation, including but not limited to using the floral dip/*Agrobacterium* vacuum infiltration method as described in Clough & Bent (1998) and incorporated herein by reference.

Accordingly, in one embodiment, at least one nucleic acid construct or sgRNA molecule as described herein can be introduced to at least one plant cell using any of the above described methods. In an alternative embodiment, any of the nucleic acid constructs described herein may be first transcribed to form a preassembled Cas9-sgRNA ribonucleoprotein and then delivered to at least one plant cell using any of the above described methods, such as lipofection, electroporation or microinjection.

Optionally, to select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility is growing the seeds, if appropriate after sterilization, on agar plates using a suitable selection agent so that only the transformed seeds can grow into plants. As described in the examples, a suitable marker can be bar-phosphinothricin or PPT. Alternatively, the transformed plants are screened for the presence of a selectable marker, such as, but not limited to, GFP, GUS (β-glucuronidase). Other examples would be readily known to the skilled person. Alternatively, no selection is performed, and the seeds obtained in the above-described manner are planted and grown and GRF1 expression or protein levels measured at an appropriate time using standard techniques in the art. This alternative, which avoids the introduction of transgenes, is preferable to produce transgene-free plants.

Following DNA transfer and regeneration, putatively transformed plants may also be evaluated, for instance using PCR to detect the presence of the gene of interest, copy number and/or genomic organisation. Alternatively or additionally, integration and expression levels of the newly introduced DNA may be monitored using Southern, Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques.

Specific protocols for using the above described CRISPR constructs would be well known to the skilled person. As one example, a suitable protocol is described in Ma & Liu ("CRISPR/Cas-based multiplex genome editing in monocot and dicot plants") incorporated herein by reference.

In a further related aspect of the invention, there is also provided, a method of obtaining a genetically modified plant as described herein, the method comprising
  a. selecting a part of the plant;
  b. transfecting at least one cell of the part of the plant of paragraph (a) with at least one nucleic acid construct as described herein or at least one sgRNA molecule as described herein, using the transfection or transformation techniques described above;
  c. regenerating at least one plant derived from the transfected cell or cells;
  d. selecting one or more plants obtained according to paragraph (c) that show increased expression or function of GRF, preferably GRF4.

In a further embodiment, the method also comprises the step of screening the genetically modified plant for SSN (preferably CRISPR)-induced mutations in the GRF gene or promoter sequence. In one embodiment, the method comprises obtaining a DNA sample from a transformed plant and carrying out DNA amplification to detect a mutation in at least one GRF gene or promoter sequence.

In a further embodiment, the methods comprise generating stable T2 plants preferably homozygous for the mutation (that is a mutation in at least one GRF gene or promoter sequence).

Plants that have a mutation in at least one GRF gene or promoter sequence can also be crossed with another plant also containing at least one different mutation in at least one GRF gene or promoter sequence to obtain plants with additional mutations in the GRF1 gene or promoter sequence. The combinations will be apparent to the skilled person. Accordingly, this method can be used to generate a T2 plants with mutations on all or an increased number of homoeologs, when compared to the number of homoeolog mutations in a single T1 plant transformed as described above.

A plant obtained or obtainable by the methods described above is also within the scope of the invention.

A genetically altered plant of the present invention may also be obtained by transference of any of the sequences of the invention by crossing, e.g., using pollen of the genetically altered plant described herein to pollinate a wild-type or control plant, or pollinating the gynoecia of plants described herein with other pollen that does not contain a mutation in at least one of the GRF gene or promoter sequence. The methods for obtaining the plant of the invention are not exclusively limited to those described in this paragraph; for example, genetic transformation of germ cells from the ear of wheat could be carried out as mentioned, but without having to regenerate a plant afterwards.

Method of Screening Plants for Naturally Occurring Increased Nitrogen Uptake and Grain Yield Phenotypes In a further aspect of the invention, there is provided a method for screening a population of plants and identifying and/or selecting a plant that carries or expresses the ngr allele of GRF, as described herein. Alternatively, there is provided a method for screening a population of plants and identifying and/or selecting a plant that has an increased nitrogen uptake and/or nitrogen assimilation and/or nitrogen use efficiency, and optionally additionally increased yield and/or C assimilation. In either aspect, the method comprises detecting in the plant or plant germplasm at least one polymorphism in the GRF gene and/or promoter. Preferably, said screening comprises determining the presence of at least one polymorphism, wherein said polymorphism is at least one insertion and/or at least one deletion and/or substitution, more preferably a substitution.

In one specific embodiment, said polymorphism may comprise at least one substitution as follows:
- a C to T substitution at position −941 or −935 from the GRF start codon or at position 60 of SEQ ID NO: 7 or position 66 of SEQ ID NO: 8; or a homologous position thereof;
- a T to A substitution at position −884 or −878 from the GRF start codon or at position 118 of SEQ ID NO: 7 or position 124 of SEQ ID NO: 8; or a homologous position thereof;
- a C to T substitution at position −855 or −849 from the GRF start codon or at position 148 of SEQ ID NO: 7 or position 154 of SEQ ID NO: 8; or a homologous position thereof;
- a C to T substitution at position −847 or −841 from the GRF start codon or at position 157 of SEQ ID NO: 7 or position 163 of SEQ ID NO: 8; or a homologous position thereof;
- a C to T substitution at position −801 or −795 from the GRF start codon or at position 204 of SEQ ID NO: 7 or position 210 of SEQ ID NO: 8; or a homologous position thereof;
- a C to T substitution at position −522 or −516 from the GRF start codon or at position 484 of SEQ ID NO: 7 or position 489 of SEQ ID NO: 8; or a homologous position thereof;
- a G to C substitution at position −157 from the GRF start codon or at position 850 of SEQ ID NO: 7 or position 516 of SEQ ID NO: 8; or a homologous position thereof;

In a preferred embodiment, the mutation is
- a T to A substitution at position −884 or −878 from the GRF start codon or at position 118 of SEQ ID NO: 7 or position 124 of SEQ ID NO: 8; or a homologous position thereof; and
- a C to T substitution at position −847 or −841 from the GRF start codon or at position 157 of SEQ ID NO: 7 or position 163 of SEQ ID NO: 8; or a homologous position thereof;
- a C to T substitution at position −801 or −795 from the GRF start codon or at position 204 of SEQ ID NO: 7 or position 210 of SEQ ID NO: 8; or a homologous position thereof.

As described above, a GRF promoter comprising all three of the above polymorphisms may be known as haplotype B.

Suitable tests for assessing the presence of a polymorphism would be well known to the skilled person, and include but are not limited to, Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs-which are also referred to as Microsatellites), and Single Nucleotide Polymorphisms (SNPs). In one embodiment, Kompetitive Allele Specific PCR (KASP) genotyping is used.

In one embodiment, the method comprises
a) obtaining a nucleic acid sample from a plant and
b) carrying out nucleic acid amplification of one or more GRF or GRF promoter alleles
using one or more primer pairs.

In a further embodiment, the method may further comprise introgressing the chromosomal region comprising a GRF polymorphism into a second plant or plant germplasm to produce an introgressed plant or plant germplasm. Preferably said second plant will display an increase in nitrogen uptake and/or nitrogen assimilation and/or nitrogen use efficiency, and optionally additionally yield and/or C assimilation.

Accordingly, in a further aspect of the invention there is provided a method for increasing nitrogen uptake and/or nitrogen assimilation and/or nitrogen use efficiency, and optionally additionally yield and/or C assimilation in a plant, the method comprising
a. screening a population of plants for at least one plant with a GRF polymorphism as described herein;
b. further modulating the expression or activity of a GRF polypeptide, as described herein, in said plant by introducing at least one mutation into the nucleic acid sequence encoding GRF and/or at least one mutation into the promoter of GRF as described herein.

GRF$^{ngr}$ Constructs

As discussed throughout, the inventors have surprisingly identified that overexpression of GRF, particularly GRF4, increases nitrogen metabolism and also yield in plants.

Accordingly, in another aspect of the invention there is provided a nucleic acid construct comprising a nucleic acid sequence encoding a polypeptide as defined in SEQ ID NO: 3 or a functional variant or homolog thereof, wherein said sequence is operably linked to a regulatory sequence. Preferably said regulatory sequence is a tissue-specific promoter or a constitutive promoter. A functional variant or homolog is as defined above. Suitable promoters are also described above. However, in one embodiment, the promoter may be the haplotype B promoter as described herein. Preferably, this promoter comprises or consists of SEQ ID NO: 9 or a variant thereof.

In another aspect of the invention there is provided a vector comprising the nucleic acid sequence described above.

In a further aspect of the invention, there is provided a host cell comprising the nucleic acid construct. The host cell may be a bacterial cell, such as *Agrobacterium tumefaciens*, or an isolated plant cell. The invention also relates to a culture medium or kit comprising a culture medium and an isolated host cell as described below.

In another embodiment, there is provided a transgenic plant expressing the nucleic acid construct as described above. In one embodiment, said nucleic acid construct is stably incorporated into the plant genome.

The nucleic acid sequence is introduced into said plant through a process called transformation as described above.

In another aspect, the invention relates to the use of a nucleic acid construct as described herein to increase at least one nitrogen uptake and/or nitrogen assimilation and/or nitrogen use efficiency, and optionally additionally yield and/or C assimilation.

In a further aspect of the invention there is provided a method of increasing at least one of nitrogen uptake and/or nitrogen assimilation and/or nitrogen use efficiency, and optionally additionally yield and/or C assimilation, the method comprising introducing and expressing in said plant the nucleic acid construct described herein.

In another aspect of the invention there is provided a method of producing a plant with an increased in at least one of nitrogen uptake and/or nitrogen assimilation and/or nitrogen use efficiency, and optionally additionally yield and/or C assimilation, the method comprising introducing and expressing in said plant the nucleic acid construct described herein said increase is relative to a control or wild-type plant.

While the foregoing disclosure provides a general description of the subject matter encompassed within the scope of the present invention, including methods, as well as the best mode thereof, of making and using this invention, the following examples are provided to further enable those skilled in the art to practice this invention and to provide a complete written description thereof. However, those skilled in the art will appreciate that the specifics of these examples should not be read as limiting on the invention, the scope of which should be apprehended from the claims and equivalents thereof appended to this disclosure. Various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

The foregoing application, and all documents and sequence accession numbers cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

The invention is now described in the following non-limiting example.

Example 1

Plants integrate regulation of metabolic assimilation with regulation of growth. However, the molecular mechanisms underlying this coordinate integration are poorly understood. To advance that understanding, we systematically analysed the growth and assimilatory properties of cereal varieties carrying mutant alleles characteristic of the 1960's 'green revolution'. The green revolution boosted yields, fed an expanding world population, and was partly driven by adoption of semi-dwarf green revolution varieties (GRVs)[1-3]. GRV semi-dwarfism is caused by the accumulation of growth-repressing DELLA proteins (DELLAs) conferred by mutant Rht (wheat)[4,5] and sd1 (indica rice)[6,7] alleles. In normal plants, the phytohormone gibberellin (GA) stimulates DELLA destruction, thus promoting growth[8,9]. However, in GRVs, DELLA destruction is inhibited. Mutant wheat GRV DELLAs[4] resist GA-stimulated destruction, whilst sd1 causes reduced GA abundance and consequent SLR1 DELLA accumulation[10]. In both cases, accumulated DELLAs inhibit growth, causing semi-dwarfism and resultant resistance to yield-reducing 'lodging' (flattening of plants by wind and rain)[3].

GRV lodging resistance is enhanced because mutant Rht and sd1 alleles confer partial growth insensitivity to increasing nitrogen (N) supply. For example, the height of Nanjing6 indica rice (NJ6) increases in response to increasing N, but this response is reduced in NJ6-sd1 isogenic plants (FIG. 1a). Rht-B1b semi-dwarf mutant wheat has similar properties (compared with isogenic Rht-B1a (WT) wheat; FIG. 1b). Whilst GRV DELLA accumulation inhibits vegetative growth N-response, allocation of N to grain continues, enabling both enhanced harvestable yield and reduced lodging risk from increased N-supply. These yield-enhancing properties have driven the rapid spread of GRV cultivation during the past 50 years[2], and ensured retention of mutant sd1 and Rht alleles in present-day elite varieties[4,5,11].

However, the partial N-insensitivity of GRVs is associated with reduced N use-efficiency[2]. Furthermore, sd1 and Rht mutant alleles inhibit N uptake. For example, $NH_4^+$ is the majority N form assimilated by anaerobically growing paddy-field rice roots[13], and rate of $^{15}NH_4^+$ uptake is itself N-regulated, being reduced by high N supply (HN; FIG. 1c). We found that NJ6-sd1 exhibits a reduced $^{15}NH_4^+$ uptake rate, in both low and high N conditions (FIG. 1c). With nitrate ($NO_3^-$) being the N form predominantly taken up in relatively aerobic soil conditions[14], the rate of RhtB1b wheat $^{15}NO_3^-$ uptake is similarly reduced (FIG. 1d). Thus, in addition to semi-dwarfism and reduced N-promotion of growth, GRV DELLA accumulation confers reduced N uptake. Consequently, achievement of high GRV yield requires excessive use of N fertiliser inputs that unsustainably damage the environment (e.g., via agricultural runoff[15]). Developing new GRVs that are high-yielding despite reduced N supply is thus an urgent global sustainable agriculture goal[1,16]. We reasoned that systematic analyses of N metabolism in GRVs might enable discovery of how growth and assimilation are coordinated, and that this discovery might in turn enable development of new GRVs having improved N use-efficiency.

OsGRF4 Counteracts SLR1-Mediated Inhibition of Rice Ammonium ($NH_4^+$) Uptake

Figure 2:
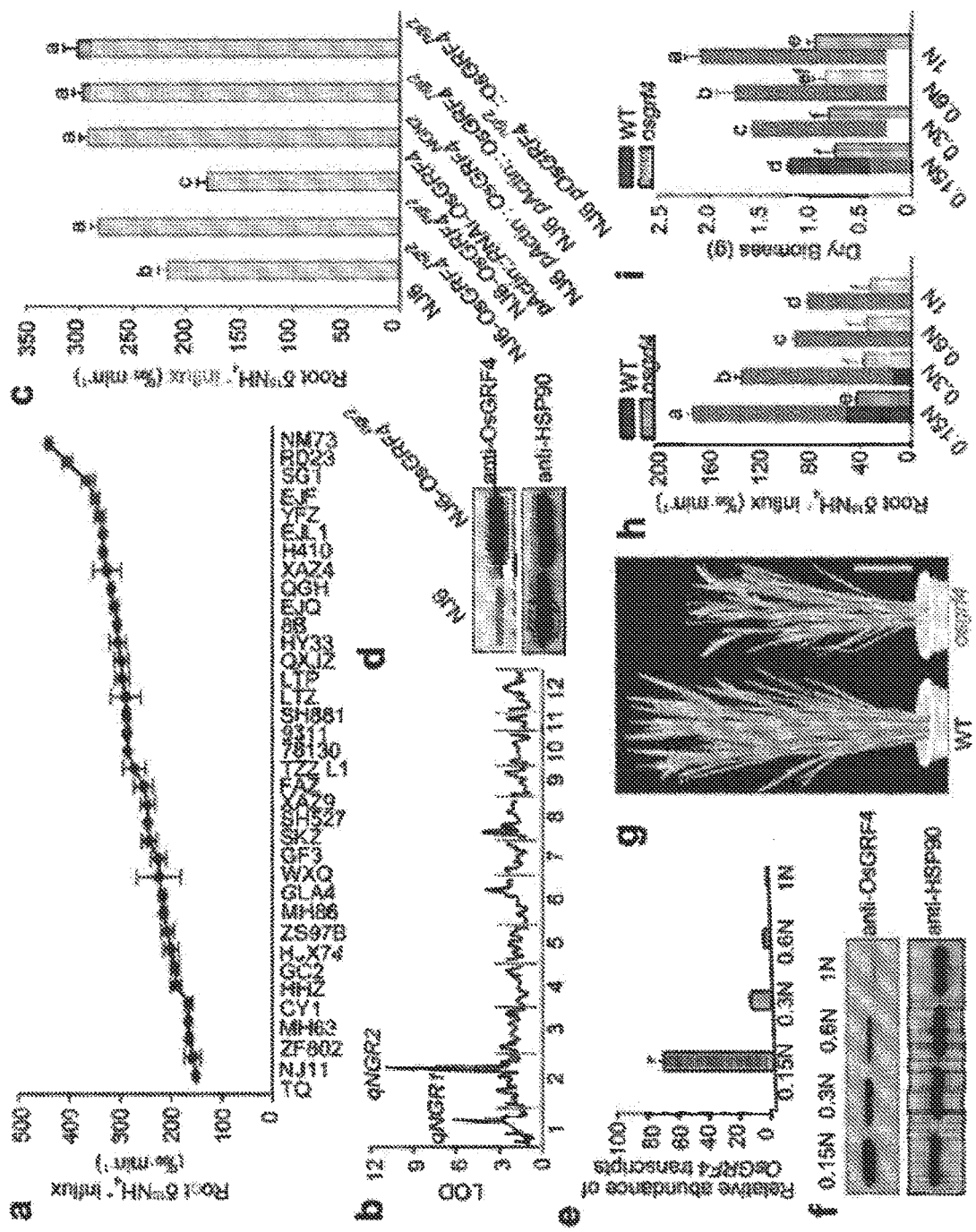
FIG. 2 shows OsGRF4 regulates rice $NH_4^+$ uptake and growth response to N availability. a, Varietal $^{15}NH_4^+$ uptake rates (arranged lowest to highest, left to right), plants grown in high N supply (1.25 mM $NH_4NO_3$). b, LOD scores from a QTL analysis of $^{15}NH_4^+$ uptake rates in a NJ6×NH73 $BC_1F_2$ population, distributed across the 12 rice chromosomes. Major peaks (qNGR1 and qNGR2) are indicated. c, $^{15}NH_4^+$ uptake rates. Data shown as mean±s.e.m. (n=9). d, OsGRF4 accumulation revealed with an anti-OsGRF4 antibody. HSP90 serves as loading control. e, Relative abundance of OsGRF4 mRNA, NJ6 roots grown at increasing N supply level (0.15N, 0.1875 mM $NH_4NO_3$; 0.3N, 0.375 mM $NH_4NO_3$; 0.6N, 0.75 mM $NH_4NO_3$; 1N, 1.25 mM $NH_4NO_3$). Abundance expressed relative to in 1N (=1). f, Anti-OsGRF4 antibody-revealed accumulation of OsGRF4 protein in NJ6 at different levels of N supply (as in i). HSP90 serves as loading control. g, Visible phenotype of loss-of-function osgrf4 mutant plants. Scale bar, 15 cm. h, $^{15}NH_4^+$ uptake rates in increasing N-supply (as in i). Data shown as mean±s.e.m. (n=9). i, Biomasses (dry weight) of plants grown in increasing N supply. Data shown as mean±s.e.m. (n=3). Statistical analyses used Duncan's multiple range tests, the same lowercase letter denotes a non-significant difference between means (P>0.05; panels c, h and i).

We first explored $^{15}NH_4^+$ uptake rates in 36 sd1-containing indica varieties, finding ~3-fold variation (FIG. 2a). Intriguingly, some higher-yielding GRVs (e.g., 9311) do not display the highest $^{15}NH_4^+$ uptake rates, despite having dominated Chinese indica rice acreage for many years. We selected NM73 (displaying the highest $^{15}NH_4^+$ uptake rate; FIG. 2a) for quantitative trait locus (QTL) analysis, discovering two LOD-score peaks (qNGR1 and qNGR2, FIG. 2b). The NM73 qngr1 allele is associated with a relatively low $^{15}NH_4^+$ uptake rate, and coincides in map position with sd1[6,7] (see FIG. 1c). However, the molecular identity of the NM73 qngr2 allele, associated with a relatively high $^{15}NH_4^+$ uptake rate, was unknown.

Figure 7:
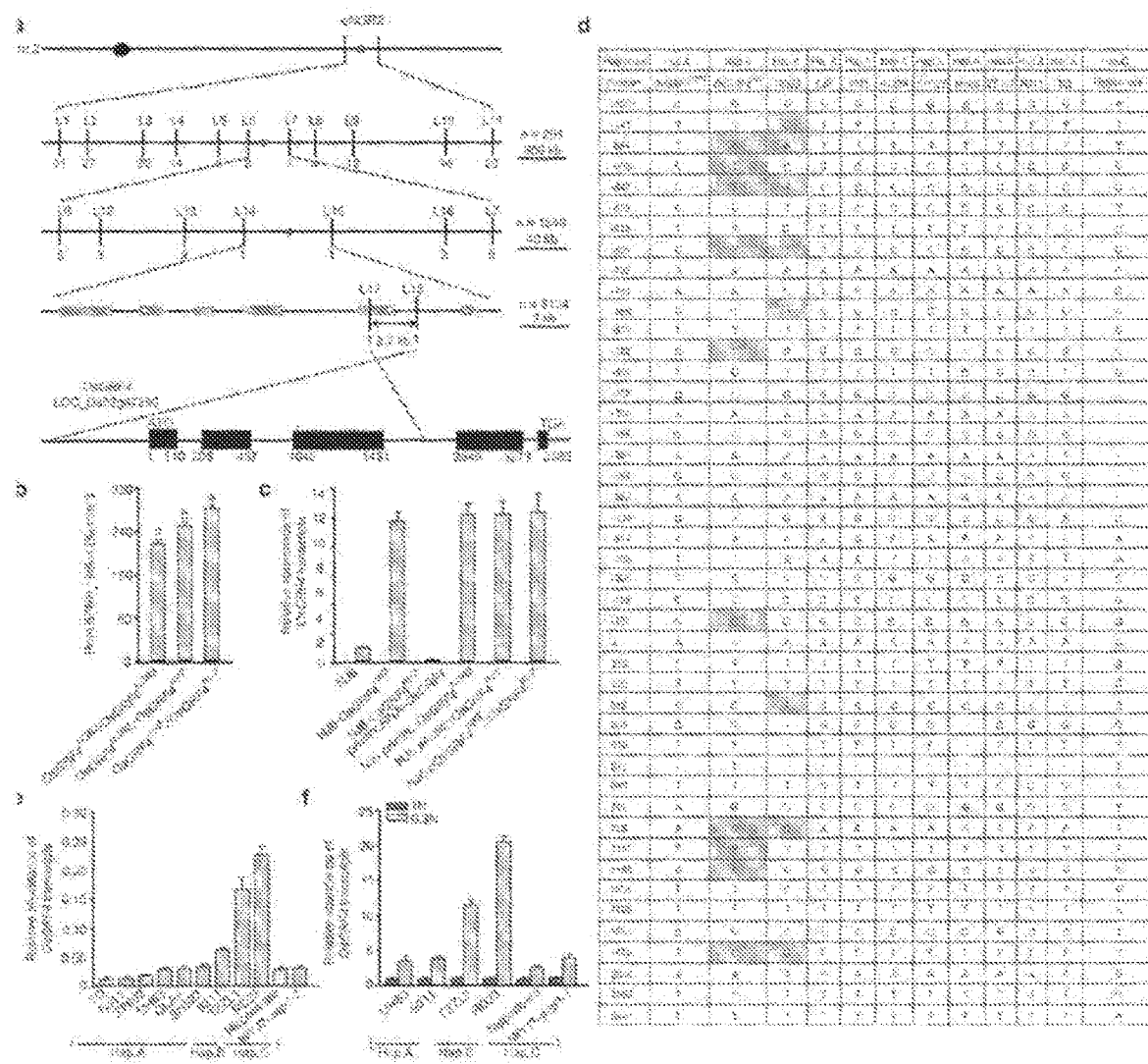
FIG. 7 shows that allelic variation at the OsGRF4 locus affects OsGRF4 mRNA abundance and root $^{15}NH_{4+}$ uptake. a, Positional cloning indicates the equivalence of OsGRF4 with qNGR2 (N-mediated growth response 2). Successive maps show progressive narrowing of focus of qNGR2 (grey dot, using recombination break points and linked DNA markers) to an ~2.7-kbp region on chromosome 2 flanked by molecular markers L17 and L18 and overlapping candidate gene LOC_Os02g47280 (also known as OsGRF4). The start ATG (nucleotide 1) and close TGA (nucleotide 3385) of OsGRF4 are shown, together with protein-encoding DNA sequence (CDS, thick black bars). The target site for OsmiR396 is indicated by an *. b, $^{15}NH_{4+}$ uptake rates of roots of $BC_2F_2$ progeny (derived from a NJ6×NM73 cross) homozygous or heterozygous for OsGRF4$^{NGR2}$ or OsGRF4$^{ngr2}$ grown in high N concentration conditions (1.25 mM $NH_4NO^3$). Data shown as mean±s.e.m. (n=9). The same lowercase letter denotes a non-significant difference between means (P>0.05). c, OsGRF4 mRNA abundance in plants (genotypes as shown) relative to the abundance in NJ6 (=1). Data shown as mean±s.e.m. (n=3). d, Natural allelic variation at the OsGRF4 locus. Nucleotide position relative to the OsGRF4 start ATG is shown. SNPs shared between varieties NM73 and RD23 are highlighted. Sequences representative of OsGRF4 promoter haplotypes A, B and C (see main text) are shown. e, OsGRF4 mRNA abundance in various rice varieties. Data shown as mean±s.e.m. (n=3). Abundance data is all relative to abundance of rice Actin2 mRNA. f, OsGRF4 mRNA in selected rice varieties grown in high (1N) or low (0.3N) N conditions. Data shown as mean±s.e.m. (n=3). Abundance data is all relative to that in 1N (=1).

Positional mapping located qngr2 to OsGRF4[17-19] (FIG. 7a), implying a previously unknown function in $NH_4^+$ uptake regulation. Furthermore, heterozygosity for the NM73 ($OsGRF4^{ngr2}$) allele confers a higher $^{15}NH_4^+$ uptake rate than homozygosity for the NJ6 allele ($OsGRF4^{NGR2}$; FIG. 7b), showing that $OsGRF4^{ngr2}$ semi-dominantly increases $NH_4^+$ uptake. An NJ6-$OsGRF4^{ngr2}$ isogenic line exhibited the expected higher $NH_4^+$ uptake rate (versus NJ6; FIG. 2c), and increased both OsGRF4 mRNA and OsGRF4 protein abundances (FIG. 2d; FIG. 7c), consistent with the semi-dominance of $OsGRF4^{ngr2}$. Furthermore, RNAi reduced the relatively high $^{15}NH_4^+$ uptake rate of NJ6-$OsGRF4^{ngr2}$ (FIG. 2e; FIG. 7c), thus confirming the equivalence of qngr2 and OsGRF4. Finally, transgenic expression of OsGRF4-encoding mRNA from the native $OsGRF4g^{ngr2}$ or constitutive rice Actin1 promoters conferred increased $^{15}NH_4^+$ uptake rates on NJ6 (FIG. 2c; FIG. 7c). Thus, $OsGRF4^{ngr2}$ confers increased $^{15}NH_4^+$ uptake on NM73, and counteracts the repressive effects of sd1 (which are due to rice DELLA protein SLR1 accumulation).

$OsGRF4^{NGR2}$ (NJ6) and $OsGRF4^{ngr2}$ (NM73) allelic comparisons revealed multiple SNPs (single nucleotide polymorphisms; FIG. 7a, d). Two of the $OsGRF4^{ngr2}$ SNPs (FIG. 7d; positions 1187T>A and 1188C>A in exon 3) prevent OsmiR396-mediated cleavage of $OsGRF4^{ngr2}$ mRNA[17-19], increasing OsGRF4 mRNA and OsGRF4 abundance (FIG. 2d; FIG. 7c), and promoting $NH_4^+$ uptake. Nevertheless, variety RD23, which also displays a relatively high $^{15}NH_4^+$ uptake rate (FIG. 2a), carries an OsGRF4 allele lacking 1187A and 1188A. However, RD23 and NM73 do share three OsGRF4 promoter SNPs (−884T>A, −847C>T and −801C>T; FIG. 7d). In all, we detected three OsGRF4 promoter haplotypes (A, as in 9311; B, with −884A, −847T and −801T, as in NM73 and RD23; and C, common in *japonica* germplasm, e.g., variety Nipponbare; FIG. 7d).

Interestingly, OsGRF4 mRNA abundance is higher in varieties TZZL1 and RD23 (both carrying haplotype B) than in elite varieties carrying haplotypes A or C (FIG. 7e). This suggests that the RD23 $NH_4^+$ uptake rate is relatively high (FIG. 1a) because promoter haplotype B confers relatively high OsGRF4 mRNA levels, whilst NM73 has a yet higher $NH_4^+$ uptake rate because it combines the effect of promoter haplotype B with the OsmiR396-resistance conferred by 1187A and 1188A[17-19].

Figure 8:
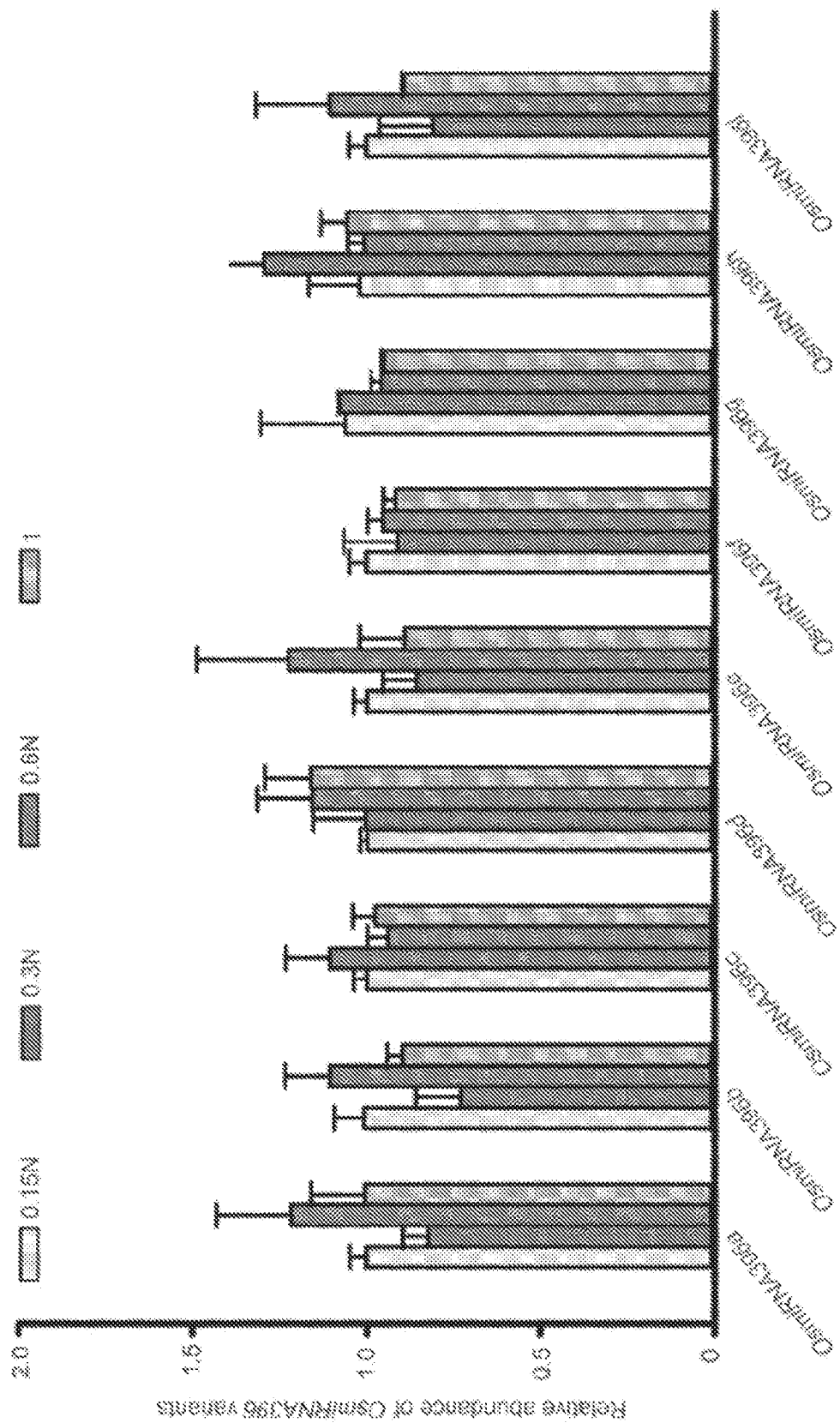
FIG. 8 shows that OsmiR396 abundance is not detectably increased by increasing N supply. Relative abundances of rice OsmiR396 family members in NJ6 plants grown at different levels of N supply (0.15N, 0.1875 mM $NH_4NO_3$; 0.3N, 0.375 mM $NH_4NO_3$; 0.6N, 0.75 mM $NH_4NO_3$; 1N, 1.25 mM $NH_4NO_3$), shown relative to abundance in plants grown in 1N conditions (=1). Data shown as mean±s.e.m. (n=3).
Figure 9:
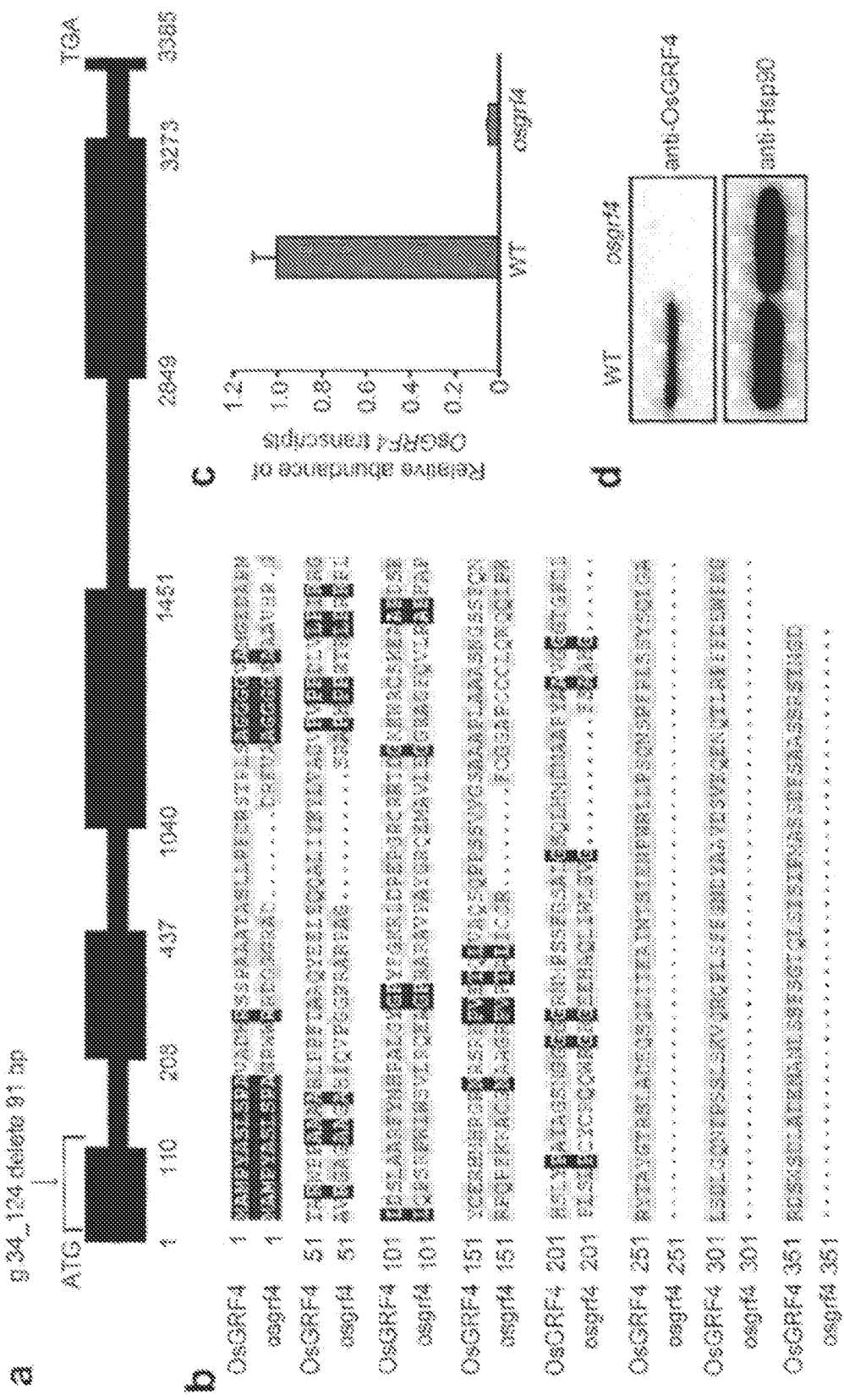
FIG. 9 shows CRISPR/cas9-generation of a rice OsGRF4 loss-of-function mutant (osgrf4). a, OsGRF4 exon-intron structure showing location of CRISPR/cas9-generated 91-bp deletion in exon 1 and intron 1 of the osgrf4 mutant allele. b, Sequence of proteins encoded by OsGRF4 (WT) and osgrf4 mutant alleles. The deletion in osgrf4 causes it to correctly encode the first 11 amino acids of OsGRF4 but protein of aberrant sequence from there on. c, OsGRF4 mRNA abundance in WT (OsGRF4) versus the osgrf4 mutant, shown relative to the abundance in WT (=1). Data shown as mean±s.e.m. (n=3). d, Anti-OsGRF4 antibody-revealed accumulation of OsGRF4 protein in the osgrf4 mutant. HSP90 serves as loading control.

Importantly, we found that whilst OsGRF4 regulates $NH_4^+$ uptake, it is in turn itself regulated by N supply. NJ6 OsGRF4 mRNA abundance decreases with increasing N (FIG. 2e), likely due to decreased OsGRF4 transcription (OsmiR396 abundance does not detectably increase with increasing N; FIG. 8), thus reducing OsGRF4 abundance (FIG. 2f). Because increased OsGRF4 abundance increases $NH_4^+$ uptake (FIG. 2c, d), promotion of OsGRF4 abundance by low N enables feedback regulation of N homeostasis. In particular, the increased OsGRF4 mRNA abundance response to low N supply is significantly amplified in varieties (e.g., TZZL1 and RD23) carrying promoter haplotype B (FIG. 7f). Finally, a CRISPR/cas9[20]-generated osgrf4 mutant lacks OsGRF4 (FIG. 9), and exhibits semi-dwarfism (FIG. 2g), reduced $^{15}NH_4^+$ influx (FIG. 2h), reduced N-mediated feedback regulation of $^{15}NH_4^+$ uptake rate (FIG. 2h) and reduced N-dependent biomass accumulation (FIG. 2i). Thus, OsGRF4 is an N-regulated transcriptional regulator promoting both rate of $NH_4^+$ uptake and growth response to N-supply, and counteracting the inhibitory effects of sd1 (SLR1) on these processes.

Competitive OsGRF4, SLR1 and OsGIF1 Interactions Regulate $NH_4^+$ Assimilation

Figure 3:
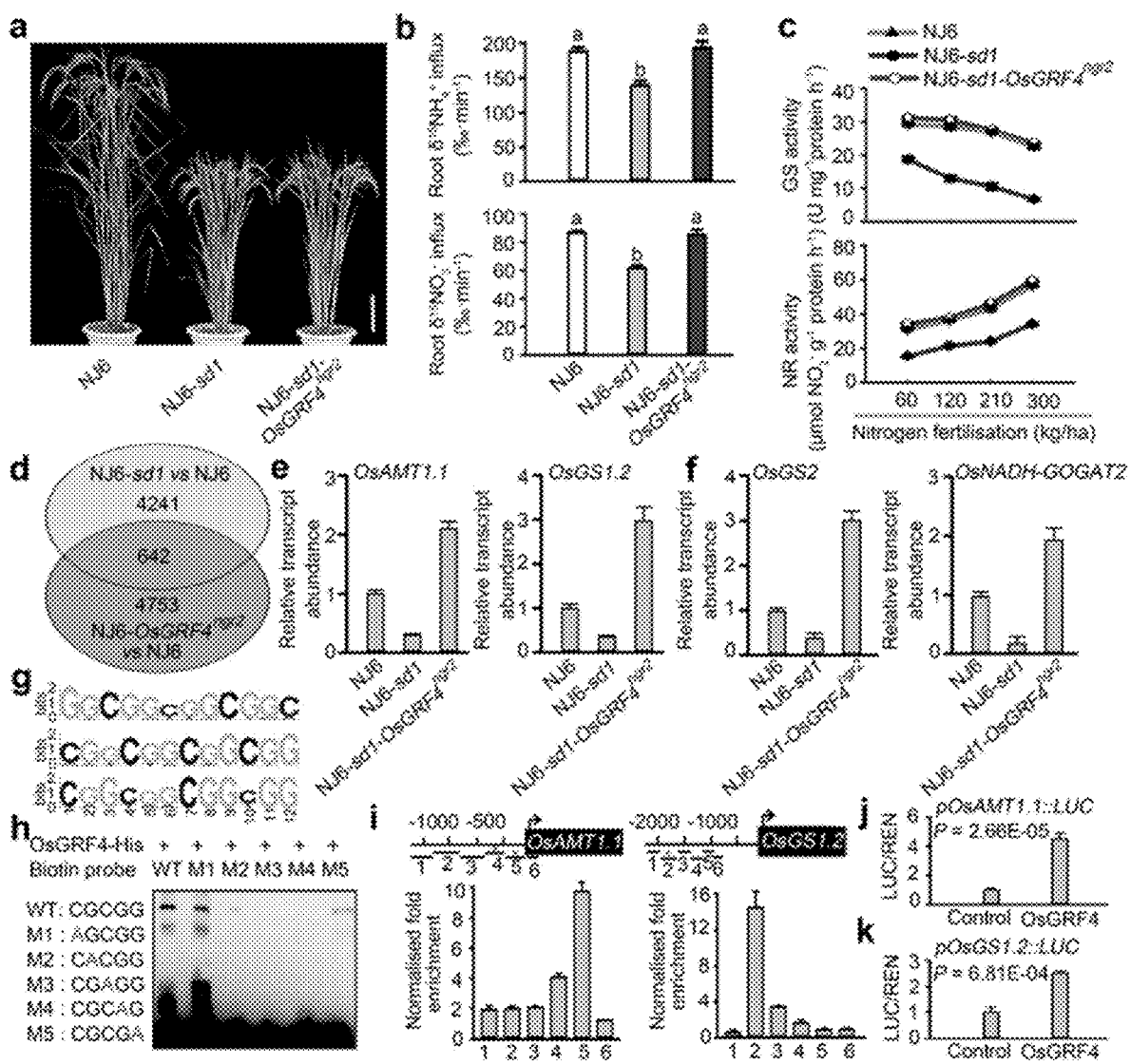
FIG. 3 shows that OsGRF4 is a master coordinator of N metabolism gene expression. a, Mature plant phenotypes. Scale bar, 15 cm. b, $^{15}NH_4^+$ and $15NO_3^-$ uptake rates. Data shown as mean±s.e.m. (n=9). Statistical analyses used Duncan's multiple range tests, the same lowercase letter denotes a non-significant difference between means (P>0.05). c, Glutamine synthase (GS) and nitrate reductase (NR) activities in shoots of rice plants grown in paddy-field conditions with increasing N supply. Data shown as mean±s.e.m. (n=3). d, RNA-seq analysis. 4883 genes had transcript abundances downregulated in NJ6-sd1 (versus NJ6), 5395 genes had transcript abundances upregulated in NJ6-OsGRF4$^{ngr2}$ (versus NJ6), with 642 genes common to both. e, Root mRNA abundances relative to NJ6 (=1). Data shown as mean±s.e.m. (n=3). f, Shoot mRNA abundances relative to NJ6. Data shown as mean±s.e.m. (n=3). g, Sequence motifs enriched in ChIP-seq with Flag-tagged OsGRF4. h, EMSAs show binding of OsGRF4-His to WT but not mutant (M1-M5) forms of a core GCGG motif. i, ChIP-PCR with Flag-OsGRF4 enriches GCGG-containing promoter fragments (marked with *). j-k, OsGRF4 activates promoter: Luciferase fusion constructs in transient transactivation assays. Data shown as mean±s.e.m. (n=3; panels e-f, i-k).
Figure 10:
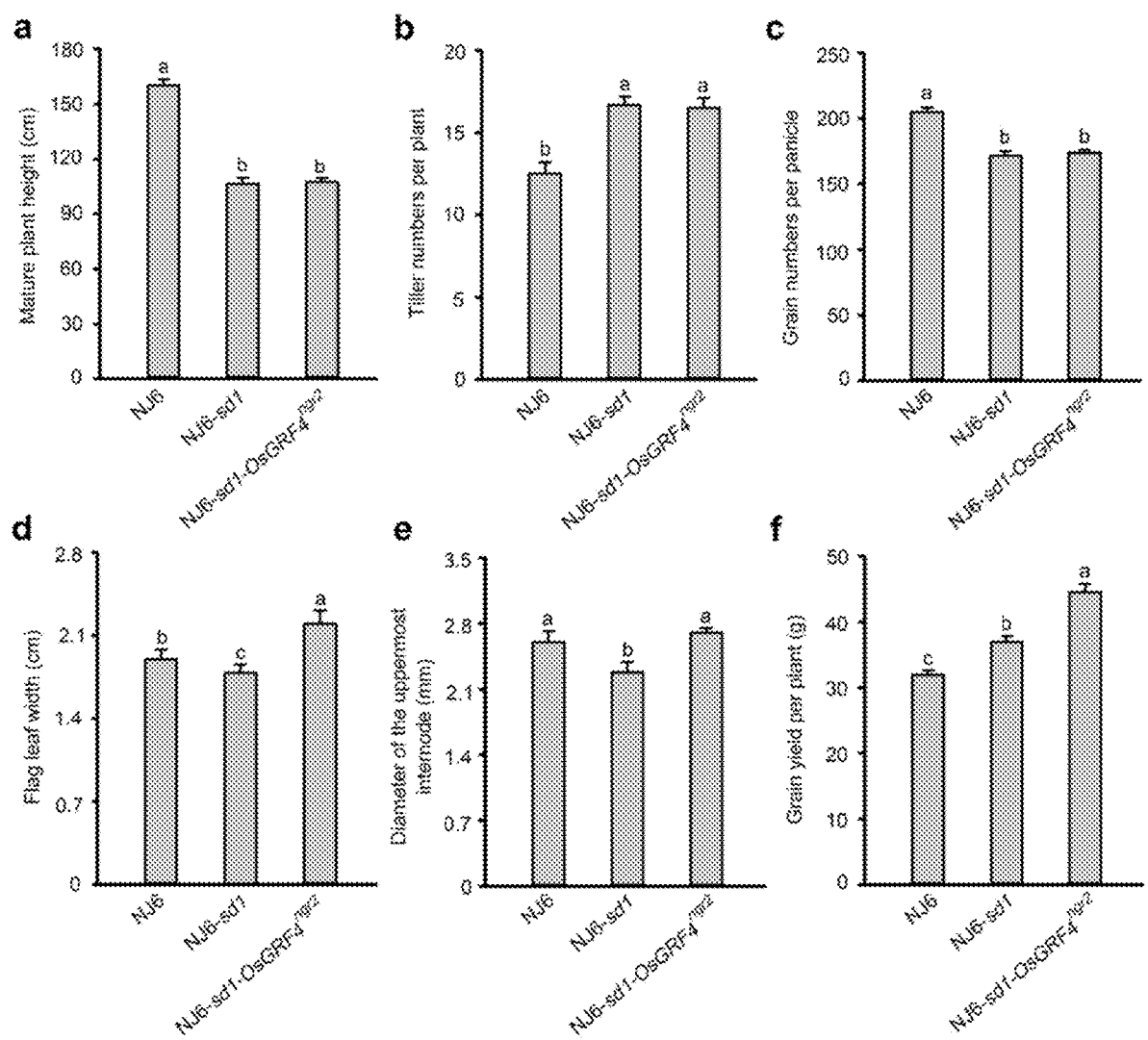
FIG. 10 shows phenotypic and yield performance traits of NJ6, NJ6-sd1 and NJ6-sd1-OsGRF4$^{ngr2}$ isogenic lines. a, Mature plant height. b, Number of tillers per plant. c, Number of grains per panicle. d, Flag-leaf width. e, Culm (stem) width expressed as diameter of the uppermost internode. Data shown as mean±s.e.m. (n=16; panels a-e). f, Grain yield per plant. Data shown as mean±s.e.m. estimated from six plots (each plot contained 220 plants) per line. The same lowercase letter denotes a non-significant difference between means (P>0.05).

We next determined how OsGRF4 and SLR1 activities counteract one another to regulate $NH_4^+$ assimilation, first finding that a NJ6-sd1-$OsGRF4^{ngr2}$ isogenic line retains the dwarfism, tiller number per plant and grain number per panicle conferred by sd1 (SLR1; FIG. 3a; FIG. 10a-c), whilst leaf and culm width are increased (FIG. 10d, e). However, grain yield is increased in NJ6-sd1-$OsGRF4^{ngr2}$ (FIG. 10f). Furthermore, multiple sd1-repressed N uptake and assimilation properties are de-repressed by $OsGRF4^{ngr2}$. First, the NJ6-sd1-$OsGRF4^{ngr2}$ $^{15}NH_4^+$ uptake rate is greater than that of NJ6-sd1 (and similar to that of NJ6), with $^{15}NO_3^-$ uptake being similarly affected (FIG. 3b). Second, the activities of key N assimilation enzymes, such as shoot glutamine synthase (GS; $NH_4^+$ assimilation)[21] and nitrate reductase (NR; $NO_3$ assimilation)[22] are, at varying N-supply levels, consistently greater in NJ6-sd1-$OsGRF4^{ngr2}$ than in NJ6-sd1, and similar to that of NJ6 (FIG. 3c). Thus, OsGRF4 promotes N uptake and assimilation, whilst SLR1 inhibits them.

Figure 11:
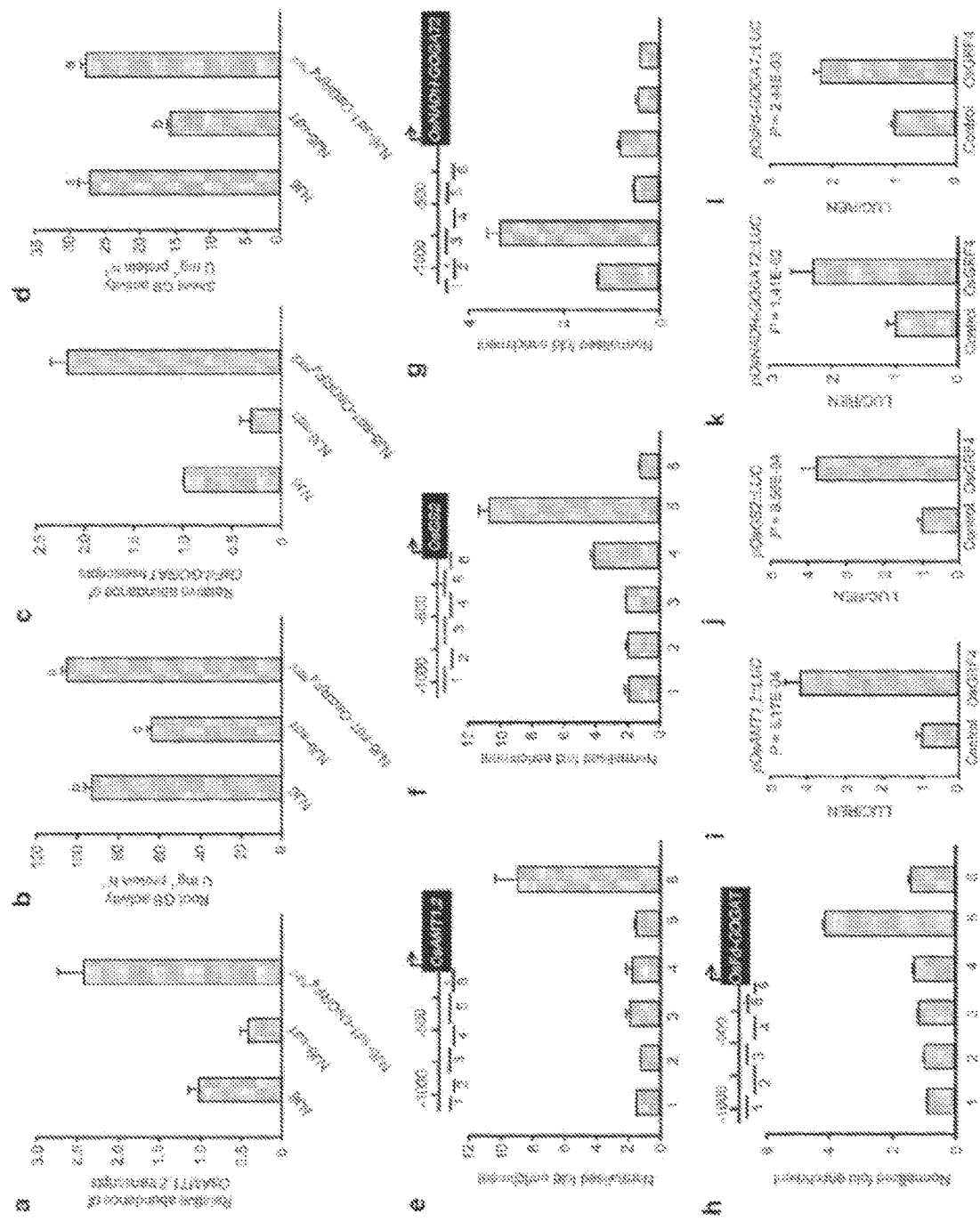
FIG. 11 shows that OsGRF4 regulates expression of multiple NH4+ metabolism genes. a, Relative root abundance of OsAMT1.2 mRNA in NILs, genotypes as indicated. Data shown as mean±s.e.m. (n=3). b, Root glutamine synthase (GS) activities. Data shown as mean±s.e.m. (n=3). c, Relative shoot abundance of OsFd-GOGAT mRNA. Data shown as mean±s.e.m. (n=3). Abundance shown relative to that in NJ6 plants (=1; panels a, c). d, Shoot glutamine synthase (GS) activities. Data shown as mean±s.e.m. (n=3). e-h, ChIP-PCR with Flag-OsGRF4 enriches GCGG-containing promoter fragments (marked with *) from OsAMT1.2, OsGS2, OsNADH-GOGAT2 and OsFd-GOGAT promoters. Diagrams depict putative OsAMT1.2, OsGS2, OsNADH-GOGAT2 and OsFd-GOGAT promoters and fragments (1-6). i-l, OsGRF4 activates (i) pOsAMT1.2, pOsGS2 (k) pOsNADH-GOGAT2 and (l) pOsFd-GOGAT promoter::Luciferase fusion constructs in transient transactivation assays. Data shown as mean±s.e.m. (n=3).

Transcriptome-wide RNA-sequencing analysis next identified 642 genes having transcript abundances upregulated (by OsGRF4) in NJ6-$OsGRF4^{ngr2}$ and downregulated (by SLR1) in NJ6-sd1 (versus NJ6) (FIG. 3d), including multiple N-uptake and assimilation genes. For example, qRT-PCR confirmed elevated root abundances of mRNAs encoding $NH_4^+$ uptake transporters (e.g., OsAMT1.1 and OsAMT1.2[13]) in NJ6-sd1-$OsGRF4^{ngr2}$, versus reduced abundances in NJ6-sd1 (FIG. 3e; FIG. 11a). Similarly, abundances of mRNAs encoding root and shoot $NH_4^+$ assimilation enzymes (e.g., OsGS1.2[23], OsGS2 and OsNADH-GOGAT2) and corresponding enzymatic activities were enhanced in NJ6-sd1-$OsGRF4^{ngr2}$ (FIG. 3e, f; FIG.

Figure 12:
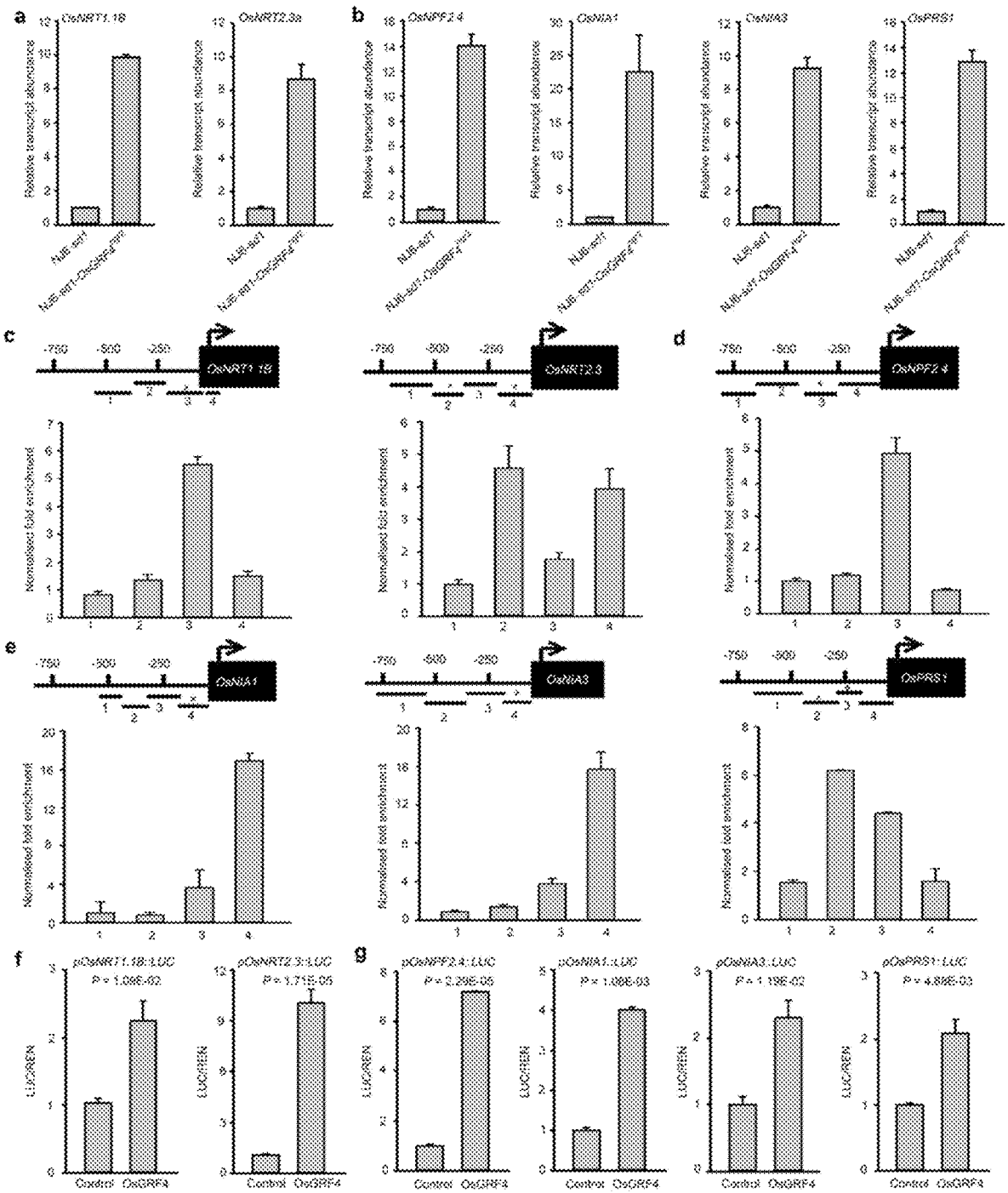
FIG. 12 shows that OsGRF4 regulates expression of multiple $NO_{3-}$ metabolism genes. a, Relative root abundance of $NO_{3-}$ uptake transporter-encoding OsNRT1.1B and OsNRT2.3a mRNA. Data shown as mean±s.e.m. (n=3). b, Relative shoot abundances of OsNPF2.4, OsNIA1, OsNIA3 and OsPRS1 mRNAs encoding $NO_{3-}$ transporters and assimilation enzymes. Data shown as mean±s.e.m. (n=3). Abundance shown relative to that in NJ6-sd1 (=1; panels a-b). c-e, ChIP-PCR with Flag-OsGRF4 enriches GCGG-containing fragments (marked with *) from (c) root $NO_{3-}$ uptake transporter-encoding OsNRT1.1B and OsNRT2.3a gene promoters, (d) the shoot $NO_{3-}$ transporter-encoding OsNPF2.4 gene promoter, and (e) shoot $NO_{3-}$ assimilation enzyme-encoding OsNIA1, OsNIA3 and OsPRS1 gene promoters. Data shown as mean±s.e.m. (n=3). f-g, OsGRF4 activates (f) pOsNRT1.1B and pOsNRT2.3 (g) pOsNPF2.4, pOsNIA1, pOsNIA3 and pOsPRS1 promoter::Luciferase fusion constructs in transient transactivation assays. Data shown as mean±s.e.m. (n=3).

11b-d). We next showed that OsGRF4 enhances N metabolism via transcriptional activation. ChIP-seq enriched several motifs (FIG. 3g), with a GGCGGCGGCGGC motif common to multiple N metabolism gene promoters being most abundant. EMSA demonstrated binding of OsGRF4-His to intact but not mutant OsAMT1.1 promoter fragments (FIG. 3h), and ChIP-PCR confirmed specific in vivo association of OsGRF4 with GCGG-containing promoter fragments from multiple $NH_4^+$ uptake and assimilation genes, including OsAMT1.1 and OsGS1.2 (FIG. 3i; FIG. 11e-h). Finally, OsGRF4 activates transcription from OsAMT1.1 and OsGS1.2 promoters in transactivation assays (FIG. 3j, k; FIG. 11i-l). Next focusing on $NO_3^-$-related genes, qRT-PCR, ChIP, transactivation assays, and enzyme activity determinations confirmed that $NO_3^-$ uptake and assimilation is promoted via OsGRF4-mediated transcriptional activation (FIG. 3b, c; FIG. 12). Thus, OsGRF4 is an overall transcriptional activator of N metabolism, and counteracts the inhibitory effects of SLR1.

Figure 4:
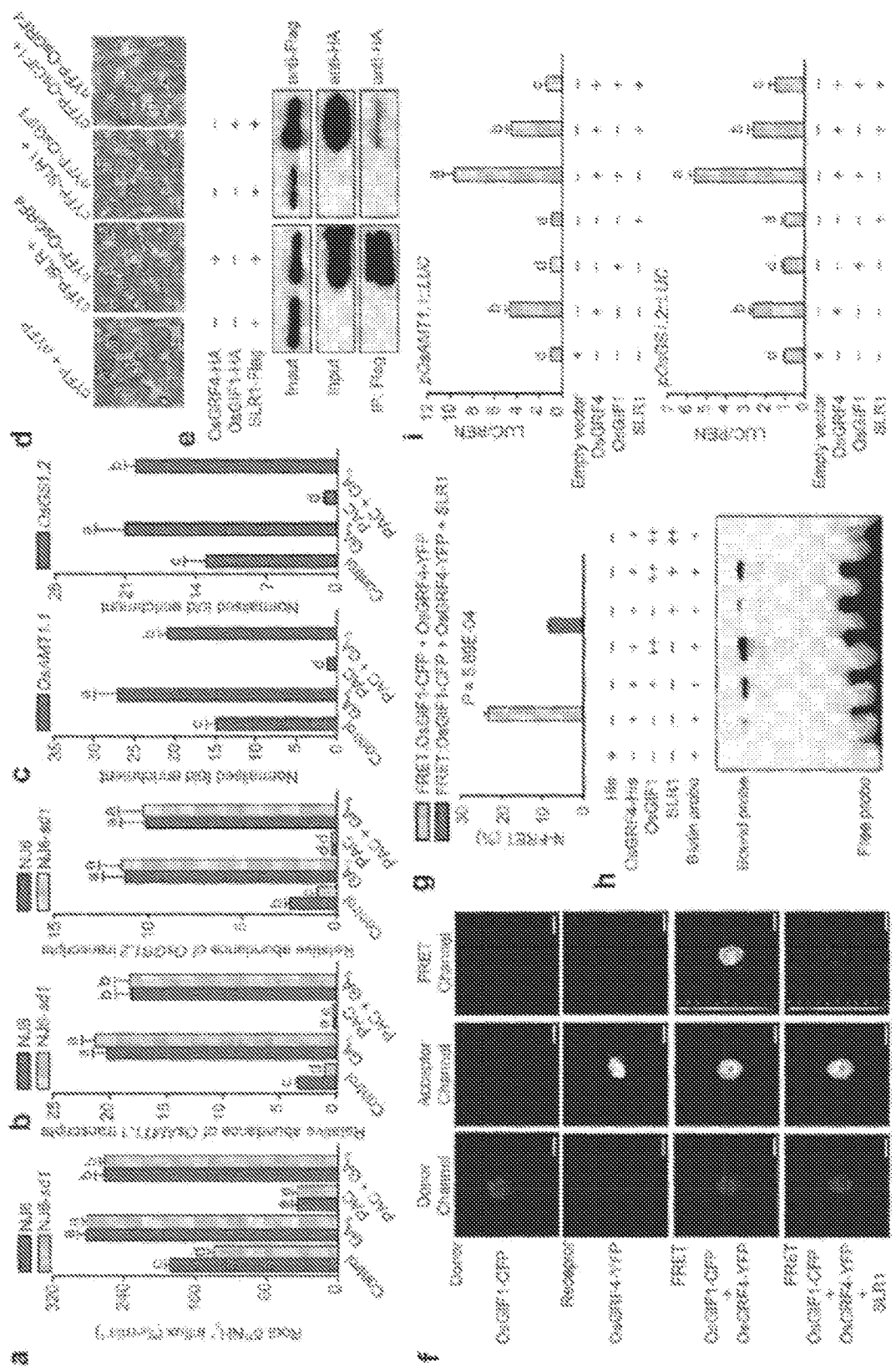
FIG. 4 shows competitive OsGRF4-OsGIF1-OsSLR1 interactions coordinate $NH_4^+$ uptake and assimilation. a, $^{15}NH_4^+$ uptake rates in plants treated with 100 μM GA ($GA_3$) and/or 2 μM paclobutrazol (PAC). Data shown as mean±s.e.m. (n=9). b, Relative root mRNA abundance in plants treated with GA and/or paclobutrazol (PAC). Data shown as mean±s.e.m. (n=3). c, Extent of ChIP-PCR OsGRF4-mediated enrichment of GCGG-containing promoter fragments from OsAMT1.1 (fragment 5) and OsGS1.2 (fragment 2) (shown in FIG. 2i) varies in response to treatment with GA and/or PAC. Data shown as mean±s.e.m. (n=3). d, BiFC assays reveal mutual interactions between SLR1, OsGRF4 and OsGIF1 in nuclei of tobacco leaf epidermal cell nuclei. Scale bar, 60 μm. e, Co-IP experiments with Flag-tagged SLR1 and HA-tagged OsGRF4 or HA-tagged OsGIF1. f, FRET images. Donor group: OsGIF1-CFP only; Acceptor group: OsGRF4-YFP only; FRET groups: OsGIF1-CFP and OsGRF4-YFP with and without SLR1. Scale bar, 200 μm. g, Mean N-FRET data for OsGIF1-CFP and OsGRF4-YFP channels. Data shown as mean±s.e.m. (n=6). A Student's t-test generated the P values. h, EMSA assays show that binding of an OsGRF4-His fusion protein to a GCGG motif-containing DNA fragment from the OsAMT1.1 promoter is promoted by OsGIF1 but inhibited by SLR1. i, Transactivation assays. OsGRF4-activated promotion of pOsAMT1.1 and pOsGS1.2 promoter::Luciferase fusion constructs is enhanced by OsGIF1 and inhibited by SLR1. Data shown as mean±s.e.m. (n=6). Statistical analyses used Duncan's multiple range tests, the same lowercase letter denotes non-significant difference between means (P>0.05; panels a-c, and i).
Figure 13:
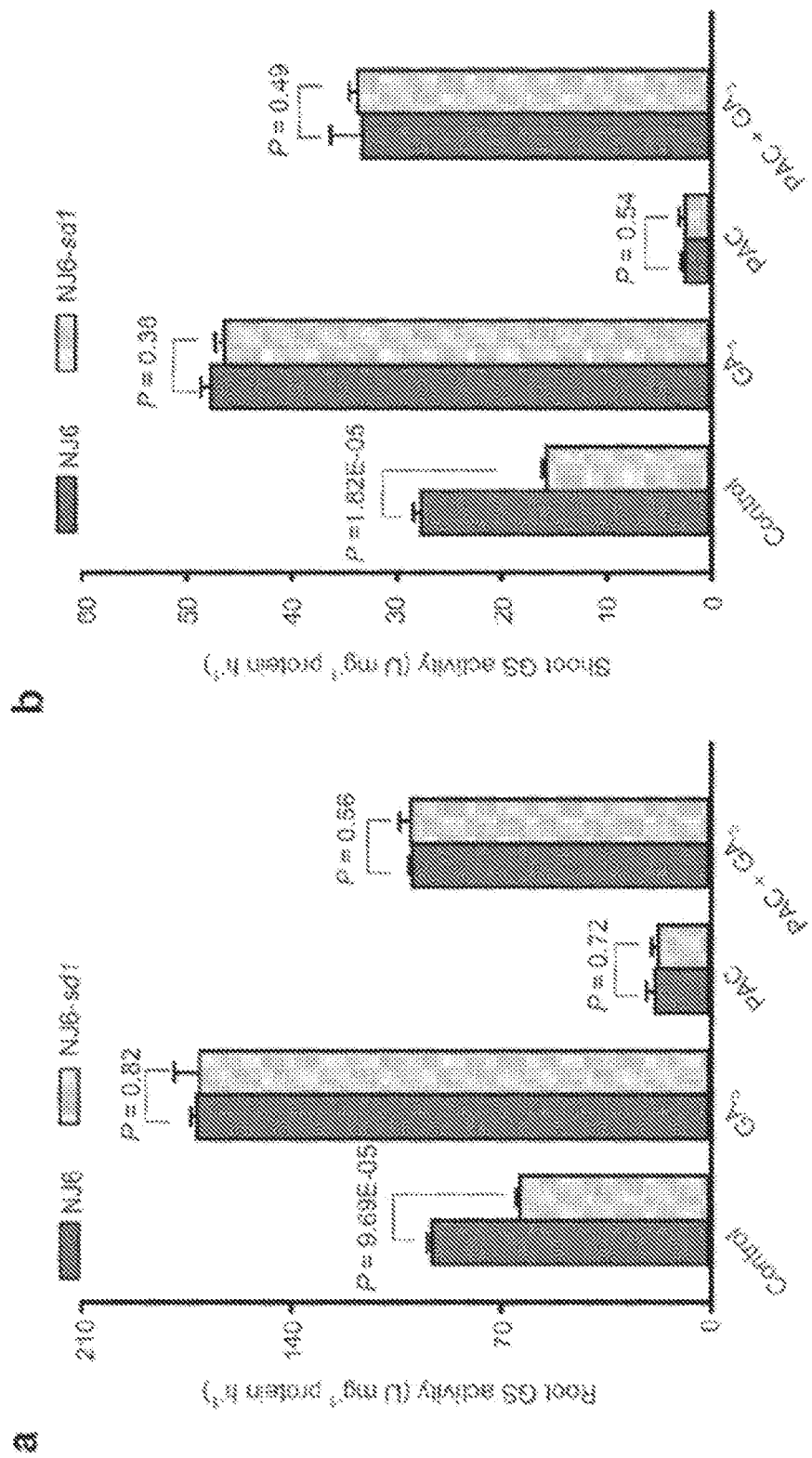
FIG. 13 shows that GA promotes GS activity. a, GS activities in roots of 2-week-old rice plants treated with 100 μM GA ($GA_3$) and/or 2 μM paclobutrazol (PAC), genotypes as indicated. Data shown as mean±s.e.m. (n=3). b, GS activities in shoots of plants treated with 100 μM GA ($GA_3$) and/or 2 μM paclobutrazol (PAC), genotypes as indicated. Data shown as mean±s.e.m. (n=3).

Because GA promotes proteasome-mediated destruction of SLR1[8,9], we next investigated how GA, SLR1, and OsGRF4 regulate N metabolism. GA promotes both NJ6 and NJ6-sd1 $^{15}NH_4^+$ uptake rates to similarly high levels (FIG. 4a). Also, whilst the GA-biosynthesis inhibitor pacolubutrazol (PAC)[24] reduces NJ6 and NJ6-sd1 $^{15}NH_4^+$ uptake, GA abolishes this effect (FIG. 4a). Thus, SLR1 accumulation (due to sd1 or PAC) reduces $NH_4^+$ uptake, whilst reduced SLR1 accumulation (due to GA) increases it. Furthermore, differential SLR1 accumulation differentially regulates the abundance of mRNAs encoding $NH_4^+$ uptake and assimilation functions: OsAMT1.1 and OsGS1.2 mRNA abundances are increased by GA, reduced by PAC, and restored to higher levels by a combination of GA and PAC (FIG. 4b). Next, we found that PAC reduces, whilst GA promotes ChIP-PCR enrichment of GCGG motif-containing fragments from the OsAMT1.1 and OsGS1.2 promoters (FIG. 4c). Thus, SLR1 accumulation inhibits, whilst reduced SLR1 abundance promotes OsGRF4 binding to OsAMT1.1 and OsGS1.2 promoters (FIG. 4c), thus affecting OsAMT1.1 and OsGS1.2 mRNA levels, $NH_4^+$ uptake, and $NH_4^+$ assimilation (FIG. 4a, b; FIG. 13).

Figure 14:
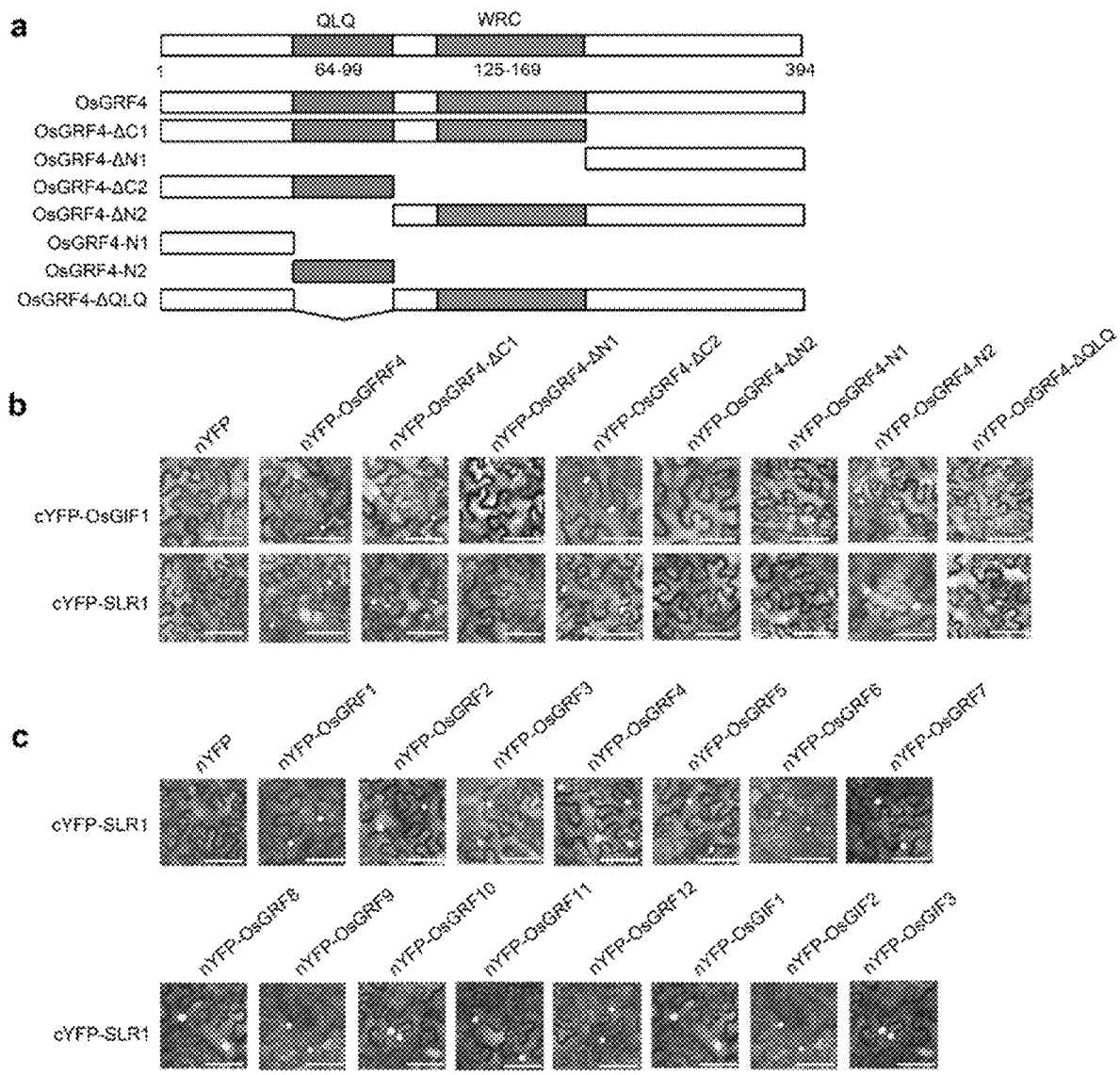
FIG. 14 shows BiFC visualisation of SLR1-OsGIF1-OsGRF4 interactions. a, Details of constructs expressing OsGRF4 and variants deleted for specific domains. OsGRF4 contains the QLQ (Gln, Leu, Gln) and WRC (Trp, Arg, Cys) domains, positions as indicated. b, BiFC assays. Constructs expressing OsGRF4 or deletion variants (as in a) tagged with the N-terminus of YFP were co-transformed into tobacco leaf epidermal cells, together with constructs expressing OsGIF1 or SLR1 tagged with the C-terminus of YFP, respectively. Scale bar, 60 μm. c, BiFC assays. Constructs expressing OsGRF1 or related OsGRF family protein tagged with the N-terminus of YFP-tagged were co-transformed into tobacco leaf epidermal cells together with a construct expressing SLR1 tagged with the C-terminus of YFP. Scale bar, 60 μm.
Figure 15:
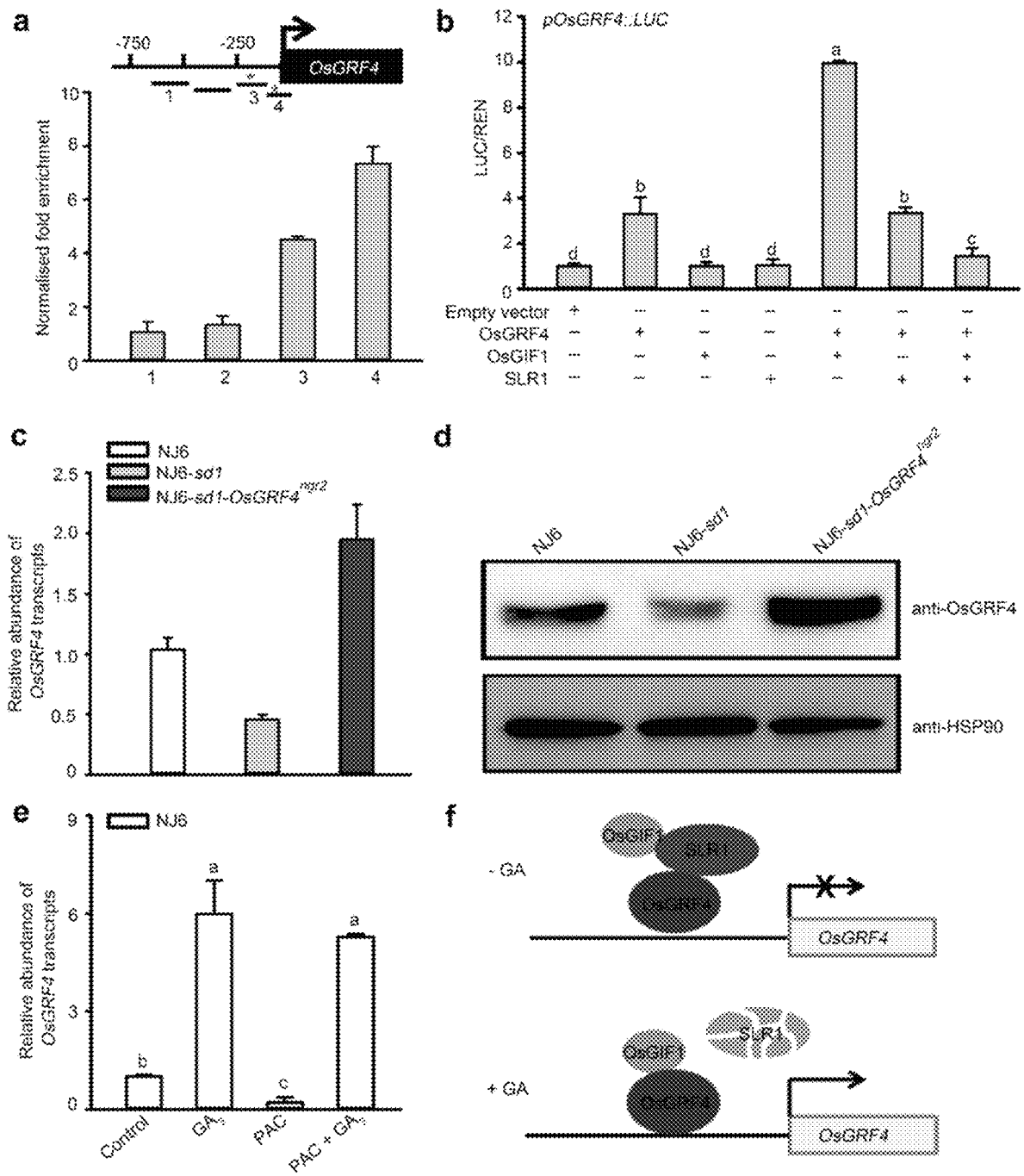
FIG. 15 shows that SLR1 inhibits OsGRF4 self-promotion of OsGRF4 mRNA and OsGRF4 protein abundance. a, ChIP-PCR OsGRF4-mediated enrichment of GCGG-containing OsGRF4 promoter fragments. b, OsGRF4-activated promotion of transcription from a pOsGRF4promoter::Luciferase fusion constructs is enhanced by OsGIF1 and inhibited by SLR1. c, OsGFR4 mRNA abundance, plant genotypes as indicated. d, OsGRF4 abundance (as detected by an anti-OsGRF4 antibody), plant genotypes as indicated. e, Effect of GA and PAC on OsGRF4 mRNA abundance. f, Diagrammatic representation of how GA promotes OsGRF4 abundance. In the absence of GA, SLR1 inhibits OsGRF4-OsGIF1 promotion of OsGRF4 transcription. In the presence of GA, SLR1 is destroyed via proteasome-mediated degradation, this promoting OsGRF4-OsGIF1 activated OsGRF4 transcription.

OsGRF4 interacts with OsGIF (GRF-interacting factor) co-activators[17]. BiFC (FIG. 4d) and Co-IP (FIG. 4e) revealed in vivo interaction between OsGRF4, OsGIF1, and SLR1. OsGRF4 interactions involve a conserved QLQ[17] domain (FIG. 14a, b), and SLR1 interacts with all rice OsGRFs and OsGIFs (FIG. 14c). In vivo FRET revealed that these interactions are competitive, with SLR1 inhibiting the OsGRF4-OsGIF1 interaction (FIG. 4f, g). Further EMSA showed that the OsGRF4-OsGIF1 interaction promotes binding of OsGRF4 to the OsAMT1.1 GCGG motif-containing promoter fragment, and that SLR1 inhibits this promotion (FIG. 4h). Accordingly, SLR1 inhibits OsGRF4-OsGIF1-mediated transcriptional activation from OsAMT1.1 and OsGS1.2 promoters (FIG. 4i). Furthermore, SLR1 inhibits OsGRF4-OsGIF1 self-activation transcription from the OsGRF4 promoter (FIG. 15a, b), causing reduced OsGRF4 mRNA and OsGRF4 abundance in NJ6-sd1 (versus NJ6; FIG. 15c, d), and OsGRF4 mRNA abundance to be GA-regulated (FIG. 15e, f). Thus, SLR1 counteracts the promotive effects of OsGRF4 on N metabolism in two ways. First, SLR1 accumulation reduces OsGRF4 accumulation (via inhibition of OsGRF4 transcription). Second, SLR1 inhibits formation of OsGRF4-OsGIF1 complexes, thus reducing transcription of OsGRF4-activated N metabolism genes.

The OsGRF4-SLR1 Interaction Integrates Assimilative Metabolism and Growth

Figure 5:
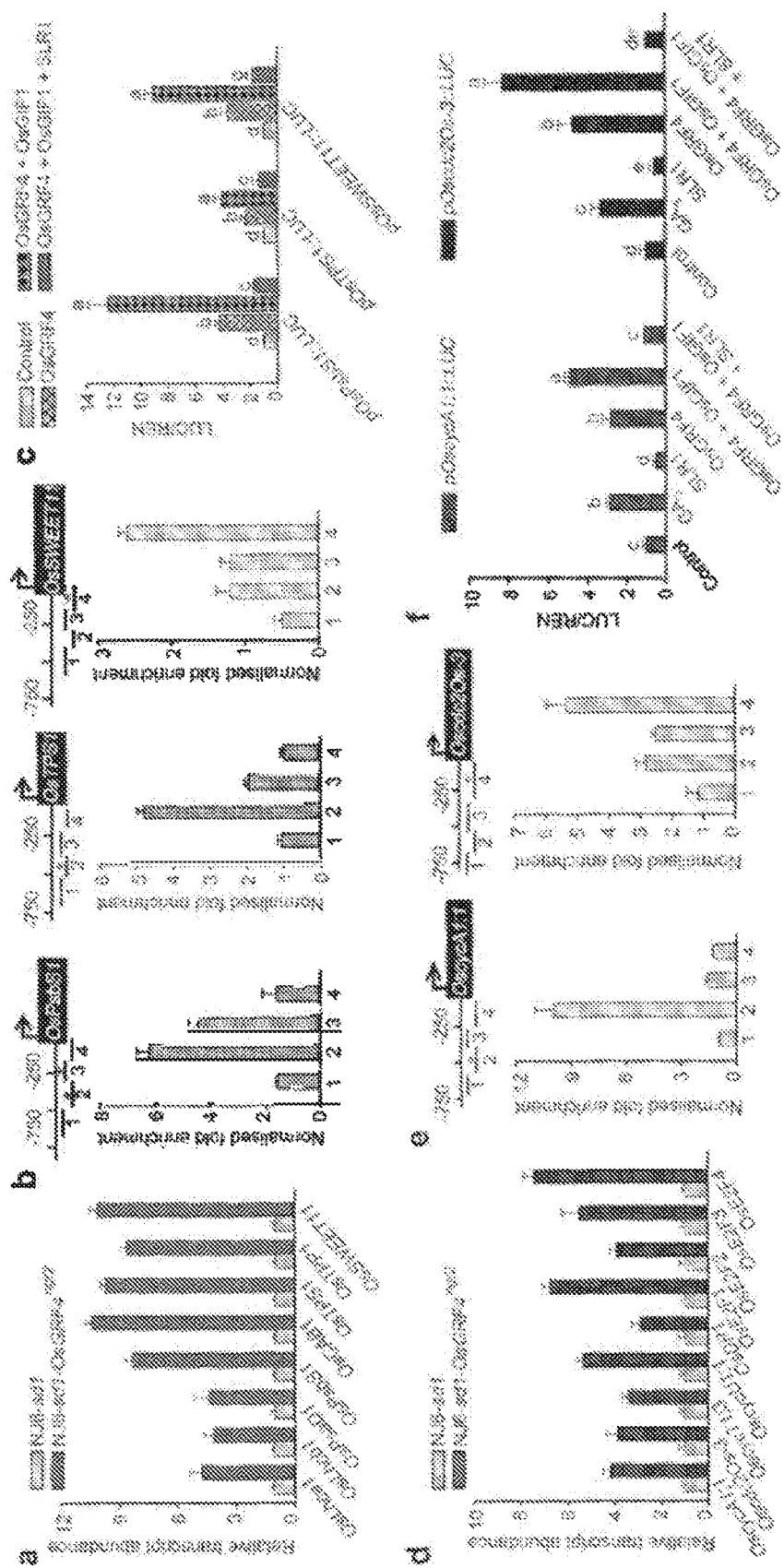
FIG. 5 shows that OsGRF4-SLR1 antagonism regulates carbon assimilation and plant growth. a, Relative abundances of mRNAs transcribed from genes regulating C-fixation. Data shown as mean±s.e.m. (n=3). Abundances expressed relative to the level in NJ6-sd1. b, ChIP-PCR assays. Diagram depicts the OsPsbS1, OsTPS1 and OsS-WEET11 promoters and regions used for ChIP-PCR. c, Transactivation assays. Data shown as mean±s.e.m. (n=9). d, Relative abundances of mRNAs transcribed from cell-cycle regulatory genes. Data shown as mean±s.e.m. (n=3). Abundances expressed relative to the level in NJ6-sd1. e, ChIP-PCR assays. Diagram depicts the OscycA1.1 and Oscdc2Os-3 promoters and regions used for ChI P-PCR. f, Transactivation assays. Data shown as mean±s.e.m. (n=12). Statistical analyses used Duncan's multiple range tests, the same lowercase letter denotes a non-significant difference between means (P>0.05).
Figure 16:
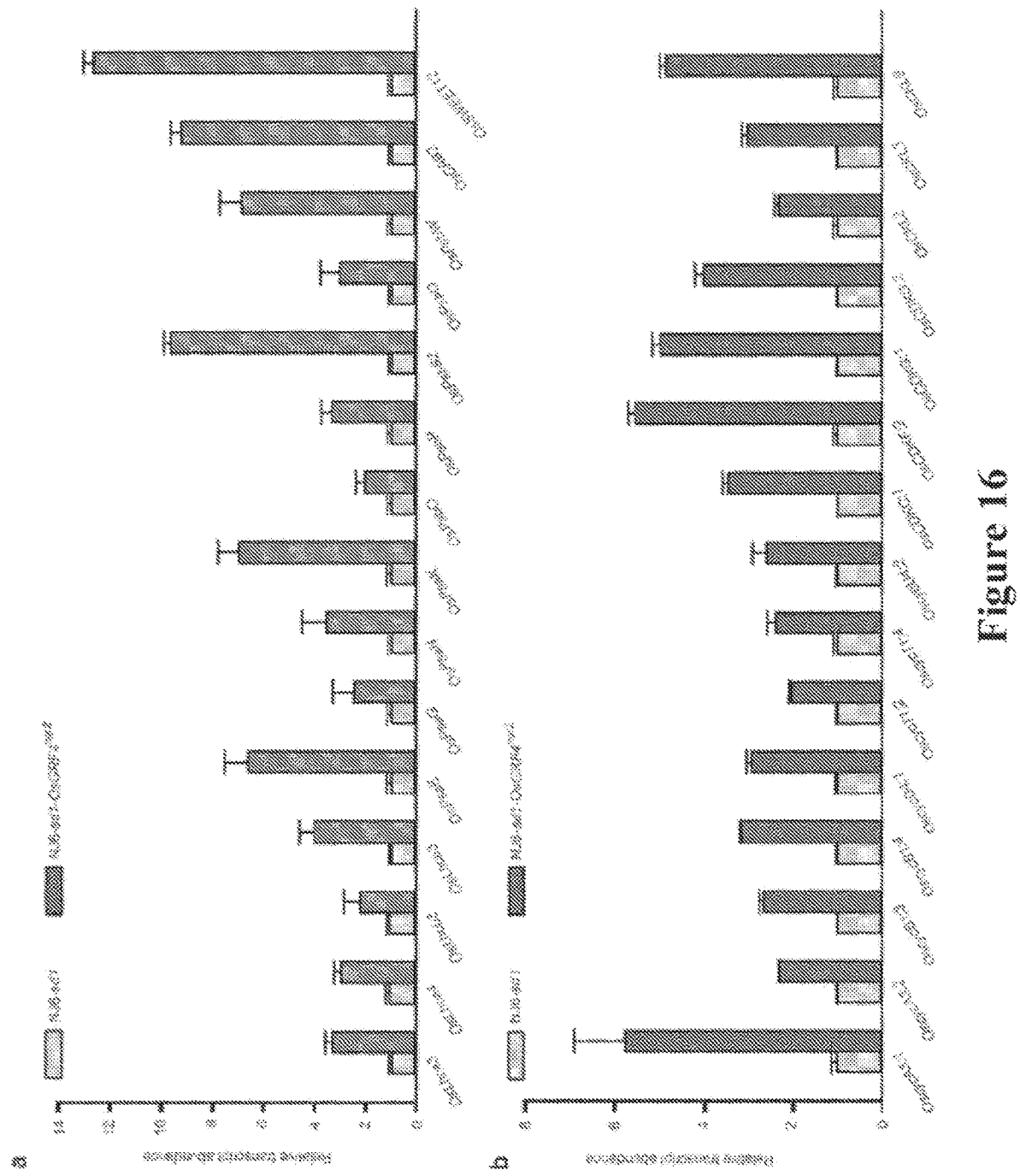
FIG. 16 shows that OsGRF4 regulates expression of multiple C metabolism and cell-cycle regulatory genes. a, Relative shoot abundances of transcripts of selected genes regulating photosynthesis, carbon signalling and sucrose transport/phloem loading in NJ6-sd1-OsGRF4$^{ngr2}$ plants, relative to abundance in NJ6-sd1 plants (=1). Data shown as mean±s.e.m. (n=3). b, Relative shoot abundances of transcripts of selected genes regulating cell cycle progression in NJ6-sd1-OsGFR4$^{ngr2}$ plants, relative to abundance in NJ6-sd1 plants (=1). Data shown as mean±s.e.m. (n=3).

Whilst it has long been known that N uptake rates are coupled with the rate of photosynthetic carbon (C) fixation[25], the balancing molecular mechanism that connects C and N metabolism remains unknown. Because the OsGRF4-SLR1 interaction regulates N assimilation, we determined if it also regulates C assimilation. First, RNA-seq data (FIG. 3d) and quantitative RT-PCR comparisons of NJ6-sd1-OsGRF4$^{ngr2}$ and NJ6-sd1 indicated that OsGRF4 upregulates, whilst SLR1 downregulates, multiple genes encoding photosynthetic (e.g., OsCAB1, OsPsbS1 and others; FIG. 5a; FIG. 16a), sugar signalling (e.g., OsTPS1; FIG. 5a) and sucrose transport/phloem loading (e.g., OsSWEET11 and others; FIG. 5a; FIG. 16a) mechanism components. In addition, OsGRF4 binds in vivo to GCGG-containing promoter fragments from OsPsbS1, OsTPS1 and OsSWEET11 (FIG. 5b), whilst SLR1 inhibits OsGRF4-OsGIF1 complex activation of transcription from pOsPsbS1, pOsTPS1 and pOsSWEET11 promoters (FIG. 5c). We therefore conclude that the balanced antagonistic relationship between OsGRF4 and SLR1 regulates both N and C assimilation, and provides a regulatory coordinating link between them.

Because SLR1 inhibits growth, we also determined if the OsGRF4-SLR1 interaction regulates cell proliferation, showing that OsGRF4 upregulates, whilst SLR1 downregulates, multiple genes promoting cell division, including those encoding cyclin dependent cdc2 protein kinases (e.g., OscycA1; 1 and Oscdc2Os-3[26,27]) and others (FIG. 5d; FIG. 16b). In addition, OsGRF4 binds in vivo to GCGG-containing promoter fragments from OscycA1;1 and Oscdc2Os-3 (FIG. 5e), and GA promotes, whilst SLR1 inhibits OsGRF4-OsGIF1 complex activation of transcription from pOscycA1;1 and pOscdc2Os-3 promoters (FIG. 5f). We conclude that the OsGRF4-SLR1 antagonism balance modulates the GA-mediated regulation of cell proliferation, and provides a coordinate controlling link that integrates growth, N, and C metabolism.

Increased OsGRF4 Abundance Increases Sustainable Yields of Rice and Wheat GRVs

Figure 6:
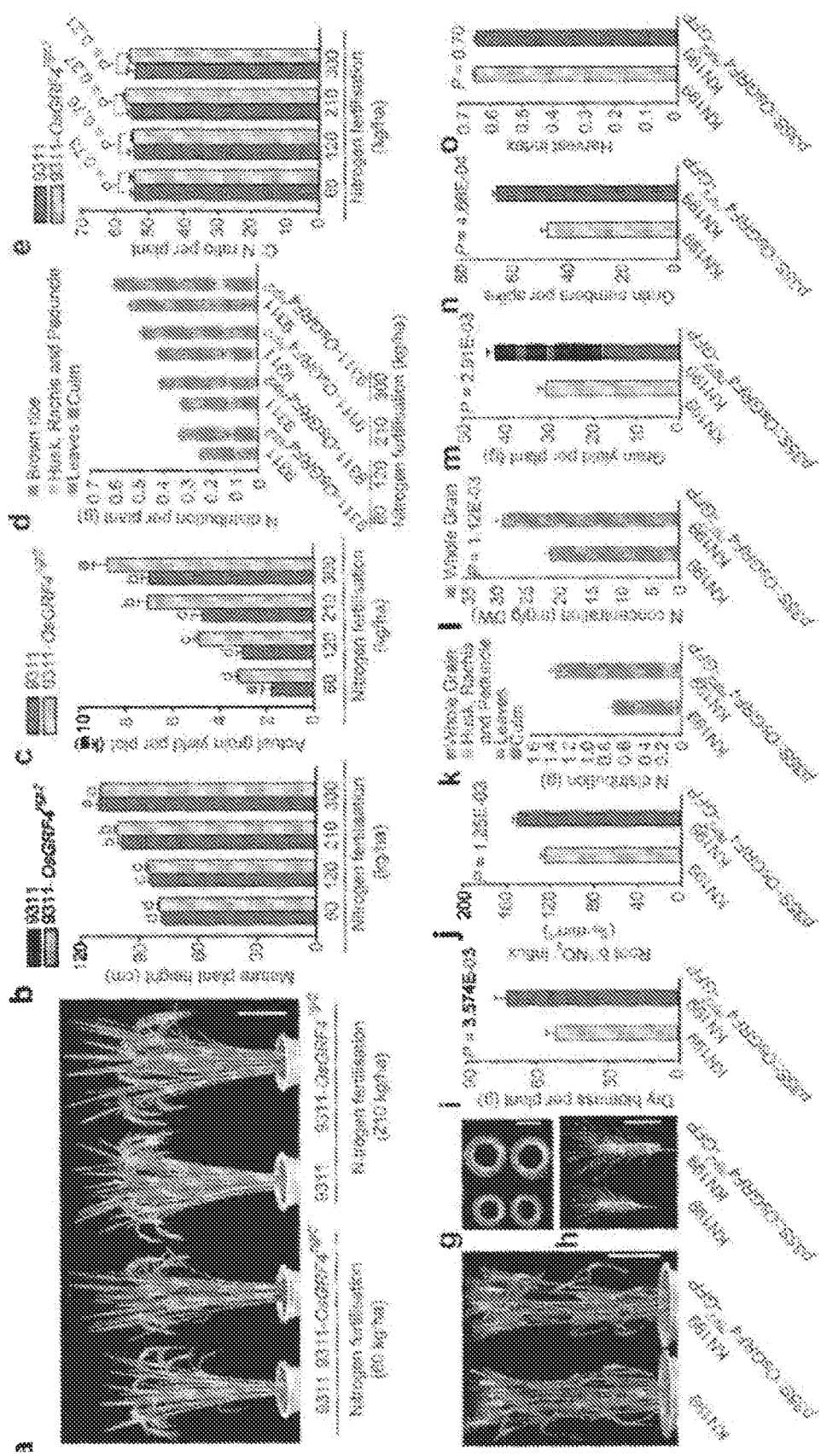
FIG. 6 shows that elevated OsGRF4 abundance increases grain yield and N use-efficiency of rice and wheat GRVs without increasing mature plant height. a, Mature plant phenotypes of 9311 and 9311-OsGRF4$^{ngr2}$ rice grown in paddy field conditions at low (LN: 60 kg/ha) and high (HN: 210 kg/ha) N supply. Scale bar, 15 cm. b, Heights of NIL plants grown in paddy field conditions increasing N supply. Data shown as mean±s.e.m. (n=30). c, Grain yield of field-grown plants in response to increasing N supply. Data shown as mean±s.e.m. of six plots (each plot contained 220 plants) per line per N level. Statistical analyses used Duncan's multiple range tests, the same lowercase letter denotes a non-significant difference between means (P>0.05; panels b, c). d, N distribution ratio in different organs of above-ground parts of plants shown in b. Data shown as mean s.e.m. (n=30). e, C:N ratio of plants shown in b. f, Mature KN199 and KN199 p35S::OsGRF4$^{ngr2}$-GFP wheat plants. Scale bar, 15 cm. g, Cross section of the uppermost internodes of (left) KN199 and (right) KN199 p35S::OsGRF4$^{ngr2}$-GFP wheat plants. Scale bar, 2 mm. h, Comparison of spike lengths of KN199 and KN199 p35S::OsGRF4$^{ngr2}$-GFP wheat plants. Scale bar, 5 cm. i, Biomass accumulation. Data shown as mean s.e.m. (n=12). j, Root $^{15}NO_3^-$ uptake rates, genotypes as indicated. Data shown as mean±s.e.m. (n=9). k, Comparison of N distribution in different organs of above-ground plant parts. Data shown as mean s.e.m. (n=9). l, N concentrations. Data shown as mean s.e.m. (n=20). m, Grain yields of KN199 and KN199 p35S::OsGRF4$^{ngr2}$-GFP wheat plants. Data shown as mean±s.e.m. (n=30). n, Grain number of grains per spike. Data shown as mean s.e.m. (n=30). o, Harvest index of KN199 and KN199 p35S:: OsGRF4$^{ngr2}$-GFP wheat plants. Data shown as mean±s.e.m. (n=6). A Student's t-test was used to generate the P values (panels e, i, j and l-o).
Figure 17:
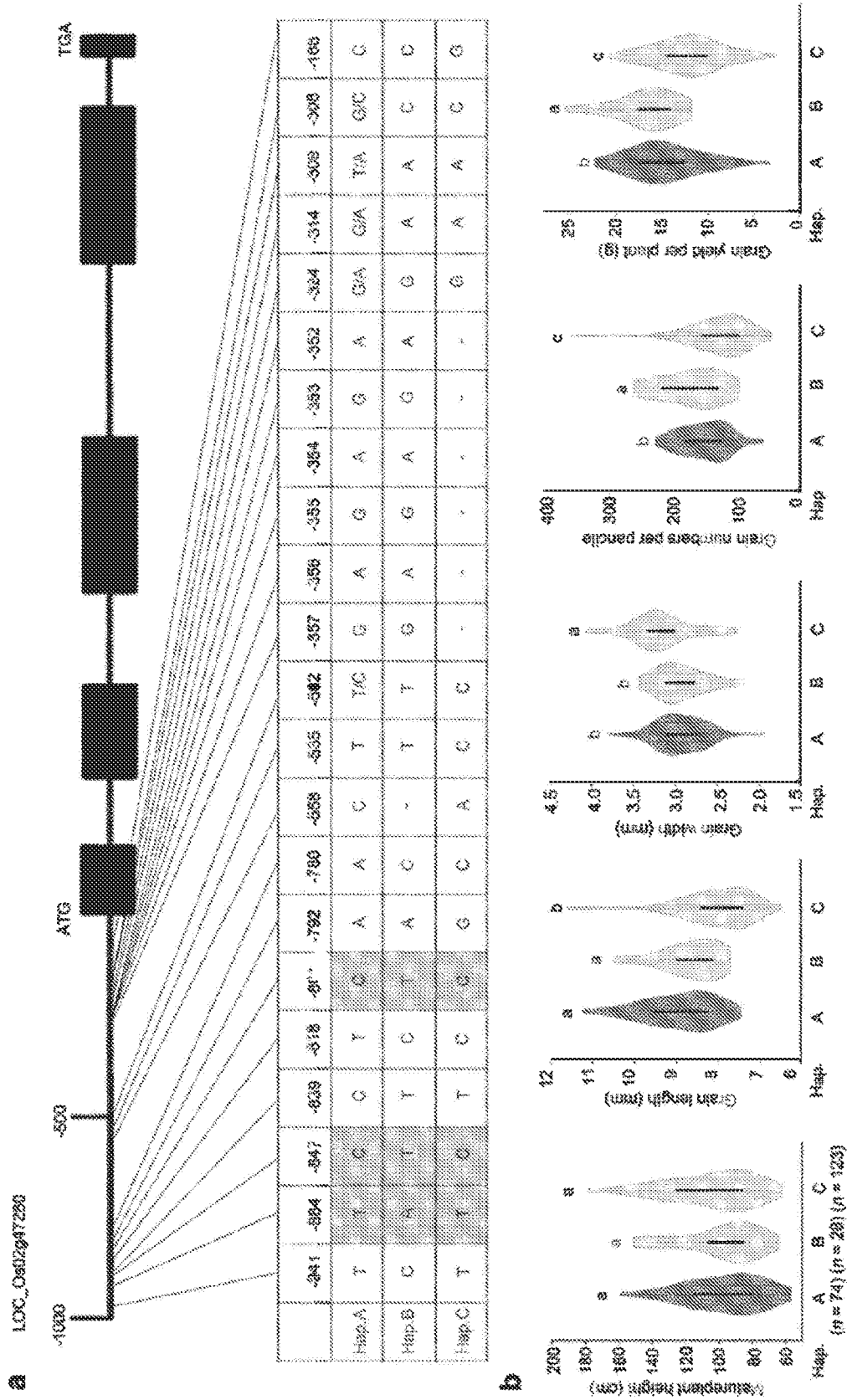
FIG. 17 shows that natural allelic variation at OsGRF4 is associated with variation in plant and grain morphology and grain yield performance. a, DNA polymorphisms in the promoter region of OsGRF4. Green-shaded regions indicate the three unique SNP variations associated with phenotypic variation in NM73 and RD23. b, Boxplots for plant height, grain length, grain width, grain numbers per panicle, and grain yield performance of rice varieties carrying different OsGRF4 promoter haplotypes (Hap.; A, B or C). All data from plants grown in normal paddy-field fertilization conditions[21]. Data shown as mean±s.e.m. (A, n=74; B, n=28; C, n=123). The same lowercase letter denotes a non-significant difference between means (P>0.05).
Figure 18:
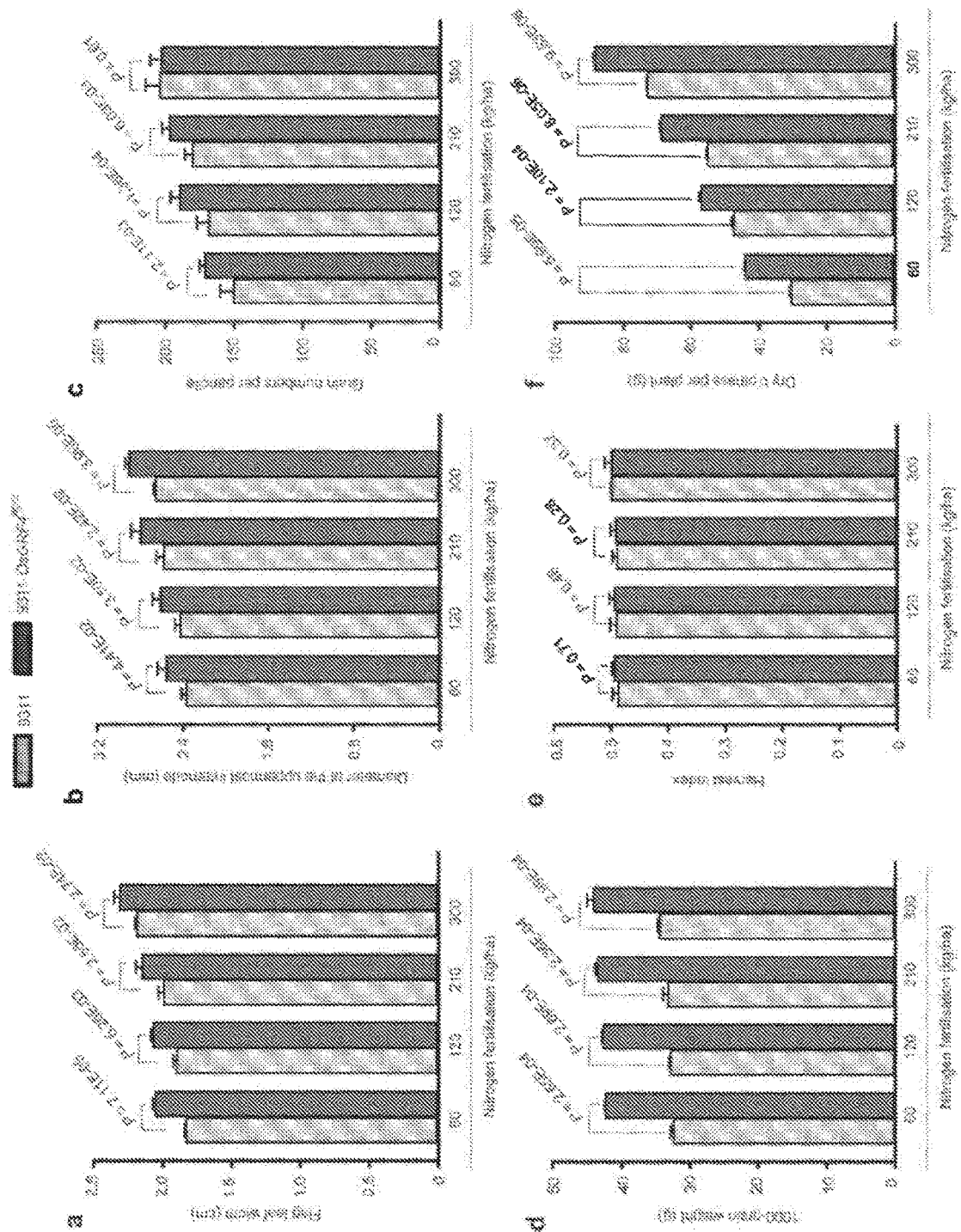
FIG. 18 shows agronomic traits displayed by 9311 and 9311-OsGRF4$^{ngr2}$ plants grown at varying N fertilisation levels. a, Flag leaf width. b, Culm width of the uppermost internode. c, The number of grains per panicle. d, 1000-grain weight. e, Harvest index. f, Dry biomass per plant. Data shown as mean±s.e.m. (n=30). A Student's t-test was used to generate the P values.
Figure 19:
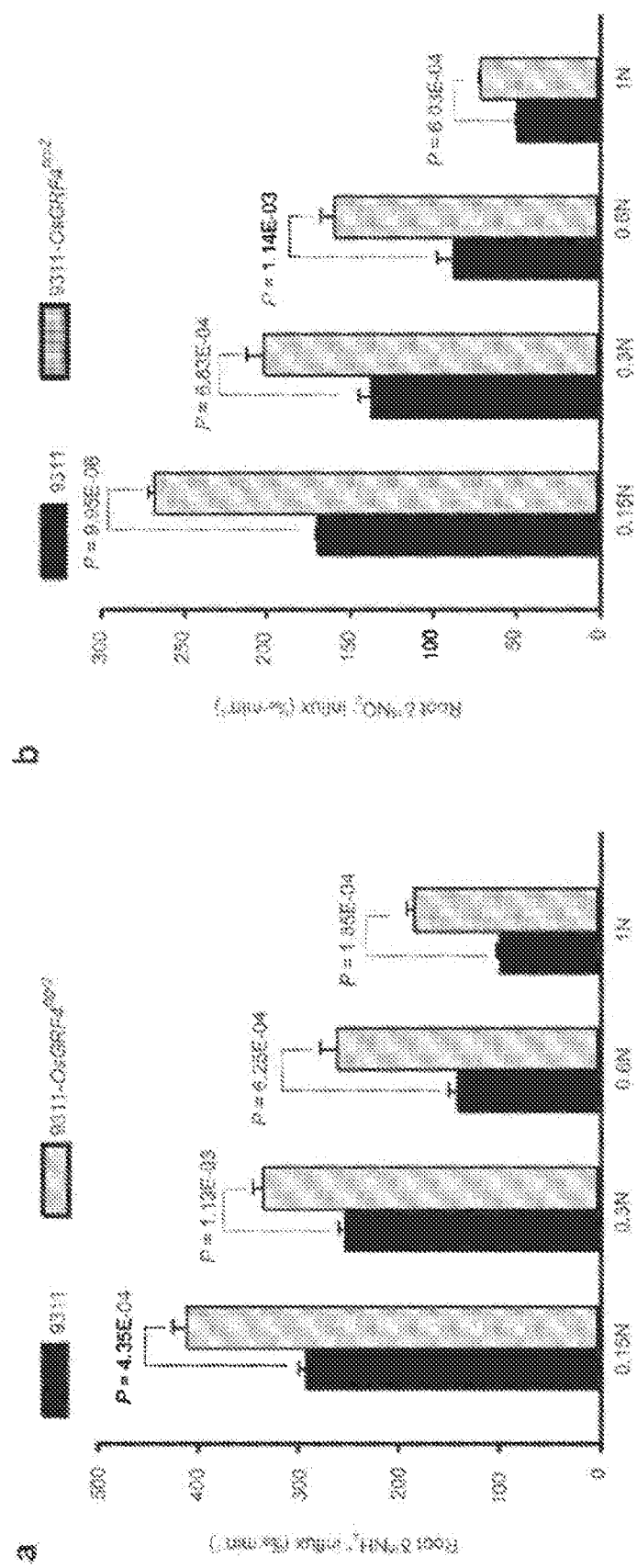
FIG. 19 shows root N-uptake rates of 9311 and 9311-OsGRF4$^{ngr2}$ plants grown at varying N fertilisation levels. a, $^{15}NH_{4+}$ uptake. b, $^{15}NO_{3-}$ uptake. Data shown as mean±s.e.m. (n=30). A Student's t-test was used to generate the P values.
Figure 20:
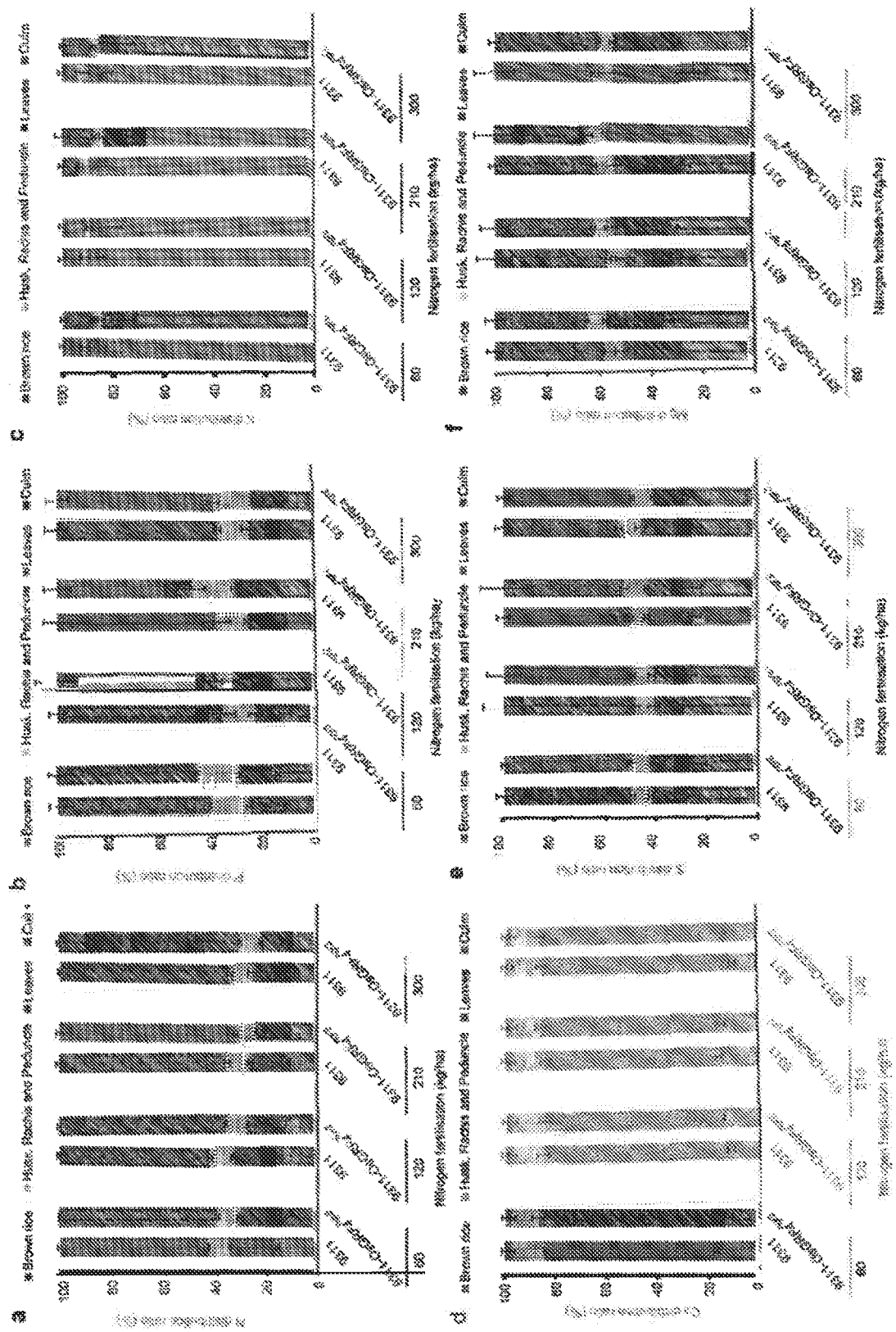
FIG. 20 shows mineral nutrient distributions in different organs of above ground parts of 9311 and 9311-OsGRF4$^{ngr2}$ plants grown at varying levels of N fertilization. a, N distribution. b, P (phosphorus) distribution. c, K (potassium) distribution. d, Ca (calcium) distribution. e, S (sulphur) distribution. f, Mg (magnesium) distribution. Data shown as mean±s.e.m. (n=9).

OsGRF4 promoter haplotype B (FIG. 7d) exists in selected indica cultivars, but not in modern elite indica or japonica varieties. Nevertheless, of 225 accessions[28], varieties carrying haplotype B exhibit relatively high yield potential (FIG. 17). We further assessed the possible impact of OsGRF4 allelic variation on indica N use-efficiency and grain yield, by constructing a 9311-OsGRF4$^{ngr2}$ isogenic line (in the high-yielding sd1-containing indica rice 9311 background; FIG. 6a). As previously found in NJ6-sd1 (FIG. 3a), OsGRF4$^{ngr2}$ does not affect the sd1-conferred semi-dwarf 9311 phenotype at low, medium or high N-input levels (FIG. 6a, b), but does increase leaf and culm width (FIG. 18a, b). Also, the increased N uptake and assimilation conferred by OsGRF4$^{ngr2}$ (FIG. 19), whilst not affecting plant height (FIG. 6a, b), increases 9311 grain yield and N use-efficiency. Grain yield was increased in 9311-OsGRF4$^{ngr2}$ (versus 9311) at a range of N-inputs, with significant yield boost being observed even at relatively low N-supply levels (FIG. 6c). These yield increases were due to an increase in grain number per plant that increased in extent with decreasing N-input (FIG. 18c), and an increase in 1,000-grain weight[17-19] (FIG. 18d). In addition, harvest index was little changed (FIG. 18e), presumably because biomass increases (FIG. 18f) balance out increases in grain yield. Whilst total N in above-ground parts of 9311-OsGRF4$^{ngr2}$ plants was substantially greater than in 9311 (FIG. 6d), the distribution ratio of N allocated to grain (versus vegetative organs) was not significantly increased in 9311-OsGRF4$^{ngr2}$ (FIG. 20a). C/N balance ratio was similarly unaffected (as expected since OsGRF4 coordinately promotes both C and N metabolism; FIG. 6e). Finally, OsGRF4$^{ngr2}$ had little effect on in planta distributions of other mineral nutrients (FIG. 20b-f). These results suggest that the increased OsGRF4 abundance conferred by OsGRF4$^{ngr2}$ partially disconnects GA-regulation of stem elongation (plant height) from N metabolic regulation. Nutrient assimilation and grain yield of indica rice GRVs are hence increased, particularly at low levels of N fertilization.

Figure 21:
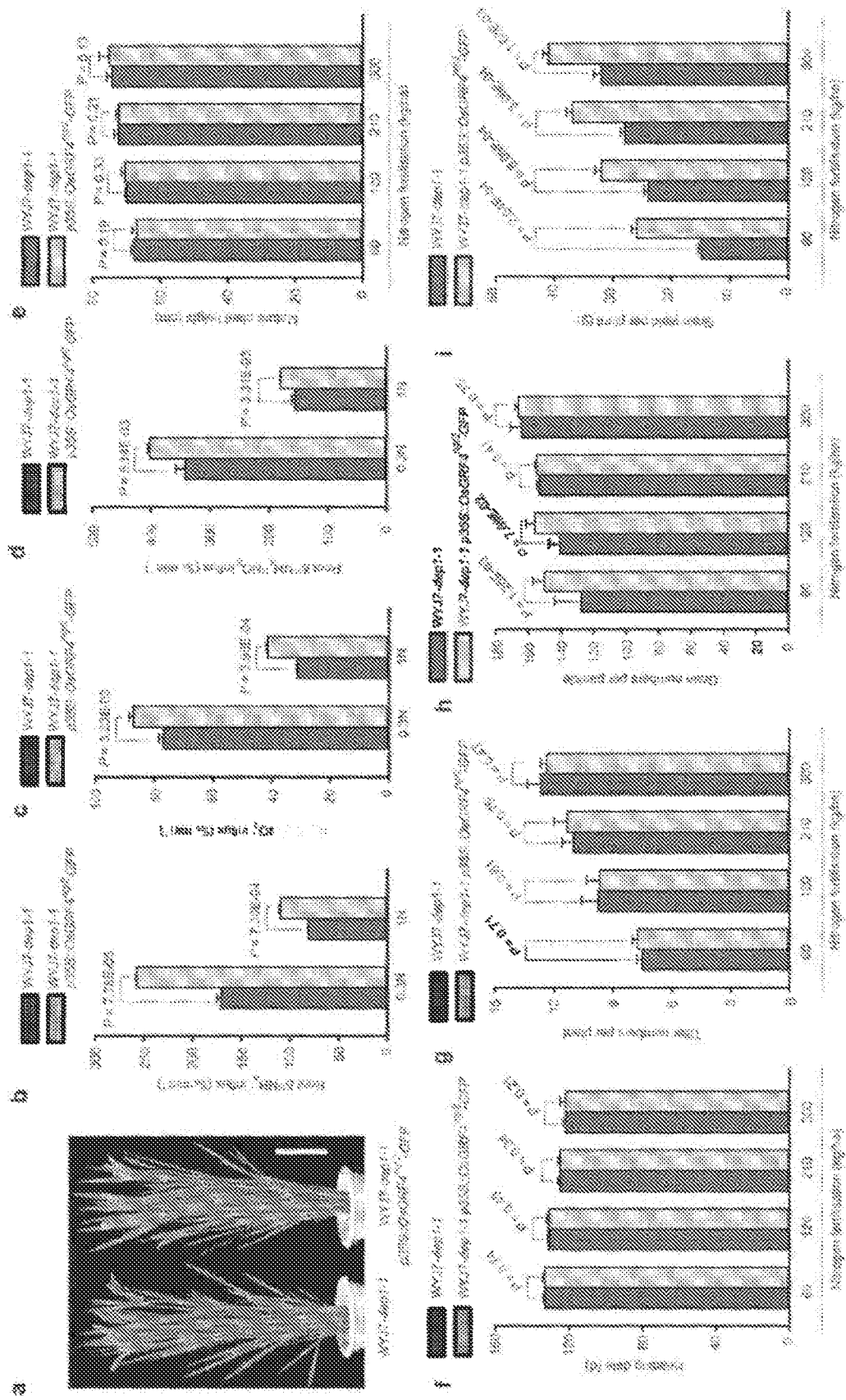
FIG. 21 shows growth, N uptake and grain yield performance of WYJ7-dep1 and transgenic WYJ7-dep1 plants expressing a p35::OsGRF4ngr2-GFP construct at varying levels of N fertilization. a, Mature plant heights. Scale bar, 15 cm. b-d, Root uptake rates for (b)$^{15}NH_{4+}$ (c)$^{15}NO_{3-}$ and (d)$^{15}NH_{4+}$ and $^{15}NO^{3-}$ combined. Rice plants grown in low N (0.3N, 0.375 mM NH$_4$NO$_3$) and high N (1N, 1.25 mM NH$_4$NO$_3$) conditions, respectively. Data shown as mean±s.e.m. (n=9). The same lowercase letter denotes a non-significant difference between means (P>0.05). e, Mature plant height. f, Heading date. g, Tiller number per plant. h, Grain number per panicle. i, Grain yield per plant. Data shown as mean±s.e.m. (n=30). A Student's t-test was used to generate the P values (panels e-i).

We next determined if increased OsGRF4 abundance similarly elevates grain yield and N use-efficiency in japonica rice and wheat GRVs. Heterotrimeric G-protein complexes (of Gα, Gβ and Gγ subunits) mediate responses to multiple external stimuli in diverse organisms. Chinese Japonica rice GRV semi-dwarfism is conferred by a variant (dep1-1) Gγ subunit[29] that reduces vegetative growth N-response and increases N use-efficiency[21]. As for indica, we found that increased OsGRF4 abundance (OsGRF4-GFP in transgenic japonica WJY7-dep1-1 isogenic plants[29] expressing p35S::OsGRF4$^{ngr2}$-GFP) did not suppress dep1-1-conferred semi-dwarfism (FIG. 21a), but did increase both $^{15}NH_4^+$ and $^{15}NO_3$ uptake rates (FIG. 21b-d). In addition, whilst plant height, heading date and tiller number per plant responses to different N input levels were unaffected (FIG. 21e-g), expression of p35S::OsGRF4$^{ngr2}$-GFP increased both the number of grains per panicle (in low N; FIG. 21h) and grain yield (FIG. 21i) of WJY7-dep1-1. Thus, elevated OsGRF4 abundance increases N use-efficiency and yield of elite indica and japonica rice varieties.

Finally, the semi-dwarfism of high-yielding Chinese wheat GRV KN199 is conferred by the mutant Rht-B1b allele[4,5]. As in rice, transgenic expression of p35S::OsGRF4$^{ngr2}$-GFP did not increase KN199 plant height (FIG. 6f), but did increase culm diameter and wall thickness (FIG. 6g), spike length (FIG. 6h) and biomass accumulation (FIG. 6i). In addition, p35S::OsGRF4$^{ngr2}$-GFP increased KN199 $^{15}NO_3^-$ uptake rate (FIG. 6j), total N in aboveground plant parts (FIG. 6k) and N concentration in dehusked grain (FIG. 6l). p35S::OsGRF4$^{ngr2}$-GFP also boosted KN199 yield (FIG. 6m) by increasing grain numbers per spike (FIG. 6n), without affecting harvest index (FIG. 6o). Increased OsGRF4 abundance thus enhances grain yield and N use-efficiency of wheat GRVs, without affecting the beneficial semi-dwarfism conferred by mutant Rht alleles. Indeed, the increased culm width and wall thickness conferred by p35S::OsGRF4$^{ngr2}$-GFP (FIG. 6g) is likely to enhance the stem robustness conferred by mutant Rht alleles, thus further reducing lodging yield-loss. In conclusion, increased OsGRF4 abundance elevates the grain yields of rice and wheat GRVs grown at moderate levels of N fertilization.

DISCUSSION

We here report combined advances in fundamental plant science and strategic plant breeding. First, we show that the OsGRF4-DELLA interaction integrates regulation of plant growth and metabolism. OsGRF4 regulates N homeostasis via transcriptional regulation of multiple N uptake and assimilation genes, and is a N-regulated coordinator of plant N metabolism. Importantly, OsGRF4 also coordinates C metabolism and growth. Because OsGRF4 abundance is itself N-regulated, OsGRF4 integrates homeostatic control of N metabolism with control of growth and C metabolism. Although long thought to exist, the identities of such integrators were previously unknown. Finally, the antagonistic balance regulatory interaction between OsGRF4 and the DELLA growth repressor is a key aspect of the mechanism via which OsGRF4 coordinates plant growth and metabolism. Essentially, physical DELLA-OsGRF4-OsGIF1 interactions enable DELLA to inhibit OsGRF4-OsGIF1 activation of target gene promoters, and the balanced OsGRF4-DELLA antagonistic interaction thus integrates coordinated regulation of plant growth and metabolism.

Second, we show that increasing the abundance of OsGRF4 in GRVs alters the OsGRF4-DELLA balance, thus partially disconnecting the effects of DELLAs (see also ref. 30) on GRV growth and metabolism. In particular, increased OsGRF4 abundance increases GRV N assimilation and cell proliferation. The increased cell proliferation increases leaf and stem width, but has little effect on stem height. The practical plant breeding consequence of this is that it enables enhanced GRV nutrient assimilation without loss of the beneficial dwarfism conferred by DELLA accumulation. Improved GRV N use-efficiency can thus be achieved, without the yield-loss penalties of increased lodging. We conclude that genetic variation at OsGRF4 (and other cereal orthologues) should now become a major target for breeders in enhancing crop yield and nutrient use-efficiency. Such enhancements will enable future green revolutions, sustainably increasing yield, yet reducing environmentally degrading agricultural N use.

Methods

Plant Materials and Field Growth Conditions.

Details of rice germplasm used for positional cloning and haplotype analysis have been described elsewhere[28,21,31]. QTL analysis and map-based cloning were performed using a population derived from a cross between NM73 and the indica rice variety NJ6 (the recurrent parent). Near Isogenic Line (NIL) plants carrying differing combinations of the qngr2 and sd1 alleles were bred by crossing NM73×NJ6 and NM73×9311 $F_1$ six times with NJ6, NJ6-sd1 and 9311 as recurrent parents respectively. Field-grown NILs and transgenic rice plants were raised in standard paddy conditions with an interplant spacing of 20 cm at three Institute of Genetics and Developmental Biology experimental station sites located in Lingshui (Hainan Province), Hefei (Anhui Province) and Beijing. Field-grown wheat plants (Chinese wheat GRV KN199 and transgenic derivatives) were planted during the winter planting season at the Experimental Station of the Institute of Cereal and Oil Crops, Hebei Academy of Agriculture and Forestry Sciences (Shijiazhuang, Hebei province).

Hydroponic Culture Conditions.

Hydroponic culture conditions were modified from those of Liu (2004)[32]. Seeds were disinfected in 20% sodium hypochlorite solution for 30 min, thoroughly washed with deionized water, and then germinated in moist Perlite. 7-day-old seedlings were then selected and transplanted to PVC pots containing 40 L+N nutrient solution (1.25 mM $NH_4NO_3$, 0.5 mM $NaH_2PO_4 \cdot 2H_2O$, 0.75 mM $K_2SO_4$, 1 mM $CaCl_2$), 1.667 mM $MgSO_4 \cdot 7H_2O$, 40 μM Fe-EDTA (Na), 19 μM $H_3BO_3$, 9.1 μM $MnSO_4 \cdot H_2O$, 0.15 μM $ZnSO_4 \cdot 7H_2O$, 0.16 μM $CuSO_4$, and 0.52 μM $(NH_4)_3Mo_7O_{24} \cdot 4H_2O$, pH 5.5). The compositions of nutrient solutions containing different levels of supplied N were as follows: 1N, 1.25 mM $NH_4NO_3$; 0.6 N, 0.75 mM $NH_4NO_3$; 0.3N, 0.375 mM $NH_4NO_3$; 0.15N, 0.1875 mM $NH_4NO_3$. All nutrient solutions were changed twice per week, pH was adjusted to 5.5 every day. The temperature was maintained at 30° C. day and 22° C. night, and the relative humidity was 70%.

Positional Cloning of qNGR2.

The map-based cloning of qngr2 was based on 1,849 $BC_2F_2$ and 3,124 $BC_3F_2$ populations derived from a backcross between NM73 and the *indica* rice variety NJ6 (with NJ6 as the recurrent parent).

Transgene Constructs.

The OsGRF4$^{NGR2}$ protein-encoding sequence (together with intron sequences) was amplified from NJ6. The OsGRF4$^{ngr2}$ coding sequence (together with introns and promoter regions lying ~3-kbp upstream of the transcription start site) were amplified from NM73. These amplified fragments were then inserted into the pActin::nos[33] and pCAMBIA1300 (CAMBIA, www.cambia.org) vectors to respectively generate the pActin::OsGRF4$^{NGR2}$ and pOsGRF4$^{ngr2}$::OsGRF4$^{ngr2}$ constructs. A full-length OsGRF4$^{ngr2}$ cDNA was introduced into the p35S::GFP-nos and p35S::Flag-nos vectors[31] to respectively generate the p35S::OsGRF4$^{ngr2}$-GFP and p35S::flag-OsGRF4$^{ngr2}$ constructs. A 300-bp OsGRF4$^{ngr2}$ cDNA fragment was amplified and used to construct the pActin::RNAi-OsGRF4 transgene, as described elsewhere[29]. gRNA constructs required for construction of the CRISPR/Cas9-enabled OsGRF4 loss of function allele (osgrf4) in the WYJ7 genetic background were generated as described elsewhere[20,31]. Transgenic rice and wheat plants were generated by *Agrobacterium*-mediated transformation as described elsewhere[29].

Quantitative Real Time PCR (qRT-PCR) Analysis.

Total RNAs were extracted from different rice plant organs using the TRIzol reagent (Invitrogen), and then treated with RNase-free DNase I (Invitrogen) according to the manufacturer's protocol. Full-length cDNA was then reverse-transcribed using a cDNA synthesis kit (TRANSGEN, AE311). Subsequent qRT-PCR was performed according to the manufacturer's instructions (TRANSGEN, AQ101), using three independent RNA preparations as biological replicates. Rice Actin2 gene transcripts were used as a reference.

Bimolecular Fluorescence Complementation (BiFC) Assays.

The full-length cDNAs corresponding to the SLR1, OsGIF1, OsGIF2, OsGIF3, OsGRF1, OsGRF2, OsGRF3, OsGRF4, OsGRF5, OsGRF6, OsGFR7, OsGRF8, OsGRF9, OsGRF10, OsGRF11 and OsGRF12 genes, along with both deleted and non-deleted versions of an OsGRF4 cDNA were amplified from NJ6. The resultant amplicons were inserted into the pSY-735-35S-cYFP-HA or pSY-736-35S-nYFP-EE vectors[34] to generate fusion constructs. Co-transfection of constructs (e.g., those encoding nYFP-OsGRF4 and cYFP-SLR1) into tobacco leaf epidermal cells by *Agrobacterium*-mediated infiltration enabled testing for protein-protein interaction. Following a 48 h incubation in the dark, the YFP signal was examined and photographed using a confocal microscope (Zeiss LSM710). Each BiFC assay was repeated at least three times.

Co-Immunoprecipitation (Co-IP) Assays.

Full-length OsGRF4, OsGIF1 and SLR1 cDNAs were amplified, and then inserted into either the pUC-35S-HA-RBS or the pUC-35S-flag-RBS vector as previously described[35]. *A. thaliana* protoplasts were transfected with 100 μg of plasmid and then incubated overnight in low light intensity conditions. Total protein was then extracted from harvested protoplasts by treating with 50 mM HEPES (pH7.5), 150 mM KCl, 1 mM EDTA (pH8), 0.3% Triton-X 100, 1 mM DTT with added proteinase inhibitor cocktail (Roche LifeScience). Lysates were incubated with magnetic beads conjugated with an anti-DDDDK-tag antibody (MBL, M185-11) at 4° C. for at least 4 hours. The magnetic beads were then rinsed 6 times with the extraction buffer and eluted with 3×Flag peptide (Sigma-Aldrich, F4709). Immunoprecipitates were electrophoretically separated by SDS-PAGE and transferred to a nitrocellulose membrane (GE Healthcare). Proteins were detected by immunoblot using the antibodies anti-Flag (Sigma, F1804) and anti-HA (Santa Cruz Biotechnology, sc-7392).

EMSA Assays.

Full-length OsGRF4, OsGIF1 and SLR1 cDNAs were amplified and cloned into the pCold-TF vector (Takara). His, OsGRF4-His and SLR1-His fusion proteins were purified using Ni-NTA agarose (QIAGEN, 30210), following the manufacturer's instructions. 47 bp DNA probes were artificially amplified and labelled using a biotin label kit (Biosune). DNA gel shift assays were performed using the LightShift Chemiluminescent EMSA kit (Thermo Fisher Scientific, 20148).

ChIP-qPCR Assays.

~2 g of two-week-old seedlings of transgenic p35S::flag-OsGRF4$^{ngr2}$ rice plants were fixed with 1% formaldehyde under vacuum for 15 min at 20-25° C., and then homogenized in liquid nitrogen. Following isolation and lysing of nuclei, chromatin was isolated and ultrasonically fragmented into fragments of average size of ~500 bp. Immunoprecipitations were performed with anti-Flag antibodies (Sigma, F1804) overnight at 4° C. The reverse-crosslinked and precipitated DNA then served as template for quantitative RT-PCR.

FRET (Förster Resonance Energy Transfer) Assay.

Cauliflower mosaic virus 35S promoter-driven fusion constructs with C-terminal tagging CFP or YFP were created to generate the donor vector p35S::OsGIF1-CFP and the acceptor vector p35S::OsGRF4-YFP. Donor and acceptor vectors, with or without a p35S::SLR1 vector, were co-transformed into tobacco leaf epidermis cells by *Agrobacterium*-mediated infiltration to provide the FRET channel. Transformation with p35S::OsGIF1-CFP vector only provided the Donor channel, and with p35S::OsGRF4-YFP vector only the Accepter channel. The FRET signal was detected and photographed using a confocal microscope (Zeiss LSM710).

In Vitro Transient Transactivation Assays.

~3-kb DNA promoter fragments from each of OsAMT1.1, OsAMT1.2, OsGS1.2, OsGS2, OsNADH-GOGAT2, OsFd-GOGAT, OsCAB1, OsTPS1, OsSWEET11, OscycA1;1 or Oscdc2Os-3 were amplified from NJ6, and then subcloned into a pUC19 vector containing the firefly LUC reporter gene driven by the 35S minimal TATA box and 5×GAL4 binding elements, thus generating reporter plasmids containing specific promoters fused to LUC. The full-length OsGRF4 cDNA was amplified and fused to sequence encoding GAL4BD, thus generating the effector plasmid pRTBD-OsGRF4. Transient transactivation assays were performed using rice protoplasts as described elsewhere[36]. The Dual-Luciferase Reporter Assay System (Promega, E1960) was used to perform the luciferase activity assay, with the *Renilla* LUC gene as an internal control.

Determination of in Planta Mineral Nutrient Concentration.

Samples from various plant organs were dried in an oven at 80° C. for 72 hours. Following tissue homogenisation, C and N concentrations were determined using an elemental analyser (IsoPrime100; Elementar), the concentrations of P and S were determined using ICP-OES (Optima5300DV; Perkin Elmer), and the concentrations of K, Ca and Mg were determined with an atomic absorption spectrophotometer (AA-6800GF; Shimadzu). All experiments were conducted with at least three replicates.

$^{15}N$ Uptake Analysis.

Following growth in hydroponic culture for 4 weeks, rice root $^{15}NO_3^-$ and $^{15}NH_4^+$ influx measurements were as described elsewhere[37,38]. Roots and shoots were separated and stored at −70° C. before freeze drying. Roots and shoots were dried overnight at 80° C., and the $^{15}N$ content was measured using the Isoprime 100 (Elementar, Germany).

Determination of Glutamine Synthase and Nitrate Reductase Activities.

Glutamine synthase and nitrate reductase activities were respectively determined with the Glutamine Synthetase Kit (Solarbio LIFE SCIENCES, BC0910) and the Nitrate Reductase Kit (Solarbio LIFE SCIENCES, BC0080) following the manufacturer's instructions.

Method for the Design of Donor DNA Sequences for CRISPR
1. Select two target sequences at both ends of the template sequence.
2. Two sequences of about 100 bp are selected at both ends of the two target sequence to create a left arm and right arm.
3. Introducing mutant locus/loci into the template sequence, results in a repair template sequence for introduction of the correct SNPs.
4. Replacing the NGG to NXX (making sure that the amino acid sequence is not changed) of the target sequences, brings mutated target 1 and mutated target 2.
5. Adding the target sequences with NGG at both ends of the arms.
6. Using KpnI to connect the donor fragment to the construct pCXUN-cas9-U3-gDNA.
7. Using AarI to connect the target sequence 1 (without NGG) to the space between the U3 promoter and the gDNA.
8. Amplify U3, target sequence 2 (without NGG) and gDNA, then using AarI to connect them to the construct pCXUN-cas9-U3-gDNA.

REFERENCES

1, Pingali, P. L. Green Revolution: Impacts, limits, and the path ahead. *Proc. Natl Acad. Sci. USA* 109, 12302-12308 (2012).
2, Evenson, R. E. and Gollin, D. Assessing the impact of the green revolution, 1960 to 2000. *Science* 300, 758-762 (2003).
3, Hedden, P. The genes of the Green Revolution. *Trends Genet* 19, 5-9 (2003).
4, Peng, J. et al. Green revolution genes encode mutant gibberellin response modulators. *Nature* 400, 256-261 (1999).
5, Zhang, C., Gao, L., Sun, J., Jia, J and Ren, Z. Haplotype variation of Green Revolution gene Rht-D1 during wheat domestication and improvement. *J Integr Plant Biol.* 56, 774-780 (2014).
6, Sasaki, A. et al. Green revolution: a mutant gibberellin-synthesis gene in rice—new insight into the rice variant that helped avert famine over thirty years ago. *Nature* 416, 701-702 (2002).
7, Speilmeyer, W. et al. Semidwarf (sd-1), green revolution rice, contains a defective gibberellin 20-oxidase gene. *Proc. Natl Acad. Sci. USA* 99, 9043-9048 (2002).
8, Harberd, N. P., Belfield, E. and Yasumura, Y. The angiosperm gibberellin-GID1-DELLA growth regulatory mechanism: how an "inhibitor of an inhibitor" enables flexible response to fluctuating environments. *Plant Cell* 21, 1328-1339 (2009).
9, Xu, H., Liu, Q., Yao, T., Fu, X. Shedding light on integrative GA signaling. *Curr Opin Plant Biol.* 21, 89-95 (2014).
10, Itoh, H., Ueguchi-Tanaka, M., Sato, Y., Ashikari, M., Matsuoka, M. The gibberellin signaling pathway is regulated by the appearance and disappearance of SLENDER RICE1 in nuclei. *Plant Cell* 14, 57-70 (2002).
11, Asano, K. et al. Artificial selection for a green revolution gene during *japonica* rice domestication. *Proc Natl Acad Sci USA.* 108, 11034-11039 (2011).
12, Gooding, M. J., Addisu, M., Uppal, R. K., Snape, J. W. and Jones, H. E. Effect of wheat dwarfing genes on nitrogen-use efficiency. *J Agric Sci* 150, 3-22 (2012).
13, Li, B.-Z. et al. Molecular basis and regulation of ammonium transporter in rice. *Rice Science* 16, 314-322 (2009).
14, Hawkesford, M. J. Reducing the reliance on nitrogen fertilizer for wheat production. *J Cereal Sci* 59, 276-283 (2014).
15, Zhao, X. et al. Nitrogen runoff dominates water nitrogen pollution from rice-wheat rotation in the Taihu Lake region of China. *Agric Ecosyst Environ* 156, 1-11 (2012).
16, Conway, G. One Billion Hungry. Can We Feed the World? Cornell Univ. Press. USA (2012).
17, Che, R. et al. Control of grain size and rice yield by GL2-mediated brassinosteroid responses. *Nature Plants* 2, 15195 (2015).
18, Duan, P. et al. Regulation of OsGRF4 by OsmiR396 controls grain size and yield in rice. *Nature Plants* 2, 15203 (2015).
19, Hu, J. et al. A rare allele of GS2 enhances grain size and grain yield in rice. *Mol Plant* 8, 1455-1465 (2015).
20, Ma, X. et al. A robust CRISPR/Cas9 system for convenient, high-efficiency multiplex genome editing in monocot and dicot plants. *Mol Plant* 8, 1274-1284 (2015).
21, Sun, H. et al. Heterotrimeric G proteins regulate nitrogen-use efficiency in rice. *Nat Genet.* 46, 652-656 2014).
22, Somers, D. A., Kuo, T., Kleinhofs A., Warner R. L., Oaks A. Synthesis and degradation of barley nitrate reductase. *Plant Physiol.* 72, 949-952 (1983).
23, Tabuchi, M., Abiko, T., Yamaya, T. Assimilation of ammonium ions and reutilization of nitrogen in rice (*Oryza sativa* L.). *J Exp Bot.* 58, 2319-2327 (2007).
24, Peng, J. et al. The *Arabidopsis* GAI gene defines a signaling pathway that negatively regulates gibberellin responses. *Genes Dev.* 11, 3194-3205 (1997).
25, Nunes-Nesi, A., Fernie, A. R., Stitt, M. Metabolic signalling aspects underpinning plant carbon nitrogen interactions. *Mol. Plant* 3, 973-996 (2010).
26, Fabian, T., Lorbiecke, R., Umeda, M., Sauter, M. The cell cycle genes cycA1;1 and cdc2Os-3 are coordinately regulated by gibberellin in planta. *Planta* 211, 376-383 (2000).
27, Sauter, M. Differential expression of a CAK (cdc2-activating kinase)-like protein kinase, cyclins and cdc2 genes from rice during the cell cycle and in response to gibberellin. *Plant J.* 11, 181-190 (1997).
28, Yu, J. et al. OsLG3 contributing to rice grain length and yield was mined by Ho-LAMap. *BMC Biol.* 15, 28 (2017).

29, Huang, X. et al. Natural variation at the DEP1 locus enhances grain yield in rice. *Nat Genet.* 41, 494-497 2009).
30, Serrano-Mislata, A., Bencivenga, S., Bush, M., Schiessl, K., Boden, S., Sablowski, R. DELLA genes restrict inflorescence meristem function independently of plant height. *Nat. Plants* 3, 749-754 (2017).
31, Wang, S. et al. Non-canonical regulation of SPL transcription factors by a human OTUB1-like deubiquitinase defines a new plant type rice associated with higher grain yield. *Cell Res.* 27, 1142-1156 (2017).
32, Liu, W. J., Zhu, Y. G., Smith, F. A., Smith, S. E. Do phosphorus nutrition and iron plaque alter arsenate (As) uptake by rice seedlings in hydroponic culture? *New Phytol.* 162, 481-488 (2004).
33, Wang, S. et al. Control of grain size, shape and quality by OsSPL16 in rice. *Nat Genet* 44, 950-954 (2012).
34, Bracha-Drori, K. et al. Detection of protein-protein interactions in plants using bimolecular fluorescence complementation. *Plant J* 40, 419-427 (2004).
35, Chen, H. et al. Firefly luciferase complementation imaging assay for protein-protein interactions in plants. *Plant Physiol.* 146, 368-376 (2008).
36, Wang, S. et al. The OsSPL16-GW7 regulatory module determines grain shape and simultaneously improves rice yield and grain quality. *Nat. Genet.* 47, 949-954 (2015).
37, Ho, C. H., Lin, S. H., Hu, H. C., Tsay, Y. F. CHL1 functions as a nitrate sensor in plants. Cell 138, 1184-1194 (2009).
38, Loqué, D. et al. Additive contribution of AMT1;1 and AMT1;3 to high-affinity ammonium uptake across the plasma membrane of nitrogen-deficient *Arabidopsis* roots. *Plant J* 48, 522-534 (2006).
39, Sun. Y et al. Engineering Herbicide-Resistant Rice Plants through CRISPR/Cas9-mediated Homologous Recombination of Acetolactate Synthase. *Mol. Plant.* 628-630 (2016).
40, Nicole M. Gaudelli et al. Programmable base editing of A•T to G•C in genomic DNA without DNA cleavage; Nature volume 551, pages 464-471 (23 Nov. 2017).
41, Kim et al. Highly efficient RNA-guided Base Editing in Mouse Embryos; Nat Biotechnol. 2017 May; 35(5):435-437.
42, Tomas Cermak, Erin L. Doyle, Michelle Christian, Li Wang, Yong Zhang, Clarice Schmidt, Joshua A. Bailer, Nikunj V. Somia, Adam J. Bogdanove & Daniel F. Voytas. Efficient design and assembly of custom TALEN and other TAL-effector-based constructs for DNA targeting, Nucleic Acids Research 2011, 39(12).
43, Neville E Sanjana, Le Cong, Yang Zhou, Margaret M Cunniff, Guoping Feng & Feng Zhang A transcription activator-like effector toolbox for genome engineering, Nature Protocols 7, 171-192 (2012
44, Meghdad Randar, Moira A. McMahon; Thazha P. Prakash, Eric E. Swayze, C. Frank Bennett and Don W. Cleveland, Synthetic CRISPR RNA-Cas9-guided genome editing in human cells PNAS 2015 112 (51) E7110-E7117; published ahead of print Nov. 16, 2015, doi: 10.1073/pnas.1520883112

SEQUENCE LISTING

Rice

SEQ ID NO: 1 OsGRF $^{NGR2}$ (wild-type genomic sequence)

```
ATGACGATGCCGTATGCCTCCCTGTCTCCGGCGGTGGCCGACCACCGCTCGTCC
CCGGCAGCCGCGACCGCCTCCCTCCTCCCCTTCTGCCGCTCCACCCCGCTCTCC
GCGTAAGCAACGCGAACCCGCGGCTACAACCCATTTTCTTGGCTCCAGTGGTGCA
TGTGACAACACGGTGAGACGTTGTGTGTGGGTGGGTGGGTGCAGGGGCGGTGG
TGTTGTCGCGATGGGGGAGGACGCGCCGATGACCGCGAGGTGGCCGCCGGCGG
CGGCGGCGAGGCTGCCGCCGTTCACCGCGGCGCAGTACGAGGAGCTGGAGCAG
CAGGCGCTCATATACAAGTACCTGGTGGCAGGCGTGCCCGTCCCGCCGGATCTC
GTGCTCCCCATCCGCCGCGGACTCGACTCCCTCGCCGCCCGCTTCTACAACCAT
CCCGCCCGTACGTCGTGTTCCTATTTCTTGCCTCTCCTCTACCATCGCTGCATTGC
TTTTGGATGCTTGTTTAGTGTCGGCCTCTTTGTTTATTCCGATCAGGCGTACTTTG
CTTCCATTTGTTAATTGGCTCCGGGTCATTTGTTAATCCGGGTTACGCGATTCAAG
AAACATGCGTGTGGTTTTTATGCTATCCTCCGGATTTGGTTATAAAAAGGCTTGTTT
TTAAATCCAAAACTCGTGCTCGCTTCACGATTAGCGCATCATTTTTTTTTATGGGG
GGGGGGGGGGAGAGTTTGCCCATCATTCTGTCTCTGTTTGATCTGATAGAGGAC
GTGCACACGCTCTTGTCTGAAATAAAATCTTTTGTTTATCAGTATGCCCATGGGAT
AAGCCATTTTCTCTGTGAACCAACACCCTGGCAAACTGTTTTTTTGCTCGCCATTTT
TGAGCGATTGCTAAGAACAGATAACTATGCCCTGCATATGGATCGGATATGGACTT
CTCAAATATTCAAATGCCATTCTATTAGGAACTCAAAATGCATTACCAACAAATGCA
TTCTTGTGTGTAACACGGTTGCTACGATGTGCCTGTTTTTGTACAGTTGGATATGG
TCCGTACTTCGGCAAGAAGCTGGACCCAGAGCCAGGGCGGTGCCGGCGTACGG
ACGGCAAGAAATGGCGGTGCTCGAAGGAGGCCGCGCCGGATTCCAAGTACTGCG
AGCGCCACATGCACCGCGGCCGCAACCGTTCAAGAAAGCCTGTGGAAACGCAGC
TGGTCGCCCAGTCCCAACCGCCCTCATCTGTTGTCGGTTCTGCGGCGGCGCCCC
TTGCTGCTGCCTCCAATGGCAGCAGCTTCCAAAACCACTCTCTTTACCCTGCTATT
GCCGGCAGCAATGGCGGGGCGGGGGAGGAACATGCCCAGCTCATTTGGCTC
GGCGTTGGGTTCTCAGCTGCACATGGATAATGCTGCCCCTTATGCAGCTGTTGGT
GGTGGAACAGGCAAAGATCTCAGGTGATTGTTCATTTCTTTTTTTTTAATCAAACG
CCATATTTACTTGTTTAGCACTGTCTTGAATCATGATATGTATCCTTCCGTTGTCTA
AAAAAAAGGTGTCATGCTCTAACTGATTGGTGTCAGGTGGATGCAGTTATGAATCT
GTATTTTTCTTTGTGATCGGTTAATAACTGTGTCCCATTTGTTTGCATTGGTGGCAA
TCGAACCAGCTGTCCATGCTCAGTAGTACTACTTCGATTTGGTGCTGCAATCACTG
AAAGTCTGAAACTTTACTCTCTGCACTGCAAAAATTTGTGTTATGTTTAGGTTTCCA
GAGTGCTGCCTCTTTGCCCTTCCCATACTTTCTGGTATCAGTTTTCAGCCCCAGAA
GCCGGGGACAGTCTCCATAAGAGATTTCTGCTCAGGTGAAACTGGGGTGCAGGG
TCTTAACATGGCTTTGGCCCAGTAGTTTGAAACATGTACTGTCCATAAAGATGATA
CTACTACATATTTGTGTCTGCCCTCGCAGTGCTTGTGCCTGCTGGTAGCTGATCAT
```

SEQUENCE LISTING

```
GGCTTCCCTTGGCATTTACTCCACTTCTTTATTCCTCCACAGAATCCAGTTGTTTCT
GTCTCTGCTCTTCAGGGGCAGTCAATTATTTGGCCCTTGCAAAATACTATCTCTGA
AGATGTCTCACCGATCACCACTATACCTGAAACATTTTCCAGTGGCCAGCGTGAG
CTGCATGATGCTCCAAGTCAACTCTATACTCATCCAATGTTGATGATTAGATTTTAA
CAATGCAACTCTTTGATTTATCTTCCCTACAAAAAAAAAGGAACTCTTTGATTTATC
TTCGGTGAATCTCAGTCTGACCTTAGTACCTAGCCTCATTATTTACTTCACCAAATG
TATAACTCTACAGTGCTTGTTCGTGTTGATTTGGTTTAGTTTAGTTATTGAATTATTC
GGTCACCTTAGTCTTTGATTGTTTTTTTCTTTCTGCTCTTGTCATCAACTGTTTAGG
GTTCAGCTGACTTGCTGCTGCAACTAAACTGTCTTCTGGTTTTACTGCAAAATAGA
ATGTTTCTTGGGCCATGATCTGCTGCTATATATGATTAGTTAAACCATGGTTCTATG
TTTTCTTATATGAATTCATGACAAGAATACTAACTTTTGGAAAAGGTAATTTTATTTT
TTTTGTATGATAATAATGCTTTGGATTCTTTCTAGTTTATCTGTCGGACTTAGGTTA
ACTACATTTCCTCCGGTACATGGATTTATTTCATTCTTACAATTGAGCCCTTATGAA
TATTTTCTTCCTAATTCTGTTCTAAAAAGTTAGAATTGACATATTTTCGATAGGTACA
TGCCTAGCACTTGCATTCGTGTTTCCTACTAATTCCCAATCACTGTATCTTCTCAAA
TTCAGGTATACTGCTTATGGCACAAGATCTTTGGCGGATGAGCAGAGTCAACTCAT
TACTGAAGCTATCAACACATCTATTGAAAATCCATGGCGGCTGCTGCCATCTCAGA
ACTCGCCATTTCCCCTTTCAAGCTATTCTCAGCTTGGGGCACTAAGTGACCTTGGT
CAGAACACCCCCAGCTCACTTTCAAAGGTTCAGAGGCAGCCACTTTCGTTCTTTG
GGAACGACTATGCGGCTGTCGATTCTGTGAAGCAAGAGAACCAGACGCTGCGTC
CCTTCTTTGATGAGTGGCCAAAGGGAAGGGATTCATGGTCAGACCTCGCTGATGA
GAATGCTAATCTTTCGTCATTCTCAGGCACCCAACTGTCGATCTCCATACCAATGG
CATCCTCTGACTTCTCGGCGGCCAGTTCTCGATCAACTAATGGTACGACTACTTGA
TCTCCCCCCAATTACTTCGTGCGTGTTTATGTCTGTATCCTGCAATGTCTGAAGAT
TTCTTACTGAAAACGTCATCTGGTCTGTGTGCAGGTGACTGA

SEQ ID NO: 2 OsGRF NGR2 (wild-type CDS sequence)

ATGACGATGCCGTATGCCTCCCTGTCTCCGGCGGTGGCCGACCACCGCTCGTCC
CCGGCAGCCGCGACCGCCTCCCTCCTCCCCTTCTGCCGCTCCACCCCGCTCTCC
GCGGGCGGTGGTGTTGTCGCGATGGGGGAGGACGCGCCGATGACCGCGAGGTG
GCCGCCGGCGGCGGCGGCGAGGCTGCCGCCGTTCACCGCGGCGCAGTACGAG
GAGCTGGAGCAGCAGGCGCTCATATACAAGTACCTGGTGGCAGGCGTGCCCGTC
CCGCCGGATCTCGTGCTCCCCATCCGCCGCGGACTCGACTCCCTCGCCGCCCGC
TTCTACAACCATCCCGCCCTTGGATATGGTCCGTACTTCGGCAAGAAGCTGGACC
CAGAGCCAGGGCGGTGCCGGCGTACGGACGGCAAGAAATGGCGGTGCTCGAAG
GAGGCCGCGCCGGATTCCAAGTACTGCGAGCGCCACATGCACCGCGGCCGCAA
CCGTTCAAGAAAGCCTGTGGAAACGCAGCTGGTCGCCCAGTCCCAACCGCCCTC
ATCGTTGTCGGTTCTGCGGCGGCGCCCCTTGCTGCCTCCAATGGCAGCAG
CTTCCAAAACCACTCTCTTTACCCTGCTATTGCCGGCAGCAATGGCGGGGGCGG
GGGGAGGAACATGCCCAGCTCATTTGGCTCGGCGTTGGGTTCTCAGCTGCACAT
GGATAATGCTGCCCCTTATGCAGCTGTTGGTGGTGGAACAGGCAAAGATCTCAGG
TATACTGCTTATGGCACAAGATCTTTGGCGGATGAGCAGAGTCAACTCATTACTGA
AGCTATCAACACATCTATTGAAAATCCATGGCGGCTGCTGCCATCTCAGAACTCG
CCATTTCCCCTTTCAAGCTATTCTCAGCTGTGGGCACTAAGTGACCTTGGTCAGAA
CACCCCCAGCTCACTTTCAAAGGTTCAGAGGCAGCCACTTTCGTTCTTTGGGAAC
GACTATGCGGCTGTCGATTCTGTGAAGCAAGAGAACCAGACGCTGCGTCCCTTCT
TTGATGAGTGGCCAAAGGGAAGGGATTCATGGTCAGACCTCGCTGATGAGAATGC
TAATCTTTCGTCATTCTCAGGCACCCAACTGTCGATCTCCATACCAATGGCATCCT
CTGACTTCTCGGCGGCCAGTTCTCGATCAACTAATGGTGACTGA

SEQ ID NO: 3 OsGRF NGR2 (amino acid sequence)

MTMPYASLSPAVADHRSSPAAATASLLPFCRSTPLSAGGGVVAMGEDAPMTARWPP
AAAARLPPFTAAQYEELEQQALIYKYLVAGVPVPPDLVLPIRRGLDSLAARFYNHPALG
YGPYFGKKLDPEPGRCRRTDGKKWRCSKEAAPDSKYCERHMHRGRNRSRKPVETQ
LVAQSQPPSSVVGSAAAPLAAASNGSSFQNHSLYPAIAGSNGGGGRNMPSSFGSA
LGSQLHMDNAAPYAAVGGGTGKDLRYTAYGTRSLADEQSQLITEAINTSIENPWRLLP
SQNSPFPLSSYSQLWALSDLGQNTPSSLSKVQRQPLSFFGNDYAAVDSVKQENQTL
RPFFDEWPKGRDSWSDLADENANLSSFSGTQLSISIPMASSDFSAASSRSTNGD*

SEQ ID NO: 4 OsGRF ngr2 (genomic sequence)

ATGACGATGCCGTATGCCTCCCTGTCTCCGGCGGTGGCCGACCACCGCTCGTCC
CCGGCAGCCGCGACCGCCTCCCTCCTCCCCTTCTGCCGCTCCACCCCGCTCTCC
GCGTAAGCAACGCGAACCCGCGGCTACAACCCATTTTCTTGGCTCCAGTGGTGCA
TGTGACAACACGGTGAGACGTTGTGTGTGGGTGGGTGGGTGCAGGGGCGGTGG
TGTTGTCGCGATGGGGGAGGACGCGCCGATGACCGCGAGGTGGCCGCCGGCGG
CGGCGGCGAGGCTGCCGCCGTTCACCGCGGCGCAGTACGAGGAGCTGGAGCAG
CAGGCGCTCATATACAAGTACCTGGTGGCAGGCGTGCCCGTCCCGCCGGATCTC
GTGCTCCCCATCCGCCGCGGACTCGACTCCCTCGCCGCCCGCTTCTACAACCAT
CCCGCCCGTACGTCGTGTTCCTATTTCTTGCCTCTCCTCTACCATCGCTGCATTGC
TTTTGGATGCTTGTTTAGTGTCGGCCTCTTTGTTTATTCCGATCAGGCGTACTTTG
CTTCCATTTGTTAATTGGCTCCGGGTCATTTGTTAATCCGGGTTACGCGATTCAAG
AAACATGCGTGTGTGTTTTTATGCTATCCTCCGGATTTGGTTATAAAAGGCTTGTT
TTTAAATCCAAAACTCGTGCTCGCTTCACGATTAGCGCATCATTTTTTTTTTGTGGG
```

SEQUENCE LISTING

```
GGGGGGGGGGGGGGAGTTTGCCCATCATTCTGTCTCTGTTTGATCTGATAGAGG
ACGTGCACACGCTCTTGTCTGAAATAAAATCTTTTGTTTATCAGTATGCCCATGG
ATAAGCCATTTTCTCTGTGAACCAACACCCTGGCAAACTGTTTTTTTGCTCGCCAT
TTTTGAGCGATTGCTAAGAACAGATAACTATGCCCTGCATATGGATCGGATATGGA
CTTCTCAAATATTCAAATGCCATTCTATTAGGAACTCAAAATGCATTACCAACAAT
GCATTCTTGTGTGTAACACGGTTGCTACGATGTGCCTGTTTTTGTACAGTTGGATA
TGGTCCGTACTTCGGCAAGAAGCTGGACCCAGAGCCAGGGCGGTGCCGGCGTA
CGGACGGCAAGAAATGGCGGTGCTCGAAGGAGGCCGCGCCGGATTCCAAGTACT
GCGAGCGCCACATGCACCGCGGCCGCAACCGTAAAAGAAAGCCTGTGGAAACGC
AGCTGGTCGCCCAGTCCCAACCGCCCTCATCTGTTGTCGGTTCTGCGGCGGCGC
CCCTTGCTGCTGCCTCCAATGGCAGCAGCTTCCAAAACCACTCTCTTTACCCTGC
TATTGCCGGCAGCAATGGCGGGGGCGGGGGAGGAACATGCCCAGCTCATTTG
GCTCGGCGTTGGGTTCTCAGCTGCACATGGATAATGCTGCCCCTTATGCAGCTGT
TGGTGGTGGAACAGGCAAAGATCTCAGGTGATTGTTCATTTCTTTTTTTTTAATCAA
ACGCCATATTTACTTGTTTAGCACTGTCTTGAATCATGATATGTATCCTTCCGTTGT
CTAAAAAAAAGGTGTCATGCTCTAACTGATTGGTGTCAGGTGGATGCAGTTATGAA
TCTGTATTTTTCTTTGTGATCGGTTAATAACTGTGTCCCATTTGTTTGCATTGGTGG
CAATCGAACCAGCTGTCCACGCTCAGTAGTACTACTTCGATTTGGTGCTGCAATCA
CTGAAAGTCTGAAACTTTACTCTCTGCACTGCAAAAATTTGTGTTATGTTTAGGTTT
CCAGAGTGCTGCCTCTTTGCCCTTCCCATACTTTCTGGTATCAGTTTTCAGCCCCA
GAAGCCGGGACAGTCTCCATAAGAGATTTCTGCTCAGGTGAAACTGGGGTGCA
GGGTCTTAACATGGCTTTGGCCCAGTAGTTTGAAACATGTACTGTCCATAAAGATG
ATACTACTACATATTTGTGTCTGCCCTCGCAGTGCTTGTGCCTGCTGGTAGCTGAT
CATGGCTTCCCTTGGCATTTACTCCACTTCTTTATTCCTCCACAGAATCCAGTTGTT
TCTGTCTCTGCTCTTCAGGGGCAGTCAATTATTTGGCCCTTGCAAAATACTATCTC
TGAAGATGTCTCACCGATCACCACTATACCTGAAACATTTTCAGTGGCCAGCGT
GAGCTGCATGATGCTCCAAGTCAACTCTATACTCATCCAATGTTGATGATTAGATT
TTAACAATGCAACTCTTTGATTTATCTTCCCTACAAAAAAAAAGGAACTCTTTGATT
TATCTTCGGTGAATCTCAGTCTGACCTTAGTACCTAGCCTCATTATTTACTTCACCA
AATGTATAACTCTACAGTGCTTGTTCGTGTTGATTTGGTTTAGTTTAGTTATTGAAT
TATTCGGTCACCTTAGTCTTTGATTGTTTTTTCTTTCTGCTCTTGTCATCAACTGTT
TAGGGTTCAGCTGACTTGCTGCTGCAACTAAACTGTCTTCTGGTTTTACTGCAAAA
TAGAATGTTTCTTGGGCCATGATCTGCTGCTATATATGATTAGTTAAACCATGGTTC
TATGTTTTCTTATATGAATTCATGACAAGAATACTAACTTTTGGAAAAGGTAATTTTA
TTTTTTTTGTATGATAATAATGCTTTGGATTCTTTCTAGTTTATCTGTCGGACTTAGG
TTAACTACATTTCCTCCGGTACATGGATTTATTTCATTCTTACAATTGAGCCCTTAT
GAATATTTTCTTCCTAATTCTGTTCTAAAAAGTTAGAATTGACATATTTTCGATAGGT
ACATGCCTAGCACTTGCATTCGTGTTTCCTACTAATTCCCAATCACTGTATCTTCTC
AAATTCAGGTATACTGCTTATGGCACAAGATCTTTGGCGGATGAGCAGAGTCAACT
CATTACTGAAGCTATCAACACATCTATTGAAAATCCATGGCGGCTGCTGCCATCTC
AGAACTCGCCATTTCCCCTTTCAAGCTATTCTCAGCTTGGGGCACTAAGTGACCTT
GGTCAGAACACCCCCAGCTCACTTTCAAAGGTTCAGAGGCAGCCACTTTCGTTCT
TTGGGAACGACTATGCGGCTGTCGATTCTGTGAAGCAAGAGAACCAGACGCTGC
GTCCCTTCTTTGATGAGTGGCCAAAGGGAAGGGATTCATGGTCAGACCTCGCTGA
TGAGAATGCTAATCTTTCGTCATTCTCAGGCACCCAACTGTCGATCTCCATACCAA
TGGCATCCTCTGACTTCTCGGCGGCCAGTTCTCGATCAACTAATGGTACGACTAC
TTGATCTCCCCCCAATTACTTCGTGCGTGTTTATGTCTGTATCCTGCAATGTCTGA
AGATTTCTTACTGAAACGTCATCTGGTCTGTGTGCAGGTGACTGA
```

SEQ ID NO: 5 OsGRF $^{ngr2}$ (CDS sequence)

```
ATGACGATGCCGTATGCCTCCCTGTCTCCGGCGGTGGCCGACCACCGCTCGTCC
CCGGCAGCCGCGACCGCCTCCCTCCTCCCCTTCTGCCGCTCCACCCCGCTCTCC
GCGGGCGGTGGTGTTGTCGCGATGGGGAGGACGCGCCGATGACCGCGAGGTG
GCCGCCGGCGGCGGCGAGGCTGCCGCCGTTCACCGCGGCGCAGTACGAG
GAGCTGGAGCAGCAGGCGCTCATATACAAGTACCTGGTGGCAGGCGTGCCCGTC
CCGCCGGATCTCGTGCTCCCCATCCGCCGCGGACTCGACTCCCTCGCCGCCGC
TTCTACAACCATCCCGCCCTTGGATATGGTCCGTACTTCGGCAAGAAGCTGGACC
CAGAGCCAGGGCGGTGCCGGCGTACGACGGCAAGAAATGGCGGTGCTCGAAG
GAGGCCGCGCCGGATTCCAAGTACTGCGAGCGCCACATGCACCGCGGCCGCAA
CCGTAAAAGAAAGCCTGTGGAAACGCAGCTGGTCGCCCAGTCCCAACCGCCCTC
ATCTGTTGTCGGTTCTGCGGCGGCGCCCCTTGCTGCTGCCTCCAATGGCAGCAG
CTTCCAAAACCACTCTCTTTACCCTGCTATTGCCGGCAGCAATGGCGGGGGCGG
GGGGAGGAACATGCCCAGCTCATTTGGCTCGGCGTTGGGTTCTCAGCTGCACAT
GGATAATGCTGCCCCTTATGCAGCTGTTGGTGGTGGAACAGGCAAAGATCTCAGG
TATACTGCTTATGGCACAAGATCTTTGGCGGATGAGCAGAGTCAACTCATTACTGA
AGCTATCAACACATCTATTGAAAATCCATGGCGGCTGCTGCCATCTCAGAACTCG
CCATTTCCCCTTTCAAGCTATTCTCAGCTGTGGGCACTAAGTGACCTTGGTCAGAA
CACCCCCAGCTCACTTTCAAAGGTTCAGAGGCAGCCACTTTCGTTCTTTGGGAAC
GACTATGCGGCTGTCGATTCTGTGAAGCAAGAGAACCAGACGCTGCGTCCCTTCT
TTGATGAGTGGCCAAAGGGAAGGGATTCATGGTCAGACCTCGCTGATGAGAATGC
TAATCTTTCGTCATTCTCAGGCACCCAACTGTCGATCTCCATACCAATGGCATCCT
CTGACTTCTCGGCGGCCAGTTCTCGATCAACTAATGGTGACTGA
```

SEQUENCE LISTING

SEQ ID NO: 6 OsGRF $^{ngr2}$ (amino acid sequence)

MTMPYASLSPAVADHRSSPAAATASLLPFCRSTPLSAGGGVVAMGEDAPMTARWPP
AAAARLPPFTAAQYEELEQQALIYKYLVAGVPVPPDLVLPIRRGLDSLAARFYNHPALG
YGPYFGKKLDPEPGRCRRTDGKKWRCSKEAAPDSKYCERHMHRGRNRKRKPVETQ
LVAQSQPPSSVVGSAAAPLAAASNGSSFQNHSLYPAIAGSNGGGGRNMPSSFGSA
LGSQLHMDNAAPYAAVGGGTGKDLRYTAYGTRSLADEQSQLITEAINTSIENPWRLLP
SQNSPFPLSSYSQLWALSDLGQNTPSSLSKVQRQPLSFFGNDYAAVDSVKQENQTL
RPFFDEWPKGRDSWSDLADENANLSSFSGTQLSISIPMASSDFSAASSRSTNGD*

SEQ ID NO: 7: OsGRF haplotype A promoter

TATCGATGGCAACAGTGCATGAGCATATATTTATTTCATTGACCTACGGTTGCATG
TCTTCGATCTCTATGGAGTAGTACCGAGGCTAAGTTTAGTTTCAAACTTTTCCTTCA
AACTTACAGCTTTTTTATCACATTAAAACTTTCCTACATACAAACTTTCAACTTTTCC
ATCACATCTTTTAATTTCAACCAAACTTCTAATTTTAACGTGAACTAAAAACACCCT
GAATTCAAAACTCTTTTTATTTTCCTTCAAGATGTCCGATGCACACGCTCTATGTAG
ACGCAAGAAGATGTTGGAGCAGCAGACTAACAGTAGCAAAAAAATGGCAGGTCGA
AAAGCAACTGCGACGGTTGCTCCGTCATCCTCTCATCGCCTTTTTATTGCTCCGG
CGTTGGGAACCGCAACAATGGAACAGCCCAAATCGACAGTCCCCTCCCCCCCCC
TCCCCCATCCTCTCTCCCCACGCAATACTTGTCACTACTCGCGCTGCTCACTAC
AGCGTCTCTGCATGTATATCCATCTATCCATCCATTCCCCCATTTTCCAAATAAAAA
TACAGCAAACCAAACACAAACGCAGCCTCGCACTGTACTCGAAGAAAAATCGGTG
CTGTACGTACTACGCCACGAGATAACGAGAGAGAGAGAGAGAGAGAGAGAGAGA
GAGGAGAAAATGGAAATGCTTCTGCTCGTACCACGCCGCTACGTCCGCTAGGTC
GACAGGCCCGGGCGGAGGCAGGTGTTTGTCGTCTAGCTCGGGTCGGAGCGCGC
CTTCTCGTGTCGGGCTCGACGTCCGCGACTCCTCGCCCCTGGTCGAGAGCTCGC
AGGCGCAGCGGAGAGAGAGAGAGAGAGAGAGAGAGAGAGAGACAAGCCGCGCAA
TAAAGGCGCGCGCGAGCGAGCGAAGCAAAGCACCATTACTAAAGACCGCGGC
GTGTGCTTGCGTTGCGAGCGAGCGAGAGCGAGAGAGAGATTGAGAGAGAGAGA
GGGAAGGG (the -941, -884, -855, -847, -801, -522 and -157 SNPs
are highlighted in bold)

SEQ ID NO: 8: OsGRF haplotype C promoter

CTAAATTATCGATGGCAACAGTGCATGAGCATATATTTATTTCATTGACCTACGGTT
GCATGTCTTCGATCTCTATGGAGTAGTACCGAGGCTAAGTTTAGTTTCAAACTTTT
CCTTCAAACTTACAGCTTTTTTATCACATTAAAACTTTCCTACATACAAACTTTCAAC
TTTTCCATCACATCTTTCAATTTCAACCAAACTTCTAATTTTAGCGTGAACTAAACA
CACCCTGAATTCAAAACTCTTTTTATTTTCCTTCAAGATGTCCGATGCACACGCTCT
ATGTAGACGCAAGAAGATGTTGGAGCAGCAGACTAACAGTAGCAAAAAAATGGCA
GGTCGAAAAGCAACTGCGACGGTTGCTCCGTCATCCTCTCATCGCCTTTTTATTG
CTCCGGCGTTGGGAACCGCAACAATGGAACAGCCCAAATCGACAGTCCCCTCCA
CCCCCCTCCCCCATCCTCTCTCCCCCACGCAATACTTGTCACTACTCGCGCTGC
CCACTACAGCGTCTCTGCATGTATATCCATCTATCCATCCATTCCCCCATTTTCCA
AATAAAAATACAGCAAACCAAACACAAACGCAGCCTCGCACTGTACTCGAAGAAAA
ATCGGTGCTGTACGTACTACGCCACGAGATAACGAGAGAGAGAGAGAGAGAGAG
AGAGGAGAAAATGGAAATGCTACTGCTCGTACCACGCCGCTACGTCCGCTAGGTC
GACAGGCCCGGGGGAGGCAGGTGTTTGTCGTCTAGCTCGGGTCGGAGCGCGC
CTTCTCGTGTCGGGCTCGACGTCCGCGACTCCTCGCCCCTGGTCGAGAGCTCGC
AGGCGCAGCGGAGAGAGAGAGAGAGAGAGAGAGAGAGAGAGACAAGCCGCGCAA
TAAAGGCGCGCGCGAGCGAGCGAAGCAAAGCACCATTACTAAAGACCGCGGC
GTGTGCTTGCGTTGCGAGCGAGCGAGAGCGAGAGAGAGATTGAGAGAGAGAGA
GGGAAGGG (the -935, -878, -849, -841, -795, -516 and -157 SNPs
are highlighted in bold)

SEQ ID NO: 9: OsGRF haplotype B promoter

TATCGATGGCAACAGTGCATGAGCATATATTTATTTCATTGACCTACGGTTGCATG
TCTCCGATCTCTATGGAGTAGTACCGAGGCTAAGTTTAGTTTCAAACTTTTCCTTC
AAACATACAGCTTTTTTATCACATTAAAACTTTCCTACATATAAACTTTTAACTTTTC
CATCACATCTTTCAATTTCAACCAAACTTTTAATTTTAACGTGAACTAAACACACCC
TGAATTCAAAACTCTTTTTATTTTCCTTCAAGATGTCCGATGCACACGCTCTATGTA
GACGCAAGAAGATGTTGGAGCAGCAGACTAACAGTAGCAAAAAAATGGCAGGTC
GAAAAGCAACTGCGACGGTTGCTCCGTCATCCTCTCATCGCCTTTTTATTGCTCCG
GCGTTGGGAACCGCAACAATGGAACAGCCCAAATCGACAGTCCCCTCC-
CCCCCCTCCCCCATCCTCTCTCCCCACGCAATACTTGTCACTACTCGCGCTGC
TCACTACAGCGTCTCTGCATGTATATCCATCTATCCATCCATTCCCCCATTTTCCAA
ATAAAAATACAGCAAACCAAACACAAACGCAGCCTCGCACTGTACTCGAAGAAAAA
TCGGTGCTGTACGTACTACGCCACGAGATAACGAGAGAGAGAGAGAGAGAGA
GAGAGAGGAGAAAATGGAAATGCTACTGCTCGTACCACGCCGCTACGTCCGC

SEQUENCE LISTING

```
TAGGTCGACAGGCCCGGGGGGAGGCAGGTGTTTGTCGTCTAGCTCGGGTCGGA
GCGCGCCTTCTCGTGTCGGGCTCGACGTCCGCGACTCCTCGCCCCTGGTCGAGA
GCTCGCAGGCGCAGCGGGAGAGAGAGAGAGAGAGAGAGAGAGAGAGACAAGCC
GCGCAATAAAGGCGCGCGCGAGCGAGCGAAGCAAAGCACCATTACTAAAGAC
CGCGGCGTGTGCTTGCGTTGCGAGCGAGCGAGAGCGAGAGAGAGATTGAGAGA
GAGAGAGGGAAGGG
```

(the -941, -884, -855, -847, -801, -522 and -157 SNPs
are highlighted in bold)

Orthologue sequences

Zea Mays

SEQ ID NO: 10: RMZM2G034876 (GRF-transcription factor 6);
2 kb promoter

```
TTCTAGTGTTTCAACGGAAGCCTAAGTTTCGATGGGAAGAAAGGACATGTACTAG
CAAGGAACCAAACTCCACGCATCATTCTTGCCTAGCCTTGCTTTATCGTGGCTACC
TTGGACCAACAAAAGAACCAAGCAGCCCCAATGTATCTGATATGGAGCTAAAAATA
CAACCAACTCATATTATACGTTGGATGTTTTGACTGCACTTGAGATGTTGTAAGAC
TTTCGGTACGCTATACATATAGAGTTAATATACAGTTGAAGACTGCTGCAGCGGT
CAACTGTCTGATCTACTGTAAACTCTATGAGGAAATCGGAAACGCTACTTCCAGAG
TAGTGTAACTCCGACTGGAAAACTGTTGCAGAATACGGATAGCCTGATCAGTTAG
ACTGTCGGCTGCGGAGTTCAACTGTTGCAGAGTTAGAAAGAAATGATAAATATAT
AGTAGTTAGTATAGAGTTGATATATAGAGTAAACATGACTGTAGAGGATTGTAGTA
TAGGGTAGATAGTTTTGCTGACCAGGACAAGATATTCCTTTTAGAGTATGAATTTA
GAGTAGTATGAGTGCGGATAGCCTAACTTTGTAAGTATTTTTAAAGCTTACTTTGC
ATACGGTCTTTGTGATCTACATCTTTACTATGGCTATTTCATGATAATAACTAGATG
AGATATATGACCAATCGAGTTGTACATATATGTTTGGGTTTTAATTAAGGGCATAGT
TAAAAGCACTGAGCTTTTAAGAAAACGATGTGGTTCTAAATATGGCAGTTTATGCT
TTGGTTTCTAGAAACTGAATTTCTAGCATATTTCCGTACTATTCTTAGTTGGTTTGG
ATAGAAACTACGACGATTATCACCGCTCTGAGGCCTAATGGCCTATGCACTTGATT
CTCTCCATGCCCACTCTGCCCTGTTCAAATGTTTAATTAATATTTAATTTAATAATTT
TGAATTCAAGAATACGAGTTCAAGGTATATTTAAAATTGACATCAAAGAGAAATGAA
ATTAAAGCAATGATAGACTTGTCTTTGGGTGTGAAAAAAAGCTAGAAACTTATTTAT
AAAAACCCAATTCTAAACATGTATACCTAATTTTTATTATAAATCGGTTTTTAGATAG
AATCGTAAAGCCCTTGATCAGAGCATCCAACGAGCCATGAGGCCATGACGGAAGA
GCGGAAGTGCAGACGGCAACGGCGTTCCGCTTCATGCCGCACCCTCCAGTGTCC
TGTGGCCTTTAAGTGCCGGCCTTGGGAACCGCGACGCAGACACAGCCCAAATCC
GCAGTCACTCCTCCAACACGATGCTTGTCACCACCCTTGCTACAGTGCCTGCATC
CATATCCACTCCGCTCGCGCAAAAAATATCCGAGTCGGAAACAAACAAAGCAGCA
TAGGAAACAGAAGAAAGCTGTACTAGTACGTGAGGACGAGGAGGGAGAGAGAGC
AATACACAGAAGCCTGCTACCGTGCTACGGACTACCACAACGCCAGAGGGACAA
CCGGACAGAGGGGGAGGCAGGCCTCGCTTGTCATCTAGCTAGGTCAGCCGGGG
ACGGGGTCGGAGCAGTAGAGCTAAAGCCAGAGGCCAGGCTCGTAGTAGTACGTA
GTAGTAGTGCCCTCCTCGTGTCATTTGGCCAGCCTTGTCCAGACGACCACACACA
CCAGATTACGCTTAACATTCTGTTTGACATCTAAAACCAGCCGGCTTGATCCAAAT
GCCTCCCTAGGTAGTAGCTTAGTCTTGCTCGCCGCCTCTCCGGGAGACGACGAC
ACGCCTGATGAGTGCCTGACGTTCCAGCGCGAGGCAGACAGCGACGCAGAGAGA
GACAAAGCGGGCAATAAAGGCAGCCGCGCGCGAGCGAGGGAAGGGAGCGAAGC
AAAGCACATCACGAGCCCAGCCTGCGCCTGCGGAGGGAGGGGGCTCATTAAAGA
GGGGGCGCGAGCGCGACCGGCCGCGGGGAGCAAGCAGCGCGCGAGAGAGACA
GGTTGAG
```

SEQ ID NO: 11: CDS

```
ATGGCGATGCCGTATGCCTCTCTTTCCCCGGCAGGCGCCGCCGACCACCGCTCC
TCCACAGCCACGGCGTCCCTCGTCCCCTTCTGCCGCTCCACTCCGCTCTCCGCG
GGCGGCGGGCTGGGCGAGGAGGACGCCCAGGCGAGCGCGAGGTGGCCGGCCG
CGAGGCCGGTGGTGCCGTTCACGCCGGCGCAGTACCAGGAGCTGGAGCAGCAG
GCGCTCATATACAAGTACCTGGTGGCGGGCGTGCCCGTTCCGCCGGATCTCGTG
GTTCCAATCCGCCGCGCCTCGACTCCCTCGCAACCCGCTTCTACGGCCAACCC
ACACTCGGGTACGGACCGTACCTGGGGAGGAAACTGGATCCGGAGCCCGGCCG
GTGCCGGCGAACGGACGGCAAGAAGTGGCGGTGCTCCAAGGAGGCGCCCCCGG
ACTCCAAGTACTGCGAGCGCCACATGCACCGCGGCCGAACCGTTCAAGAAAGC
CTGTGGAAACGCAGCTCGCGCCCCAGTCCCAACCGCCCGCCGCCGCAGCCGTC
TCCGCCGCTCCGCCCCTGGCAGCCGCCGCCGCCGCCACCACCAACGGCAGCGG
CTTCCAGAACCACTCTCTCTACCCGGCCATCGCCGGCAGCACTGGTGGTGGAGG
AGGAGTTGGCGGGTCCGGCAATATCTCCTCCCCGTTCTCCTCGTCTGATGGGGGG
ATCGTCTCAGCTGCACATGGACAGTGCTGCCAGCTACTCCTACGCAGCTCTTGGT
GGTGGAACTGCAAAGGATCTCAGGTACAACGCTTACGGAATAAGATCTCTGGCGG
ACGAGCACAACCAGCTGATCGCAGAAGCCATCGACTCGTCGATAGAGAGCCAGT
GGCGCCTCCCCAGCTCGTCGTTCCCGCTCTCGAGCTACCCACATCTCGGGGCGC
TGGGCGACCTGGGCGGCCAGAACAGCACGGTGAGCTCGCTGCCGAAGATGGAG
AAGCAGCAGCCGCCCTCGTCCTTCCTAGGGAACGACACCGGGGCCGGCATGGC
```

SEQUENCE LISTING

CATGGGCTCCGCCTCCGCGAAGCAGGAGGGCCAGACGCTGCGGCACTTCTTCGA
CGAGTGGCCCAAGGCGCGGGACTCCTGGCCGGGCCTCTCCGACGAGACCGCCA
GCCTCGCCTCGTTCCCCCCGGCGACCCAGCTGTCGATGTCCATACCCATGGCGT
CCTCCGACTTCTCCGTGGCCAGCTCCCAGTCGCCCAACGATGACTAA (miR396 recognition site is highlighted in bold)

SEQ ID NO: 12: amino acid sequence

MAMPYASLSPAGAADHRSSTATASLVPFCRSTPLSAGGGLGEEDAQASARWPAA
RPVVPFTPAQYQELEQQALIYKYLVAGVPVPPDLVVPIRRGLDSLATRFYGQPT
LGYGPYLGRKLDPEPGRCRRTDGKKWRCSKEAAPDSKYCERHMHRGRNRSRKPV
ETQLAPQSQPPAAAAVSAAPPLAAAAATTNGSGFQNHSLYPAIAGSTGGGGGV
GGSGNISSPFSSSMGGSSQLHMDSAASYSYAALGGGTAKDLRYNAYGIRSLADE
HNQLIAEAIDSSIESQWRLPSSSFPLSSYPHLGALGDLGGQNSTVSSLPKMEKQ
QPPSSFLGNDTGAGMAMGSASAKQEGQTLRHFFDEWPKARDSWPGLSDETASLA
SFPPATQLSMSIPMASSDFSVASSQSPNDD*

SEQ ID NO: 13 GRMZM2G041223 (GRF-transcription factor 8);
2 kb promoter

AAACAAATACTTATCGTTAATAAACATGACATATGATCTGATGCATAAATTTGT
ATTTTTATTTTTAACATTGATTTTTTAAAGATTCCCAAAAGATAAACATCAAAT
TTATCATATAATTCCTCAAATGATACATATAAAATTTGAATACGAATATATTTT
TACTTTGTTTATTACTGGGAGTAAATATTGTATAAAAAATATGCAAAATTTATT
CTTATTTATAGTAATATGCAAATAATGTATAAATAGTCCATGCTCATAAATTTT
ATTAGTAGCCCGCAACCCAGGCGACCGCGAACAGTGCCAAGCCGAGCGGGGTG
TGCATGTTGGAGATGGAGAGAGAGAGAGAGAGCCCGAAAAATATCGCTGATGAC
TCGACGAGATAGAGGAGGGAGGGAGGGAGGCGCAGTAGGACAGGGCTGCA
GGCAGGTGCTTGTCCTTAGCTGGAACCCTCCCGTGTCGGCCTCATCCCACCGCC
CCGCCCTGCCGTCCTGCCCTGCGCGGCTGCGGTCGCCTATAAGGCTAGCCCAGG
CCATTTGCCCTTTGCCCCCGTCCGTCCGTCCCTCACCTCACCTCACCTCACCTC
GGCCCGCCTCCCTCATCAGGTAGCCGTAGCGAGCAGTATAGCACGCACAGCCGC
CGCCCTGCCCTGCCCTGCCCTGCTCGGCGTAGGCACAGGCACAGCCCAGAGCGA
GCGAGACAGAGGGAAAGAGACAGAGCCAGCCAGGTAAAAGGCAAAAGCACAGCA
CATTAAAAGAGAGGCCGGAAGCAGCGGCAGAGCGGAGAGAGAGAGAGAACTAGA
AGCATATATGGCGATGCCCTTTGCCTCCCTGTCTCCGGCAGCCGACCACCGCCC
CTCCTCCCTCCTCCCCTACTGCCGCGCCGCCCCTCTCTCCGCGTAAGCCACCTC
CCTTTCGCCCGTCCGGGAAAAAACCCTCTTCTTCGCTCGGTTTATGCCACCCGG
AGCCGTGCTGCAGCCTGCAGGTATCTGATGCCGCGAGCTTTGCCTTGCAGGGTG
GGAGAGGACGCCGCCGCGCAGGCGCAACAGCAGCAGCAGCACGCTATGAGCGGC
AGGTGGGCAGCGAGGCCGCCGGCGCTCTTCACCGCGCGCAGTACGAGGAGCTG
GAGCACCAGGCGCTTATATACAAGTACCTCGTCGCCGGCGTGCCCGTCCCGCCG
GACCTCCTCCTCCCCCTACGCCGAGGCTTCGTCTACCACCAACCCGCCCGTAAG
CAAGCACGGCCCCCGCGCCGCCTCCGCACCCCTTCACACTCACACGCACGTTTA
ACCGCTTTTGCACTGCACAACCCCGGCCGCCCGGCGGCGGCGTCCGTGCCTTGA
TCTGGTTGTTTACTCGGATCGAGGGATTCAGATGTCCTCTCCGTCCGTTTGTTA
ATCGGCTCCGGTCATTTCTTAATCTCGTCCTGGATTCGGTCACGAAAAGCTAGA
GGTCAAGATTTTGCTCTCGATTACTATATCCTTGCCTCATGTTCTAATGGAGTT
TATTTTATTGGTCTGATGTGATTAGATAGGATGCTAGCCAGGCTTGTCTCCGGC
CAAAAGCGGCGGTTTAGTTTATTGATGATTGCTTCTTTCCTTGGGGGATTTATT
CCTGTCTGGTTGTTGGGAGCCTAACCACGCTCCTATTGCTGCTGCGGTTTACTA
ACCATCTGCGCCAGTACACCTACTCCATGGACCCCAAAATACAGTTCTTCCAAC
CATTCCCCCCTCCATCTGCTTTCTCGCGGGCAAATAAAAACGTGTAGAACGAC
GGTGTAGTAGGCAGATCTACTCCTTGTGCCGCTACGCTAGCCCGCTACCGAAGA
TCGGGCCCGTTTCAACCGGTTCGTTGGTCTGAGCGGAGCTAAGATGGGGCGCAT
TTCATTTTTTGGTCCTTTCGTCTGATTGGAGAAGTGCCCATTCCGGTATCGCTC
CCCGGCCTCCAAATACGCACCGACACAGAACGTGTTCGTACGCACGTACACATG
GT

SEQ ID NO: 14: CDS

ATGCGCACCGTGCTGCTGGCCATAGCCGTTGACTCACCGGGATTCACTCCTCTCT
CGCGTGTGTGTGTGTGGCTTCCTTGCAGTTGGGTACGGGCCCTACTTCGGCAAG
AAGGTGGACCCGGAGCCCGGGCGGTGCCGGCGTACGGACGGCAAGAAGTGGC
GGTGCTCCAAGGAGGCCGCCCCGGACTCCAAGTACTGCGAGCGCCACATGCACC
GCGGCCGCAACCGTTCAAGAAAGCCTGTGGAAGCGCAGCTCGTGCCCCCGCCG
CACGCCCAGCAGCAGCAGCAGCAGGCCCCCGCGCCCACCGCTGGCTTCCA
GAGCCACCCCATGTACCCATCCATCCTCGCCGGCAACGGCGGCGGCGGCGGCG
GGGTAGGTGGTGGTGCTGGTGGCGGTGGCACGTTCGGCCTGGGGCCCACCTCT
CAGCTGCACATGGACAGTGCCGCTGCTTACGCGACTGCTGCTGGTGGTGGAGGGAGC
AAAGATCTCAGGTACTCTGCCTACGGGGTGAAGTCTCTGTCGGACGAGCACAGC
CAGCTCTTGTCCGGCGGCGGCGGCATGGACGCGTCAATGGACAACTCGTGGCG
CCTGTTGCCGTCCCAAACCGCCGCCACGTTCCAGGCCACAAGCTACCCTCTGTTC
GGCGCGCTGAGCGGTCTGGACGAGAGCACCATCGCCTCGCTGCCCAAGACGCA
GAGGGAGCCCCTCTCCTTCTTCGGGAGCGACTTCGTGACCCCGAAGCAGGAGAA

```
CCAGACGCTGCGCCCCTTCTTCGACGAGTGGCCCAAGTCGAGGGACTCGTGGCC
GGAGCTGAACGAGGACAACAGCCTCGGCTCCTCGGCCACCCAGCTCTCCATCTC
CATCCCCATGGCGCCCTCCGACTTCAACACCAGCTCCAGATCGCCGAATGGAATA
CCGTCAAGATGAACCTGAGTAACCATGCGGACCCCAACATCTCAGAGCTGACGAC
TCTTTGCTGCTGGCCTGGCCTCATCGTACCTTGA
```

(miR396 recognition site is highlighted in bold)

SEQ ID NO: 15: amino acid sequence

```
MAMPFASLSPAADHRPSSLLPYCRAAPLSAVGEDAAAQAQQQQQHAMSGRWAAR
PPALFTAAQYEELEHQALIYKYLVAGVPVPPDLLLPLRRGFVYHQPALGYGPYF
GKKVDPEPGRCRRTDGKKWRCSKEAAPDSKYCERHMHRGRNRSRKPVEAQLVPP
PHAQQQQQQAPAPTAGFQSHPMYPSILAGNGGGGGGVGGGAGGGGTFGLGPTS
QLHMDSAAAYATAAGGGSKDLRYSAYGVKSLSDEHSQLLSGGGGMDASMDNSWR
LLPSQTAATFQATSYPLFGALSGLDESTIASLPKTQREPLSFFGSDFVTPKQEN
QTLRPFFDEWPKSRDSWPELNEDNSLGSSATQLSISIPMAPSDFNTSSRSPNGI
PSR*
```

Triticum aestivum

SEQ ID NO: 16: Traes_6AL_06A78C520 2 kb promoter

```
GATAGTGTGGGAAGGGAGTGGAGTGGAGTGGAATGCGGCTAGGGTTTTAGCCGG
AGTGCGGCCTATTTAGGTGGGGTCGGGTGAGCCAGATCCAACATGGCAGGTAGG
TTCGGGCATCCCCGTACTCGCCCTAAATTTGGGCTGGACTGGGGAGTGACCGGA
AGTCCGAACGTTTGCGCGTCAAAAATGCGGCGCTCGGTTGGGCATTGACCATGC
AACTTGCTCGGACATTTGGGGCAAGTATAGGGACTCCGATTGTAGATGCTCCTAC
GTCTAATTTGATACTTCATTGAGATGTGGTGTCCGATGCGTGAAAATGCTTCGAGA
AGTGAGAGCATCTACAGCCGGACTTAGCAAATCTGGCATCTATAAGTCAGCGGGC
GCCTCCGCGGACGGCCCCTCACTTGAGTTGCCGCACATTGACACACCGCAAATA
CGGATTCTTGAATTCATGCAATCCATTGACGTCCATCAAACGATACAAATCATCCC
AATTCAACAGTTCGAAACAAAATAAGACAAAGCAAAACAAATCATAATTCAACAATC
CGGACATGCTAAAATAAAATCAATGTCCGAGCGTGATGGTTCACTCCTTGACCGG
CTGGATCACTCGCCCGACGCCATCCATATTCCGCTTGCTCCGTGGCCATCCTTAT
GGGCAGCGAGGATGAGGAGCAAGGATGGCGGACGACAAGGGCTTGAACACGGG
AATAGGTGGAGGGAGTCGGGAGGGGGAAGGGTTTAGGGCCTCTTTGATTCACAG
GATTGTCAAAATAAAGGAATAGAAAAAATGCAGGAATAGGGTGACATGTCCCATAG
TATCCTACAGGATTTGAAAGAATGTTTGATAGCATAGGAAAAACAAAGGAATTCTA
CAAAGAGGTTTGAGTGGATGGAAATTTTTTTTCAAAATGTAGTACAAATGGATCATA
TGGAAAAATTCCTAAGGATGCCAATCCTACGAATCAAACGAGCATCACATGAAAAA
TTTCTAAGGATTTAAATCCTCCAAAAATCCTATATAATTCCTTTAAATCAAAGGAGC
GCTAGTGAATTGATGCAATTTGTGCTGAAGTAAGCCTGTCGGGTTCGACGTGACG
GGCGCGCCGAGACATCGCTTTCATATTTGGACTGGGTATATGGAGTGCTAGTCAG
CTCAAGTGTTTGAGACGCTCGTCTCGGTTTTTTCATTTGACCTGTAATCGGGCCGT
TCGTCCGGACGTTCGATAGAGGTTTGTGGTGCAGGGATGTAGATGCACACTGCTT
CCGTTATCAGTTATCACCACGACACAAGAAGCAAGCACATAGTACTGTAGTAAAAA
AATTGACGAGGGAAAAGTGGCGCAAACGGTTGCCCCGCACCCTCTCACGGACGG
ACTTTAAAAGTCGGCATTGGTAACCGCAACACAGCACAGAGAGACTCACCCCCAA
ATCTCTCTCTTCTCTCTCTATTCCTATGCAATGCAATAGTTGTCACCACTCGCTACA
GTGCCGGCAGCATTGCATCGCATCGCATCCATATCCATTCCTCCTCACGAGAAAA
AGAGAGAGAGACGAGCAATACTAGTCGTCGTCGTCGTCGTAGCCTGGTACGTCTA
CGCTAGAGCGACAGGGAAAGAGGAGGGAGGGGGCGCTTGTCATCTACTCCTCCT
CGCTACTACCCCTAGCTGGGATCCACAGCCTCCTCCTCCTCCTCGTGTCGGCCTC
GTCCACATCCACCGTCTCCTCCGAGCGAGGCGGACAGCGACGCGGCCACGGAG
CGAGGGAGGGAGAGAGACAAAGCCGGTAATAAAGGCGGGCGGGCGCGCGCGC
GCACAAGCCAAGCAAAGCACATTAACGACGCCAGCCAGCCAGCCAGCCAGCCAG
CCCGCGGGGAACCCCATTAAAGACGCTTCCGGGGGAGCGCCGTGGGCAAGCAA
GCACAGGGGCTTAGCTTAGCTTGGCTTGTGCATCGCGTGTTGTGTGCGCGAGAG
GGAGACAGCGGCCGAGAGAGAAAG
```

SEQ ID NO: 17: CDS

```
atggcgatgccgtatgcctctcttttccccggcaggcgaccgccgctcctccccgg
ccgccaccgccaccgcctcctcctcccctttctgccgctcctccccttctccgc
cggcggcaatggcggcatgggggaggaggcgccgatggacgggaggtggatggcg
aggccggtgccttcacggcggcgcagtacgaggagctggagcaccaggcgctca
tatacaagtacctggtggccggcgtgccgtccgccggatctcgtgctccccat
ccgccgcggcatcgagtccctcgccgcccgcttctaccacaacccctcgccatc
gggtacggatcgtacctgggcaagaagtggatccggagccgggccggtgccggc
gcacggacggcaagaagtggcggtgcgccaaggaggccgcctccgactccaagta
ctgcgagcgccacatgcaccgcggccgcaaccgttcaagaaagcctgtggaaacg
cagctcgtgccccactcccagccgccggccgcctccgccgtgccgccctcgcca
ccggcttccacggccactccctctaccccgccgtcggcggcggcaccaacggtgg
tggaggcgggggaacaacggcatgtccatgcccggcacgttctcctccgcgctg
gggccgcctcagcagcacatgggcaacaatgccgcctctccctacgcggctctcg
```

SEQUENCE LISTING gcggcgccggaacatgcaaagatttcaggtataccgcatatggaataagatcttt
ggcagatgagcagagtcagctcatgacagaagccatgaacacctccgtggagaac
ccatggcgcctgccgccatcttctcaaacgactacattcccgctctcaagctact
ctcctcagcttggagcaacgagtgacctgggtcagaacaacagcagcaacaacaa
cagcggcgtcaaggccgagcgacagcagcagcagcagccgctctccttcccgggg
tgcggcgacttcggcggcggcgactccgcgaagcaggagaaccagacgctgcggc
cgttcttcgacgagtggccgaagacgagggactcgtggtcggacctgaccgacga
caactcgaacgtcgcctccttctcggccacccagctgtcgatctcgatacctatg
acgtcccccgacttctccgccgccagctcccagtcgcccaacggcatgctgttcg
ccggcgagatgtactag (miR396 recognition site is highlighted in bold)

SEQ ID NO: 18: amino acid sequence

MAMPYASLSPAGDRRSSPAATATASLLPFCRSSPFSAGGNGGMGEEAPMDGRWMA
RPVPFTAAQYEELEHQALIYKYLVAGVPVPPDLVLPIRRGIESLAARFYHNPLAI
GYGSYLGKKVDPEPGRCRRTDGKKWRCAKEAASDSKYCERHMHRGRNRSRKPVET
QLVPHSQPPAASAVPPLATGFHGHSLYPAVGGGTNGGGGGNNGMSMPGTFSSALG
PPQQHMGNNAASPYAALGGAGTCKDFRYTAYGIRSLADEQSQLMTEAMNTSVENPW
RLPPSSQTTTFPLSSYSPQLGATSDLGQNNSSNNNSGVKAERQQQQQPLSFPGCGD
FGGGDSAKQENQTLRPFFDEWPKTRDSWSDLTDDNSNVASFSATQLSISIPMTSPD
FSAASSQSPNGMLFAGEMY*

SEQ ID NO: 19: TRIAE_CS42_6BL_TGACv1_500422_AA1604330:
2 kb promoter

TTTTCGCACGCAACGCCCACTTGAGTTCCTCCTCTCTCAAGAGAGCATGTTGGCC
TTGCTCAGCCTCAGACTTGGTTCGATGCTCATTAACAGAAAGAAGTGTGGTTTCAG
CCTTTACATCTAGTGTCTCAATGAGTTGAGTTAGACGTTCTTTTTTCTGCTTATAAA
TCCCAGTCTCATTCCTGGCCCATCCTCTCAGAAATTGTCGGAGGTTCTAATCTTA
TTCTGCCATCTCTCGACATGTGTCCTTCCTGTAATTGGCTTAGCCCATTCGCATGC
AATCATCTCCATAAATCCTTCTCGCTCAAACCAGCTTTACTCGAAAGAGAAGATGT
TTTTGTTTGCAACATGGGTAGCCTCACCCGAATCTAAAAAGAGTGGTGTATGATCT
GAGATCCCTCTATGCATTGCATGGACCGACACCAACGGATATTTTTGTTCCCACTC
CACACTAGCAAGTACCCTATCCAGCTTTTCATAAGTCAGAACAGGTAACGAGTTGG
CCCATGTAAACTGTCTACCGGTGAGCTCAATTTCTCTCAAATTGAGGCTCTCGATA
ATCATGTTAAACATCATAGACCAACGTCCATCGAAATTGTCATTATTCTTTTCTTCT
CTTCTCCGAATGATATTAAAATCACCCCCGACTAGCAGTGGCAGATTTTCATCTCC
ACAAATCCGCACTAGATGGGCAAGAAAATCGGGTTTAAATTGCTTGGAGGAGTGA
GAGCATCTACAACCGGACTTAGCGAATCTGGGCTCTATAAGCCCGCGGGTGCCT
CCGCGGACGGCCCTCCCTTGAGTTGCCGCACATTCACACATCTCAAATACGGATT
CTTGAATCCATGTATCCATGCACGTCCATCATACGATATAAATCATCCCAATTCAAA
TGTTTGAAAACAAAATACGACAATGCAAAGCAAATCATAGTTTCAATAATTCAGACAT
GCCAAATTAAAATCAATATCCGAGCATGATAGATCACTCGTTGGACGCCATCCATG
CCCGCTTGCTCCGCGGCCATCCTTGCGGGCGGCGAGGATGGGGAGCAAGGGTG
GCGGACGGCAAGGGCTTGGACACGAAAATAGGTGGATGAAGGCGGGAGAGAGG
AGGGTTTAGTGAATTTTATGCAATTTATGTGGGGGGTTGGCCTGTCGGGTTCTAC
GTAATGGACGCGCCGAGGCATGAGGGATGCCGGTCAGCTTGGGTGTTTTAGATG
CCCGTCCGGTCTTTTATTTTTAAGTCCGTAATTGGGCCGTTCGCCGGACGTTCCAT
AGAGGTTTGGGGTGCCGGGAAGTAGATGCACAGTACTTCCGTTATCACCACGACA
CAAGAAGCAAGCACATAGTACTGTTGTAAAAAAATGACGAGGGAAAAGTGGCGCA
AACGGTTGCCCCGCACCCTCTCACGGACGGACTTTAAAAGTCGGCATTGGTAACC
GCAACACAACACAGACAGACGCACCCCAAATCTCTCTCTCTCTCTTCCCATGCA
ATAGTTGTCGCCACTCGCTCGCTACAGTGACCGCATCGCATCGCATCCATGTCCA
TTCCTCCCCACGAGAAAAAGAGAGAGACAGCAGAAATACCAGTCGTCGTCGTCGT
CGTCGTAGCCTGGTACGTCTACGCTAGAGCGACAGGGAAAGAGGAGGGCGCTTG
TCATCTACTCCTCCTCCTCGCCCGCTACTAGCTGGGATCCACAGCCTCCTCCTCC
TCCTCGTGTCGGCCTCGTCCACATCCACCATCTCCTCCGAGCGAGGTGGACAGC
GACGCGGCCACGGAGCGAGTGAGAGAGACAAAGCCGGTAATAAAGGCGGGCGC
GCGCGCGCGCACAAGCCAAGCAAAGCACATTAACGAGGCCAGCCAGCCCGCAG
GGAACCCCATTAAAGACGCTTCCGTGGGAGCGCCGTGGGAAGCAAGCGAGCG
AGCACAGGGGCTTGGCTTGCGCGTCGTGTGCTGTGTGCGCGAGAGGGAGACAG
CGGCCGAGAGAGAAAG

SEQ ID NO: 20: CDS

ATGGCGATGCCGTATGCCTCTCTTTCCCCGGCAGGCGACCGCCGCTCCTCCCCG
GCCGCCACCGCCTCCCTCCTCCCCTTCTGCCGCTCCTCCCCGTTCTCCGCCGGC
AATGGCGGCATGGGGGAGGAGGCGCGGATGGCCGGTAGGTGGATGGCGAGGC
CGGCGCCCTTCACGGCGGCGCAGTACGAGGAGCTGGAGCACCAGGCGCTGATA
TACAAGTACCTGGTGGCCGGCGTGCCCGTCCCGCCGGATCTCGTGCTCCCCATC
CGCCGCGGCATCGAGACCCTCGCCGCCCGCTTCTACCACAACCCCCTCGCCATC
GGGTATGGATCGTACCTGGGCAAGAAGGTGGATCCGGAGCCCGGCCGGTGCCG
GCGCACGGACGGCAAGAAGTGGCGGTGCGCCAAGGAGGCCGCCTCCGACTCCA
AGTATTGCGAGCGCCACATGCACCGCGGCCGCAACCGTTCAAGAAAGCCTGTGG

SEQUENCE LISTING

AAACGCAGCTCGTCTCGCACTCCCAGCCGCCGGCCGCCTCCGTCGTGCCGCCC
CTCGCCACCGGCTTCCACAACCACTCCCTCTACCCCGCCATCGGCGGCACCAAC
GGTGGTGGAGGCGGGGGGAACAACGGCATGCCCAACACGTTCTCCTCCGCGCT
GGGGCCTCCTCAGCAGCACATGGGCAACAATGCCTCCTCACCCTACGCGGCTCT
CGGTGGCGCCGGAACATGCAAAGATTTCAGGTATACCGCATATGGAATAAGATCT
TTGGCAGACGAGCACAGTCAGCTCATGACAGAAGCCATGAATACCTCCGTGGAGA
ACCCATGGCGCCTGCCGCCATCGTCTCAAACGACCACATTCCCGCTCTCAAGCTA
CGCTCCTCAGCTTGGAGCAACTAGTGACCTGGGTCAGAACAACAACAGCAGCAG
CAGCAACAGTGCCGTCAAGTCCGAACGGCAGCAGCAGCAGCAGCCCCTCTCCTT
CCCGGGGTGCGGCGACTTCGGCGGCGGCGGCGCCATGGACTCCGCGAAGCAG
GAGAACCAGACGCTGCGGCCGTTCTTCGACGAGTGGCCCAAGACGAGGGACTCG
TGGTCGGACCTGACCGACGACAACTCCAGCCTCGCCTCCTTCTCGGCCACCCAG
CTGTCGATCTCGATACCCATGACGTCCTCCGACTTCTCGGCCGCCAGCTCCCAGT
CGCCCAACGGTATGCTGTTCGCCGGCGAAATGTACTAG (miR396 recognition site is highlighted in bold)

SEQ ID NO: 21: amino acid sequence

MAMPYASLSPAGDRRSSPAATASLLPFCRSSPFSAGNGGMGEEARMAGRVVMARPA
PFTAAQYEELEHQALIYKYLVAGVPVPPDLVLPIRRGIETLAARFYHNPLAIGYGS
YLGKKVDPEPGRCRRTDGKKWRCAKEAASDSKYCERHMHRGRNRSRKPVETQLVSH
SQPPAASVVPLATGFHNHSLYPAIGGTNGGGGGNNGMPNTFSSALGPPQQHMGNN
ASSPYAALGGAGTCKDFRYTAYGIRSLADEHSQLMTEAMNTSVENPWRLPPSSQTT
TFPLSSYAPQLGATSDLGQNNNSSSSNSAVKSERQQQQQPLSFPGCGDFGGGGAMD
SAKQENQTLRPFFDEWPKTRDSWSDLTDDNSSLASFSATQLSISIPMTSSDFSAAS
SQSPNGMLFAGEMY*

SEQ ID NO: 22: TRIAE_CS42_6DL_TGACv1_527461_AA1704370
2 kb promoter

GTATGCGTTACCTTGATTTGCCACATTAGCTAGCTGAAGTTGGTTGCCCGTACATT
TGTCAGCGTTAGCGCCCTGTGACGAAACTTGCCATGCTGCCCCCCTGATTGTGGT
TTGGTCATAAGAACCTNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNGCAGCA
ATGGCCCTGAAGAAATGAGTTGATTGTACTCTGCTGCATCCCAAGGTGGCGTTTC
CGGCCTTTGAGAAAGCCAAGGATCAGTGCCATCTTCGTGATTCATTCTTCTGCTTT
TTCTTTTCTGCTACTATGCTTTTAGTCACTGCATGAACAAGAACGCATCAACAATCC
ACAAAAAGCGTTCTTGCTGTTTGCACGTAGAAGATAACACGGCAATCTCATAATAT
TTTTTGCGTAGGCAACCAACACCTCATGGCAAGTAGGACATGCACATCCATTTTTC
TTTTCTGAATTCTGGATGCCATCTATCATTTTGAAGCGATGGCAACAGAAAATAAA
TAGGATGGCAAGCAATAATACATGGTGGCAACTATGGACAACGATAGATGGCAAC
TGACGTTAGATACAAGTGGCAATTATTTTTCCTCCCTCCCCATGCCAAATTCCTCC
TTTCTCTCCCTATTTTATAGTGATTACTACGCTACCAACTACTCGCATCAAAGCCAA
CCCAGAAGCTTGGCACAAGTCTAGCATAGTATATGGCAGATCTGGCGTATGTTGG
TGGGAAAATGCAAAGACACACAAATTCGTGGGGTGTTTGCCCTGATAGCGTGGAT
CCAGTCGCCATCTTCGTGGGCAAATTTTGCAAATTCAGATTTCTGGACAAAAGAAG
ATCGGGGATCCACCTGTTTTAGCTCGTCGTCTTGGGAGTGCGGGAGGGGGGTA
GGGTGGGGTGGGGTGGTTGGTTAGCTGTGGGAAAGGCGCTAGGGATTTGCTC
TGGTTGCCATGGCAACCAGAGAAGGAAGGCGACGGAGGTAGGGGATCGGGAGA
TGCGAGACAATGGCGGCAGGGCGGACCGGGGATCGGAAGGAGCCCGGGACAG
CTGGCGTGCTGAGTCGTGCGGGCAGCGCGGTCGTTTGGCCCGGACGTGTGGGC
GGTTTTGCCACACACCGGACGTGCGGGTTGTGGCTGCGCGCGCCCGGATGCGG
TTTTGCGGGCGAGTTCTTCTCCATGCCACACGAGGCGTGCGGCACAACCACCCG
ATACACCACACGTGTGGCAGTTATCGGTGTTAAAAAAATGACGAGAGAAAAGTGG
CGCAAACGTTGCCCCGCACCCTCTCACGGACGGACTTTAAAAGTCGGCATTGGT
AACCGCAACACAACACAGACAGACGCACCCCAAGCCTCTCTCTATCTCTCTCTTC
CCATGCAATAGTTGTCACCACTCGCTCGCTACAGTGCCCGCATTGCATCGCATCC
ACATCCATATGACCATATCCATTCCTCCCCACGAGAAAAGGAGAGAGAGGGGAGA
AATACTAGTCGTCGTCGTCGTAGTAGCTGGTACGTCTACGCTAGAGCGACAGGGA
AAGAGGAGGGAGGGGGCGCTTGTCATCTACTCCTCCTCCTCGCCCCTAGCTGGG
ATCCACAGCCTCCTCCTCCTCCTCGTGTCGGCCTCGTCCACATCCACCGTCTCCT
CCGAGCGAGGTGGACAGCGACGCGGCCACGGAGCGAGGGAGGGAGAGAGACA
AAGCCGGTAATAAAGGCGGGGGCGCGCGCGCACAAGCCAAGCAAAGCACATT
AACGACGCCAGCCAGCCCGCGGGGAACCCCATTAAAGACGCTTCCGGGGGAGC
GCCGTGGGCAAGCACAGGGGCTTAGCTTAGCTTGGCTTGTGTGTTGTGTGCGCG
AGAGGGAGACAGCGGCCGAGAGAGAAAGATGGCG

SEQ ID NO: 23: CDS

ATGGCGATGCCGTATGCCTCTCTTTCCCCGGCAGGCGACCGCCGCTCCTCCCCG
GCCGCCACCGCCTCCCTCCTCCCCTTCTGCCGCTCCTCCCCCTTCTCCGCCGGC
GGCGGCAATGGCGGCATGGGGGAGGAGGCGCGGATGGACGGGAGGTGGATGG
CGAGGCCGGTGCCCTTCACGGCGGCGCAGTACGAGGAGCTGGAGCACCAGGCG
CTGATATACAAGTACCTGGTGGCCGGCGTGCCCGTCCCGCCGGATCTCGTGCTC

```
CCCATCCGCCGCGGCATCGAATCCCTCGCCGCCCGCTTCTACCACAACCCCCTC
GCCATCGGGTACGGATCGTACCTAGGCAAGAAGGTGGATCCGGAGCCGGGCCG
GTGCCGGCGCACGGACGGCAAGAAGTGGCGGTGCGCCAAGGAGGCCGCCTCCG
ATTCCAAGTATTGCGAGCGCCACATGCACCGCGGCCGCAACCGTTCAAGAAAGC
CTGTGGAAACGCAGCTCGTCCCGCACACCCAGCCGCCGGCCGCCTCCGCCGTG
CCGCCCCTCGCCACCGGCTTCCACAGCCACTCCCTCTACCCCGCCATCGGCGGC
AGCACCAACGGTGGTGGAGGCGGGGGGAACAACGGCATGTCCATGCCCAGCAC
GTTCTCCTCCGCGCTGGGGCCGCCTCAGCAGCACATGGGCAGCAATGCCGCCTC
TCCCTACGCGGCTCTCGGTGGCGCCGGTTCAGGTATACCGCATATGGAATAAGAT
CTTTGGCAGACGAGCACAGTCAGCTCATGACAGAAGCCATGAATACCTCCGTGGA
GAACCCATGGCGCCTGCCGCCGTCGTCTCAAACGACCTCATTCCCGCTTTCAAGC
TACGCTCCTCAGCTTGGAGCAACGAGTGACCTGGGTCAGAACAACAACCACAACA
ACAGCAGCAGCAACAGTGCCGTCAAGTCCGAGCGGCAGCAGCCGCTCTCCTTCC
CGGGGTGCGGCGACTTTGGCGGCGGCGGCATGGACTCCGCGAAGCAGGAGAAC
CAGACGCTGCGGCCGTTCTTCGACGAGTGGCCGAAGACGAGGGACTCGTGGTC
GGACCTGACGGACGACAACTCCAGCCTCGCCTCCTTCTCGGCCACCCAGCTGTC
GATCTCGATACCCATGACGTCCTCCGACTTCTCCGCCGCCAGCTCCCAGTCGCCC
AACGGTATGCTGTTCGCCGGCGAGATGTACTAG
```

(miR396 recognition site is highlighted in bold)

SEQ ID NO: 24: amino acid sequence

```
MAMPYASLSPAGDRRSSPAATASLLPFCRSSPFSAGGGNGGMGEEARMDGRVVMA
RPVPFTAAQYEELEHQALIYKYLVAGVPVPPDLVLPIRRGIESLAARFYHNPLAI
GYGSYLGKKVDPEPGRCRRTDGKKWRCAKEAASDSKYCERHMHRGRNRSRKPVET
QLVPHTQPPAASAVPPLATGFHSHSLYPAIGGSTNGGGGGNNGMSMPSTFSSAL
GPPQQHMGSNAASPYAALGGAGTCKDFRYTAYGIRSLADEHSQLMTEAMNTSVEN
PWRLPPSSQTTSFPLSSYAPQLGATSDLGQNNNHNNSSSNSAVKSERQQPLSFPG
CGDFGGGGMDSAKQENQTLRPFFDEWPKTRDSWSDLTDDNSSLASFSATQLSISI
PMTSSDFSAASSQSPNGMLFAGEMY*
```

*Hordeum vulgare L.*

SEQ ID NO: 25: HORVU2Hr1G101770 2 kb promoter

```
AAAGTTCAAATAAGTTTTTCAGACCCTACCGTCATACACCTTGACGGTAGAATGTG
AAACCCTACCATTATATAAACGAATTCCCGTTACAACAACTTTACACACGAGGTCA
GACTCCTACCGCCATAGTTCCTAATGGTAAGGTCTTGCATCCTATCGTCTTATACT
TGGCGGTACGGCCGTTACGCCACGTGAGCCCTTCGGCTGGCAGTTGACGGCCG
CTGTTGTTACTCGACTGTCAGATACCTATAAACCTATCGCCAACCTGTGTAACAAT
GAAAAACGGTCAAATCCCGAAAAAATTTTCGAAGCAGGATCGCATCCTGCTAAACTT
TTGACAAATGGTCAAAACACGAAATTTTTGCCGCTCGTTGTGCCTCTGTAAGCTGG
AAGCCTACGGTGTCGGCCTCACCCCCCACACGGTGCTGCCGCTGCTGCGCCCAT
CGCCAGCGCTTCACGCTATATATCCACCCCGTCGTCGTGTGAGTCTCACCAGGCA
GATCGAGCCCTGCGCAGCGAGGGGAAAGAGACACACACAGCGCCACCAGGCAA
GTAGTAGTAAAAGGCAAAAGCACGGCACATTAAAAGAGAGGCCAGCCCAGCCCC
GGACCGGACCGGAGCCAAGCAGCAGCCGCAGCCGCAGCCGCAGCAGAGGAGA
GAGAGAGGGAGGGAGAAGCATATATGGCGATGCCCTTTGCCTCCCTGTCGCGG
CAGCCGACCACCACCGCTCCTCCCCCATCTTCCCCTTCTGCCGCTCCTCCCCTCT
CTACTCGTAAGCCGGCCGGCCGGCCGGCCAACCGCCTCACTTCTTTCTTCGTATC
TGCTTCCATCTTAGCTCGAGGGGTTCGCTAATGCGGTGACCGTCTCCGGCGCCT
GTGTTGTGTTCCGTGTGTGCAGGGTAGGGGAGGAGGCGGCGCATCAGCATCCTC
ATCCTCAGCAGCAGCAGCACGCGATGAGCGGCGCGCGGTGGGCGGCGAGGCCG
GCGCCCTTCACGGCGGCGCAGTACGAGGAGCTGGAGCAGCAGGCGCTCATCTA
CAAGTACCTCGTCGCCGGCGTCCCCGTCCCGCAGGACCTCCTCCTCCCCATCCG
CCGCGGCTTCGAGACCCTCGCCTCGCGCTTCTACCACCACCACGCCCGTACGTA
CCCCATCCCTTCCTCCTCCTACCCCGGCCAGGAGTAGTACTTGCTTTTTTGCATTC
GCCATGCGATTTGCCCGGTTGTTTATTCGGATCGAGCACTTGCTTTTGCATTCGCC
ATGCGATTTGCCCGGCTTGTTTATTGGGATCGAGAGATTCAGGTGTGCTCGACCC
CCATCCCATGATTCCCATCTCTTTGTTAATTGCTCCGGTCATTTGTTAATCCCTCCC
CGGATTTGGCCGAGCAAAAGTCTCATTATTCTAATCCGAGCAAGCCTCGTGCCC
TGTTCAAAGATTTGCTCCTACCATCACCACCTACCACCATCCAGCAAGCATCCCCT
GCCTCGCCGGGTCTTTTAATTTACTTGGGATTTCATTCTCATGTCATGTCATGTGC
TATGATTTGATTAGATGGCGCTAGTCGAGTCTTGGGTTAGTTTCCATTGGTCCTTC
CGTGGCAAGGGGGTTATTCCTGTCTGGTTGTTGGGAGCCTCACCCACGCATTCAC
TCGCTCGCTCGCTGGTCATGTCCTGCCACGGCCGATCTCACCGATCCATCCTGCA
TCGCATCACATGGACCCCCGACGAAAAAGATCGGCAATCAACCACGCACAGCTCC
TCCTTTCCCCGGAAATTATTTCGCATACGTCCTTCCTTCCTTCGTTCCTTCCTTCTT
GCGGGGTAAATGATTGGTTTGGTGGGGTGGGCACACAGATAGATCCAGGACGAG
GACGACCGCTTCGTCCGTCCCTCCGGCCGGCCGGCGTCATGATTGATTGCTAC
CTGCTACGGCCTTGGACTGGACGCGTCTCCGTTCTTCCGATCTCGCGTCTCCTCC
TGAGTTGATTTCTTGGTCCCTCCGG
```

SEQUENCE LISTING

SEQ ID NO: 26: CDS

ATGAGCACCGACACATTCCAAGTGCGTACAGATGTATGGGGTATTTATCATGAAAA
AGCATTCTTGACGTGGGTGTTTTTCGTTGTTTGCAGTTGGGTACGGGTCCTACTTC
GGGAAGAAGCTGGATCCGGAGCCGGGGCGGTGCCGGCGGACGGACGGCAAGA
AGTGGCGGTGCTCCAAGGAGGCCGCTCAGGACTCCAAGTACTGCGAGCGCCACA
TGCACCGCGGCCGCAACCGTTCAAGAAAGCCTGTGGAAACGCAGCTCGTCGCC
AGCTCCCACTCCCAGTCCCAGCAGCACGCCACCGCCGCCTTCCACAACCACTCG
CCGTATCCGGCGATCGCCACTGGCGGTGGCTCCTTCGCCCTGGGGTCTGCTCAG
CTGCACATGGACACTGCTGCGCCTTACGCGACGACCGCCGGTGCTGCCGGAAAC
AAAGATTTCAGGTGACCTCTTCTCTGCATATACTCTGCTGCCGTCGTGTTGATTAG (miR396 recognition site is highlighted in bold)

SEQ ID NO: 27: amino acid sequence

MSTDTFQVRTDVWGIYHEKAFLTVVVFFVVCSVVVRVLLREEAGSGAGAVPADGRQEV
AVLQGGRSGLQVLRAPHAPRPQPFKKACGNAARRQLPLPVPAARHRRLPQPLAVSG
DRHWRWLLRPGVCSAAHGHCCALRDDRRCCRKQRFQVTSSLHILCCRRVD*

*Sorghum bicolor (L.)*

SEQ ID NO: 28: SORBI_004G269900 2 kb promoter

TAAATATTGTTTATTATAGACTAACTAGGCTTAAAAAATTCGTCTCACAAATTACAAT
TGAACTGTCTAATTAGTTTATATTTTTGTCTATATTTAATGCTTCATGCATAAGTATA
AAGATTTGACGTGACAGAGAATCTAAAAAATTTTACAAAATTGTTTGGAACTAAACA
AGGCCCTAGAATACAAGGCTAAGGCCTTGTTTAGATGCACCCAAAAATCCAAAACT
TTACAAGATTCTCCGTCACATCGAATCTTACAGCACATGCATGAAGTATTAAATATA
GATAAAAATAAAAACTAATTACACAGTTTATCTGTAAATCGCGAGACAAATCTTTTA
AGCCTAGTTACTCCATGATTGGACAATGTTTGTCAAATAAAAACGAAAGTGCTACA
GTGTCAAAATCCAAAAAGTTTTTGCATCTAAACAAGCCCTAAATATAAGGCCTCGT
TTAGTTCACCCCAAAAATCAAAAACTTTTCAAGATTCTCCGTCACATCGAATCTTGC
GGCACATGCATAAAGCACTAAATAAAGATGAAAATAAAAACTAATTGTACAGTTTAC
GTGTAAATGAATCTTTTAAGCCTAATTACTCCATGATTAGATAATATTTATCAAATAA
AAACGAAAGTTTTACGGTTTGGAAAACCAAAAAGTTTTCGGAACTAGCCCTGTTTA
AATTGAAGTTAAAATTTTTTTAGATGTCACGTTGTATGTGTCGGAAGGATATCGGG
AGGGGTTTTAAGAAACTAATAAAAGAACAAATTACATAGCTCGTCTAGAAACTGCA
AGACAAATCTATTAATCATAATTAATATATCATTAGCACATATGAGTTATTATAGAAC
TTAAGGCTAATCATAGACTAACTAGGCTTAAAAGATTCATCTCGCAATTCTAAACCA
AACTGTGTAATTAGTTTATTTTTTATTTACATTTAGTGATCAATGTATGTGTCCAAAG
ATTTGATATGATGAATCTAAACACAAATCTAGGCCTTGTTTAGTTTCAAAATATTTT
GCAAAATGGACACGGTAGCTCTTTCGTTTGTATTTGACAAATATTGTCCAATCATG
GACTAAATAGGCTCAAAAGATTTATCTCGTCAATTCCGACCAAACTGTGCAATTAG
TTTTTATTTTTGTCTATATTTAGTAATTCATGCATGTGTCTAAAGATTCGATATGACG
TGGAATCTGAAAAATTTTGTAAAATTTTTTGGGAACTAAACAAGACCCTAACCATCA
ACAAATGACCGGATGTACAGTACTAGTTTCCAGTCGGCTGTCCAAACGCCCCCGC
TGCTCGCTCGCCGCCTCGCCGGGAGTCTCGACACGCCTGACGCTCCAGCGCGA
GGCAGACAGCGACGCAGAGAGAGACAAAGGGGGCAATAAAGGCAGCGCGCGCG
AGCACCAGCGAGGGAGCGAAGCAAAGCACATCACGAGCCCGGAAGCTCATTAAG
AGCAACTCCAGCATTAGACCCTAAAACTAAACCCCTACTTTTAATTTGGGTGCTCT
TCCTACTTCGTGGGGCTCAATTTTTTTGCTTCAACTCCAACAGTAGCACCCAAATT
TAGGCCCCCAAACTTATTCCAGAGAGAATGACACAAGGGACCCACTCGTCAGTGT
CCTTTTCTTCTTCCTCTTTCTTCTTCCTTTGGACATGGACACAATTAGAGCATCGAG
CCGGTTACCGTAGGGTGTCATGCACATACAAGGGTAGAGAGAGAAGGAGCATGA
GCTGAGGCTAGGACACGCGATGGAGGATGGGGGCTGCCCTGTTGGGCCAACAG
GAATGGGGTCTAGGAGAGAAATATGGGTGCCCAGCCAAATATGGGGTCTGGAGT
AGGGACCGTGCTGGAGTAATGTTTTTAGTCTGAGCACCCATATTTAGCTATTGGG
GCTTGAGTAGAAGCTCTGCTGGAGTTGCTCTAAAGAGGGGTGCCGTCCGGCCGG
CCGCGGGGAGCAAGCAGCGCGCGCGAGAGACAGGTTGAG

SEQ ID NO: 29: CDS

ATGGCGATGCCGTATGCCTCTCTTTCCCCGGCAGGCGCCGACCACCGCTCCTCC
ACGGCCACGGCGGCGTCGCTCCTCCCCTTCTGCCGCTCCACCCCGCTCTCCGCG
GGCGGCGGCGGCGGCCTGGGGGAGGACGCCCAGTTGAGCTCGCGGTGGCCGG
CCGCGAGGCCGGTGGTGCCGTTCACGCCGGCGCAGTACGAGGAGCTGGAGCAG
CAGGCGCTCATATACAAGTACCTGGTGGCCGGCGTGCCCGTCCCGCCGGATCTC
GTGGTTCCAATCCGCCGCGGTCTCGACTCCCTCGCAACCCGCTTCTACGGCCAT
CCCACACTTGGTGGGTACGGGACGTACTACTTAGGCAAGAAACTGGATCCGGAG
CCGGGGCGGTGCCGGCGTACGGACGGCAAGAAGTGGCGGTGCTCCAAGGAGGC
CGCCCCAGACTCCAAGTACTGCGAGCGCCACATGCACCGCGGCCGCAA**CCGTTC
AAGAAAGCCTGTGGAA**ACGCAGCTCGTGCCCCAGTCCCAACCGCCCGCCACCG
CCGCTGCCGTCTCCGCCGCTCCGCCCTTGGCCTTGGCCGCCGCCACCACCACCA
CCAACGGCAGCTGCTTCCAGAATCACTCTCTTTACCCGGCCATTGCAGGCAGCAC

CGGTGGAGGTGGCGGGGCCAGCAATATCTCTACCCCGTTCTCCTCGTCGATGGG
GTCGTCTCAGCTGCACATGGACAATGCTGCCAGCTACGCAGCTCTTGGTGGTGG
AACTGCAAAGGATCTCAGGTACAACGCCTACGGAATAAGATCTTTGGCGGAGGAG
CACAACCAGCTGATTGCAGAAGCCATTGACTCATCAATGGAGAACCAGTGGCGCC
TCCCGCCATCCCAAACCTCTTCGTTTCCGCTCTCGAGCTACCCCCAGCTTGGGGC
GCTGAGCAACCTGGGTCAGAGCACAGTCACCTCGCTGTCGAAGATGGAGCGGCA
GCAGCCACTCTCCTTCCTAGGGAACTCCGAGTTCGGGGCCATGGAATCCGCCGC
CAAGCAGCAGGAGAACCAGACGCTGCGGCCCTTCTTCGACGAGTGGCCCAAGGC
GAGGGACTCCTGGCCGGGCCTCTCCGACGACAACGCCGCAAGCCTCGCTCCGT
CGTTCCCGGCGACCCAGCTGTCGATGTCCATACCGATGGCGTCCTCGGACTTCT
CCGTGGCCAGCTCCCAGTCGCCCAACGATGACTAA (miR396 recognition site is highlighted in bold)

SEQ ID NO: 30: amino acid sequence

MAMPYASLSPAGADHRSSTATAASLLPFCRSTPLSAGGGGGLGEDAQLSSRWPAAR
PVVPFTPAQYEELEQQALIYKYLVAGVPVPPDLVVPIRRGLDSLATRFYGHPTLG
GYGTYYLGKKLDPEPGRCRRTDGKKWRCSKEAAPDSKYCERHMHRGRNRSRKPVET
QLVPQSQPPATAAAVSAAPPLALAAATTTTNGSCFQNHSLYPAIAGSTGGGGGASN
ISTPFSSSMGSSQLHMDNAASYAALGGGTAKDLRYNAYGIRSLAEEHNQLIAEAID
SSMENQWRLPPSQTSSFPLSSYPQLGALSNLGQSTVTSLSKMERQQPLSFLGNSEF
GAMESAAKQQENQTLRPFFDEWPKARDSWPGLSDDNAASLAPSFPATQLSMSIPMA
SSDFSVASSQSPNDD*

*Glycine max (L.)*

SEQ ID NO: 31: GLYMA11G11826; 2 kb promoter

ACATACACTCTTTCTCTCCAAAAATAAATAAATTAATATACACTAGTTTGGCTTTTAA
TTCCCAAATTACACCATTTTTTGTGACATTGAGATGTAGGGATTTGACAACCCGA
CTTCTCAGTGATTTTTATTTTTTTTAATTTAAATTTTATTTTTATTCTAAATTTATGTT
TTAGTTTAAATTATTATACACAAAAGTTAAGAAGTTAAAAAGTTGGGATTCATCCCT
ATTTTTTATCTATGGTTTTACTCCAATTTACTCTAATCAAGAATTAAGAGAATCTAAC
TTACTTGAATGTTATAAATCCTTCATACCTTATTTAATTCTTACCTATAAAAAATCCC
AATCAAGAAAAAAATCCCAATTAAGAGAATCTAACTTACTTTAATTATAACCGAAAC
AAAGCTACGTAACTTGATTACAAAATGTACGAGAAACCAAAATTAGTGATGGTGAA
AAAAATCACCGACAAAAGTAAGAATCTACACGTGATCTGAGATCAGAGACATACTT
TAAGAAGCAACAATCAACAGCCGAAAACCAAAATTAAAGGTATATATTCCTTAAATT
GCTTTGTCCCTTTGACTTTTGCCATCGTGATGATTAATTAAAGGTTTAGCAAACCC
CTTCGAACTTCATACAATTGACTGAATTGAGAATTTTATTTTCACATTCGAGGAAGC
GATGCTACAACATCACTTTTTTTGTTCTGTATTGTGCTTTTTAACTGCCTTTTTTCTT
CTTCTTTTTTGCCTCCCTAACAAAGACATGTAAAAGTAATTGTAATAATATTCGTTT
CTTATGGAATGCAATCAGTTGATTGATGTAACTATAAACTATTATCTCCTTAATATC
GAAAGACAAGTGAAGCCAAACACAAACAAGATAGGGCCTAGGGAGAGGTGTGGT
CCATGAATGATGAGGTATGGGTGACCAAACAATGAATGAATAATTGAAGCATCCTT
GACCGTTGCTTGAGTTTGTGTCATCCTCAATAATATACTAGTCCCTTGGCTACAGA
AACCGATAAGCCTAAAACTGGAATTGCACACATTTACGTTTTTGATTTTGATTTTGT
TTTTGGCAATCTCGCCCCACATCAAATGTCACCCGCATTCCGGCAAGTAGTGGAT
GGTTTCCTCTAGCGGTGCTTTGCCTTTGGGCCACTGGGCCCGCAATTACTCCAGC
CCATCATGCCTTGTTGCTGTCCGTTAAAGGGTAGCATAATAAAATAAAAGTAGATC
AACAAAATGAGAGCAAGTATTTCAAAAAAAAAAAAACATAGTAAAAAAACACTTCCT
CTATTTATATTATCAAGATTTATTTATCTTAAAACATTCATTATCTCAAAAATACCTAT
ATTACTTAATAGTATTTCATGAATTTAAATCTAAGTTTACTATCAAACTCACCTTTTA
AAACAATTATTACACAACAAGTTATAATTGAATGTCATAAAAAAAATTGATTATTGTG
CTAACACGTGAAAAAAATTTATATTTAATTTTTTTATGTATAATTTGTTTGGACCAAT
GATAGAGATTAATTGTGATCTAATGAGTTATAAGAAATACGTGGCACATGATCCTA
GACAAAAATAAATAAGAATTGTAAAATAATGTATTTTATAGCTTTTCTGAAAGATTTT
TTTTTTTAATTTCTTCATGCCCATACATGAATACATGAATGAGAATTTTTATTTTT
ATTTTTTTGTCTGAAATAAAGTTAAAAATTGGGAGCAGTGAATGTTAAGGATGACTT
TTGACTTGAATGCAACAAGAAGTAAAGTTCACTTTAAGTTGGAGGCTTGGAGCATC
GCCATCCATAACACAACACAATCGACAATCCTAATGGTTCCGACAAAGCTCGACCT
GAGTGTGATCTCATGATGTTTCTGCTCTAACTATGTTTGATTTGGATACCCAACAA
CAAAAAGAGTGTTGTCGTGTTGTTGTAGTTAATAGTAATAGGACTAAGTAAGAGTA
GTGGAAAAC

SEQ ID NO: 32: CDS

ATGAACAACAGCAGTGGCGGAGGAGGACGAGGAACTTTGATGGGTTTGAGTAAT
GGGTATTGTGGAGGTCGCCATTCACAGTGTCTCAGTGGCAGGAACTGGAGCAC
CAAGCTTTGATCTTCAAGTACATGCTTGCGGGTCTTCCTGTTCCTCTCGATCTCGT
GTTCCCCATTCAGAACAGCTTCCACTCTACTATCTCGCTCTCGCACGCTTTCTTTC
ACCATCCCACGTTGAGTTACTGTTCCTTCTATGGGAAGAAGGTGGACCCTGAGCC
AGGACGATGCAGGAGGACTGATGGAAAAAAGTGGAGGTGCTCCAAGGAAGCATA
CCCAGACTCCAAGTACTGCGAGCGCCACATGCACCGTGGCCGCAACCGTTCAAG

AAAGCCTGTGGAATCACAAACTATGACTCACTCATCTTCAACTGTCACATCACTCA
CTGTCACTGGGGGTAGTGGTGCCAGCAAAGGAACTGTAAATTTCCAAAACCTTTC
TACAAATACCTTTGGTAATCTCCAGGGTACCGATTCTGGAACTGACCACACCAATT
ATCATCTAGATTCCATTCCCTATGCGATTCCAAGTAAAGAATACAGGTATGTTCAA
GGACTTAAATCTGAGGGTGGTGAGCACTGCTTTTTTTCTGAAGCTTCTGGAAGCAA
CAAGGTTCTCCAAATGGAGTCACAGCTGGAAAACACATGGCCTTTGATGTCAACC
AGAGTTGCCTCTTTTTCTACGTCAAAATCAAGTAATGATTCCCTGTTGCATAGTGAT
TATCCCCGGCATTCGTTTTATCTGGTGAATATGTGTCGGGAGAACACGTAAAGGA
GGAGGGCCAGCCTCTTCGACCTTTTTTTAATGAATGGCCTAAAAGCAGGGAGTCA
TGGTCTGGTCTAGAAGATGAGAGATCCAACCAAACAGCCTTCTCCACAACTCAAC
TCTCAATATCCATTCCTATGTCTTCCAATTTCTCTGCAACGAGCTCTCAGTCCCCA
CATGGTGAAGATGAGATTCAATTTAGGTAA (miR396 recognition site is highlighted in bold)

SEQ ID NO: 33: amino acid sequence

MNNSSGGGGRGTLMGLSNGYCGRSPFTVSQWQELEHQALIFKYMLAGLPVPLDLVF
PIQNSFHSTISLSHAFFHHPTLSYCSFYGKKVDPEPGRCRRTDGKKWRCSKEAYPDS
KYCERHMHRGRNRSRKPVESQTMTHSSSTVTSLTVTGGSGASKGTVNFQNLSTNTF
GNLQGTDSGTDHTNYHLDSIPYAIPSKEYRYVQGLKSEGGEHCFFSEASGSNKVLQM
ESQLENTWPLMSTRVASFSTSKSSNDSLLHSDYPRHSFLSGEYVSGEHVKEEGQPLR
PFFNEWPKSRESWSGLEDERSNQTAFSTTQLSISIPMSSNFSATSSQSPHGEDEIQF
R*

*Brassica napus*

SEQ ID NO: 34: BnaA03g16700D: 2 kb promoter

CATACCTTCAGGATGTGTGAAGCATTCCTATTGAATTTTGTCGATAAAATAGAAATT
GCAAGTTGAACAAATTGCAATATATATGGAAAGATGCTAGCTAGTGCCAATAATAT
ATTAACGGAACAATTCATATTTCATTTTATATTATATAATGATTATTTTAGTTTTTAGT
TAATACTAATAAATAATAAGAAATATAACTACATAGTTTAAAATGATAGTGTGTTCTA
AATTTGTTAAATGGATATCTAAATCAGTTTAGGTGGCTTTTAAATGTTATTTTATGTT
CATGTAAATTAATTATTGTTTTACATTTAACATTGTATTACTTTTTATCATATTAGTTA
ATTAATGACACTCGTTTTCATTCTAAAATCAAATATCAGACATATTCATCTTTATAA
CAATATGAAAATTAATTTTCAGTATTAATCTAAAAAATCTATTTAAATTTTGATGCGT
CTGACTTATAAAAACACACACATATATATATATATATATGTATATATTTTATTAATT
AGTAAAATTTATTTTAAGAAAAATTGAAACTAATTAAATTTTGGGAAAGTAGTGATTA
TATAATAGTTTTGTTATTTTATATGCTAAAATTTATTAAGTACTTTTTTTTTAATTTG
AGACTTACCAAATTACGGATCCTAAATATATTGATCTTGAATTATGATATATTAATTA
AATTTTAAAGTTATCATAAATTTGTTGTGAATTCAGTTTAGGTAATTGTCTATTAAAT
TAGAAAAAAGATAAATAATGATAAAGTTATGTTAGTTATTAGTTTAATAGTATTGAG
GTGTAAATAAATTAAAGTTGTAATGGTTAATTTATAAGTGTATTTGTGTTTTAATTAT
ATTAGATTTCAATTGATTCCACAGATAATTCAACATGTTCCATGTAATTAATGTTACA
GCAGAAATCTAGATAAATTTTTTTTTTAACACTGGATAATGCGATTATAAACGATAA
GACGATTCTATATGCGACATGTCTTATAATGATTCATGTCTGAATACATCATTTGAA
CCGTTTTATAAGATCTACGTTTGGTGGTATTTTTTGTGCTATGCTGCAGATTTTTTA
TAAGTATTTATTTCATTAATTCGCATAATTTTATTTTTTTTCTAAAGATCGAAACTCC
GATTTTTATGGTGTTGAACATCTAGATAGAGATCTATGGATAAAACAAATATAGAGG
AAGCTACACAATTTAAAGGGTCAAAATAGAAACACAGAACTGAAAAGTATACTCAG
TGCCATATGATTTAATAGTATGAATTTAACTTGAACTTAATGTCGTTTGGTTTGTCA
TCAAATGCAACTGCAAATCATATCGAAGTAACGCCCGTGTCATAATATATCTGATT
AAGGACTATTATTTTCTGTTTGACAAAAAAAAAGGACTATTATTTTCTCACTAATCA
GGCTATTGTTTTTTTCTCAATAAACTAATTTAAAGAAATACAGATTATTCAAGTGCTA
TTTCCAAGGCAGATGCAGGTTACTATCTCTCGATCTTCATCTCGGAGTGTGGTTCT
TTATGTGTTTTCTGACTTGCTTTATTATACTAATATTATTAATAGATTAATGAAGATT
AATAGTTTAATAGATTAATGAAGACATAAACTATAATTTAATAATCATAGATTAATGA
AGATTTGTGAACCCCATTAATAAAGTTTAATAGTTGTTGTTCTTTATAGTCTTTTACC
GTATAGTTTTCTCCCCCCATCTGTCTCGTCTCACTGTCTTTTCCTCTCAAGTTTCAA
GTGCCCTAAATAAAAACCTCTTTCCCCTTCTCTCTCTGCAGAAGAAGGTCAGAT
ACAGAAACTGACTGCAAAGAACAAAGCTGCAAGGTGCAGCTATTCCTTAGTAAAAA
GCTTTGTTCTCTTTCTTCTTTTGCTCTTCACATCCCCCCCAACAGAGACTTTTCTGC
TATTTAAAACCAGACCCTGGAAAAAGTAGCCAACACTCTCTCTTTCCC

SEQ ID NO: 35: CDS

ATGGATTTGCAACTGAAACAATGGAGGAGCAAGCAGGTGCAGACAGAGTCAGAAC
CACAACCTTCTGCAGCTAAGATACCAAGACATGCCTTTGATCCGATTCAGTCCCAA
ACTGCAACTTCTACTGTTCTTCCACTCTTTGCCCCTGAACCTGCGTCTTCTAAACT
CTCCTCCTTATGTCCTGATTCTTCTTCCAGGTTCTCCAAGATGGGGAGTTTCTTTA
GCTCGGCACAGTGGCAAGAGCTTGAACTACAGGCACTGATCTACAGGTACATGCT
GGCTGGAGCTGCTGTTCCACAAGAGCTCCTTCTACCAATCAAGAAAAGTCTTCTC
CATCTATCTCCTTCCTACTTTCTTCACCACCTACCTCATTACCAGCCTGCTTGGTAT
TTGGGGAGGGGGCGATGGATCCTGAGCCAGGGAGATGCAGGAGAACGGATGG
TAAGAAGTGGAGATGTTCAAGGGACGTCTTCGCTGGCCACAAGTACTGCGAGCG

```
CCACATGCACCGAGGCCGCAACCGTTCAAGAAAGCCTGTGGAAACTCCCATAGT
CAATGCTACCACCACCACTTCCATGGCTTCCCCAGCCACAGCGGCACCGTCATCA
ACACCATCCTCCTTTGCTTTTGGCGGTGGTGAGAAAGTGGGTCAAGGTGGATCAT
CTAGCTTCTTCTTCTCAAGTCAAAGTTGTTCAGAGATGAAACAAGAAAGCAACAAC
AACAAGAGGCCATACGAGTCCCATAATGGATTTGGGAGCAATGGATCAGACGGAG
GCCACATCTTGAGGCACTTCTTTGATGATTGGCCTCGTTCTGAAGCCGACAATAGT
TCAAGCCCCATGAGCTCAGCCACTTGTCTCTCCATCTCTATGCCTGGAAACTCTTC
CTCAGACGTCTCTCTGAAGCTGTCCACTGGTAATGAAGAGGAAGCTAGGAGCAAC
AACATTGGGAGGGACCAGCAAAACATGAGCTGGTGGAGCGGTGGAGGTACCAAC
CACAACCACCATCACATGGGAGGACCATTGGCTGAAGCCCTGAGATCTTCCTCAT
CATCTTCCCCGACCAGTGTTCTCCATCAGCTCGGTGTTTCAACGCAAGCCTTTCAT
TGA
```

(miR396 recognition site is highlighted in bold)

SEQ ID NO: 36: amino acid sequence

```
MDLQLKQWRSKQVQTESEPQPSAAKIPRHAFDPIQSQTATSTVLPLFAPEPASSKLSS
LCPDSSSRFSKMGSFFSSAQWQELELQALIYRYMLAGAAVPQELLLPIKKSLLHLSPS
YFLHHLPHYQPAVVYLGRGAMDPEPGRCRRTDGKKWRCSRDVFAGHKYCERHMHR
GRNRSRKPVETPIVNATTTTSMASPATAAPSSTPSSFAFGGGEKVGQGGSSSFFFSS
QSCSEMKQESNNNKRPYESHNGFGSNGSDGGHILRHFFDDWPRSEADNSSSPMSS
ATCLSISMPGNSSSDVSLKLSTGNEEEARSNNIGRDQQNMSVWVSGGGTNHNHHHM
GGPLAEALRSSSSSSPTSVLHQLGVSTQAFH*
```

*Solanum lycopersicum*

SEQ ID NO: 37: Solyc08g075950; 2 kb promoter

```
CATTTAATTAGTTAAATCAAATACATACATATATAATTGTTATTAATTTTTAGGTATG
ATGTACCATTAAGACTAAGAAGATCAGTGATGACGCAACGTATTTCAATTTTTTGT
GGGTTAAGTATATGTCTTAAACTTAACATAGATTTAAAATTATTTAAATTGTTAATAC
CTAAAGTTTATTTTTATTTTCATTTTTGAAAGAACAATAATTCAAGTGGGTAATTGAC
AAATTATTTTGAATATAAAAAAAATGAAAAACAGAGAAAAAAAACATTAGTAAAATC
ATTAAATTACACCAAACAAATTTGGAGAATTGAAAAAGAACATTTATAACAACTCTA
ATATAAATAAAAAGAAAATTAAATTACAAAAGTTTTTTTTAAAAAAAATAAAGGGTTA
GTTTAGTCATTTAGGAATCTTATCCGAGGTTTAACAAATTTTGAATTAGTTATCCCT
CCATTTCGAAGGGATAAGATAATACTAGATATGATGGATAAGCAATCCATGAGTTA
AATTAAATGAAGTAACCAAAACAATGTATTAGTTGAATTAAATTTTAATCCATAAATT
ATTCTACCTAATATTGTCTATCAAACGGGTCCTTAGTATTAGTTAACTGGTGACGA
GGATCATATAATTTAAAGAGTTGGGTCCAGTTTTAAAGCGTGATTATAGCGAAATG
AAATGTTTCTTATCCCACCAAAAATTTGATTATAAAACGAAAATGACTCTCGTTGAG
AAAAGAAAATTTACAAATGATATTCATCCTCCCGTAATTCTCATATAATTTGTTTTTG
ATGTACATGAATATTTTTTAAAATAGTTTTTTTAGTTTTTACAAAAATATATAATCTCA
CTCAACACAAACTCGTTAGGAATTAAATTAAACTTTTGTGTTGATCAACATAAGTCG
CATAACTTATGAGTTTTGATATCGAACTTTGTCGGACTGGATATAAATTAGAAAACA
GAGTCATGAAATACTTAATATAAGTCACATAATTTATGAATTTTGATATTAGACTTTG
TCTTGCTCGAAACAAGTTTTGAATAAAAAAAATTATGCAATACGACATAACTAATGA
GATTAATCACATTTGCATTATTCAAGACTCATAAATACAAAATTTCTAAATTGAGTAA
TCTCATCTATGTCATCTGTTCACATACAAAACTAAAAACTATCTATGCCACCACACT
TCTTGATGATGTGTTGGAGCTTATTTCTCAAGATATTTCACATTCTTGCTCAAACAA
AAAGCACAAAGTTTCAAAAAGTAAAAAAAAAAAGAGAGAAAAACAATCATATATATA
TATATATATCAAACTAGAATAAGATCTTTTGTAGGTCATCTTAATTATTGTTGAACCT
TAAAGGACAAAGTTTACATCTTTAGGGTCATGATACATTCACATGACTAAATTTTGA
AAGATATAAAAAGAGGTGTTACATCATTTGGACCACAATAAGACATTATCCATTCTA
CCCCACTCCATAAGGTCCCCCTTCTTTCAATCCCCTTTTCTCCCCCCCATGCCCCA
ATGCTTCCTTAAACCCTTCATTATCTTTCACAAAACTTATACTATAATGTCATCATTC
ATATTGTTATTGTCATTTATTCTTCTCACCATAAAGTTCAATGTAAGTTTGTTAATTT
TGTCTTGTACATTAATAAGTACTAGTGTTATGAATGTTTCTTGATTTCACTCTAATTA
AATCTCACTCTCTTTCTTCAGCTTTTATCTCTCTGCTCTTTCTTCCATGCTTGTCCA
AACCCTAGATCTGTCCCCCTCTTAGGTAACCTCAACAAACTTTGCTCTCTATAACT
CACACACAACACACAAAAACACATTCTTTTTCTCTTTCTCTGTGTATATGTTTGTAT
ATTAACTGATATTGTGTTGATTTCTAGGTGCAGCTTTTTGAGTGAAGTGAAAAAGG
GGAAAGGGGGTGGGTAAAATTTGGAAAGATTAGTTTTTTAGTGAAGGGAGAAG
```

SEQ ID NO: 38: CDS

```
ATGAGTGGCACCTCTACATCAGTAGTGGGGGTGGGGGTGGAGGGGAGGGGGG
AATGGGGTATGGGTATGGTTACCGGCCGCCATTTACGGCGGTGCAATGGCAGGA
GCTGGAGCATCAAGCAATGATATACAAGTACTTGGTGGCAGGTCTTCCTGTGCCA
CCTGATCTTGTTGTCCCTATTCGTCGTAGCTTTGAAGCCATCTCAGCTAGGTTCTT
TCATCATCCAAGCTTGGGCTATTGTTCCTATTATGGGAAGAAGTTTGATCCTGAGC
CAGGAAGGTGTAGAAGGACTGACGGAAAAAAGTGGAGATGCTCAAAGATGCATA
TCCTGACTCCAAATATTGCGAGCGGCACATGCATCGAGGCCGCAACCGTTCAAG
AAAGCCTGTGGAATCTCAATCTACTCCCCAGTCCTTGTCGACTAGTATGTCACAA
ATTACAGCTGGGAGCAGCAATACAAGAGGAAGTTTCCAAAATAGCAGCAGCGGAA
```

```
GCTTCCAAAACATGCCATTGTATTCTGTTGCTAATTCGGGAACGCTGAATTATGGA
AGCACTGGAACAAAGCTGCAGATGGAGCCTGTCTCCTATGGAATAGATAACAAGG
ACTATAGGTATCTCCATGGAATTACTCCTGATGCTGATGAGCACAATTTATCTTCA
GAGGCTTCTGCTACTGTCAGAAGTTTAGGGATGAGGACCAACACAGACAGTACCT
GGGTATTGCCTTCTCAAATTTCTTCAAGCCCCATGGCAAGATCAAAAAATGATTCT
CAGCTGCTAGGTAGCTCAACAGAGATGCATCTACCTAATCTACTTGAGCCTATGAT
TGATGCAACAATTTCAAAACGACGACACCAGCATTGCTTCTTTGGCAGTGACATCG
ATTCACCTGGAACAGTAAAGGAGGAGCAGCATTCAATGCGCCCTTTCTTTAACGA
ATGGCCCACTGCTAAAGAATCGTGGTCCAACCTCGACGATGAGGGATCCAACAAA
AACAATTTCTCCACAACACAGCTCTCCATGTCCATTCCAATCGCTCCTTCCAACTT
CTCTTCAAGGAGTGCTTGCTCTCCAAATGATACTTGA
```

(miR396 recognition site is highlighted in bold)

SEQ ID NO: 39: amino acid sequence

```
MSGTSTSVVGGGGGEGGMGYGYGYRPPFTAVQWQELEHQAMIYKYLVAGLPVPP
DLVVPIRRSFEAISARFFHHPSLGYCSYYGKKFDPEPGRCRRTDGKKWRCSKDAYPD
SKYCERHMHRGRNRSRKPVESQSTPQSLSTSMSQITAGSSNTRGSFQNSSSGSFQN
MPLYSVANSGTLNYGSTGTKLQMEPVSYGIDNKDYRYLHGITPDADEHNLSSEASAT
VRSLGMRTNTDSTVVVLPSQISSSPMARSKNDSQLLGSSTEMHLPNLLEPMIDATISKR
RHQHCFFGSDIDSPGTVKEEQHSMRPFFNEWPTAKESWSNLDDEGSNKNNFSTTQL
SMSIPIAPSNFSSRSACSPNDT*
```

SEQ ID NO: 40: p35S promoter

```
aattcccatggagtcaaagattcaaatagaggacctaacagaactcgccgtaaaga ctggcgaacagttcatacagagtctcttacgactcaatgacaagaagaaaatcttc gtcaacatggtggagcacgacacgcttgtctactccaaaaatatcaaagatacagt ctcagaagaccaaagggcaattgagacttttcaacaaagggtaatatccggaaacc tcctcggattccattgcccagctatctgtcactttattgtgaagatagtggaaaag gaaggtggctcctacaaatgccatcattgcgataaaggaaaggccatcgttgaaga tgcctctgccgacagtggtcccaaagatggacccccacccacgaggagcatcgtgg aaaaagaagacgttccaaccacgtcttcaaagcaagtggattgatgtgatatctcc actgacgtaagggatgacgcacaatcccactatccttcgcaagacccttcctctat ataaggaagttcatttcatttggagaggacagggtac
```

SEQ ID NO: 41 pUbi promoter
```
CTGCAGTGCAGCGTGACCCGGTCGTGCCCCTCTCTAGAGATAATGAGCATTGCAT
GTCTAAGTTATAAAAAATTACCACATATTTTTTTGTCACACTTGTTTGAAGTGCAG
TTTATCTATCTTTATACATATATTTAAACTTTACTCTACGAATAATATAATCTATAGTA
CTACAATAATATCAGTGTTTTAGAGAATCATATAAATGAACAGTTAGACATGGTCTA
AAGGACAATTGAGTATTTTGACAACAGGACTCTACAGTTTTATCTTTTTAGTGTGCA
TGTGTTCTCCTTTTTTTTTGCAAATAGCTTCACCTATATAATACTTCATCCATTTTAT
TAGTACATCCATTTAGGGTTTAGGGTTAATGGTTTTTATAGACTAATTTTTTTAGTA
CATCTATTTTATTCTATTTTAGCCTCTAAATTAAGAAAACTAAAACTCTATTTTAGTT
TTTTTATTTAATAATTTAGATATAAAATAGAATAAAATAAAGTGACTAAAAATTAAAC
AAATACCCTTTAAGAAATTAAAAAAACTAAGGAAACATTTTTCTTGTTTCGAGTAGA
TAATGCCAGCCTGTTAAACGCCGTCGACGAGTCTAACGGACACCAACCAGCGAAC
CAGCAGCGTCGCGTCGGGCCAAGCGAAGCAGACGGCACGGCATCTCTGTCGCT
GCCTCTGGACCCCTCTCGAGAGTTCCGCTCCACCGTTGGACTTGCTCCGCTGTC
GGCATCCAGAAATGCGTGGCGGAGCGGCAGACGTGAGCCGGCACGGCAGGCGG
CCTCCTCCTCCTCTCACGGCACGGCAGCTACGGGGGATTCCTTTCCCACCGCTC
CTTCGCTTTCCCTTCCTCGCCCGCCGTAATAAATAGACACCCCCTCCACACCCTCT
TTCCCCAACCTCGTGTTGTTCGGAGCGCACACACACACAACCAGATCTCCCCCAA
ATCCACCCGTCGGCACCTCCGCTTCAAGGTACGCCGCTCGTCCTCCCCCCCCCC
CCCTCTCTACCTTCTCTAGATCGGCGTTCCGGTCCATGGTAGGGCCCGGTAGTT
CTACTTCTGTTCATGTTTGTGTTAGATCCGTGTTTGTGTTAGATCCGTGCTGCTAG
CGTTCGTACACGGATGCGACCTGTACGTCAGACGTTCTGATTGCTAACTTGCC
AGTGTTTCTCTTTGGGGAATCCTGGGATGGCTCTAGCCGTTCCGCAGACGGGATC
GATTTCATGATTTTTTTGTTTCGTTGCATAGGGTTTGGTTTGCCCTTTTCCTTTATT
TCAATATATGCCGTGCACTTGTTTGTCGGGTCATCTTTTCATGCTTTTTTTTGTCTT
GGTTGTGATGATGTGGTCTGGTTGGGCGGTCGTTCTAGATCGGAGTAGAATTCTG
TTTCAAACTACCTGGTGGATTTATTAATTTTGGATCTGTATGTGTGTGCCATACATA
TTCATAGTTACGAATTGAAGATGATGGATGGAAATATCGATCTAGGATAGGTATAC
ATGTTGATGCGGGTTTTACTGATGCATATACAGAGATGCTTTTTGTTCGCTTGGTT
GTGATGATGTGGTGTGGTTGGGCGGTCGTTCATTCGTTCTAGATCGGAGTAGAAT
```

ACTGTTTCAAACTACCTGGTGTATTTATTAATTTTGGAACTGTATGTGTGTCATA
CATCTTCATAGTTACGAGTTTAAGATGGATGGAAATATCGATCTAGGATAGGTATA
CATGTTGATGTGGGTTTTACTGATGCATATACATGATGGCATATGCAGCATCTATT
CATATGCTCTAACCTTGAGTACCTATCTATTATAATAAACAAGTATGTTTTATAATTA
TTTTGATCTTGATATACTTGGATGATGGCATATGCAGCAGCTATATGTGGATTTTTT
TAGCCCTGCCTTCATACGCTATTTATTTGCTTGGTACTGTTTCTTTTGTCGATGCTC
ACCCTGTTGTTTGGTGTTACTTCTGCAG

SEQ ID NO: 42: Cas 9 nucleic acid

GTCACCCCCAAGCTGTGACAAATCTATCCGAGTTTCATATAATCCCGTGATGGATT
GGTGAATCAGTGTCGCGTCTAGCACCTCCTTGGTAGAAGTGTATCGTTTGCGATC
TATCGTTGTGTCAAATACTTGAATGCGGCTGGAGCGCCGAGGTTGGTAAGAGTA
AACAAATGGATAATATTTTCCGCCTGCTCACGTATGGGTTTATCCCTGTGCTTGTT
GTATGCGCTTAATACTTTGTCCAGATTGGCATCAGCTAGGATGACTCTCTTACTGA
ATTCCGAAATTTGCTCTATGATTTCGTCGAGATAATGTTTGTGCTGCTCAACAAAA
GTTGCTTCTGTTCGTTATCTTCAGGTGAACCTTTCAACTTCTCGTAATGGGACGCT
AAATACAGGAAATTCACGTATTTAGACGGTAGTGCGAGTTCGTTCCCCTTTTGAAG
CTCTCCGGCGCTAGCCAACATCCGTTTTCGGCCATTTTCTAACTCAAACAGACTAT
ACTTTGGTAGTTTAATTATGAGATCCTTTTTTACTTCCTTGTAACCTTTCGCCTCAA
GGAAGTCGATGGGGTTCTTTTCAAAGACGAGCGCTCCATAATCGTTATCCCCAA
TAATTCTTTGACTGACTTCAGTTTCTTGGATTTTCCCTTCTCAACTTTTGCCACTAC
TAGGACAGAATAGGCAACTGTAGGGCTATCGAAGCCACCGTACTTTTTCGGGTCC
CAGTCCTTTTTACGAGCGATGAGCTTATCACTATTCCTTTTTGGAAGAATCGATTC
CTTTGAAAACCCTCCGGTCTGCACCTCAGTTTTCTTTACTATGTTGACTTGGGGCA
TGGACAAAACTTTTCTCACCGTCGCGAAGTCCCGGCCCTTATCCCATACGATTTCA
CCTGTCTCCCATTGGTTTCAATTAAAGGTCGTTTGCGTATCTCTCCGTTTGCCAG
AGTGATTTCCGTCTTAAAGAAATTCATAATGTTAGAATAAAAGAAGTATTTGGCTGT
AGCCTTGCCTATCTCCTGTTCGCTTTTCGCGATCATCTTACGGACGTCATAAACTT
TGTAATCACCATACACAAACTCACTTTCTAGCTTCGGGTATTTCTTAATGAGTGCG
GTCCCTACGACGGCATTAAGATAAGCGTCGTGCGCATGGTGGTAGTTATTTATCT
CCCTAACTTTATAGAATTGAAAATCCTTTCTGAAGTCCGACACCAATTTTGACTTTA
AAGTGATTACTTTGACTTCCCGAATCAGCTTATCGTTCTCGTCGTATTTCGTATTCA
TTCGGGAATCTAGTATCTGTGCAACATGCTTTGTGATTTGGCGGGTTTCCACGAG
CTGACGTTTAATAAATCCGGCCTTGTCAAGTTCAGACAAGCCACCCCTCTCAGCTT
TAGTTAAGTTATCGAACTTTCTTTGCGTTATCAGTTTCGCATTTAGGAGCTGCCGC
CAATAGTTCTTCATTTTCTTTACGACTTCCTCGCTTGGAACATTGTCACTTTTCCCT
CGGTTCTTATCCGAGCGTGTAAGCACTTTATTGTCGATTGAATCGTCCTTCAAAAA
GGATTGGGGTACAATGTGATCGACGTCGTAATCAGATAAACGGTTTATGTCCAGTT
CCTGATCAACATACATGTCCCTTCCATTTTGTAGGTAATAGAGGTAAAGTTTCTCG
TTCTGCAATTGGGTATTTTCCACAGGATGCTCCTTTAAGATCTGGCTGCCCAGTTC
TTTAATACCCTCTTCTATTCTCTTCATCCGCTCTCGACTGTTTTTTTGCCCCTTCTG
AGTCGTTTGATTTTCGCGTGCCATCTCGATTACAATGTTTTCCGGTTTGTGACGTC
CCATGACCTTAACTAGCTCATCCACTACTTTGACTGTCTGGAGTGATGCCCTTTTTG
ATGGCTGGCGAACCAGCAAGATTCGCAATATGTTCGTGCAATGAGTCCCCTTGTC
CGGAAACCTGTGCCTTTTGTATATCCTCTTTGAAGGTTAAAGAGTCATCATGGATC
AGCTGCATAAAGTTCCTATTGGCGAAGCCGTCGCTCTTTAGAAAATCGAGAATAGT
TTTACCACTTTGCTTGTCTCTTATCCCGTTGATAAGTTTCCGCGACAATCGTCCCC
AGCCCGTATAGCGACGCCTCTTTAACTGTTTCATAACCTTATCGTCGAACAGGTGA
GCGTATGTTTTTAGTCTTTCCTCAATCATTTCCCGATCTTCAAAGAGGGTAAGAGT
CAACACTATATCTTCTAAGATATCTTCATTCTCTTCGTTATCCAGGAAGTCCTTATC
TTTAATTATCTTTAGGAGGTCATGATACGTACCAAGTGACGCATTAAATCGATCTTC
TACCCCGGAGATCTCGACAGAATCGAAGCATTCAATTTTCTTAAAGTAGTCCTCTT
TCAATTGCTTAACTGTCACTTTGCGGTTGGTCTTGAATAACAGATCTACTATTGCTT
TCTTCTGTTCTCCGCTTAGAAAGGCGGGTTTACGCATGCCCTCAGTGACATACTTA
ACTTTCGTGAGTTCATTGTACACTGTGAAATACTCGTAAAGTAAACTGTGCTTAGG
CAATACTTTTTCGTTCGGTAAATTCTTGTCAAAGTTGGTCATCCTCTCGATGAACGA
TTGAGCTGACGCACCTTTATCGACAACTTCCTCAAAATTCCATGGAGTAATCGTTT
CTTCGGACTTTCTTGTCATCCATGCGAACCGAGAGTTCCCTCGGGCCAGGGGTCC
CACATAGTAAGGTATGCGAAAGGTTAGGATTTTCTCAATCTTTTCACGATTGTCTTT
GAGGAACGGATAAAAATCCTCCTGCCTTCTAAGTATAGCATGCAATTCGCCTAAGT
GGATTTGATGTGGAATGCTACCGTTGTCGAAAGTCCGCTGCTTTCGCAGTAGATC
TTCGCGATTGAGTTTTACAAGCAACTCTTCCGTCCCATCCATCTTCTCTAATATGG
GTTTGATAAACTTGTAGAATTCCTCTTGACTCGCTCCGCCGTCAATATAACCTGCG
TACCCGTTTTTCGACTGATCAAAGAATATTTCCTTATATTTCTCAGGCAGTTGCTGA
CGGACTAGGGCCTTGAGAAGTGTCAAGTCTTGGTGATGTTCATCGTACCTTTTGAT
CATTGAAGCGGATAACGGCGCCTTGGTAATCTCAGTATTAACTCTCAGTATGTCAG
ATAGGAGGATTGCATCGCTAAGGTTTTTGGCAGCCAAAAATAAGTCCGCATACTG
ATCTCCAATTTGTGCCAGTAGATTGTCGAGATCGTCATCGTACGTGTCCTTACTAA
GCTGCAATTTGGCATCTTCAGCTAAGTCGAAGTTCGACTTAAAATTTGGTGTCAGG
CCTAGTGAGAGCGCTATAAGGTTACCGAACAACCCATTTTTCTTCTCTCCGGGTAA
TTGTGCGATCAGGTTTTCTAGCCGTCGGGATTTAGAGAGGCGGGCGCTAAGAATA
GCCTTCGCATCCACGCCACTTGCATTTATAGGGTTCTCTTCAAACAACTGATTATA
GGTTTGTACTAACTGGATGAACAGTTTGTCGACATCCGAGTTGTCCGGATTTAGAT
CACCCTCAATGAGAAAGTGCCCACGGAACTTTATCATATGGGCAAGAGCCAAGTA
GATTAACCTCAGGTCCGCTTTATCAGTTGAGTCAACTAGCTTTTTTCTGAGGTGAT

```
AAATCGTTGGGTACTTTTCATGATATGCCACCTCATCTACTATGTTTCCAAAGATG
GGGTGCCGTTCATGTTTCTTGTCCTCTTCGACAAGGAAGGACTCTTCCAAACGGT
GAAAGAAAGAATCGTCAACTTTGGCCATCTCATTGCTAAAAATTTCTTGTAAGTAAC
ATATTCGGTTCTTGCGACGTGTATACCTTCTCCGAGCGGTTCGTTTCAGGCGAGT
CGCCTCTGCCGTTTCGCCACTATCGAATAGGAGGGCACCGATAAGATTCTTTTTAA
TCGAATGACGGTCTGTGTTCCCCAACACCTTAAATTTCTTTGAAGGTACTTTGTATT
CATCGGTTATGACAGCCCATCCAACGGAATTAGTGCCGATGGCTAAACCAATAGA
ATACTTTTTATC
```

SEQ ID NO: 43; Cys 4 endoribonuclease nucleic acid sequence

```
5'ATGGACCACTACCTCGACATCAGGCTCAGGCCAGACCCAGAGTTCCCACCAGC
CCAGCTCATGTCCGTCCTCTTCGGCAAGCTCCACCAGGCCCTCGTGGCCCAGGG
CGGCGACAGGATCGGCGTGTCCTTCCCAGACCTCGACGAGTCCAGGTCCAGGCT
CGGCGAGAGGCTCCGCATCCACGCCTCCGCCGACGACCTCAGGGCCCTCCTCG
CCAGGCCGTGGCTGGAGGGCCTCAGGGACCACCTCCAGTTCGGCGAGCCAGCC
GTGGTGCCACACCCAACCCCATACAGGCAAGTGTCCAGGGTGCAAGCCAAGTCC
AACCCAGAGAGGCTCAGGAGGAGGCTCATGAGGAGGCACGACCTCTCCGAGGAA
GAGGCCAGGAAGCGCATCCCAGACACCGTGGCCAGGGCCCTCGACCTCCCATTC
GTGACCCTCAGGTCCCAGTCCACCGGCCAGCACTTCCGCCTCTTCATCAGGCAC
GGCCCACTCCAGGTGACCGCCGAGGAGGGCGGCTTTACCTGCTACGGCCTCTCC
AAGGGCGGCTTCGTGCCGTGGTTC
```

CRISPR constructs

SEQ ID NO: 46; tracrRNA nucleic acid sequence

```
GTTTTAGAGCTAGAAATAGCAAGTTAAAATAAGGCTAGTCCGTTATCAACTTGAAA
AAGTGGCACCGAGTCGGTGCTTTTTTT
```

Rice

Information for gain of function mutant g.1187-1188 TC>AA (mutation at the miRNA396 binding site)

SEQ ID NO: 47: a repair template sequence for introduction of the correct SNP

```
CCGCGCCGGATTCCAAGTACTGCGAGCGCCACATGCACCGCGGCCGCAACCGTA
AAAGAAAGCCTGTGGAAACGCAGCTGGTCGCCCAGTCCCAACCGCCCTC
```

SEQ ID NO: 48: donor DNA sequence for introduction of the correct SNP

```
GAAATGGCGGTGCTCGAAGGAGGACGGTTGCTACGATGTGCCTGTTTTTGTACAG
TTGGATATGGTCCGTACTTCGGCAAGAAGCTGGACCCAGAGCCAGGGCGGTGCC
GGCGTACGGACGGCAAGAAATGGCGGTGCTCGAAGGAAGCCGCGCCGGATTCC
AAGTACTGCGAGCGCCACATGCACCGCGGCCGCAACCGTAAAAGAAAGCCTGTG
GAAACGCAGCTGGTCGCCCAGTCCCAACCGCCCTCATCTGTTGTCGGTTCTGCG
GCAGCGCCCTTGCTGCTGCCTCCAATGGCAGCAGCTTCCAAAACCACTCTCTTT
ACCCTGCTATTGCCGGCAGCAATGGCGGGGGCGGGGGAGGAACATGCCATCT
GTTGTCGGTTCTGCGGCGG
```

SEQ ID NO: 49: target 1 target sequence:

GAAATGGCGGTGCTCGAAGGAGG

SEQ ID NO: 50: target 1 protospacer sequence:

GAAATGGCGGTGCTCGAAGG

SEQ ID NO: 51: target 1 complete sgRNA nucleic acid sequence:

```
GAAATGGCGGTGCTCGAAGGGTTTTAGAGCTAGAAATAGCAAGTTAAAATAAGGC
TAGTCCGTTATCAACTTGAAAAGTGGCACCGAGTCGGTGCTTTTTTT
```

SEQ ID NO: 52: target 2 target sequence:

ATCTGTTGTCGGTTCTGCGGCGG

SEQ ID NO: 53: target 2 protospacer sequence:

ATCTGTTGTCGGTTCTGCGG

SEQUENCE LISTING

SEQ ID NO: 54: target 2 complete sgRNA nucleic acid sequence:
ATCTGTTGTCGGTTCTGCGGGTTTTAGAGCTAGAAATAGCAAGTTAAAATAAGGCT
AGTCCGTTATCAACTTGAAAAAGTGGCACCGAGTCGGTGCTTTTTTT

Information for repairing promoter in Hap.A/C -884 T>A

SEQ ID NO: 55: a repair template sequence for introduction of the correct SNP

CTAAGTTTAGTTTCAAACTTTTCCTTCAAACATACAGCTTTTTTATCACATTAAAACT
TTCCTACATACAAACTTTCAACTTTTCCATCACATCTTTTAATTTCAACCAAACTTCT
AATTTTAACGTGAACTAAAAACACCCTGAATTCAAAACTCTTTTTATTTTCCTTCAAG
ATGTCCGATGCACACGCTCT

SEQ ID NO: 56: donor DNA sequence for introduction of the correct SNP

ATCTCTATGGAGTAGTACCGAGGCCATGGATAAAATGTAATTTCTATGCATACAAC
TAAATTATCGATGGCAACAGTGCATGAGCATATATTTATTTCATTGACCTACGGTTG
CATGTCTTCGATCTCTATGGAGTAGTACCGATTCTAAGTTTAGTTTCAAACTTTTCC
TTCAAACATACAGCTTTTTTATCACATTAAAACTTTCCTACATACAAACTTTCAACTT
TTCCATCACATCTTTTAATTTCAACCAAACTTCTAATTTTAACGTGAACTAAAAACAC
CCTGAATTCAAAACTCTTTTTATTTTCCTTCAAGATGTCCGATGCACACGCTCTATG
TAGACGCAAGAAGATGTTAAAGCAGCAGACTAACAGTAGCAAAAAAATGGCAGGT
CGAAAAGCAACTGCGACGGTTGCTCCGTCATCCTCTCATCGCCTTTTTATTGCTCC
GGCGTTGGGATGTAGACGCAAGAAGATGTTGG

SEQ ID NO: 57: target 1 target sequence:

ATCTCTATGGAGTAGTACCGAGG

SEQ ID NO: 58: target 1 protospacer sequence:

ATCTCTATGGAGTAGTACCG

SEQ ID NO: 59: target 1 complete sgRNA nucleic acid sequence:

ATCTCTATGGAGTAGTACCGGTTTTAGAGCTAGAAATAGCAAGTTAAAATAAGGCT
AGTCCGTTATCAACTTGAAAAAGTGGCACCGAGTCGGTGCTTTTTTT

SEQ ID NO: 60: target 2 target sequence:

ATGTAGACGCAAGAAGATGTTGG

SEQ ID NO: 61: target 2 protospacer sequence:

ATGTAGACGCAAGAAGATGT

SEQ ID NO: 62: target 2 complete sgRNA nucleic acid sequence:

ATGTAGACGCAAGAAGATGTGTTTTAGAGCTAGAAATAGCAAGTTAAAATAAGGCT
AGTCCGTTATCAACTTGAAAAAGTGGCACCGAGTCGGTGCTTTTTTT

Information for repairing promoter in Hap.A/C -847 C>T

SEQ ID NO: 63: a repair template sequence for introduction of the correct SNP

CTAAGTTTAGTTTCAAACTTTTCCTTCAAACTTACAGCTTTTTTATCACATTAAAACT
TTCCTACATATAAACTTTCAACTTTTCCATCACATCTTTTAATTTCAACCAAACTTCT
AATTTTAACGTGAACTAAAAACACCCTGAATTCAAAACTCTTTTTATTTTCCTTCAAG
ATGTCCGATGCACACGCTCT

SEQ ID NO: 64: donor DNA sequence for introduction of the correct SNP

ATCTCTATGGAGTAGTACCGAGGCCATGGATAAAATGTAATTTCTATGCATACAAC
TAAATTATCGATGGCAACAGTGCATGAGCATATATTTATTTCATTGACCTACGGTTG
CATGTCTTCGATCTCTATGGAGTAGTACCGATTCTAAGTTTAGTTTCAAACTTTTCC
TTCAAACTTACAGCTTTTTTATCACATTAAAACTTTCCTACATATAAACTTTCAACTT
TTCCATCACATCTTTTAATTTCAACCAAACTTCTAATTTTAACGTGAACTAAAAACAC
CCTGAATTCAAAACTCTTTTTATTTTCCTTCAAGATGTCCGATGCACACGCTCTATG

TAGACGCAAGAAGATGTTAAAGCAGCAGACTAACAGTAGCAAAAAAATGGCAGGT
CGAAAAGCAACTGCGACGGTTGCTCCGTCATCCTCTCATCGCCTTTTTATTGCTCC
GGCGTTGGGATGTAGACGCAAGAAGATGTTGG

SEQ ID NO: 65: target 1 target sequence:

ATCTCTATGGAGTAGTACCGAGG

SEQ ID NO: 66: target 1 protospacer sequence:

ATCTCTATGGAGTAGTACCG

SEQ ID NO: 67: target 1 complete sgRNA nucleic acid sequence:

ATCTCTATGGAGTAGTACCGGTTTTAGAGCTAGAAATAGCAAGTTAAAATAAGGCT
AGTCCGTTATCAACTTGAAAAAGTGGCACCGAGTCGGTGCTTTTTTT

SEQ ID NO: 68: target 2 target sequence:

ATGTAGACGCAAGAAGATGTTGG

SEQ ID NO: 69: target 2 protospacer sequence:

ATGTAGACGCAAGAAGATGT

SEQ ID NO: 70: target 2 complete sgRNA nucleic acid sequence:

ATGTAGACGCAAGAAGATGTGTTTTAGAGCTAGAAATAGCAAGTTAAAATAAGGCT
AGTCCGTTATCAACTTGAAAAAGTGGCACCGAGTCGGTGCTTTTTTT

Information for repairing promoter in Hap.A/C -801 C>T

SEQ ID NO: 71: a repair template sequence for introduction of the correct SNP

CTAAGTTTAGTTTCAAACTTTTCCTTCAAACTTACAGCTTTTTTATCACATTAAAACT
TTCCTACATACAAACTTTCAACTTTTCCATCACATCTTTTAATTTCAACCAAACTTTT
AATTTTAACGTGAACTAAAAACACCCTGAATTCAAAACTCTTTTTATTTTCCTTCAAG
ATGTCCGATGCACACGCTCT

SEQ ID NO: 72: donor DNA sequence for introduction of the correct SNP

ATCTCTATGGAGTAGTACCGAGGCCATGGATAAAATGTAATTTCTATGCATACAAC
TAAATTATCGATGGCAACAGTGCATGAGCATATATTTATTTCATTGACCTACGGTTG
CATGTCTTCGATCTCTATGGAGTAGTACCGATTCTAAGTTTAGTTTCAAACTTTTCC
TTCAAACTTACAGCTTTTTTATCACATTAAAACTTTCCTACATACAAACTTTCAACTT
TTCCATCACATCTTTTAATTTCAACCAAACTTTTAATTTTAACGTGAACTAAAAACAC
CCTGAATTCAAAACTCTTTTTATTTTCCTTCAAGATGTCCGATGCACACGCTCTATG
TAGACGCAAGAAGATGTTAAAGCAGCAGACTAACAGTAGCAAAAAAATGGCAGGT
CGAAAAGCAACTGCGACGGTTGCTCCGTCATCCTCTCATCGCCTTTTTATTGCTCC
GGCGTTGGGATGTAGACGCAAGAAGATGTTGG

SEQ ID NO: 73: target 1 target sequence:

ATCTCTATGGAGTAGTACCGAGG

SEQ ID NO: 74: target 1 protospacer sequence:

ATCTCTATGGAGTAGTACCG

SEQ ID NO: 75: target 1 complete sgRNA nucleic acid sequence:

ATCTCTATGGAGTAGTACCGGTTTTAGAGCTAGAAATAGCAAGTTAAAATAAGGCT
AGTCCGTTATCAACTTGAAAAAGTGGCACCGAGTCGGTGCTTTTTTT

SEQ ID NO: 76: target 2 target sequence:

ATGTAGACGCAAGAAGATGTTGG

SEQ ID NO: 77: target 2 protospacer sequence:

ATGTAGACGCAAGAAGATGT

SEQ ID NO: 78: target 2 complete sgRNA nucleic acid sequence:

ATGTAGACGCAAGAAGATGTGTTTTAGAGCTAGAAATAGCAAGTTAAAATAAGGCT
AGTCCGTTATCAACTTGAAAAAGTGGCACCGAGTCGGTGCTTTTTTT

Information for repairing promoter in Hap.A/C -884 T>A, -847 C>T

SEQ ID NO: 79: a repair template sequence for introduction of the correct SNP

CTAAGTTTAGTTTCAAACTTTTCCTTCAAACATACAGCTTTTTTATCACATTAAAACT
TTCCTACATATAAACTTTCAACTTTTCCATCACATCTTTTAATTTCAACCAAACTTCT
AATTTTAACGTGAACTAAAAACACCCTGAATTCAAAACTCTTTTTATTTTCCTTCAAG
ATGTCCGATGCACACGCTCT

SEQ ID NO: 80: donor DNA sequence for introduction of the correct SNP

ATCTCTATGGAGTAGTACCGAGGCCATGGATAAAATGTAATTTCTATGCATACAAC
TAAATTATCGATGGCAACAGTGCATGAGCATATATTTATTTCATTGACCTACGGTTG
CATGTCTTCGATCTCTATGGAGTAGTACCGATTCTAAGTTTAGTTTCAAACTTTTCC
TTCAAACATACAGCTTTTTTATCACATTAAAACTTTCCTACATATAAACTTTCAACTT
TTCCATCACATCTTTTAATTTCAACCAAACTTCTAATTTTAACGTGAACTAAAAACAC
CCTGAATTCAAAACTCTTTTTATTTTCCTTCAAGATGTCCGATGCACACGCTCTATG
TAGACGCAAGAAGATGTTAAAGCAGCAGACTAACAGTAGCAAAAAAATGGCAGGT
CGAAAAGCAACTGCGACGGTTGCTCCGTCATCCTCTCATCGCCTTTTTATTGCTCC
GGCGTTGGGATGTAGACGCAAGAAGATGTTGG

SEQ ID NO: 81: target 1 target sequence:

ATCTCTATGGAGTAGTACCGAGG

SEQ ID NO: 82: target 1 protospacer sequence:

ATCTCTATGGAGTAGTACCG

SEQ ID NO: 83: target 1 complete sgRNA nucleic acid sequence:

ATCTCTATGGAGTAGTACCGGTTTTAGAGCTAGAAATAGCAAGTTAAAATAAGGCT
AGTCCGTTATCAACTTGAAAAAGTGGCACCGAGTCGGTGCTTTTTTT

SEQ ID NO: 85: target 2 target sequence:

ATGTAGACGCAAGAAGATGTTGG

SEQ ID NO: 86: target 2 protospacer sequence:

ATGTAGACGCAAGAAGATGT

SEQ ID NO: 87: target 2 complete sgRNA nucleic acid sequence:

ATGTAGACGCAAGAAGATGTGTTTTAGAGCTAGAAATAGCAAGTTAAAATAAGGCT
AGTCCGTTATCAACTTGAAAAAGTGGCACCGAGTCGGTGCTTTTTTT

Information for repairing promoter in Hap.A/C -884 T>A, -801 C>T

SEQ ID NO: 88: a repair template sequence for introduction of the correct SNP

CTAAGTTTAGTTTCAAACTTTTCCTTCAAACATACAGCTTTTTTATCACATTAAAACT
TTCCTACATACAAACTTTCAACTTTTCCATCACATCTTTTAATTTCAACCAAACTTTT
AATTTTAACGTGAACTAAAAACACCCTGAATTCAAAACTCTTTTTATTTTCCTTCAAG
ATGTCCGATGCACACGCTCT

SEQ ID NO: 89: donor DNA sequence for introduction of the correct SNP

ATCTCTATGGAGTAGTACCGAGGCCATGGATAAAATGTAATTTCTATGCATACAAC
TAAATTATCGATGGCAACAGTGCATGAGCATATATTTATTTCATTGACCTACGGTTG
CATGTCTTCGATCTCTATGGAGTAGTACCGATTCTAAGTTTAGTTTCAAACTTTTCC
TTCAAACATACAGCTTTTTTATCACATTAAAACTTTCCTACATACAAACTTTCAACTT
TTCCATCACATCTTTTAATTTCAACCAAACTTTTAATTTTAACGTGAACTAAAAACAC
CCTGAATTCAAAACTCTTTTTATTTTCCTTCAAGATGTCCGATGCACACGCTCTATG

TAGACGCAAGAAGATGTTAAAGCAGCAGACTAACAGTAGCAAAAAAATGGCAGGT
CGAAAAGCAACTGCGACGGTTGCTCCGTCATCCTCTCATCGCCTTTTTATTGCTCC
GGCGTTGGGATGTAGACGCAAGAAGATGTTGG

SEQ ID NO: 90: target 1 target sequence:

ATCTCTATGGAGTAGTACCGAGG

SEQ ID NO: 91: target 1 protospacer sequence:

ATCTCTATGGAGTAGTACCG

SEQ ID NO: 92: target 1 complete sgRNA nucleic acid sequence:

ATCTCTATGGAGTAGTACCGGTTTTAGAGCTAGAAATAGCAAGTTAAAATAAGGCT
AGTCCGTTATCAACTTGAAAAAGTGGCACCGAGTCGGTGCTTTTTTT

SEQ ID NO: 93: target 2 target sequence:

ATGTAGACGCAAGAAGATGTTGG

SEQ ID NO: 94: target 2 protospacer sequence:

ATGTAGACGCAAGAAGATGT

SEQ ID NO: 95: target 2 complete sgRNA nucleic acid sequence:

ATGTAGACGCAAGAAGATGTGTTTTAGAGCTAGAAATAGCAAGTTAAAATAAGGCT
AGTCCGTTATCAACTTGAAAAAGTGGCACCGAGTCGGTGCTTTTTTT

Information for repairing promoter in Hap.A/C -884 T>A, -847 C>T, -801 C>T

SEQ ID NO: 96: a repair template sequence for introduction of the correct SNP

CTAAGTTTAGTTTCAAACTTTTCCTTCAAACATACAGCTTTTTTATCACATTAAAACT
TTCCTACATATAAACTTTCAACTTTTCCATCACATCTTTTAATTTCAACCAAACTTTT
AATTTTAACGTGAACTAAAAACACCCTGAATTCAAAACTCTTTTTATTTTCCTTCAAG
ATGTCCGATGCACACGCTCT

SEQ ID NO: 97: donor DNA sequence for introduction of the correct SNP

ATCTCTATGGAGTAGTACCGAGGCCATGGATAAAATGTAATTTCTATGCATACAAC
TAAATTATCGATGGCAACAGTGCATGAGCATATATTTATTTCATTGACCTACGGTTG
CATGTCTTCGATCTCTATGGAGTAGTACCGATTCTAAGTTTAGTTTCAAACTTTTCC
TTCAAACATACAGCTTTTTTATCACATTAAAACTTTCCTACATATAAACTTTCAACTT
TTCCATCACATCTTTTAATTTCAACCAAACTTTTAATTTTAACGTGAACTAAAAACAC
CCTGAATTCAAAACTCTTTTTATTTTCCTTCAAGATGTCCGATGCACACGCTCTATG
TAGACGCAAGAAGATGTTAAAGCAGCAGACTAACAGTAGCAAAAAAATGGCAGGT
CGAAAAGCAACTGCGACGGTTGCTCCGTCATCCTCTCATCGCCTTTTTATTGCTCC
GGCGTTGGGATGTAGACGCAAGAAGATGTTGG

SEQ ID NO: 98: target 1 target sequence:

ATCTCTATGGAGTAGTACCGAGG

SEQ ID NO: 99: target 1 protospacer sequence:

ATCTCTATGGAGTAGTACCG

SEQ ID NO: 100: target 1 complete sgRNA nucleic acid sequence:

ATCTCTATGGAGTAGTACCGGTTTTAGAGCTAGAAATAGCAAGTTAAAATAAGGCT
AGTCCGTTATCAACTTGAAAAAGTGGCACCGAGTCGGTGCTTTTTTT

SEQ ID NO: 101: target 2 target sequence:

ATGTAGACGCAAGAAGATGTTGG

SEQ ID NO: 102: target 2 protospacer sequence:

ATGTAGACGCAAGAAGATGT

SEQUENCE LISTING

SEQ ID NO: 103: target 2 complete sgRNA nucleic acid sequence:

ATGTAGACGCAAGAAGATGTGTTTTAGAGCTAGAAATAGCAAGTTAAAATAAGGCT
AGTCCGTTATCAACTTGAAAAAGTGGCACCGAGTCGGTGCTTTTTTT

Information for repairing promoter in Hap.A/C -847 C>T, -801 C>T

SEQ ID NO: 104: a repair template sequence for introduction of the correct SNP

CTAAGTTTAGTTTCAAACTTTTCCTTCAAACTTACAGCTTTTTTATCACATTAAAACT
TTCCTACATATAAACTTTCAACTTTTCCATCACATCTTTTAATTTCAACCAAACTTTT
AATTTTAACGTGAACTAAAAACACCCTGAATTCAAAACTCTTTTTATTTTCCTTCAAG
ATGTCCGATGCACACGCTCT

SEQ ID NO: 105: donor DNA sequence for introduction of the correct SNP

ATCTCTATGGAGTAGTACCGAGGCCATGGATAAAATGTAATTTCTATGCATACAAC
TAAATTATCGATGGCAACAGTGCATGAGCATATATTTATTTCATTGACCTACGGTTG
CATGTCTTCGATCTCTATGGAGTAGTACCGATTCTAAGTTTAGTTTCAAACTTTTCC
TTCAAACTTACAGCTTTTTTATCACATTAAAACTTTCCTACATATAAACTTTCAACTT
TTCCATCACATCTTTTAATTTCAACCAAACTTTTAATTTTAACGTGAACTAAAAACAC
CCTGAATTCAAAACTCTTTTTATTTTCCTTCAAGATGTCCGATGCACACGCTCTATG
TAGACGCAAGAAGATGTTAAAGCAGCAGACTAACAGTAGCAAAAAAATGGCAGGT
CGAAAAGCAACTGCGACGGTTGCTCCGTCATCCTCTCATCGCCTTTTTATTGCTCC
GGCGTTGGGATGTAGACGCAAGAAGATGTTGG

SEQ ID NO: 106: target 1 target sequence:

ATCTCTATGGAGTAGTACCGAGG

SEQ ID NO: 107: target 1 protospacer sequence:

ATCTCTATGGAGTAGTACCG

SEQ ID NO: 108: target 1 complete sgRNA nucleic acid sequence:

ATCTCTATGGAGTAGTACCGGTTTTAGAGCTAGAAATAGCAAGTTAAAATAAGGCT
AGTCCGTTATCAACTTGAAAAAGTGGCACCGAGTCGGTGCTTTTTTT

SEQ ID NO: 109: target 2 target sequence:

ATGTAGACGCAAGAAGATGTTGG

SEQ ID NO: 110: target 2 protospacer sequence:

ATGTAGACGCAAGAAGATGT

SEQ ID NO: 111: target 2 complete sgRNA nucleic acid sequence:

ATGTAGACGCAAGAAGATGTGTTTTAGAGCTAGAAATAGCAAGTTAAAATAAGGCT
AGTCCGTTATCAACTTGAAAAAGTGGCACCGAGTCGGTGCTTTTTTT

CRISPR constructs for the introduction of SNPs at the miRNA396 recognition site (i.e. CCGT░AAGAAAGCCTGTGGAA>CCGT░AAGAAAGCCTGTGGAA)

*Zea mays*

GRMZM2G034876 (GRF-transcription factor 6)

SEQ ID NO: 112: a repair template sequence for introduction of the correct SNP

CGGTGCTCCAAGGAGGCCGCCCCGGACTCCAAGTACTGCGAGCGCCACATGCAC
CGCGGCCGCAACCGTAAAAGAAAGCCTGTGGAAACGCAGCTCGCGCCCCAGTCC
CAACCGCCCGCCGCCGCAGC

SEQUENCE LISTING

SEQ ID NO: 113: donor DNA sequence for introduction of the
correct SNP

GGCGAACGGACGGCAAGAAGTGGCGCGGCCTCGACTCCCTCGCAACCCGCTTCT
ACGGCCAACCCACACTCGGGTACGGACCGTACCTGGGGAGGAAACTGGATCCGG
AGCCCGGCCGGTGCCGGCGAACGGACGGCAAGAAGTGCCGGTGCTCCAAGGAG
GCCGCCCCGGACTCCAAGTACTGCGAGCGCCACATGCACCGCGGCCGCAACCG
TAAAAGAAAGCCTGTGGAAACGCAGCTCGCGCCCCAGTCCCAACCGCCCGCCGC
CGCCAGCCGTCTCCGCCGCTCCGCCCCTAGCAGCCGCCGCCGCCGCCACCACCA
ACGGCAGCGGCTTCCAGAACCACTCTCTCTACCCGGCCATCGCCGGCAGCACTG
GTGGTGGAGGAGGAGTTGGCGGCGTCTCCGCCGCTCCGCCCCTGG

SEQ ID NO: 114: target 1 target sequence:

GGCGAACGGACGGCAAGAAGTGG

SEQ ID NO: 115: target 1 protospacer sequence:

GGCGAACGGACGGCAAGAAG

SEQ ID NO: 116: target 1 complete sgRNA nucleic acid sequence:

GGCGAACGGACGGCAAGAAGGTTTTAGAGCTAGAAATAGCAAGTTAAAATAAGGC
TAGTCCGTTATCAACTTGAAAAAGTGGCACCGAGTCGGTGCTTTTTTT

SEQ ID NO: 117: target 2 target sequence:

CGTCTCCGCCGCTCCGCCCCTGG

SEQ ID NO: 118: target 2 protospacer sequence:

CGTCTCCGCCGCTCCGCCCC

SEQ ID NO: 119: target 2 complete sgRNA nucleic acid sequence:

CGTCTCCGCCGCTCCGCCCCGTTTTAGAGCTAGAAATAGCAAGTTAAAATAAGGC
TAGTCCGTTATCAACTTGAAAAAGTGGCACCGAGTCGGTGCTTTTTTT

GRMZM2G041223

SEQ ID NO: 120: a repair template sequence for introduction
of the correct SNP

CCGCCCCGGACTCCAAGTACTGCGAGCGCCACATGCACCGCGGCCGCAACCGTA
AAAGAAAGCCTGTGGAAGCGCAGCTCGTGCCCCCGCCGCACGCCCAGCAGCAG
CAGCAGCAG

SEQ ID NO: 121: donor DNA sequence for introduction of the
correct SNP

AAGTGGCGGTGCTCCAAGGGAGGTCCTCTCTCGCGTGTGTGTGTGTGGCTTCCT
TGCAGTTGGGTACGGGCCCTACTTCGGCAAGAAGGTGGACCCGGAGCCCGGGC
GGTGCCGGCGTACGGACGGCAAGAAGTGGCGGTGCTCCAAGGAAGCCGCCCCG
GACTCCAAGTACTGCGAGCGCCACATGCACCGCGGCCGCAACCGTAAAAGAAAG
CCTGTGGAAGCGCAGCTCGTGCCCCCGCCGCACGCCCAGCAGCAGCAGCAGCA
GCAGGCCCCCGCGCCCACCGCTAGCTTCCAGAGCCACCCCATGTACCCATCCAT
CCTCGCCGGCAACGGCGGCGGCGGCGGCGGGGTAGGTGGTGGTGCTGGTGGC
GGTGGCACGTTCGGCCTGGGGCCCCAGGCCCCCGCGCCCACCGCTGG

SEQ ID NO: 122: target 1 target sequence:

AAGTGGCGGTGCTCCAAGGGAGG

SEQ ID NO: 123: target 1 protospacer sequence:

AAGTGGCGGTGCTCCAAGGG

SEQ ID NO: 124: target 1 complete sgRNA nucleic acid sequence:

AAGTGGCGGTGCTCCAAGGGGTTTTAGAGCTAGAAATAGCAAGTTAAAATAAGGC
TAGTCCGTTATCAACTTGAAAAAGTGGCACCGAGTCGGTGCTTTTTTT

SEQ ID NO: 125: target 2 target sequence:

CAGGCCCCCGCGCCCACCGCTGG

SEQUENCE LISTING

SEQ ID NO: 126: target 2 protospacer sequence:

CAGGCCCCGCGCCCACCGC

SEQ ID NO: 127: target 2 complete sgRNA nucleic acid sequence:

CAGGCCCCGCGCCCACCGCGTTTTAGAGCTAGAAATAGCAAGTTAAAATAAGGC
TAGTCCGTTATCAACTTGAAAAAGTGGCACCGAGTCGGTGCTTTTTTT

*Triticum aestivum*

Traes_6AL_06A78C520

SEQ ID NO: 128: a repair template sequence for introduction of the correct SNP ccgcctccgactccaagtactgcgagcgccacatgcaccgcggccgcaaccgtAAaagaa
agcctgtggaaacgcagctcgtgccccactcccagccgccggccgcctccgccgtgccgc
ccctcgccaccggcttccacggccactccctctacccgccgtcggcggcg SEQ ID NO: 129: donor DNA sequence for introduction of the correct SNP GAAGTGGCGGTGCGCCAAGGAGGCCCTCGCCGCCCGCTTCTACCACAACCCCCT
CGCCATCGGGTACGGATCGTACCTGGGCAAGAAGGTGGATCCGGAGCCGGGCC
GGTGCCGGCGCACGGACGGCAAGAAGTGGCGGTGCGCCAAGGAGccgcctcc
gactccaagtactgcgagcgccacatgcaccgcggccgcaaccgtAAaagaaag
cctgtggaaacgcagctcgtgccccactcccagccgccggccgcctccgccgtg
ccgcccctcgccaccggcttccacggccactccctctacccgccgtcggcggc
ggcaccaacggtggtggaggcggAgggaacaacggcatgtccatgcccggcacg
ttctcctccgcgctggggccgcctcagcagcacatgggcaacaatgccgcctct
ccctacgcggctctcggcggcggcaccaacggtggtggaggcggg SEQ ID NO: 130: target 1 target sequence:

GAAGTGGCGGTGCGCCAAGGAGG

SEQ ID NO: 131: target 1 protospacer sequence:

GAAGTGGCGGTGCGCCAAGG

SEQ ID NO: 132: target 1 complete sgRNA nucleic acid sequence:

GAAGTGGCGGTGCGCCAAGGGTTTTAGAGCTAGAAATAGCAAGTTAAAATAAGGC
TAGTCCGTTATCAACTTGAAAAAGTGGCACCGAGTCGGTGCTTTTTTT

SEQ ID NO: 133: target 2 target sequence:

gcaccaacggtggtggaggcggg

SEQ ID NO: 134: target 2 protospacer sequence:

gcaccaacggtggtggaggc

SEQ ID NO: 135: target 2 complete sgRNA nucleic acid sequence:

gcaccaacggtggtggaggcGTTTTAGAGCTAGAAATAGCAAGTTAAAATAAGGCTAGTCC
GTTATCAACTTGAAAAAGTGGCACCGAGTCGGTGCTTTTTTT TRIAE_CS42_6BL_TGACv1_500422_AA1604330

SEQ ID NO: 136: a repair template sequence for introduction of the correct SNP

AGGAGGCCGCCTCCGACTCCAAGTATTGCGAGCGCCACATGCACCGCGGCCGCA
ACCGTAAAAGAAAGCCTGTGGAAACGCAGCTCGTCTCGCACTCCCAGCCGCCGG
CCGCCTCCGTCGTGCCGCCCCTCGCCACCGGCTTCCACAACCACTCCCTCTACC
CCGCCATCGGCG

SEQ ID NO: 137: donor DNA sequence for introduction of the correct SNP

CAAGAAGTGGCGGTGCGCCAAGGGCCGCCCGCTTCTACCACAACCCCCTCGCCA
TCGGGTATGGATCGTACCTGGGCAAGAAGGTGGATCCGGAGCCCGGCCGGTGC

```
CGGCGCACGGACGGCAAGAAGTGGCGGTGCGCCAAAGAGGCCGCCTCCGACTC
CAAGTATTGCGAGCGCCACATGCACCGCGGCCGCAACCGTAAAAGAAAGCCTGT
GGAAACGCAGCTCGTCTCGCACTCCCAGCCGCCGGCCGCCTCCGTCGTGCCGC
CCCTCGCCACCGGCTTCCACAACCACTCCCTCTACCCCGCCATCGGCGGCACCA
ACGGTGGTGGAGGCGGAGGGAACAACGGCATGCCCAACACGTTCTCCTCCGCG
CTGGGGCCTCCTCAGCAGCACATGGGCAACAATGCCTCCTCACCCTACGCGGCT
CTCGGTGGCGCCGGAGCACCAACGGTGGTGGAGGCGGG
```

SEQ ID NO: 138: target 1 target sequence:

CAAGAAGTGGCGGTGCGCCAAGG

SEQ ID NO: 139: target 1 protospacer sequence:

CAAGAAGTGGCGGTGCGCCA

SEQ ID NO: 140: target 1 complete sgRNA nucleic acid sequence:

```
CAAGAAGTGGCGGTGCGCCAGTTTTAGAGCTAGAAATAGCAAGTTAAAATAAGGC
TAGTCCGTTATCAACTTGAAAAAGTGGCACCGAGTCGGTGCTTTTTTT
```

SEQ ID NO: 141: target 2 target sequence:

GCACCAACGGTGGTGGAGGCGGG

SEQ ID NO: 142: target 2 protospacer sequence:

GCACCAACGGTGGTGGAGGC

SEQ ID NO: 143: target 2 complete sgRNA nucleic acid sequence:

```
GCACCAACGGTGGTGGAGGCGTTTTAGAGCTAGAAATAGCAAGTTAAAATAAGGC
TAGTCCGTTATCAACTTGAAAAAGTGGCACCGAGTCGGTGCTTTTTTT
```

TRIAE_CS42_6DL_TGACv1_527461_AA1704370

SEQ ID NO: 144: a repair template sequence for introduction of the correct SNP

```
AGGCCGCCTCCGATTCCAAGTATTGCGAGCGCCACATGCACCGCGGCCGCAACC
GTAAAAGAAAGCCTGTGGAAACGCAGCTCGTCCCGCACACCCAGCCGCCGGCCG
CCTCCGCCGTGCCGCCCCTCGCCACCGGCTTCCACAGCCACTCCCTCTACCCCG
CCATCGGCGGCA
```

SEQ ID NO: 145: donor DNA sequence for introduction of the correct SNP

```
CAAGAAGTGGCGGTGCGCCAAGGTCGCCGCCCGCTTCTACCACAACCCCCTCGC
CATCGGGTACGGATCGTACCTAGGCAAGAAGGTGGATCCGGAGCCGGGCCGGT
GCCGGCGCACGGACGGCAAGAAGTGGCGGTGCGCCAAAGAGGCCGCCTCCGAT
TCCAAGTATTGCGAGCGCCACATGCACCGCGGCCGCAACCGTAAAAGAAAGCCT
GTGGAAACGCAGCTCGTCCCGCACACCCAGCCGCCGGCCGCCTCCGCCGTGCC
GCCCCTCGCCACCGGCTTCCACAGCCACTCCCTCTACCCCGCCATCGGCGGCAG
CACCAACGGTGGTGGAGGCGGAGGGAACAACGGCATGTCCATGCCCAGCACGTT
CTCCTCCGCGCTGGGGCCGCCTCAGCAGCACATGGGCAGCAATGCCGCCTCTCC
CTACGCGGCTCTCGGTGCACCAACGGTGGTGGAGGCGGG
```

SEQ ID NO: 146: target 1 target sequence:

CAAGAAGTGGCGGTGCGCCAAGG

SEQ ID NO: 147: target 1 protospacer sequence:

CAAGAAGTGGCGGTGCGCCA

SEQ ID NO: 148: target 1 complete sgRNA nucleic acid sequence:

```
CAAGAAGTGGCGGTGCGCCAGTTTTAGAGCTAGAAATAGCAAGTTAAAATAAGGC
TAGTCCGTTATCAACTTGAAAAAGTGGCACCGAGTCGGTGCTTTTTTT
```

SEQ ID NO: 149: target 2 target sequence:

GCACCAACGGTGGTGGAGGCGGG

SEQUENCE LISTING

SEQ ID NO: 150: target 2 protospacer sequence:

GCACCAACGGTGGTGGAGGC

SEQ ID NO: 151: target 2 complete sgRNA nucleic acid sequence:

GCACCAACGGTGGTGGAGGCGTTTTAGAGCTAGAAATAGCAAGTTAAAATAAGGC
TAGTCCGTTATCAACTTGAAAAAGTGGCACCGAGTCGGTGCTTTTTTT

*Hordeum vulgare L.*

HORVU2Hr1G101770

SEQ ID NO: 152: a repair template sequence for introduction of the correct SNP

CAAGAAGTGGCGGTGCTCCAAGGAGGCCGCTCAGGACTCCAAGTACTGCGAGCG
CCACATGCACGCGGCCGCAACCGTAAAAGAAAGCCTGTGGAAACGCAGCTCGTC
GCCAGCTCCCACTCCCAGTCCCAGCAGCACGCCACCGCCGCCTTCCACAACCAC
TCGCCG

SEQ ID NO: 153: donor DNA sequence for introduction of the correct SNP

GGGCGGTGCCGGCGGACGGACGGACAGATGTATGGGGTATTTATCATGAAAAAG
CATTCTTGACGTGGGTGTTTTTCGTTGTTTGCAGTTGGGTACGGGTCCTACTTCGG
GAAGAAGCTGGATCCGGAGCCGGGGCGGTGCCGGCGGACGGACGACAAGAAGT
GGCGGTGCTCCAAGGAGGCCGCTCAGGACTCCAAGTACTGCGAGCGCCACATGC
ACGCGGCCGCAACCGTAAAAGAAAGCCTGTGGAAACGCAGCTCGTCGCCAGCTC
CCACTCCCAGTCCCAGCAGCACGCCACCGCCGCCTTCCACAACCACTCGCCGTA
TCCGGCGATCGCCACTGGCGATGGCTCCTTCGCCCTGGGGTCTGCTCAGCTGCA
CATGGACACTGCTGCGCCTTACGCGACGACCGCCGGTGCTGCCGGAAACAAAGA
TTTCAGGTGACCTCTTCTTATCCGGCGATCGCCACTGGCGG

SEQ ID NO: 154: target 1 target sequence:

GGGCGGTGCCGGCGGACGGACGG

SEQ ID NO: 155: target 1 protospacer sequence:

GGGCGGTGCCGGCGGACGGA

SEQ ID NO: 156: target 1 complete sgRNA nucleic acid sequence:

GGGCGGTGCCGGCGGACGGAGTTTTAGAGCTAGAAATAGCAAGTTAAAATAAGG
CTAGTCCGTTATCAACTTGAAAAAGTGGCACCGAGTCGGTGCTTTTTTT

SEQ ID NO: 157: target 2 target sequence:

TATCCGGCGATCGCCACTGGCGG

SEQ ID NO: 158: target 2 protospacer sequence:

TATCCGGCGATCGCCACTGG

SEQ ID NO: 159: target 2 complete sgRNA nucleic acid sequence:

TATCCGGCGATCGCCACTGGGTTTTAGAGCTAGAAATAGCAAGTTAAAATAAGGC
TAGTCCGTTATCAACTTGAAAAAGTGGCACCGAGTCGGTGCTTTTTTT

*Sorghum bicolor (L.)*

SORBI_004G269900

SEQ ID NO: 160: a repair template sequence for introduction of the correct SNP

TGCCGGCGTACGGACGGCAAGAAGTGGCGGTGCTCCAAGGAGGCCGCCCCAGA
CTCCAAGTACTGCGAGCGCCACATGCACCGCGGCCGCAACCGTAAAAGAAAGCC
TGTGGAAACGCAGCTCGTGCCCCAGTCCCAACCGCCCGCCACCGCCGCTGC

SEQUENCE LISTING

SEQ ID NO: 161: donor DNA sequence for introduction of the correct SNP

AACTGGATCCGGAGCCGGGGCGGGATCTCGTGGTTCCAATCCGCCGCGGTCTCG
ACTCCCTCGCAACCCGCTTCTACGGCCATCCCACACTTGGTGGGTACGGGACGT
ACTACTTAGGCAAGAAACTGGATCCGGAGCCGGGGCGATGCCGGCGTACGGACG
GCAAGAAGTGGCGGTGCTCCAAGGAGGCCGCCCCAGACTCCAAGTACTGCGAGC
GCCACATGCACCGCGGCCGCAACCGTAAAAGAAAGCCTGTGGAAACGCAGCTCG
TGCCCCAGTCCCAACCGCCCGCCACCGCCGCTGCCGTCTCCGCCGCTCCGCCCT
TAGCCTTGGCCGCCGCCACCACCACCACCAACGGCAGCTGCTTCCAGAATCACT
CTCTTTACCCGGCCATTGCAGGCAGCACCGGTGGAGGTGGCGGGGCCAGCAATC
GTCTCCGCCGCTCCGCCCTTGG

SEQ ID NO: 162: target 1 target sequence:

AACTGGATCCGGAGCCGGGGCGG

SEQ ID NO: 163: target 1 protospacer sequence:

AACTGGATCCGGAGCCGGGG

SEQ ID NO: 164: target 1 complete sgRNA nucleic acid sequence:

AACTGGATCCGGAGCCGGGGGTTTTAGAGCTAGAAATAGCAAGTTAAAATAAGGC
TAGTCCGTTATCAACTTGAAAAAGTGGCACCGAGTCGGTGCTTTTTTT

SEQ ID NO: 165: target 2 target sequence:

CGTCTCCGCCGCTCCGCCCTTGG

SEQ ID NO: 166: target 2 protospacer sequence:

CGTCTCCGCCGCTCCGCCCT

SEQ ID NO: 167: target 2 complete sgRNA nucleic acid sequence:

CGTCTCCGCCGCTCCGCCCTGTTTTAGAGCTAGAAATAGCAAGTTAAAATAAGGC
TAGTCCGTTATCAACTTGAAAAAGTGGCACCGAGTCGGTGCTTTTTTT

*Glycine max (L.)*

GLYMA11G11826

SEQ ID NO: 168: a repair template sequence for introduction of the correct SNP

AAGCATACCCAGACTCCAAGTACTGCGAGCGCCACATGCACCGTGGCCGCAACC
GTAAAAGAAAGCCTGTGGAATCACAAACTATGACTCACTCATCTTCAACTGTC

SEQ ID NO: 169: donor DNA sequence for introduction of the correct SNP

AAAAAAGTGGAGGTGCTCCAAGGTCTCGCACGCTTTCTTTCACCATCCCACGTTG
AGTTACTGTTCCTTCTATGGGAAGAAGGTGGACCCTGAGCCAGGACGATGCAGGA
GGACTGATGGAAAAAAGTGGAGGTGCTCCAAAGAAGCATACCCAGACTCCAAGTA
CTGCGAGCGCCACATGCACCGTGGCCGCAACCGTAAAAGAAAGCCTGTGGAATC
ACAAACTATGACTCACTCATCTTCAACTGTCACATCACTCACTGTCACTGGGAGTA
GTGGTGCCAGCAAAGGAACTGTAAATTTCCAAAACCTTTCTACAAATACCTTTGGT
AATCTCCAGGGTACCGATTCTGGAACTGACCACACCAATTATCATCTAGACATCAC
TCACTGTCACTGGGG

SEQ ID NO: 170: target 1 target sequence:

AAAAAAGTGGAGGTGCTCCAAGG

SEQ ID NO: 171: target 1 protospacer sequence:

AAAAAAGTGGAGGTGCTCCA

SEQ ID NO: 172: target 1 complete sgRNA nucleic acid sequence:

AAAAAAGTGGAGGTGCTCCAGTTTTAGAGCTAGAAATAGCAAGTTAAAATAAGGCT
AGTCCGTTATCAACTTGAAAAAGTGGCACCGAGTCGGTGCTTTTTTTT

SEQUENCE LISTING

SEQ ID NO: 173: target 2 target sequence:

GACATCACTCACTGTCACTGGGG

SEQ ID NO: 174: target 2 protospacer sequence:

GACATCACTCACTGTCACTG

SEQ ID NO: 175: target 2 complete sgRNA nucleic acid sequence:

GACATCACTCACTGTCACTGGTTTTAGAGCTAGAAATAGCAAGTTAAAATAAGGCT
AGTCCGTTATCAACTTGAAAAAGTGGCACCGAGTCGGTGCTTTTTTT

Brassica napus

BnaA03g16700D

SEQ ID NO: 176: a repair template sequence for introduction of the correct SNP

GACGTCTTCGCTGGCCACAAGTACTGCGAGCGCCACATGCACCGAGGCCGCAAC
CGTAAAAGAAAGCCTGTGGAAACTCCCATAGTCAATGCTACCACCACCACTTC

SEQ ID NO: 177: donor DNA sequence for introduction of the correct SNP

GTAAGAAGTAAAGATGTTCAAGGCTTCTCCATCTATCTCCTTCCTACTTTCTTCACC
ACCTACCTCATTACCAGCCTGCTTGGTATTTGGGGAGGGGGGCGATGGATCCTGA
GCCAGGGAGATGCAGGAGAACGGATGGTAAGAAGTAAAGATGTTCAAGAGACGT
CTTCGCTGGCCACAAGTACTGCGAGCGCCACATGCACCGAGGCCGCAACCGTAA
AAGAAAGCCTGTGGAAACTCCCATAGTCAATGCTACCACCACCACTTCCATGGCT
TCCCCAGCCACAGCAGCACCGTCATCAACACCATCCTCCTTTGCTTTTGGCGGTG
GTGAGAAAGTGGGTCAAGGTGGATCATCTAGCTTCTTCTTCTCAAGTCAAAGTTGT
TCAGAGATGCATGGCTTCCCCAGCCACAGCGG

SEQ ID NO: 178: target 1 target sequence:

GTAAGAAGTAAAGATGTTCAAGG

SEQ ID NO: 179: target 1 protospacer sequence:

GTAAGAAGTAAAGATGTTCA

SEQ ID NO: 180: target 1 complete sgRNA nucleic acid sequence:

GTAAGAAGTAAAGATGTTCAGTTTTAGAGCTAGAAATAGCAAGTTAAAATAAGGCT
AGTCCGTTATCAACTTGAAAAAGTGGCACCGAGTCGGTGCTTTTTTT

SEQ ID NO: 181: target 2 target sequence:

CATGGCTTCCCCAGCCACAGCGG

SEQ ID NO: 182: target 2 protospacer sequence:

CATGGCTTCCCCAGCCACAG

SEQ ID NO: 183: target 2 complete sgRNA nucleic acid sequence:

CATGGCTTCCCCAGCCACAGGTTTTAGAGCTAGAAATAGCAAGTTAAAATAAGGCT
AGTCCGTTATCAACTTGAAAAAGTGGCACCGAGTCGGTGCTTTTTTT

Solanum lycopersicum

Solyc08g075950

SEQ ID NO: 184: a repair template sequence for introduction of the correct SNP

ACTGACGGAAAAAAGTGGAGATGCTCAAAAGATGCATATCCTGACTCCAAATATTG
CGAGCGGCACATGCATCGAGGCCGCAACCGTTCAAGAAAGCCTGTGGAATCTCA
ATCTACTCCCCAGTCCTTGTCGACTA

SEQUENCE LISTING

SEQ ID NO: 185: donor DNA sequence for introduction of the correct SNP

CTGAGCCAGGAAGGTGTAGAAGGTGGTGGTTTCAGCTATATGCATTAGCTCATGA
TGGAGCTTAATGATTTGTTTCTTCTTTGTACAGTGGGCTATTGTTCCTATTATGGGA
AGAAGTTTGATCCTGAGCCAGGAAGGTGTAGAAGAACTGACGGAAAAAAGTGGAG
ATGCTCAAAAGATGCATATCCTGACTCCAAATATTGCGAGCGGCACATGCATCGA
GGCCGCAACCGTTCAAGAAAGCCTGTGGAATCTCAATCTACTCCCCAGTCCTTGT
CGACTAGTATGTCACAAATTACAGCTGGAAGCAGCAATACAAGAGGAAGTTTCCA
AAATAGCAGCAGCGGAAGCTTCCAAAACATGCCATTGTATTCTGTTGCTAATTCGG
GAACGCTGAATTATGGAAGTATGTCACAAATTACAGCTGGG

SEQ ID NO: 186: target 1 target sequence:

CTGAGCCAGGAAGGTGTAGAAGG

SEQ ID NO: 187: target 1 protospacer sequence:

CTGAGCCAGGAAGGTGTAGA

SEQ ID NO: 188: target 1 complete sgRNA nucleic acid sequence:

CTGAGCCAGGAAGGTGTAGAGTTTTAGAGCTAGAAATAGCAAGTTAAAATAAGGC
TAGTCCGTTATCAACTTGAAAAAGTGGCACCGAGTCGGTGCTTTTTTT

SEQ ID NO: 189: target 2 target sequence:

GTATGTCACAAATTACAGCTGGG

SEQ ID NO: 190: target 2 protospacer sequence:

GTATGTCACAAATTACAGCT

SEQ ID NO: 191: target 2 complete sgRNA nucleic acid sequence:

GTATGTCACAAATTACAGCTGTTTTAGAGCTAGAAATAGCAAGTTAAAATAAGGCT
AGTCCGTTATCAACTTGAAAAAGTGGCACCGAGTCGGTGCTTTTTTT

Orthologue promoter sequences

| OsGRF4-884 | TTTTCCTTCAAACTTACAGCTTTT |
| OsGRF4-847 | TTTCCTACATACAAACTTTCAACTT |
| OsGRF4-801 | TTTCAACCAAACTTCTAATTTTA |

SEQ ID NO: 192: Z.mays; GRMZM2G034876 (GRF-transcription factor 6); 2 kb promoter TTCTAGTGTTTCAACGGAAGCCTAAGTTTCGATGGGAAGAAAGGACATGTACTAGCA
AGGAACCAAACTCCACGCATCATTCTTGCCTAGCCTTGCTTTATCGTGGCTACCTTG
GACCAACAAAAGAACCAAGCAGCCCCAATGTATCTGATATGGAGCTAAAAATACAAC
CAACTCATATTATACGTTGGATGTTTTGACTGCACTTGAGATGTTGTAAGACTTTCG
GTACGCTATACATATAGAGTTGAATATACAGTTGAAGACTGCTGCAGCGGTCAACTG
TCTGATCTACTGTAAACTCTATGAGGAAATCGGAAACGCTACTTCCAGAGTAGTGTA
ACTCCGACTGGAAAACTGTTGCAGAATACGGATAGCCTGATCAGTTAGACTGTCGGC
TGCGGAGTTCAACTGTTGCAGAGTTAGAAAGAAATGATAAAATATATAGTAGTTAGT
ATAGAGTTGATATATAGAGTAAACATGACTGTAGAGGATTGTAGTATAGGGTAGATA
GTTTTGCTGACCAGGACAAGATATTCCTTTTAGAGTATGAATTTAGAGTAGTATGAG
TGCGGATAGCCTAACTTTGTAAGTATTTTTAAAGCTTACTTTGCATACGGTCTTTGT
GATCTACATCTTTACTATGGCTATTTCATGATAATAACTAGATGAGATATATGACCA
ATCGAGTTGTACATATATGTTGGGTTTAATTAAGGGCATAGTTAAAGCACTGAGCTT
TTAAGAAAACGATGTGGTTCTAAATATGGCAGTTTATGCTTGGTTTCTAGAAACTGA
ATTTCTAGCATATTTCCGTACTATTCTTAGTTGGTTTGGATAGAAACTACGACGATT
ATCACCGCTCTGAGGCCTAATGGCCTATGCACTTGATTCTCTCCATGCCCACTCTGC
CCTGTTCAAATGTTTAATTAATATTTAATTTAATAATTTTGAATTCAAGAATACGAG
TTCAAGGTATATTTAAAATTGAGCATCAAAGAGAAATGAAATTAAAGCAATGATAGA
CTTGTCTTTGGGTGTGAAAAAAAGCTAGAACTTATTTATAAAAACCCAATTCTAAAC
ATGTATACCTAATTTTTATTATAAATCGGTTTAGATAGAATCGTAAGCCCTTGATC
AGAGCATCCAACGAGCCATGAGGCCATGACGGAAGAGCGGAAGTGCAGACGGCAAC
GGCGTTCCGCTTCATGCCGCACCCTCCAGTGTCCTGTGGCCTTTAAGTGCCGGCCT
TGGGAACCGCGACGCAGACACAGCCCAAATCCGCAGTCACTCCTCCAACACGATGC
TTGTCACCACCCTTGCTACAGTGCCTGCATCCATATCCACTCCGCTCGCGCAAAA
ATATCCGAGTCGGAAACAAACAAAGCAGCATAGGAAACAGAAGAAAGCTGTACTAG
TACGTGAGGACGAGGAGGGAGAGAGAGCAATACACAGAAGCCTGCTACCGTGCTAC
GGACTACCACAACGCCAGAGGGACAACCGGACAGAGGGGGAGGCAGGCCTCGCTTG

```
TCATCTAGCTAGGTCAGCCGGGGACGGGGTCGGAGCAGTAGAGCTAAAGCCAGAGG
CCAGGCTCGTAGTAGTACGTAGTAGTAGTGCCCTCCTCGTGTCATTTGGCCAGCCT
TGTCCAGACGACCACACACACCAGATTACGCTTAACATTCTGTTTGACATCTAAAA
CCAGCCGGCTTGATCCAAATGCCTCCCTAGGTAGTAGCTTAGTCTTGCTCGCCGCC
TCTCCGGGAGACGACGACACGCCTGATGAGTGCCTGACGTTCCAGCGCGAGGCAGA
CAGCGACGCAGAGAGAGACAAAGCGGGCAATAAAGGCAGCCGCGCGCGAGGAGGG
AAGGGAGCGAAGCAAAGCACATCACGAGCCCAGCCTGCGCCTGCGGAGGGAGGGGG
CTCATTAAAGAGGGGCGCGAGCGCGACCGGCCGCGGGGAGCAAGCAGCGCGCGAG
AGAGACAGGTTGAG
```

SEQ ID NO: 193: Z.mays; GRMZM2G041223 (GRF-transcription factor 8); 2 kb promoter

```
AAACAAATACTTATCGTTAATAAACATGACATATGATCTGATGCATAAATTTGTAT
TTTTATTTTTAACATTGATTTTTTAAAGATTCCCAAAAGATAAACATCAAATTTAT
CATATAATTCCTCAAATGATACATATAAAATTTGAATACGAATATATTTTTACTTT
GTTTATTACTGGGAGTAAATATTGTATAAAAAATATGCAAAATTTATTCTTATTTA
TAGTAATATGCAAATAATGTATAAATAGTCCATGCTCATAAATTTTTTAGTAGCCC
GCAACCCAAGGCGACCGCGAACAGTGCCAAGCCGAGCGGGGGTGTGCATGTTGGAG
ATGGAGAGAGAGAGAGAGAGCCCGAAAAATATCGCTGATGACTCGACGAGATAGAG
GAGGGAGGGAGGGAGGGAGGCGCAGTAGGACAGGGCTGCAGGCAGGTGCTTGTCCT
TAGCTGGAACCCTCCCGTGTCGGCCTCATCCCACCGCCCCGCCCTGCCGTCCTGCC
CTGCGCGGCTGCGGTCGCCTATAAGGCTAGCCCAGGCCATTTGCCCTTTGCCCCCG
TCCGTCGTCCCTCACCTCACCTCACCTCACCTCGGCCCGCCTCCCTCATCAGGTA
GCCGTAGCGAGCAGTATAGCACGCACAGCCGCCGCCCTGCCCTGCCCTGCCCTGCT
CGGCGTAGGCACAGGCACAGCCCAGAGCGAGCGAGACAGAGGGAAAGAGACAGAGC
CAGCCAGGTAAAAGGCAAAAGCACAGCACATTAAAAGAGAGGCCGGAAGCAGCGGC
AGAGCGGAGAGAGAGAGAGAACTAGAAGCATATATGGCGATGCCCTTTGCCTCCCT
GTCTCCGGCAGCCGACCACCGCCCCTCCTCCCTCCTCCCCTACTGCCGCGCCGCCC
CTCTCTCCGCGTAAGCCACCTCCCTTTCGCCCGTCCGGGAAAAACCCTCTTCTTC
GCTCGGTTTATGCCACCCGGAGCCGTGCTGCAGCCTGCAGGTATCTGATGCCGCGA
GCTTTGCCTTGCAGGGTGGGAGGACGCCGCCGCGCAGGCGCAACAGCAGCAGCA
GCACGCTATGAGCGGCAGGTGGGCAGCGAGGCCGCCGGCGCTCTTCACCGCGGCGC
AGTACGAGGAGCTGGAGCACAGGCGCTTATATACAAGTACCTCGTCGCCGGCGTGCC
CGTCCCCCGGACCTCCTCCTCCCCCTAGCCGAGGCTTCGTCTACCACCAACCCGCCC
GTAAGCAAGCACGGCCCCCGCGCCGCCTCCGCACCCCTTCACACTCACACGCACGTT
TAACCGCTTTGCACTGCACAACCCCGGCCGCCCGGCGGCGGCGTCCGTGCCTTGATC
TGGTTGTTTACTCGGATCGAGGGATTCAGATGTCCTCTCCGTCCGTTTGTTAATCGG
CTCCGGTCATTTCTTAATCTCGTCCTGGATTCGGTCACGAAAAGCTAGAGGTCAAGA
TTTGCTCTCGATTACTATATCCTTGCCTCATGTTCCTAATGGAGTTTATTTTATTGG
TCTGATGTGATTAGATAGGATGCTAGCCAGGCTTGTCTCCGGCCAAAAGCGGCGGTT
TAGTTTATTGATGATTGCTTCTTTCCTTGGGGGATTTATTCCTGTCTGGTTGTTGGG
AGCCTAACCACGCTCCTATTGCTGCTGCGGTTTACTAACCATCTGCGCCAGTACACC
TACTCCATGGACCCCAAAATACAGTTCTTCCAACCATTCCCCCCCTCTGCTTTCTCG
CGGGCAAATAAAAACGTGTAGAACGACGGTGTAGTAGGCAGATCTACTCCTTGTGCC
GCTACGCTAGCCCGCTACCGAAGATCGGGCCCGTTTCAACCGGTTCGTTGGTCTGAG
CGGAGCTAAGATGGGGCGCATTTCATTTTTTGGTCCTTTCGTCTGATTGGAGAAGTG
CCCATTCCGGTATCGCTCCCCGGCCTCCAAATACGCACCGACACAGAACGTGTTCGT
ACGCACGTACACATGGT
```

SEQ ID NO: 194: Triticum aestivum; Traes_6AL_06A78C520; 2 kb promoter

```
GATAGTGTGGGAAGGGAGTGGAGTGGAGTGGAATGCGGCTAGGGTTTTAGCCGAGTG
CGGCCTATTTAGGTGGGGTCGGGTGAGCCAGATCCAACATGGCAGGTAGGTTCGGGC
ATCCCCGTACTCGCCCTAAATTTGGGCTGGACTGGGGAGTGACCGGAAGTCCGAACG
TTTGCGCGTCAAAAATGCGGCGCTCGGTTGGGCATTGACCATGCAACTTGCTCGGAC
ATTTGGGGCAAGTATAGGGACTCCGATTGTAGATGCTCCTACGTCTAATTTGATACT
TCATTGAGATGTGGTGTCCGATGCGTGAAAATGCTTCGAGAAGTGAGAGCATCTACA
GCCGGACTTAGCAAATCTGGCATCTATAAGTCAGCGGGCGCCGCCGCGGACGGCCCC
CACTTGAGTTGCCGCACATTGACACACCGCAAATACGGATTCTTGAATTCATGCAAT
CCATTGACGTCCATCAAACGATACAAATCATCCCAATTCAACAGTTCGAAACAAAAT
AAGACAAAGCAAAACAAATCATAATTCAACAATCCGGACATGCTAAAATAAAATCAA
TGTCCGAGCGTGATGGTTCACTCCTTGACCGGCTGGATCACTCGCCCGACGCCATCC
ATATTCCGCTTGCTCCGTGGCCATCCTTATGGGCAGCGAGGATGAGGAGCAAGGATG
GCGGACGACAAGGGCTTGAACACGGGAATAGGTGGAGGGAGTCGGGAGGGGGAAGGG
TTTAGGGCCTCTTTGATTCACAGGATTGTCAAAATAAAGGAATAGAAAAAATGCAGG
AATAGGGTGACATGTCCCATAGTATCCTACAGGATTTGAAAGAATGTTTGATAGCAT
AGGAAAAACAAAGGAATTCTACAAAGAGGTTTGAGTGGATGGAATTTTTTTTCAAAA
TGTAGTACAAATGGATCATATGGAAAATTCCTAAGGATGCCAATCCTACGAATCAAA
CGAGCATCACATGAAAAATTTCTAAGGATTTAAATCCTCCAAAAATCCTATATAATT
CCTTTAAATCAAAGGAGCGCTAGTGAATTGATGCAATTTGTGCTGAAGTAAGCCT
GTCGGGTTCGACGTGACGGGCGCGCCGAGACATCGCTTTCATATTTGGACTGGGT
ATATGGAGTGCTAGTCAGCTCAAGTGTTTGAGACGCTCGTCCGGTTTTTTCATT
TGACCTGTAATCGGGCCGTTCGTCCGGACGTTCGATAGAGGTTTGTGGTGCAGGG
ATGTAGATGCACACTGCTTCCGTTATCAGTTATCACCACGACACAAGAAGCAAGC
ACATAGTACTGTAGTAAAAAAATTGACGAGGGAAAAGTGGCGCAAACGGTTGCCC
```

CGCACCCTCTCACGGACGGACTTTAAAAGTCGGCATTGGTAACCGCAACACAGCA
CAGAGAGACTCACCCCCAAATCTCTCTCTTCTCTCTCTATTCCTATGCAATGCAA
TAGTTGTCACCACTCGCTACAGTGCCGGCAGCATTGCATCGCATCGCATCCATAT
CCATTCCTCCTCACGAGAAAAAGAGAGAGAGACGAGCAATACTAGTCGTCGTCGT
CGTCGTAGCCTGGTACGTCTACGCTAGAGCGACAGGGAAAGAGGAGGGAGGGGGC
GCTTGTCATCTACTCCTCCTCGCTACTACCCCTAGCTGGGATCCACAGCCTCCTC
CTCCTCCTCGTGTCGGCCTCGTCCACATCCACCGTCTCCTCCGAGCGAGGCGGAC
AGCGACGCGGCCACGGAGCGAGGGAGGGAGAGAGACAAAGCCGGTAATAAAGGCG
GGCGGGCGCGCGCGCACAAGCCAAGCAAAGCACATTAACGACGCCAGCCAGCC
AGCCAGCCAGCCAGCCCGCGGGGAACCCCATTAAAGACGCTTCCGGGGGAGCGCC
GTGGGCAAGCAAGCACAGGGGCTTAGCTTAGCTTGGCTTGTGCATCGCGTGTTGT
GTGCGCGAGAGGGAGACAGCGGCCGAGAGAGAAAG

SEQ ID NO: 195: *Triticum aestivum*;
TRIAE_CS42_6BL_TGACv1_500422_AA1604330;2 kb promoter TTTTCGCACGCAACGCCCACTTGAGTTCCTCCTCTCTCAAGAGAGCATGTTGGCCTTGCTCAGCCTCA
GACTTGGTTCGATGCTCATTAACAGAAAGAAGTGTGGTTTCAGCCTTTACATCTAGTGTCTCAATGAGT
TGAGTTAGACGTTCTTTTTTCTGCTTATAAATCCCAGTCTCATTCCTGGCCCATCCTCTCAGAAATTGT
CGGAGGTTTCTAATCTTATTCTGCCATCTCTCGACATGTGTCCTTCCTGTAATTGGCTTAGCCCATTCG CATGCAATCATCTCCATAAATCCTTCTCGCTCAAACCAGCTTTACTCGAAAGAGAAGATGTTTTTGTTT
GCAACATGGGTAGCCTCACCCGAATCTAAAAAGAGTGGTGTATGATCTGAGATCCCTCTATGCATTGC
ATGGACCGACACCAACGGATATTTTTGTTCCCACTCCACACTAGCAAGTACCCTATCCAGCTTTTCATA
AGTCAGAACAGGTAACGAGTTGGCCCATGTAAACTGTCTACCGGTGAGCTCAATTTCTCTCAAATTGA
GGCTCTCGATAATCATGTTAAACATCATAGACCAACGTCCATCGAAATTGTCATTATTCTTTTCTTCTCT
TCTCCGAATGATATTAAAATCACCCCCGACTAGCAGTGGCAGATTTTCATCTCCACAAATCCGCACTA
GATGGGCAAGAAATCGGGTTTAAATTGCTTGGAGGAGTGAGAGCATCTACAACCGGACTTAGCGAA
TCTGGGCTCTATAAGCCCGCGGGTGCCTCCGCGGACGGCCCTCCCTTGAGTTGCCGCACATTCACA
CATCTCAAATACGGATTCTTGAATCCATGTATCCATGCACGTCCATCATACGATATAAATCATCCCAAT
TCAAATGTTTGAAAACAAAATACGACAATGCAAAGCAAATCATAGTTCAATAATTCAGACATGCCAAAT
TAAAATCAATATCCGAGCATGATAGATCACTCGTTGACGCCATCCATGCCCGCTTGCTCCGCGGCC
ATCCTTGCGGGCGGCGAGGATGGGGAGCAAGGGTGGCGGACGGCAAGGGCTTGGACACGAAAATA
GGTGGATGAAGGCGGGAGAGAGGAGGGTTTAGTGAATTTTATGCAATTTATGTGGGGGGTTGGCCTG
TCGGGTTCTACGTAATGGACGCGCCGAGGCATGAGGGATGCCGGTCAGCTTGGGTGTTTTAGATGC
CCGTCCGGTCTTTTATTTTTAAGTCCGTAATTGGGCCGTTCGCCGGACGTTCCATAGAGGTTTGGGGT
GCCGGGAAGTAGATGCACAGTACTTCCGTTATCACCACGACACAAGAAGCAAGCACATAGTACTGTT
GTAAAAAAATGACGAGGGAAAAGTGGCGCAAACGGTTGCCCCGCACCCTCTCACGGACGGACTTTAA
AAGTCGGCATTGGTAACCGCAACACAACACAGACAGACGCCACCCCAAATCTCTCTCTCTCTCTTCC
CATGCAATAGTTGTCGCCACTCGCTCGCTACAGTGACCGCATCGCATCGCATCATGTCCATTCCTCC
CCACGAGAAAAAGAGAGAGACAGCAGAAATACCAGTCGTCGTCGTCGTCGTAGCCTGGTACGTC
TACGCTAGAGCGACAGGGAAAGAGGAGGGCGCTTGTCATCTACTCCTCCTCCTCGCCCGCTACTAGC
TGGGATCCACAGCCTCCTCCTCCTCCTCGTGTCGGCCTCGTCCACATCCACCATCTCCTCCGAGCGA
GGTGGACAGCGACGCGGCCACGGAGCGAGTGAGAGAGACAAAGCCGGTAATAAAGGCGGGCGCGC
GCGCGCGCACAAGCCAAGCAAAGCACATTAACGAGGCCAGCCAGCCCGCAGGGAACCCCATTAAAG
ACGCTTCCGTGGGAGCGCCGTGGGAAGCAAGCGAGCGAGCACAGGGGCTTGGCTTGCGCGTCGT
GTGCTGTGTGCGCGAGAGGGAGACAGCGGCCGAGAGAGAAAG SEQ ID NO: 44 amino_acid sequence MAMPYASLSPAGDRRSSPAATASLLPFCRSSPFSAGNGGMGEEARMAGRWMARPAPFTAAQYEELEHQ
ALIYKYLVAGVPVPPDLVLPIRRGIETLAARFYHNPLAIGYGSYLGKKVDPEPGRCRRTDGKKWRCAK
EAASDSKYCERHMHRGRNRSRKPVETQLVSHSQPPAASVVPLATGFHNHSLYPAIGGTNGGGGGNNG
MPNTFSSALGPPQQHMGNNASSPYAALGGAGTCKDFRYTAYGIRSLADEHSQLMTEAMNTSVENPWRL
PPSSQTTTFPLSSYAPQLGATSDLGQNNNSSSSNSAVKSERQQQQQPLSFPGCGDFGGGGAMDSAKQE
NQTLRPFFDEWPKTRDSWSDLTDDNSSLASFSATQLSISIPMTSSDFSAASSQSPNGMLFAGEMY SEQ ID NO: 196: *Triticum aestivum*
TRIAE_CS42_6DL_TGACv1_527461_AA1704370 2 kb promoter GTATGCGTTACCTTGATTTGCCACATTAGCTAGCTGAAGTTGGTTGCCCGTACATTTGTCAGCGTTAG
CGCCCTGTGACGAAACTTGCCATGCTGCCCCCCTGATTGTGGTTTGGTCATAAGAACCTNNNNNNNN
NNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNN
GCAGCAATGGCCCTGAAGAAATGAGTTGATTGTACTCTGCTGCATCCCAAGGTGGCGTTTCCGGCCT
TTGAGAAAGCCAAGGATCAGTGCCATCTTCGTGATTCATTCTTCTGCTTTTTCTTTTCTGCTACTATGC
TTTTAGTCACTGCATGAACAAGAACGCATCAACAATCCACAAAAAGCGTTCTTGCTGTTTGCACGTAGA
AGATAACACGGCAATCTCATAATATTTTTTGCGTAGGCAACCAACACCTCATGGCAAGTAGGACATGC
ACATCCATTTTTCTTTTCTGAATTCTGGATGCCATCTATCATTTTGAAGCGATGGCAACAGAAAATAAAA
TAGGATGGCAAGCAATAATACATGGTGGCAACTATGGACAACGATAGATGGCAACTGACGTTAGATACA
AGTGGCAATTATTTTTCCTCCCTCCCCATGCCAAATTCCTCCTTTTCTCCCTATTTTATAGTGATTAC
TACGCTACCAACTACTCGCATCAAAGCCAACCCAGAAGCTTGGCACAAGTCTAGCATAGTATATGGCA
GATCTGCGTATGTTGGTGGGAAAATGCAAAGACACACAAATTCGTGGGTGTTTGCCCTGATAGCG
TGGATCCAGTCGCCATCTTCGTGGGCAAATTTTGCAAATTCAGATTTCTGGACAAAAGAAGATCGGGG
ATCCACCTGTTTTAGCTCGTCGTCTTGGGAGTGCGGGGAGGGGGTAGGGTGGGGTGGGTGGG
TGGTTAGCTGTGGGAAAGGCGCTAGGGATTTGCTCTGGTTGCCATGGCAACCAGAGAAGGAAGGCG

```
ACGGAGGTAGGGGATCGGGAGATGCGAGACAATGGCGGCAGGGCGGACCGGGGATCGGAAGGAG
CCCGGGACAGCTGGCGTGCTGAGTCGTGCGGGCAGCGCGGTCGTTTGGCCCGGACGTGTGGCGG
TTTTGCCACACACCGGACGTGCGGGTTGTGGCTGCGCGCGCCCGGATGCGGTTTTGCGGGCGAGTT
CTTCTCCATGCCACACGAGGCGTGCGGCACAACCACCCGATACACCACACGTGTGGCAGTTATCGGT
GTTAAAAAAATGACGAGAGAAAAGTGGCGCAAACGGTTGCCCCGCACCCTCTCACGGACGGACTTTA
AAAGTCGGCATTGGTAACCGCAACACAACACAGACAGACGCACCCCAAGCCTCTCTCTATCTCTCTCT
TCCCATGCAATAGTTGTCACCACTCGCTCGCTACAGTGCCCGCATTGCATCGCATCCACATCCATATG
ACCATATCCATTCCTCCCCACGAGAAAAGGAGAGAGAGGGGAGAAATACTAGTCGTCGTCGTCGTAG
TAGCTGGTACGTCTACGCTAGAGCGACAGGGAAGAGGAGGGAGGGGGCGCTTGTCATCTACTCCT
CCTCCTCGCCCCTAGCTGGGATCCACAGCCTCCTCCTCCTCCTCGTGTCGGCCTCGTCCACATCCAC
CGTCTCCTCCGAGCGAGGTGGACAGCGACGCGGCCACGGAGCGAGGGAGGGAGAGAGACAAAGCC
GGTAATAAAGGCGGGGGCGCGCGCGCACAAGCCAAGCAAAGCACATTAACGACGCCAGCCAGC
CCGCGGGGAACCCCATTAAAGACGCTTCCGGGGGAGCGCCGTGGGCAAGCACAGGGGCTTAGCTTA
GCTTGGCTTGTGTGTTGTGTGCGCGAGAGGGAGACAGCGGCCGAGAGAGAAAGATGGCG

SEQ ID NO: 197: Hordeum vulgare L; HORVU2Hr1G101770; 2 kb promoter

AAAGTTCAAATAAGTTTTTCAGACCCTACCGTCATACACCTTGACGGTAGAATGTGA
AACCCTACCATTATATAAACGAATTCCCGTTACAACAACTTTACACACGAGGTCAGA
CTCCTACCGCCATAGTTCCTAATGGTAAGGTCTTGCATCCTATCGTCTTATACTTGG
CGGTACGGCCGTTACGCCACGTGAGCCCTTCGGCTGGCAGTTGACGGCCGCTGTTGT
TACTCGACTGTCAGATACCTATAAACCTATCGCCAACCTGTGTAACAATGAAAAACG
GTCAAATCCCGAAAAAATTTCGAAGCAGGATCGCATCCTGCTAAACTTTTGACAAAT
GGTCAAAACACGAAATTTTTGCCGCTCGTTGTGCCTCTGTAAGCTGGAAGCCTACGG
TGTCGGCCTCACCCCCCACACGGTGCTGCCGCTGCTGCGCCCATCGCCAGCGCTTCA
CGCTATATATCCACCCCGTCGTCGTGTGAGTCTCACCAGGCAGATCGAGCCCTGCGC
AGCGAGGGGAAAGAGACACACACAGCGCCACCAGGCAAGTAGTAGTAAAAGGCAAAA
GCACGGCACATTAAAAGAGAGGCCAGCCCAGCCCCGGACCGGACCGGAGCCAAGCAG
CAGCCGCAGCCGCAGCCGCAGCAGAGGAGAGAGAGAGGGAGGGAGAAGCATATATGG
CGATGCCCTTTGCCTCCCTGTCGCCGGCAGCCGACCACCACCGCTCCTCCCCCATCT
TCCCCTTCTGCCGCTCCTCCCCTCTCTACTCGTAAGCCGGCCGGCCGGCCGGCCAAC
CGCCTCACTTCTTTCTTCGTATCTGCTTCCATCTTAGCTCGAGGGGTTCGCTAATGC
GGTGACCGTCTCCGGCGCCTGTGTTGTGTTCCGTGTGTGCAGGGTAGGGGAGGAGGC
GGCGCATCAGCATCCTCATCCTCAGCAGCAGCAGCACGCGATGAGCGGCGCGCGGTG
GGCGGCGAGGCCGGCGCCCTTCACGGCGGCGCAGTACGAGGAGCTGGAGCAGCAGGC
GCTCATCTACAAGTACCTCGTCGCCGGCGTCCCCGTCCCGCAGGACCTCCTCCTCCC
CATCCGCCGCGGCTTCGAGACCCTCGCCTCGCGCTTCTACCACCACCACGCCCGTAC
GTACCCCATCCCTTCCTCCTCCTACCCCGGCCAGGAGTAGTACTTGCTTTTTTGCAT
TCGCCATGCGATTTGCCCGGTTGTTTATTCGGATCGAGCACTTGCTTTTGCATTCGC
CATGCGATTTGCCCGGCTTGTTTATTGGGATCGAGAGATTCAGGTGTGCTCGACCCC
CATCCCATGATTCCCATCTCTTTGTTAATTGCTCCGGTCATTTGTTAATCCCTCCCC
GGATTTGGCCGAGCAAAAGTCTCATTATTCTAATCCGAGCAAGCCTCGTGCCCCTGT
TCAAAGATTTGCTCCTACCATCACCACCTACCACCATCCAGCAAGCATCCCCTGCCT
CGCCGGGTCTTTTAATTTACTTGGGATTTCATTCTCATGTCATGTCATGTGCTATGA
TTTGATTAGATGGCGCTAGTCGAGTCTTGGGTTAGTTTCCATTGGTCCTTCCGTGGC
AAGGGGGTTATTCCTGTCTGGTTGTTGGGAGCCTCACCCACGCATTCACTCGCTCGC
TCGCTGGTCATGTCCTGCCACGGCCGATCTCACCGATCCATCCTGCATCGCATCACA
TGGACCCCCGACGAAAAGATCGGCAATCAACCACGCACAGCTCCTCCTTTCCCCGG
AAATTATTTCGCATACGTCCTTCCTTCCTTCGTTCCTTCCTTCTTGCGGGGTAAATG
ATTGGTTTGGTGGGGTGGGCACACAGATAGATCCAGGACGAGGACGACCGCTTCGA
TCCGTCCCTCCGGCCGGCCGGCGTCATGTTGATTGCTACCTGCTACGGCCTTGGACT
GGACGCGTCTCCGTTCTTCCGATCTCGCGTCTCCTCCTGAGTTGATTTCTTGGTCCC
TCCGG
```

SEQUENCE LISTING

SEQ ID NO: 198; *Sorghum bicolor* (L.); SORBI_004G269900; 2 kb promoter

```
TAAATATTGTTTATTATAGACTAACTAGGCTTAAAAAATTCGTCTCACAAATTACAA
TTGAACTGTCTAATTAGTTTATATTTTTGTCTATATTTAATGCTTCATGCATAAGTA
TAAAGATTTGACGTGACAGAGAATCTAAAAAATTTTACAAAATTGTTTGGAACTAAA
CAAGGCCCTAGAATACAAGGCTAAGGCCTTGTTTAGATGCACCCAAAAATCCAAAAC
TTTACAAGATTCTCCGTCACATCGAATCTTACAGCACATGCATGAAGTATTAAATAT
AGATAAAAATAAAAACTAATTACACAGTTTATCTGTAAATCGCGAGACAAATCTTTT
AAGCCTAGTTACTCCATGATTGGACAATGTTTGTCAAATAAAAACGAAAGTGCTACA
GTGTCAAAATCCAAAAGTTTTTGCATCTAAACAAGCCCTAAATATAAGGCCTCGTT
TAGTTCACCCCAAAAATCAAAAACTTTTCAAGATTCTCCGTCACATCGAATCTTGCG
GCACATGCATAAAGCACTAAATAAAGATGAAAATAAAAACTAATTGTACAGTTTACG
TGTAAATGAATCTTTTAAGCCTAATTACTCCATGATTAGATAATATTTATCAAATAA
AAACGAAAGTTTTACGGTTTGGAAAACCAAAAAGTTTTCGGAACTAGCCCTGTTTAA
ATTGAAGTTAAAATTTTTTTAGATGTCACGTTGTATGTGTCGGAAGGATATCGGGAG
GGGTTTTAAGAAACTAATAAAAGAACAAATTACATAGCTCGTCTAGAAACTGCAAGA
CAAATCTATTAATCATAATTAATATATCATTAGCACATATGAGTTATTATAGAACTT
AAGGCTAATCATAGACTAACTAGGCTTAAAAGATTCATCTCGCAATTCTAAACCAAA
CTGTGTAATTAGTTTATTTTTTATTTACATTTAGTGATCAATGTATGTGTCCAAAGA
TTTGATATGATGAATCTAAACACAAATCTAGGCCTTGTTTAGTTTCAAAATATTTTG
CAAAATGGACACGGTAGCTCTTTCGTTTGTATTTGACAAATATTGTCCAATCATGGA
CTAAATAGGCTCAAAAGATTTATCTCGTCAATTCCGACCAAACTGTGCAATTAGTTT
TTATTTTTGTCTATATTTAGTAATTCATGCATGTGTCTAAAGATTTCGATATGACGTG
GAATCTGAAAAATTTTGTAAAATTTTTTGGGAACTAAACAAGACCCTAACCATCAAC
AAATGACCGGATGTACAGTACTAGTTTCCAGTCGGCTGTCCAAACGCCCCCGCTGCT
CGCTCGCCGCCTCGCCGGGAGTCTCGACACGCCTGACGCTCCAGCGCGAGGCAGACA
GCGACGCAGAGAGAGACAAAGGGGCAATAAAGGCAGCGCGCGCGAGCACCAGCGAG
GGAGCGAAGCAAAGCACATCACGAGCCCGGAAGCTCATTAAGAGCAACTCCAGCATT
AGACCCTAAAACTAAACCCCTACTTTTAATTTGGGTGCTCTTCCTACTTCGTGGGGC
TCAATTTTTTTGCTTCAACTCCAACAGTAGCACCCAAATTTAGGCCCCCAAACTTAT
TCCAGAGAGAATGACACAAGGGACCCACTCGTCAGTGTCCTTTTCTTCTTCCTCTTT
CTTCTTCCTTTGGACATGGACACAATTAGAGCATCGAGCCGGTTACCGTAGGGTGTC
ATGCACATACAAGGGTAGAGAGAGAAGGAGCATGAGCTGAGGCTAGGACACGCGATG
GAGGATGGGGGCTGCCCTGTTGGGCCAACAGGAATGGGGTCTAGGAGAGAAATATGG
GTGCCCAGCCAAATATGGGGTCTGGAGTAGGGACCGTGCTGGAGTAATGTTTTTAGT
CTGAGCACCCATATTTAGCTATTGGGCTTGAGTAGAAGCTCTGCTGGAGTTGCTCT
AAAGAGGGGTGCCGTCCGGCCGGCCGCGGGGAGCAAGCAGCGCGCGCGAGAGACAGG
TTGAG
```

SEQ ID NO: 199: *Glycine max* (L.); GLYMA11G11826; 2 kb promoter

```
ACATACACTCTTTCTCTCCAAAAATAAATAAATTAATATACACTAGTTTGGCTTTT
AATTCCCAAATTACACCATTTTTTTGTGACATTGAGATGTAGGGATTTGACAACCC
GACTTCTCAGTGATTTTTATTTTTTTTAATTTAAATTTTATTTTTATTCTAAATT
TATGTTTTAGTTTAAATTATTATACACAAAAGTTAAGAAGTTAAAAAGTTGGGATT
CATCCCTATTTTTATCTATGGTTTTACTCCAATTTACTCTAATCAAGAATTAAGA
GAATCTAACTTACTTGAATGTTATAAATCCTTCATACCTTATTTAATTCTTACCTA
TAAAAAATCCCAATCAAGAAAAAAATCCCAATTAAGAGAATCTAACTTACTTTAAT
TATAACCGAAACAAAGCTACGTAACTTGATTACAAAATGTACGAGAAACCAAAATT
AGTGATGGTGAAAAAAATCACCGACAAAAGTAAGAATCTACACGTGATCTGAGATC
AGAGACATACTTTAAGAAGCAACAATCAACAGCCGAAAACCAAAATTAAAGGTATA
TATTCCTTAAATTGCTTTGTCCCTTTGACTTTTGCCATCGTGATGATTAATTAAAG
GTTAGCAAACCCTTCGACCTTCATACAATTGACTGAATGAGAATTTATTTCACATT
CGAGGAAGCGATGCTACAACATCACTTTTTTGTTCTGTATTGTGCTTTTTAACTGC
CTTTTTTCTTCTTCTTTTTTGCCTCCCTAACAAAGACATGTAAAAGTAATTGTAA
TAATATTCGTTTCTTATGGAATGCAATCAGTTGATTGATGTAACTATAAACTATTA
TCTCCTTAATATCGAAAGACAAGTGAAGCCAAACACAAACAAGATAGGGCCTAGGG
AGAGGTGTGGTCCATGAATGATGAGGTATGGGTGACCAAACAATGAATGAATAATT
GAAGCATCCTTGACCGTTGCTTGAGTTTGTGTCATCCTCAATAATATACTAGTCCC
TTGGCTACAGAAACCGATAAGCCTAAAACTGGAATTGCACACATTTACGTTTTTGAT
TTTGATTTTGTTTTGGCAATCTCGCCCCACATCAAATGTCACCCGCATTCCGGCAA
GTAGTGGATGGTTCCTCTAGCGGTGCTTTGCCTTTGGGCCACTGGGCCCGCAATTA
CTCCAGCCCATCATGCCTTGTTGCTGTCCGTTAAAGGGTAGCATAATAAAATAAA
AGTAGATCAACAAAATGAGAGCAAGTATTTCAAAAAAAAAAAAAACATAGTAAAAA
AACACTTCCTCTATTTATATTATCAAGATTTATTTATCTTAAAACATTCATTATCT
CAAAAATACCTATATTACTTAATAGTATTTCATGAATTTAAATCTAAGTTTACTAT
CAAACTCACCTTTTAAAACAATTATTACACAACAAGTTATAATTGAATGTCATAAA

AAAAATTGATTATTGTGCTAACACGTGAAAAAAATTTATATTTAATTTTTTTATGT
ATAATTTGTTTGGACCAATGATAGAGATTAATTGTGATCTAATGAGTTATAAGAAA
TACGTGGCACATGATCCTAGACAAAAATAAATAAGAATTGTAAAATAATGTATTTT
ATAGCTTTTCTGAAAGATTTTTTTTTTAATTTCTTCTCATGCCCATACATGAATA
CATGAATGAGAATTTTTATTTTTATTTTTTTGTCTGAAATAAAGTTAAAAATTGGG
AGCAGTGAATGTTAAGGATGACTTTTGACTTGAATGCAACAAGAAGTAAAGTTCAC
TTTAAGTTGGAGGCTTGGAGCATCGCCATCCATAACACAACACAATCGACAATCCTA
```

ATGGTTCCGACAAAGCTCGACCTGAGTGTGATCTCATGATGTTTCTGCTCTAACTA
TGTTTGATTTGGATACCCAACAACAAAAAGAGTGTTGTCGTGTTGTTGTAGTTAA
TAGTAATAGGACTAAGTAAGAGTAGTGGAAAAC

SEQ ID NO: 200: *Brassica napus*; BnaA03g16700D; 2 kb promoter

CATACCTTCAGGATGTGTGAAGCATTCCTATTGAATTTTGTCGATAAAATAGAAATTGCAAGTTGAACA
AATTGCAATATATATGGAAAGATGCTAGCTAGTGCCAATAATATATTAACGGAACAATTCATATTTCAT
TTTATATTATATAATGATTATTTTAGTTTTTAGTTAATACTAATAAATAATAAGAAATATAACTACATA
GTTTAAATGATAGTGTGTTCTAAATTTGTTAAATGGATATCTAAATCAGTTTAGGTGGCTTTTAAATG
TTATTTTATGTTCATGTAAATTAATTATTGTTTTACATTTAACATTGTATTACTTTTTATCATATTAGT
TAATTAATGACACTCGTTTTCATTCTAAAATCAAATATCAGACATATTCATCTTTATAACAATATGAA
AATTAATTTTCAGTATTAATCTAAAAAATCTATTTAAATTTTGATGCGTCTGACTTATAAAAACACACA
CACATATATATATATATATGTATATATTTATTAATTAGTAAAATTTATTTTAAGAAAAATTGAAACT
AATTAAATTTTGGGAAAGTAGTGATTATATAATAGTTTTGTTATTTTATATGCTAAATTTATTAAGTA
CTTTTTTTTTTAATTTGAGACTTACCAAATTACGGATCCTAAATATATTGATCTTGAATTATGATATAT
TAATTAAATTTTAAAGTTATCATAAATTTGTTGTGAATTCAGTTTAGGTAATTGTCTATTAAATTAGAA
AAAAGATAAATAATGATAAAGTTATGTTAGTTATTAGTTTAATAGTATTGAGGTGTAAATAAATTAAAG
TTGTAATGGTTAATTTATAAGTGTATTTGTGTTTTAATTATATTAGATTTCAATTGATTCCACAGATAA
TTCAACATGTTCCATGTAATTAATGTTACAGCAGAAATCTAGATAAATTTTTTTTTAACACTGGATAA
TGCGATTATAAACGATAAGACGATTCTATATGCGACATGTCTTATAATGATTCATGTCTGAATACATCA
TTTGAACCGTTTTATAAGATCTACGTTTGGTGGTATTTTTTGTGCTATGCTGCAGATTTTTTATAAGTA
TTTATTTCATTAATTCGCATAATTTTATTTTTTTCTAAAGATCGAAACTCCGATTTTATGGTGTTGAA
CATCTAGATAGAGATCTATGGATAAAACAAATATAGAGGAAGCTACACAATTTAAAGGGTCAAAATAGA
AACACAGAACTGAAAAGTATACTCAGTGCCATATGATTTAATAGTATGAATTTAACTTGAACTTAATGT
CGTTTGGTTTGTCATCAAATGCAACTGCAAATCATATCGAAGTAACGCCCGTGTCATAATATATCTGAT
TAAGGACTATTATTTTCTGTTTGACAAAAAAAAAGGACTATTATTTTCTCACTAATCAGGCTATTGTT
TTTTTCTCAATAAACTAATTAAAGAAATACAGATTATTCAAGTGCTATTTCCAAGGCAGATGCAGGTT
ACTATCTCTCGATCTTCATCTCGGAGTGTGGTTCTTTATGTGTTTTCTGACTTGCTTTATTATACTAAT
ATTATTATTAGATTAATGAAGATTAATAGTTTAATAGATTAATGAAGACATAAACTATAATTTAATAAT
CATAGATTAATGAAGATTTGTGAACCCCATTAATAAAGTTTAATAGTTGTTGTTCTTATAGTCTTTTAC
CGTATAGTTTTCTCCCCCATCTGTCTCGTCTCACTGTCTTTTCCTCTCAAGTTTCAAGTGCCCTAAAT
AAAAACCTCTTTCCCCTTCTCTCTCTGCAGAAGAAGGTCAGATACAGAAACTGACTGCAAAGAACAA
AGCTGCAAGGTGCAGCTATTCCTTAGTAAAAAGCTTTGTTCTCTTTCTTCTTTTGCTCTTCACATCCCC
CCCAACAGAGACTTTTCTGCTATTTAAAACCAGACCCTGGAAAAAGTAGCCAACACTCTCTCTTTCCC

SEQ ID NO: 201; *Solanum lycopersicum*;Solyc08g075950; 2 kb promoter

CATTTAATTAGTTAAATCAAATACATACATATATAATTGTTATTAATTTTTAGGTATGATGTACCATTA
AGACATAAGAAGATCAGTGATGACGCAACGTATTTCAATTTTTTTGTGGGTTAAGTATATGTCTTAAAC
TTAACATAGATTTAAAATTATTTAAATTGTTAATACCTAAAGTTTATTTTTATTTTCATTTTTGAAAGA
ACAATAATTCAAGTGGGTAATTGACAAATTATTTTGAATATAAAAAAATGAAAAACAGAGAAAAAAAA
CATTAGTAAAATCATTAAATTACACCAAACAAATTTGGAGAATTGAAAAAGAACATTTATAACAACTCT
AATATAAATAAAAAGAAATTAAATTACAAAAGTTTTTTTTAAAAAAAATAAAGGGTTAGTTTAGTCAT
TTAGGAATCTTATCCGAGGTTTAACAAATTTTGAATTAGTTATCCCTCCATTTCGAAGGGATAAGATAA
TACTAGATATGATGGATAAGCAATCCATGAGTTAAATTAAATGAAGTAACCAAAACAATGTATTAGTTG
AATTAAATTTTAATCCATAAATTATTCTACCTAATATTGTCTATCAAACGGGTCCTTAGTATTAGTTAA
CTGGTGACGAGGATCATATAATTTAAAGAGTTGGGTCCAGTTTTAAAGCGTGATTATAGCGAAATGAAA
TGTTTCTTATCCCACCAAAAATTTGATTATAAAACGAAAATGACTCTCGTTGAGAAAAGAAAATTTACA
AATGATATTCATCCTCCCGTAATTCTCATATAATTTGTTTTTGATGTACATGAATATTTTTTAAAATAG
TTTTTTTAGTTTTTACAAAAATATATAATCTCACTCAACACAAACTCGTTAGGAATTAAATTAAACTTT
TGTGTTGATCAACATAAGTCGCATAACTTATGAGTTTTGATATCGAACTTTGTCGGACTGGATATAAAT
TAGAAAACAGAGTCATGAAATACTTAATATAAGTCACATAATTTATGAATTTTGATATTAGACTTTGTC
TTGCTCGAAACAAGTTTTGAATAAAAAAAATTATGCAATACGACATAACTAATGAGATTAATCACATTT
GCATTATTCAAGACTCATAAATACAAAATTTCTAAATTGAGTAATCTCATCTATGTCATCTGTTCACAT
ACAAAACTAAAAACTATCTATGCCACCACACTTCTTGATGATGTGTTGGAGCTTATTTCTCAAGATATT
TCACATTCTTGCTCAAACAAAAAGCACAAGTTTCAAAAAGTAAAAAAAAAAAGAGAGAAAACAATCA
TATATATATATATATATCAAACTAGAATAAGATCTTTTGTAGGTCATCTTAATTATTGTTGAACCTTAA
AGGACAAAGTTTACATCTTTAGGGTCATGATACATTCACATGACTAAATTTTGAAGATATAAAAAGAG
GTGTTACATCATTTGGACCACAATAAGACATTATCCATTCTACCCCACTCCATAAGGTCCCCCTTCTTT
CAATCCCCTTTTCTCCCCCATGCCCAATGCTTCCTTAAACCCTTCATTATCTTTCACAAAACTTAT
ACTATAATGTCATCATTCATATTGTTATTGTCATTTATTCTTCTCACCATAAAGTTCAATGTAAGTTTG
TTAATTTTGTCTTGTACATTATAAGTACTAGTGTTATGAATGTTTCTTGATTTCACTCTAATTAAATC
TCACTCTCTTTCTTCAGCTTTATCTCTCTGCTCTTTCTTCCATGCTTGTCCAAACCCTAGATCTGTCCC
CCTCTTAGGTAACCTCAACAAACTTTGCTCTCTATAACTCACACACAACACACAAAAACACATTCTTTT
TCTCTTTCTCTGTGTATATGTTTGTATATTAACTGATATTGTGTTGATTTCTAGGTGCAGCTTTTTGAG
TGAAGTGAAAAGGGGAAAGGGGGTGGGTAAAATTTGGAAAGATTAGTTTTTTAGTGAAGGGAGAAG

The invention claimed is:

1. A genetically altered plant, part thereof or plant cell, wherein the plant is characterised by an increase in at least one of nitrogen uptake and/or nitrogen assimilation and/or nitrogen use efficiency compared to a control plant, wherein
a) the genetically altered plant, part thereof or plant cell comprises a nucleic acid construct comprising a GRF4 nucleic acid, wherein the GRF4 nucleic acid encodes a GRF polypeptide comprising SEQ ID NO: 3 or 6; or
b) the genetically altered plant, part thereof or plant cell comprises at least one mutation in a GRF4 promoter operably linked to a gene encoding SEQ ID NO: 3 or 6, wherein the GRF4 promoter comprises SEQ ID NO: 7 or 8; and wherein the mutation is a T to A substitution at position −884 or −878 from the GRF4 start codon ATG of an open reading frame for a polypeptide with SEQ ID NO: 3 or 6; and a C to T substitution at position −847 or −841 from the GRF4 start codon ATG of the open reading frame for the polypeptide with SEQ ID NO: 3 or 6; and a C to T substitution at position −801 or −795 from the GRF4 start codon ATG of the open reading frame for the polypeptide with SEQ ID NO: 3 or 6,
and wherein the control plant does not comprise the nucleic acid construct of a) or the at least one mutation of b).

2. The genetically altered plant of claim 1, wherein the plant is selected from the group consisting of rice, maize, wheat, barley, sorghum, potato, tomato, soybean and *B. napus*.

3. The plant part of claim 1, wherein said plant part is grain or a seed.

4. A recombinant nucleic acid construct comprising:
a nucleic acid sequence encoding at least one protospacer element, wherein the sequence of the protospacer element is selected from SEQ ID NOs: 50, 53, 58, 61, 66, 69, 74, 77, 82, 86, 91, 94, 99, 102, 107, 110, 115, 118, 123, 126, 131, 134, 139, 142, 147, 150, 155, 158, 163, 166, 171, 174, 179, 182, 187 and 190, and a nucleic acid sequence encoding at least one tracrRNA sequence, wherein the sequence of the tracrRNA is SEQ ID NO: 46; and/or wherein the recombinant nucleic acid construct comprises at least one DNA donor nucleic acid selected from SEQ ID NOs: 48, 56, 64, 72, 80, 84, 89, 97, 105, 113, 121, 129, 137, 145, 153, 161, 169, 177 and 185.

5. A single guide RNA molecule for introducing a TC to AA mutation in a miRNA396 binding site, wherein the single guide RNA is encoded by a nucleic acid sequence selected from the group consisting of:

SEQ ID NOs: 51 or 54 when used in rice,
116, 119, 124, or 127 when used in maize,
132, 135, 140, 143, 184, or 151 when used in wheat,
156, or 159 when used in barley,
164, or 167 when used in sorghum,
172, or 175 when used in soybean,
180, or 183 when used in *B. Napus*, and
181 or 191 when used in tomato.

6. The genetically altered plant, part thereof or plant cell of claim 1, wherein the genetically altered plant additionally comprises at least one mutation in a miR396 binding site, wherein the miR396 binding site comprises a nucleic acid sequence comprising SEQ ID NO: 45, and wherein the mutation prevents cleavage of the sequence by miR396.

7. The genetically altered plant, part thereof or plant cell of claim 6, wherein the at least one mutation in a miR396 binding site comprises a T to A substitution at position 4 of SEQ ID NO: 45; and a C to A substitution at position 5 of SEQ ID NO: 45.

8. The genetically altered plant, part thereof or plant cell of claim 2 wherein the plant is not rice.

9. The genetically altered plant of claim 2, wherein the plant is wheat.

10. The genetically altered plant of claim 2, wherein the plant is soybean.

11. The genetically altered plant of claim 2, wherein the plant is maize.

12. A method for producing the genetically altered plant of claim 1, wherein the method comprises:

i) introducing a nucleic acid construct comprising the nucleic acid of a) or introducing at least one mutation into the GRF promoter of b) into a plant, a part thereof or plant cell to produce a genetically altered plant, a part thereof or plant cell;

ii) growing a progeny plant from the genetically altered plant, the part thereof or plant cell;

iii) measuring nitrogen uptake and/or nitrogen assimilation and/or nitrogen use efficiency in the progeny plant in comparison to the control plant; and iv) selecting the progeny plant with an increase in at least one of nitrogen uptake and/or nitrogen assimilation and/or nitrogen use efficiency in comparison to the control plant.

13. The method of claim 12, wherein the method further comprises measuring grain yield and/or carbon assimilation in the progeny plant in comparison to the control plant and selecting the progeny plant with an increase in grain yield and/or carbon assimilation in comparison to the control plant.

14. The method of claim 12, wherein the method further comprises introducing at least one mutation into a micro RNA binding site of the GRF4 nucleic acid, wherein the micro RNA binding site is a miRNA396 binding site, wherein the miR396 binding site comprises a nucleic acid sequence comprising SEQ ID NO: 45, and wherein the mutation prevents cleavage of the sequence by miR396.

15. The method of claim 14, wherein the at least one mutation in a miR396 binding site comprises a T to A substitution at position 4 of SEQ ID NO: 45 and a C to A substitution at position 5 of SEQ ID NO: 45.

16. A single guide RNA molecule for introducing a mutation into a GRF4 promoter operably linked to a gene encoding a GRF polypeptide comprising SEQ ID NO: 3 or 6, wherein the single guide RNA is encoded by a nucleic acid sequence selected from the group consisting of: 59, 62, 67, 70, 75, 78, 83, 87, 92, 95, 100, 103, 108, and 111.

\* \* \* \* \*

SEQUENCE LISTING

<160> NUMBER OF SEQ ID NOS: 207

<210> SEQ ID NO 1
<211> LENGTH: 3385
<212> TYPE: DNA
<213> ORGANISM: Oryza sativa

<400> SEQUENCE: 1

| | | | | | |
|---|---|---|---|---|---:|
| atgacgatgc | cgtatgcctc | cctgtctccg | gcggtggccg | accaccgctc | gtccccggca | 60 |
| gccgcgaccg | cctccctcct | ccccttctgc | cgctccaccc | cgctctccgc | gtaagcaacg | 120 |
| cgaacccgcg | gctacaaccc | attttcttgg | ctccagtggt | gcatgtgaca | cacggtgag | 180 |
| acgttgtgtg | tgggtgggtg | ggtgcagggg | cggtggtgtt | gtcgcgatgg | gggaggacgc | 240 |
| gccgatgacc | gcgaggtggc | cgccggcggc | ggcggcgagg | ctgccgccgt | tcaccgcggc | 300 |
| gcagtacgag | gagctggagc | agcaggcgct | catatacaag | tacctggtgg | caggcgtgcc | 360 |
| cgtcccgccg | gatctcgtgc | tccccatccg | ccgcggactc | gactccctcg | ccgcccgctt | 420 |
| ctacaaccat | cccgcccgta | cgtcgtgttc | ctatttcttg | cctctcctct | accatcgctg | 480 |
| cattgctttt | ggatgcttgt | ttagtgtcgg | cctctttgtt | tattccgatc | aggcgtactt | 540 |
| tgcttccatt | tgttaattgg | ctccgggtca | tttgttaatc | cgggttacgc | gattcaagaa | 600 |
| acatgcgtgt | ggttttttatg | ctatcctccg | gatttggtta | taaaaaggct | tgtttttaaa | 660 |
| tccaaaactc | gtgctcgctt | cacgattagc | gcatcatttt | tttttatgg | ggggggggg | 720 |
| gggagagttt | gccatcatt | ctgtctctgt | ttgatctgat | agaggacgtg | cacacgctct | 780 |
| tgtctgaaat | aaaatctttt | gtttatcagt | atgcccatgg | gataagccat | tttctctgtg | 840 |
| aaccaacacc | ctggcaaact | gtttttttgc | tcgccatttt | tgagcgattg | ctaagaacag | 900 |
| ataactatgc | cctgcatatg | gatcggatat | ggacttctca | aatattcaaa | tgccattcta | 960 |
| ttaggaactc | aaaatgcatt | accaacaaat | gcattcttgt | gtgtaacacg | gttgctacga | 1020 |
| tgtgcctgtt | tttgtacagt | tggatatggt | ccgtacttcg | gcaagaagct | ggacccagag | 1080 |
| ccagggcggt | gccggcgtac | ggacggcaag | aaatggcggt | gctcgaagga | ggccgcgccg | 1140 |
| gattccaagt | actgcgagcg | ccacatgcac | cgcggccgca | accgttcaag | aaagcctgtg | 1200 |
| gaaacgcagc | tggtcgccca | gtcccaaccg | ccctcatctg | ttgtcggttc | tgcggcggcg | 1260 |
| cccccttgctg | ctgcctccaa | tggcagcagc | ttccaaaacc | actctctta | ccctgctatt | 1320 |
| gccggcagca | atggcggggg | cgggggagg | aacatgccca | gctcatttgg | ctcggcgttg | 1380 |
| ggttctcagc | tgcacatgga | taatgctgcc | ccttatgcag | ctgttggtgg | tggaacaggc | 1440 |
| aaagatctca | ggtgattgtt | catttctttt | tttttaatca | aacgccatat | ttacttgttt | 1500 |
| agcactgtct | tgaatcatga | tatgtatcct | tccgttgtct | aaaaaaaagg | tgtcatgctc | 1560 |
| taactgattg | gtgtcaggtg | gatgcagtta | tgaatctgta | tttttctttg | tgatcggtta | 1620 |
| ataactgtgt | cccatttgtt | tgcattggtg | gcaatcgaac | cagctgtcca | tgctcagtag | 1680 |
| tactacttcg | atttggtgct | gcaatcactg | aaagtctgaa | actttactct | ctgcactgca | 1740 |
| aaaatttgtg | ttatgtttag | gtttccagag | tgctgcctct | tgcccttcc | catactttct | 1800 |
| ggtatcagtt | ttcagcccca | gaagccgggg | acagtctcca | taagagattt | ctgctcaggt | 1860 |
| gaaactgggg | tgcagggtct | taacatggct | ttggcccagt | agtttgaaac | atgtactgtc | 1920 |
| cataaagatg | atactactac | atatttgtgt | ctgccctcgc | agtgcttgtg | cctgctggta | 1980 |
| gctgatcatg | gcttcccttg | gcatttactc | cacttcttta | ttcctccaca | gaatccagtt | 2040 |
| gtttctgtct | ctgctcttca | ggggcagtca | attatttggc | ccttgcaaaa | tactatctct | 2100 |

-continued

```
gaagatgtct caccgatcac cactatacct gaaacatttt ccagtggcca gcgtgagctg    2160
catgatgctc caagtcaact ctatactcat ccaatgttga tgattagatt ttaacaatgc    2220
aactctttga tttatcttcc ctacaaaaaa aaaggaactc tttgatttat cttcggtgaa    2280
tctcagtctg accttagtac ctagcctcat tatttacttc accaaatgta taactctaca    2340
gtgcttgttc gtgttgattt ggtttagttt agttattgaa ttattcggtc accttagtct    2400
ttgattgttt ttttctttct gctcttgtca tcaactgttt agggttcagc tgacttgctg    2460
ctgcaactaa actgtcttct ggttttactg caaaatagaa tgtttcttgg gccatgatct    2520
gctgctatat atgattagtt aaaccatggt tctatgtttt cttatatgaa ttcatgacaa    2580
gaatactaac ttttggaaaa ggtaatttta ttttttttgt atgataataa tgctttggat    2640
tctttctagt ttatctgtcg gacttaggtt aactacattt cctccggtac atggatttat    2700
ttcattctta caattgagcc cttatgaata ttttcttcct aattctgttc taaaaagtta    2760
gaattgacat attttcgata ggtacatgcc tagcacttgc attcgtgttt cctactaatt    2820
cccaatcact gtatcttctc aaattcaggt atactgctta tggcacaaga tctttggcgg    2880
atgagcagag tcaactcatt actgaagcta tcaacacatc tattgaaaat ccatggcggc    2940
tgctgccatc tcagaactcg ccatttcccc tttcaagcta ttctcagctt ggggcactaa    3000
gtgaccttgg tcagaacacc cccagctcac tttcaaaggt tcagaggcag ccactttcgt    3060
tctttgggaa cgactatgcg gctgtcgatt ctgtgaagca agagaaccag acgctgcgtc    3120
ccttctttga tgagtggcca aagggaaggg attcatggtc agacctcgct gatgagaatg    3180
ctaatctttc gtcattctca ggcacccaac tgtcgatctc cataccaatg gcatcctctg    3240
acttctcggc ggccagttct cgatcaacta atggtacgac tacttgatct ccccccaatt    3300
acttcgtgcg tgtttatgtc tgtatcctgc aatgtctgaa gatttcttac tgaaaacgtc    3360
atctggtctg tgtgcaggtg actga                                          3385
```

```
<210> SEQ ID NO 2
<211> LENGTH: 1185
<212> TYPE: DNA
<213> ORGANISM: Oryza sativa

<400> SEQUENCE: 2
```

```
atgacgatgc cgtatgcctc cctgtctccg gcggtggccg accaccgctc gtccccggca     60
gccgcgaccg cctccctcct ccccttctgc cgctccaccc cgctctccgc gggcggtggt    120
gttgtcgcga tgggggagga cgcgccgatg accgcgaggt ggccgccggc ggcggcggcg    180
aggctgccgc cgttcaccgc ggcgcagtac gaggagctgg agcagcaggc gctcatatac    240
aagtacctgt ggcaggcgt gcccgtcccg ccggatctcg tgctccccat ccgccgcgga    300
ctcgactccc tcgccgcccg cttctacaac catcccgccc ttggatatgg tccgtacttc    360
ggcaagaagc tggacccaga gccagggcgg tgccggcgta cggacggcaa gaaatgcgg    420 tgctcgaagg aggccgcgcc ggattccaag tactgcgagc gccacatgca ccgcggccgc    480
aaccgttcaa gaaagcctgt ggaaacgcag ctggtcgccc agtcccaacc gccctcatct    540
gttgtcggtt ctgcggcggc gccccttgct gctgcctcca atggcagcag cttccaaaac    600
cactctcttt accctgctat tgccggcagc aatggcgggg cgggggggag gaacatgccc    660
agctcatttg gctcggcgtt gggttctcag ctgcacatgg ataatgctgc cccttatgca    720
gctgttggtg gtggaacagg caaagatctc aggtatactg cttatggcac aagatctttg    780
```

```
gcggatgagc agagtcaact cattactgaa gctatcaaca catctattga aaatccatgg    840
cggctgctgc catctcagaa ctcgccattt ccccttcaa gctattctca gctgtgggca     900
ctaagtgacc ttggtcagaa caccccagc tcactttcaa aggttcagag cagccactt      960 tcgttctttg ggaacgacta tgcggctgtc gattctgtga agcaagaaa ccagacgctg    1020 cgtcccttct ttgatgagtg gccaaaggga agggattcat ggtcagacct cgctgatgag   1080
aatgctaatc tttcgtcatt ctcaggcacc caactgtcga tctccatacc aatggcatcc   1140
tctgacttct cggcggccag ttctcgatca actaatggtg actga                   1185
```

<210> SEQ ID NO 3
<211> LENGTH: 394
<212> TYPE: PRT
<213> ORGANISM: Oryza sativa

<400> SEQUENCE: 3

```
Met Thr Met Pro Tyr Ala Ser Leu Ser Pro Ala Val Ala Asp His Arg
1               5                   10                  15

Ser Ser Pro Ala Ala Thr Ala Ser Leu Leu Pro Phe Cys Arg Ser
                20                  25                  30

Thr Pro Leu Ser Ala Gly Gly Val Val Ala Met Gly Glu Asp Ala
        35                  40                  45

Pro Met Thr Ala Arg Trp Pro Ala Ala Ala Arg Leu Pro Pro
50                  55                  60

Phe Thr Ala Ala Gln Tyr Glu Glu Leu Glu Gln Gln Ala Leu Ile Tyr
65                  70                  75                  80

Lys Tyr Leu Val Ala Gly Val Pro Val Pro Asp Leu Val Leu Pro
                85                  90                  95

Ile Arg Arg Gly Leu Asp Ser Leu Ala Ala Arg Phe Tyr Asn His Pro
            100                 105                 110

Ala Leu Gly Tyr Gly Pro Tyr Phe Gly Lys Lys Leu Asp Pro Glu Pro
        115                 120                 125

Gly Arg Cys Arg Arg Thr Asp Gly Lys Lys Trp Arg Cys Ser Lys Glu
    130                 135                 140

Ala Ala Pro Asp Ser Lys Tyr Cys Glu Arg His Met His Arg Gly Arg
145                 150                 155                 160

Asn Arg Ser Arg Lys Pro Val Glu Thr Gln Leu Val Ala Gln Ser Gln
                165                 170                 175

Pro Pro Ser Ser Val Val Gly Ser Ala Ala Pro Leu Ala Ala Ala
            180                 185                 190

Ser Asn Gly Ser Ser Phe Gln Asn His Ser Leu Tyr Pro Ala Ile Ala
        195                 200                 205

Gly Ser Asn Gly Gly Gly Gly Arg Asn Met Pro Ser Ser Phe Gly
    210                 215                 220

Ser Ala Leu Gly Ser Gln Leu His Met Asp Asn Ala Ala Pro Tyr Ala
225                 230                 235                 240

Ala Val Gly Gly Gly Thr Gly Lys Asp Leu Arg Tyr Thr Ala Tyr Gly
                245                 250                 255

Thr Arg Ser Leu Ala Asp Glu Gln Ser Gln Leu Ile Thr Glu Ala Ile
            260                 265                 270

Asn Thr Ser Ile Glu Asn Pro Trp Arg Leu Leu Pro Ser Gln Asn Ser
        275                 280                 285

Pro Phe Pro Leu Ser Ser Tyr Ser Gln Leu Trp Ala Leu Ser Asp Leu
    290                 295                 300
```

```
Gly Gln Asn Thr Pro Ser Ser Leu Ser Lys Val Gln Arg Gln Pro Leu
305                 310                 315                 320

Ser Phe Phe Gly Asn Asp Tyr Ala Ala Val Asp Ser Val Lys Gln Glu
                325                 330                 335

Asn Gln Thr Leu Arg Pro Phe Phe Asp Glu Trp Pro Lys Gly Arg Asp
            340                 345                 350

Ser Trp Ser Asp Leu Ala Asp Glu Asn Ala Asn Leu Ser Ser Phe Ser
        355                 360                 365

Gly Thr Gln Leu Ser Ile Ser Ile Pro Met Ala Ser Ser Asp Phe Ser
370                 375                 380

Ala Ala Ser Ser Arg Ser Thr Asn Gly Asp
385                 390

<210> SEQ ID NO 4
<211> LENGTH: 3386
<212> TYPE: DNA
<213> ORGANISM: Oryza sativa

<400> SEQUENCE: 4
atgacgatgc cgtatgcctc cctgtctccg gcggtggccg accaccgctc gtccccggca      60
gccgcgaccg cctccctcct cccttctgc cgctccaccc cgctctccgc gtaagcaacg     120
cgaacccgcg gctacaaccc attttcttgg ctccagtggt gcatgtgaca acacggtgag     180
acgttgtgtg tgggtgggtg ggtgcagggg cggtggtgtt gtcgcgatgg gggaggacgc     240
gccgatgacc gcgaggtggc cgccggcggc ggcggcgagg ctgccgccgt tcaccgcggc     300
gcagtacgag gagctggagc agcaggcgct catatacaag tacctggtgg caggcgtgcc     360
cgtcccgccg gatctcgtgc tccccatccg ccgcggactc gactccctcg ccgccgctt     420 ctacaaccat cccgcccgta cgtcgtgttc ctatttcttg cctctcctct accatcgctg     480
cattgctttt ggatgcttgt ttagtgtcgg cctctttgtt tattccgatc aggcgtactt     540
tgcttccatt tgttaattgg ctccgggtca tttgttaatc cgggttacgc gattcaagaa     600
acatgcgtgt gtgtttttat gctatcctcc ggatttggtt ataaaaaggc ttgttttaa     660 atccaaaact cgtgctcgct tcacgattag cgcatcattt ttttttttgtg gggggggggg     720 gggggagtt tgcccatcat tctgtctctg tttgatctga tagaggacgt gcacacgctc     780
ttgtctgaaa taaatctttt tgtttatcag tatgcccatg gataagcca ttttctctgt     840 gaaccaacac cctggcaaac tgttttttg ctcgccattt ttgagcgatt gctaagaaca     900
gataactatg ccctgcatat ggatcggata tggacttctc aaatattcaa atgccattct     960
attaggaact caaaatgcat taccaacaaa tgcattcttg tgtgtaacac ggttgctacg    1020
atgtgcctgt ttttgtacag ttggatatgg tccgtacttc ggcaagaagc tggacccaga    1080
gccagggcgg tgccggcgta cggacggcaa gaaatggcgg tgctcgaagg aggccgcgcc    1140
ggattccaag tactgcgagc gccacatgca ccgcggccgc aaccgtaaaa gaaagcctgt    1200
ggaaacgcag ctggtcgccc agtcccaacc gccctcatct gttgtcggtt ctgcggcggc    1260 gcccttgct gctgcctcca atggcagcag cttccaaaac cactctcttt accctgctat    1320
tgccggcagc aatggcgggg gcggggggag gaacatgccc agctcatttg gctcggcgtt    1380
gggttctcag ctgcacatgg ataatgctgc cccttatgca gctgttggtg gtggaacagg    1440
caaagatctc aggtgattgt tcatttcttt tttttaatc aaacgccata tttacttgtt    1500
tagcactgtc ttgaatcatg atatgtatcc ttccgttgtc taaaaaaaag gtgtcatgct    1560
ctaactgatt ggtgtcaggt ggatgcagtt atgaatctgt attttctttt gtgatcggtt    1620
```

| | |
|---|---|
| aataactgtg tcccatttgt ttgcattggt ggcaatcgaa ccagctgtcc acgctcagta | 1680 |
| gtactacttc gatttggtgc tgcaatcact gaaagtctga aactttactc tctgcactgc | 1740 |
| aaaaatttgt gttatgttta ggtttccaga gtgctgcctc tttgcccttc ccatactttc | 1800 |
| tggtatcagt tttcagcccc agaagccggg gacagtctcc ataagagatt tctgctcagg | 1860 |
| tgaaactggg gtgcagggtc ttaacatggc tttggcccag tagtttgaaa catgtactgt | 1920 |
| ccataaagat gatactacta catatttgtg tctgccctcg cagtgcttgt gcctgctggt | 1980 |
| agctgatcat ggcttcsscctt ggcatttact ccacttcttt attcctccac agaatccagt | 2040 |
| tgtttctgtc tctgctcttc aggggcagtc aattatttgg ccsttgcaaa atactatctc | 2100 |
| tgaagatgtc tcaccgatca ccactatacc tgaaacattt tccagtggcc agcgtgagct | 2160 |
| gcatgatgct ccaagtcaac tctatactca tccaatgttg atgattagat tttaacaatg | 2220 |
| caactctttg atttatcttc cctacaaaaa aaaaggaact ctttgattta tcttcggtga | 2280 |
| atctcagtct gaccttagta cctagcctca ttatttactt caccaaatgt ataactctac | 2340 |
| agtgcttgtt cgtgttgatt tggtttagtt tagttattga attattcggt caccttagtc | 2400 |
| tttgattgtt tttttctttc tgctcttgtc atcaactgtt tagggttcag ctgacttgct | 2460 |
| gctgcaacta aactgtcttc tggttttact gcaaaataga atgtttcttg ggccatgatc | 2520 |
| tgctgctata tatgattagt taaaccatgg ttctatgttt tcttatatga attcatgaca | 2580 |
| agaatactaa cttttggaaa aggtaatttt attttttttg tatgataata atgctttgga | 2640 |
| ttctttctag tttatctgtc ggacttaggt taactacatt tcctccggta catggattta | 2700 |
| tttcattctt acaattgagc ccttatgaat attttcttcc taattctgtt ctaaaaagtt | 2760 |
| agaattgaca tattttcgat aggtacatgc ctagcacttg cattcgtgtt tcctactaat | 2820 |
| tcccaatcac tgtatcttct caaattcagg tatactgctt atggcacaag atctttggcg | 2880 |
| gatgagcaga gtcaactcat tactgaagct atcaacacat ctattgaaaa tccatggcgg | 2940 |
| ctgctgccat ctcagaactc gccatttccc cttcaagct attctcagct tggggcacta | 3000 |
| agtgaccttg gtcagaacac ccccagctca cttcaaagg ttcagaggca gccactttcg | 3060 |
| ttctttggga acgactatgc ggctgtcgat tctgtgaagc aagagaacca gacgctgcgt | 3120 |
| cccttctttg atgagtggcc aaagggaagg gattcatggt cagacctcgc tgatgagaat | 3180 |
| gctaatcttt cgtcattctc aggcacccaa ctgtcgatct ccataccaat ggcatcctct | 3240 |
| gacttctcgg cggccagttc tcgatcaact aatggtacga ctacttgatc tccccccaat | 3300 |
| tacttcgtgc gtgtttatgt ctgtatcctg caatgtctga agatttctta ctgaaaacgt | 3360 |
| catctggtct gtgtgcaggt gactga | 3386 |

<210> SEQ ID NO 5
<211> LENGTH: 1185
<212> TYPE: DNA
<213> ORGANISM: Oryza sativa

<400> SEQUENCE: 5

| | |
|---|---|
| atgacgatgc cgtatgcctc cctgtctccg gcggtggccg accaccgctc gtccccggca | 60 |
| gccgcgaccg cctccctcct cccttctgc cgctccaccc cgctctccgc gggcggtggt | 120 |
| gttgtcgcga tgggggagga cgcgccgatg accgcgaggt ggccgccggc ggcggcggcg | 180 |
| aggctgccgc cgttcaccgc ggcgcagtac gaggagctgg agcagcaggc gctcatatac | 240 |
| aagtacctgg tggcaggcgt gcccgtcccg ccggatctcg tgctccccat ccgccgcgga | 300 |

-continued

```
ctcgactccc tcgccgcccg cttctacaac catcccgccc ttggatatgg tccgtacttc      360
ggcaagaagc tggacccaga gccagggcgg tgccggcgta cggacggcaa gaaatggcgg      420
tgctcgaagg aggccgcgcc ggattccaag tactgcgagc gccacatgca ccgcggccgc      480
aaccgtaaaa gaaagcctgt ggaaacgcag ctggtcgccc agtcccaacc gccctcatct      540
gttgtcggtt ctgcggcggc gccccttgct gctgcctcca atggcagcag cttccaaaac      600
cactctcttt accctgctat tgccggcagc aatggcgggg cgggggggag gaacatgccc      660
agctcatttg gctcggcgtt gggttctcag ctgcacatgg ataatgctgc cccttatgca      720
gctgttggtg gtggaacagg caaagatctc aggtatactg cttatggcac aagatctttg      780
gcggatgagc agagtcaact cattactgaa gctatcaaca catctattga aaatccatgg      840
cggctgctgc catctcagaa ctcgccattt cccctttcaa gctattctca gctgtgggca      900
ctaagtgacc ttggtcagaa cacccccagc tcactttcaa aggttcagag gcagccactt      960
tcgttctttg gaacgactta tgcggctgtc gattctgtga agcaagagaa ccagacgctg     1020
cgtcccttct ttgatgagtg gccaaaggga agggattcat ggtcagacct cgctgatgag     1080
aatgctaatc tttcgtcatt ctcaggcacc caactgtcga tctccatacc aatggcatcc     1140
tctgacttct cggcggccag ttctcgatca actaatggtg actga                    1185
```

<210> SEQ ID NO 6
<211> LENGTH: 394
<212> TYPE: PRT
<213> ORGANISM: Oryza sativa

<400> SEQUENCE: 6

| Met | Thr | Met | Pro | Tyr | Ala | Ser | Leu | Ser | Pro | Ala | Val | Ala | Asp | His | Arg |
|---|---|---|---|---|---|---|---|---|---|---|---|---|---|---|---|
| 1 | | | | 5 | | | | | 10 | | | | | 15 | |

| Ser | Ser | Pro | Ala | Ala | Ala | Thr | Ala | Ser | Leu | Leu | Pro | Phe | Cys | Arg | Ser |
|---|---|---|---|---|---|---|---|---|---|---|---|---|---|---|---|
| | | | 20 | | | | | 25 | | | | | 30 | | |

| Thr | Pro | Leu | Ser | Ala | Gly | Gly | Gly | Val | Val | Ala | Met | Gly | Glu | Asp | Ala |
|---|---|---|---|---|---|---|---|---|---|---|---|---|---|---|---|
| | | 35 | | | | | 40 | | | | | 45 | | | |

| Pro | Met | Thr | Ala | Arg | Trp | Pro | Pro | Ala | Ala | Ala | Arg | Leu | Pro | Pro |
|---|---|---|---|---|---|---|---|---|---|---|---|---|---|---|
| 50 | | | | | 55 | | | | | 60 | | | | |

| Phe | Thr | Ala | Ala | Gln | Tyr | Glu | Glu | Leu | Glu | Gln | Gln | Ala | Leu | Ile | Tyr |
|---|---|---|---|---|---|---|---|---|---|---|---|---|---|---|---|
| 65 | | | | | 70 | | | | | 75 | | | | | 80 |

| Lys | Tyr | Leu | Val | Ala | Gly | Val | Pro | Val | Pro | Asp | Leu | Val | Leu | Pro |
|---|---|---|---|---|---|---|---|---|---|---|---|---|---|---|
| | | | | 85 | | | | | 90 | | | | | 95 |

| Ile | Arg | Arg | Gly | Leu | Asp | Ser | Leu | Ala | Ala | Arg | Phe | Tyr | Asn | His | Pro |
|---|---|---|---|---|---|---|---|---|---|---|---|---|---|---|---|
| | | | 100 | | | | | 105 | | | | | 110 | | |

| Ala | Leu | Gly | Tyr | Gly | Pro | Tyr | Phe | Gly | Lys | Lys | Leu | Asp | Pro | Glu | Pro |
|---|---|---|---|---|---|---|---|---|---|---|---|---|---|---|---|
| | | 115 | | | | | 120 | | | | | 125 | | | |

| Gly | Arg | Cys | Arg | Arg | Thr | Asp | Gly | Lys | Lys | Trp | Arg | Cys | Ser | Lys | Glu |
|---|---|---|---|---|---|---|---|---|---|---|---|---|---|---|---|
| | 130 | | | | | 135 | | | | | 140 | | | | |

| Ala | Ala | Pro | Asp | Ser | Lys | Tyr | Cys | Glu | Arg | His | Met | His | Arg | Gly | Arg |
|---|---|---|---|---|---|---|---|---|---|---|---|---|---|---|---|
| 145 | | | | | 150 | | | | | 155 | | | | | 160 |

| Asn | Arg | Lys | Arg | Lys | Pro | Val | Glu | Thr | Gln | Leu | Val | Ala | Gln | Ser | Gln |
|---|---|---|---|---|---|---|---|---|---|---|---|---|---|---|---|
| | | | | 165 | | | | | 170 | | | | | 175 | |

| Pro | Pro | Ser | Ser | Val | Val | Gly | Ser | Ala | Ala | Pro | Leu | Ala | Ala | Ala |
|---|---|---|---|---|---|---|---|---|---|---|---|---|---|---|
| | | | 180 | | | | | 185 | | | | | 190 | |

| Ser | Asn | Gly | Ser | Ser | Phe | Gln | Asn | His | Ser | Leu | Tyr | Pro | Ala | Ile | Ala |
|---|---|---|---|---|---|---|---|---|---|---|---|---|---|---|---|
| | | 195 | | | | | 200 | | | | | 205 | | | |

| Gly | Ser | Asn | Gly | Gly | Gly | Gly | Gly | Arg | Asn | Met | Pro | Ser | Ser | Phe | Gly |
|---|---|---|---|---|---|---|---|---|---|---|---|---|---|---|---|
| | 210 | | | | | 215 | | | | | 220 | | | | |

Ser Ala Leu Gly Ser Gln Leu His Met Asp Asn Ala Ala Pro Tyr Ala
225                 230                 235                 240

Ala Val Gly Gly Gly Thr Gly Lys Asp Leu Arg Tyr Thr Ala Tyr Gly
            245                 250                 255

Thr Arg Ser Leu Ala Asp Glu Gln Ser Gln Leu Ile Thr Glu Ala Ile
        260                 265                 270

Asn Thr Ser Ile Glu Asn Pro Trp Arg Leu Leu Pro Ser Gln Asn Ser
    275                 280                 285

Pro Phe Pro Leu Ser Ser Tyr Ser Gln Leu Trp Ala Leu Ser Asp Leu
290                 295                 300

Gly Gln Asn Thr Pro Ser Ser Leu Ser Lys Val Gln Arg Gln Pro Leu
305                 310                 315                 320

Ser Phe Phe Gly Asn Asp Tyr Ala Ala Val Asp Ser Val Lys Gln Glu
            325                 330                 335

Asn Gln Thr Leu Arg Pro Phe Phe Asp Glu Trp Pro Lys Gly Arg Asp
        340                 345                 350

Ser Trp Ser Asp Leu Ala Asp Glu Asn Ala Asn Leu Ser Ser Phe Ser
    355                 360                 365

Gly Thr Gln Leu Ser Ile Ser Ile Pro Met Ala Ser Ser Asp Phe Ser
370                 375                 380

Ala Ala Ser Ser Arg Ser Thr Asn Gly Asp
385                 390

<210> SEQ ID NO 7
<211> LENGTH: 1000
<212> TYPE: DNA
<213> ORGANISM: Oryza sativa

<400> SEQUENCE: 7
tatcgatggc aacagtgcat gagcatatat ttatttcatt gacctacggt tgcatgtctt      60
cgatctctat ggagtagtac cgaggctaag tttagtttca aactttccct tcaaacttac     120 agcttttttta tcacattaaa actttcctac atacaaactt tcaactttc catcacatct     180 tttaatttca accaaacttc taattttaac gtgaactaaa acaccctga attcaaaact     240 cttttttattt tccttcaaga tgtccgatgc acacgctcta tgtagacgca agaagatgtt     300
ggagcagcag actaacagta gcaaaaaaat ggcaggtcga aaagcaactg cgacggttgc     360
tccgtcatcc tctcatcgcc ttttttattgc tccggcgttg ggaaccgcaa caatggaaca     420
gcccaaatcg acagtcccct cccccccct ccccatcct ctctctcccc acgcaatact     480
tgtcactact cgcgctgctc actacagcgt ctctgcatgt atatccatct atccatccat     540
tcccccattt tccaaataaa aatacagcaa accaaacaca aacgcagcct cgcactgtac     600
tcgaagaaaa atcggtgctg tacgtactac gccacgagat aacgagagag agagagagag     660
agagagagag agaggagaaa atggaaatgc ttctgctcgt accacgccgc tacgtccgct     720
aggtcgacag gcccgggcgg aggcaggtgt ttgtcgtcta gctcgggtcg gagcgcgcct     780
tctcgtgtcg ggctcgacgt ccgcgactcc tcgcccctgg tcgagagctc gcaggcgcag     840
cgggagagag agagagagag agagagagag agacaagccg cgcaataaag gcgcgcgcgc     900
gagcgagcga agcaaagcac cattactaaa gaccgcggcg tgtgcttgcg ttgcgagcga     960
gcgagagcga gagagagatt gagagagaga gagggaaggg                         1000

<210> SEQ ID NO 8
<211> LENGTH: 1000

```
<212> TYPE: DNA
<213> ORGANISM: Oryza sativa

<400> SEQUENCE: 8
ctaaattatc gatggcaaca gtgcatgagc atatatttat ttcattgacc tacggttgca      60
tgtcttcgat ctctatggag tagtaccgag gctaagttta gtttcaaact tttccttcaa     120
acttacagct tttttatcac attaaaactt tcctacatac aaactttcaa cttttccatc     180
acatctttca atttcaacca aacttctaat tttagcgtga actaaacaca ccctgaattc     240
aaaactcttt ttattttcct tcaagatgtc cgatgcacac gctctatgta gacgcaagaa     300
gatgttggag cagcagacta acagtagcaa aaaatggca ggtcgaaaag caactgcgac      360
ggttgctccg tcatcctctc atcgcctttt tattgctccg gcgttgggaa ccgcaacaat     420
ggaacagccc aaatcgacag tccctccac ccccctcccc catcctctct cccccacgc       480
aatacttgtc actactcgcg ctgcccacta cagcgtctct gcatgtatat ccatctatcc     540
atccattccc ccatttttca ataaaaata cagcaaacca acacaaacg cagcctcgca       600
ctgtactcga agaaaaatcg gtgctgtacg tactacgcca cgagataacg agagagagag     660
agagagagag agaggagaaa atggaaatgc tactgctcgt accacgccgc tacgtccgct     720
aggtcgacag gcccgggggg aggcaggtgt tgtcgtcta gctcgggtcg gagcgcgcct      780
tctcgtgtcg ggctcgacgt ccgcgactcc tcgcccctgg tcgagagctc gcaggcgcag     840
cgggagagag agagagagag agagagagag agacaagccg cgcaataaag gcgcgcgcgc     900
gagcgagcga agcaaagcac cattactaaa gaccgcggcg tgtgcttgcg ttgcgagcga     960
gcgagagcga gagagagatt gagagagaga gagggaaggg                          1000

<210> SEQ ID NO 9
<211> LENGTH: 999
<212> TYPE: DNA
<213> ORGANISM: Oryza sativa

<400> SEQUENCE: 9
tatcgatggc aacagtgcat gagcatatat ttatttcatt gacctacggt tgcatgtctc      60
cgatctctat ggagtagtac cgaggctaag tttagtttca aacttttcct tcaaacatac     120
agcttttta tcacattaaa actttcctac atataaactt ttaacttttc catcacatct      180
ttcaatttca accaaacttt taattttaac gtgaactaaa cacaccctga attcaaaact     240
cttttttatt tccttcaaga tgtccgatgc acacgctcta tgtagacgca agaagatgtt     300
ggagcagcag actaacagta gcaaaaaat ggcaggtcga aaagcaactg cgacggttgc      360
tccgtcatcc tctcatcgcc tttttattgc tccggcgttg gaaccgcaa caatggaaca      420
gcccaaatcg acagtcccct cccccccctc cccatcctc tctctcccca cgcaatactt     480
gtcactactc gcgctgctca ctacagcgtc tctgcatgta tatccatcta tccatccatt     540
cccccatttt ccaaataaaa atacagcaaa ccaaacacaa acgcagcctc gcactgtact     600
cgaagaaaaa tcggtgctgt acgtactacg ccacgagata acgagagaga gagagagaga     660
gagagagaga gaggagaaaa atggaaatgct actgctcgta ccacgccgct acgtccgcta    720
ggtcgacagg cccgggggga ggcaggtgtt gtcgtctag ctcgggtcgg agcgcgcctt      780
ctcgtgtcgg gctcgacgtc cgcgactcct cgcccctggt cgagagctcg caggcgcagc     840
gggagagaga gagagagaga gagagagaga gacaagccgc gcaataaagg cgcgcgcgcg     900
agcgagcgaa gcaaagcacc attactaaag accgcggcgt gtgcttgcgt tgcgagcgag     960
```
cgagagcgag agagagattg agagagagag agggaaggg 999

<210> SEQ ID NO 10
<211> LENGTH: 2000
<212> TYPE: DNA
<213> ORGANISM: Zea mays

<400> SEQUENCE: 10

| | |
|---|---|
| ttctagtgtt tcaacggaag cctaagtttc gatgggaaga aaggacatgt actagcaagg | 60 |
| aaccaaactc cacgcatcat tcttgcctag ccttgcttta tcgtggctac cttggaccaa | 120 |
| caaaagaacc aagcagcccc aatgtatctg atatggagct aaaaatacaa ccaactcata | 180 |
| ttatacgttg gatgttttga ctgcacttga gatgttgtaa gactttcggt acgctataca | 240 |
| tatagagttg aatatacagt tgaagactgc tgcagcggtc aactgtctga tctactgtaa | 300 |
| actctatgag gaaatcggaa acgctacttc cagagtagtg taactccgac tggaaaactg | 360 |
| ttgcagaata cggatagcct gatcagttag actgtcggct gcggagttca actgttgcag | 420 |
| agttagaaag aaatgataaa atatatagta gttagtatag agttgatata tagagtaaac | 480 |
| atgactgtag aggattgtag tatagggtag atagttttgc tgaccaggac aagatattcc | 540 |
| ttttagagta tgaatttaga gtagtatgag tgcggatagc ctaactttgt aagtattttt | 600 |
| aaagcttact ttgcatacgg tctttgtgat ctacatcttt actatggcta tttcatgata | 660 |
| ataactagat gagatatatg accaatcgag ttgtacatat atgtttgggt tttaattaag | 720 |
| ggcatagtta aaagcactga gcttttaaga aaacgatgtg gttctaaata tggcagttta | 780 |
| tgctttggtt tctagaaact gaatttctag catatttccg tactattctt agttggtttg | 840 |
| gatagaaact acgacgatta tcaccgctct gaggcctaat ggcctatgca cttgattctc | 900 |
| tccatgccca ctctgccctg ttcaaatgtt taattaatat ttaatttaat aattttgaat | 960 |
| tcaagaatac gagttcaagg tatatttaaa attgacatca aagagaaatg aaattaaagc | 1020 |
| aatgatagac ttgtctttgg gtgtgaaaaa aagctagaaa cttatttata aaaacccaat | 1080 |
| tctaaacatg tatacctaat ttttattata aatcggtttt tagatagaat cgtaaagccc | 1140 |
| ttgatcagag catccaacga gccatgaggc catgacggaa gagcggaagt gcagacggca | 1200 |
| acggcgttcc gcttcatgcc gcaccctcca gtgtcctgtg gccttaagt gccggccttg | 1260 |
| ggaaccgcga cgcagacaca gcccaaatcc gcagtcactc ctccaacacg atgcttgtca | 1320 |
| ccacccttgc tacagtgcct gcatccatat ccactccgct cgcgcaaaaa atatccgagt | 1380 |
| cggaaacaaa caaagcagca taggaaacag aagaaagctg tactagtacg tgaggacgag | 1440 |
| gagggagaga gagcaataca cagaagcctg ctaccgtgct acggactacc acaacgccag | 1500 |
| agggacaacc ggacagaggg ggaggcaggc ctcgcttgtc atctagctag gtcagccggg | 1560 |
| gacggggtcg gagcagtaga gctaaagcca gaggccaggc tcgtagtagt acgtagtagt | 1620 |
| agtgccctcc tcgtgtcatt tggccagcct tgtccagacg accacacaca ccagattacg | 1680 |
| cttaacattc tgtttgacat ctaaaaccag ccggcttgat ccaaatgcct ccctaggtag | 1740 |
| tagcttagtc ttgctcgccg cctctccggg agacgacgac acgcctgatg agtgcctgac | 1800 |
| gttccagcgc gaggcagaca gcgacgcaga gagagacaaa gcgggcaata aaggcagccg | 1860 |
| cgcgcgagcg agggaaggga gcgaagcaaa gcacatcacg agcccagcct gcgcctgcgg | 1920 |
| agggaggggg ctcattaaag aggggcgcg agcgcgaccg gccgcgggga gcaagcagcg | 1980 |
| cgcgagagag acaggttgag | 2000 |

```
<210> SEQ ID NO 11
<211> LENGTH: 1227
<212> TYPE: DNA
<213> ORGANISM: Zea mays

<400> SEQUENCE: 11
atggcgatgc cgtatgcctc tctttccccg gcaggcgccg ccgaccaccg ctcctccaca      60
gccacggcgt ccctcgtccc cttctgccgc tccactccgc tctccgcggg cggcgggctg     120
ggcgaggagg acgcccaggc gagcgcgagg tggccggccg cgaggccggt ggtgccgttc     180
acgccggcgc agtaccagga gctggagcag caggcgctca tatacaagta cctggtggcg     240
ggcgtgcccg ttccgccgga tctcgtggtt ccaatccgcc gcggcctcga ctccctcgca     300
acccgcttct acggccaacc cacactcggg tacggaccgt acctggggag gaaactggat     360
ccggagcccg gccggtgccg gcgaacggac ggcaagaagt ggcggtgctc caaggaggcc     420
gccccggact ccaagtactg cgagcgccac atgcaccgcg ccgcaaccg ttcaagaaag      480 cctgtgaaa cgcagctcgc gccccagtcc aaccgcccg ccgccgcagc cgtctccgcc       540
gctccgcccc tggcagccgc cgccgccgcc accaccaacg gcagcggctt ccagaaccac     600
tctctctacc cggccatcgc cggcagcact ggtggtggag gaggagttgg cgggtccggc     660
aatatctcct ccccgttctc ctcgtcgatg gggggatcgt ctcagctgca catggacagt     720
gctgccagct actcctacgc agctcttggt ggtggaactg caaaggatct caggtacaac     780
gcttacggaa taagatctct ggcggacgag cacaaccagc tgatcgcaga agccatcgac     840
tcgtcgatag agagccagtg gcgcctcccc agctcgtcgt tcccgctctc gagctaccca     900
catctcgggg cgctgggcga cctgggcggc cagaacagca cggtgagctc gctgccgaag     960
atggagaagc agcagccgcc ctcgtccttc ctagggaacg acaccggggc cggcatggcc    1020
atgggctccg cctccgcgaa gcaggagggc cagacgctgc ggcacttctt cgacgagtgg    1080
cccaaggcgc gggactcctg gccgggcctc tccgacgaga ccgccagcct cgcctcgttc    1140 ccccggcga cccagctgtc gatgtccata cccatggcgt cctccgactt ctccgtggcc     1200
agctcccagt cgcccaacga tgactaa                                        1227

<210> SEQ ID NO 12
<211> LENGTH: 408
<212> TYPE: PRT
<213> ORGANISM: Zea mays

<400> SEQUENCE: 12
```

Met Ala Met Pro Tyr Ala Ser Leu Ser Pro Ala Gly Ala Ala Asp His
1               5                   10                  15

Arg Ser Ser Thr Ala Thr Ala Ser Leu Val Pro Phe Cys Arg Ser Thr
            20                  25                  30

Pro Leu Ser Ala Gly Gly Gly Leu Gly Glu Glu Asp Ala Gln Ala Ser
        35                  40                  45

Ala Arg Trp Pro Ala Ala Arg Pro Val Val Pro Phe Thr Pro Ala Gln
    50                  55                  60

Tyr Gln Glu Leu Glu Gln Gln Ala Leu Ile Tyr Lys Tyr Leu Val Ala
65                  70                  75                  80

Gly Val Pro Val Pro Pro Asp Leu Val Val Pro Ile Arg Arg Gly Leu
                85                  90                  95

Asp Ser Leu Ala Thr Arg Phe Tyr Gly Gln Pro Thr Leu Gly Tyr Gly
            100                 105                 110

Pro Tyr Leu Gly Arg Lys Leu Asp Pro Glu Pro Gly Arg Cys Arg Arg

```
                    115                 120                 125
Thr Asp Gly Lys Lys Trp Arg Cys Ser Lys Glu Ala Ala Pro Asp Ser
        130                 135                 140

Lys Tyr Cys Glu Arg His Met His Arg Gly Arg Asn Arg Ser Arg Lys
145                 150                 155                 160

Pro Val Glu Thr Gln Leu Ala Pro Gln Ser Gln Pro Pro Ala Ala Ala
                165                 170                 175

Ala Val Ser Ala Ala Pro Pro Leu Ala Ala Ala Ala Ala Thr Thr
        180                 185                 190

Asn Gly Ser Gly Phe Gln Asn His Ser Leu Tyr Pro Ala Ile Ala Gly
                195                 200                 205

Ser Thr Gly Gly Gly Gly Val Gly Gly Ser Gly Asn Ile Ser Ser
        210                 215                 220

Pro Phe Ser Ser Ser Met Gly Gly Ser Ser Gln Leu His Met Asp Ser
225                 230                 235                 240

Ala Ala Ser Tyr Ser Tyr Ala Ala Leu Gly Gly Gly Thr Ala Lys Asp
                245                 250                 255

Leu Arg Tyr Asn Ala Tyr Gly Ile Arg Ser Leu Ala Asp Glu His Asn
                260                 265                 270

Gln Leu Ile Ala Glu Ala Ile Asp Ser Ser Ile Glu Ser Gln Trp Arg
        275                 280                 285

Leu Pro Ser Ser Ser Phe Pro Leu Ser Ser Tyr Pro His Leu Gly Ala
290                 295                 300

Leu Gly Asp Leu Gly Gly Gln Asn Ser Thr Val Ser Ser Leu Pro Lys
305                 310                 315                 320

Met Glu Lys Gln Gln Pro Pro Ser Ser Phe Leu Gly Asn Asp Thr Gly
                325                 330                 335

Ala Gly Met Ala Met Gly Ser Ala Ser Ala Lys Gln Glu Gly Gln Thr
                340                 345                 350

Leu Arg His Phe Phe Asp Glu Trp Pro Lys Ala Arg Asp Ser Trp Pro
        355                 360                 365

Gly Leu Ser Asp Glu Thr Ala Ser Leu Ala Ser Phe Pro Pro Ala Thr
        370                 375                 380

Gln Leu Ser Met Ser Ile Pro Met Ala Ser Ser Asp Phe Ser Val Ala
385                 390                 395                 400

Ser Ser Gln Ser Pro Asn Asp Asp
                405

<210> SEQ ID NO 13
<211> LENGTH: 2000
<212> TYPE: DNA
<213> ORGANISM: Zea mays

<400> SEQUENCE: 13
aaacaaatac ttatcgttaa taaacatgac atatgatctg atgcataaat ttgtatttt     60 atttttaaca ttgattttt aaagattccc aaaagataaa catcaaattt atcatataat    120
tcctcaaatg atacatataa aatttgaata cgaatatatt tttactttgt ttattactgg    180
gagtaaatat tgtataaaaa atatgcaaaa tttattctta tttatagtaa tatgcaaata    240
atgtataaat agtccatgct cataaatttt ttagtagccc gcaacccaag gcgaccgcga    300
acagtgccaa gccgagcggg ggtgtgcatg ttggagatgg agagagagag agagagcccg    360
aaaaatatcg ctgatgactc gacgagatag aggaggagg gagggaggga ggcgcagtag    420
gacagggctg caggcaggtg cttgtcctta gctggaaccc tcccgtgtcg gcctcatccc    480
```

```
accgccccgc cctgccgtcc tgccctgcgc ggctgcggtc gcctataagg ctagcccagg      540
ccatttgccc tttgccccg tccgtccgtc cctcacctca cctcacctca cctcggcccg       600
cctccctcat caggtagccg tagcgagcag tatagcacgc acagccgccg ccctgccctg      660
ccctgccctg ctcggcgtag gcacaggcac agcccagagc gagcgagaca gagggaaaga     720
gacagagcca gccaggtaaa aggcaaaagc acagcacatt aaagagagg ccggaagcag       780 cggcagagcg gagagagaga gagaactaga agcatatatg gcgatgccct ttgcctccct     840
gtctccggca gccgaccacc gcccctcctc cctcctcccc tactgccgcg ccgcccctct     900
ctccgcgtaa gccacctccc tttcgccgt ccgggaaaaa accctcttct tcgctcggtt       960
tatgccaccc ggagccgtgc tgcagcctgc aggtatctga tgccgcgagc tttgccttgc    1020
agggtgggag aggacgccgc cgcgcaggcg caacagcagc agcagcacgc tatgagcggc    1080
aggtgggcag cgaggccgcc ggcgctcttc accgcggcgc agtacgagga gctggagcac    1140
caggcgctta tatacaagta cctcgtcgcc ggcgtgcccg tccgccggga cctcctcctc    1200
cccctacgcc gaggcttcgt ctaccaccaa cccgcccgta agcaagcacg gcccccgcgc    1260
cgcctccgca ccccttcaca ctcacacgca cgtttaaccg cttttgcact gcacaacccc    1320
ggccgcccgg cggcggcgtc cgtgccttga tctggttgtt tactcggatc gagggattca    1380
gatgtcctct ccgtccgttt gttaatcggc tccggtcatt tcttaatctc gtcctggatt    1440
cggtcacgaa aagctagagg tcaagatttt gctctcgatt actatatcct tgcctcatgt    1500
tctaatggag tttattttat tggtctgatg tgattagata ggatgctagc caggcttgtc    1560
tccggccaaa agcggcggtt tagtttattg atgattgctt cttcttgg gggatttatt      1620 cctgtctggt tgttgggagc ctaaccacgc tcctattgct gctgcggttt actaaccatc    1680
tgcgccagta cacctactcc atggaccca aaatacagtt cttccaacca ttccccccct     1740
ccatctgctt tctcgcgggc aaataaaaac gtgtagaacg acggtgtagt aggcagatct    1800
actccttgtg ccgctacgct agcccgctac cgaagatcgg gcccgtttca accggttcgt    1860
tggtctgagc ggagctaaga tgggggcgat ttcatttttt ggtcctttcg tctgattgga    1920
gaagtgccca ttccggtatc gctccccggc ctccaaatac gcaccgacac agaacgtgtt    1980
cgtacgcacg tacacatggt                                                 2000
```

<210> SEQ ID NO 14
<211> LENGTH: 1002
<212> TYPE: DNA
<213> ORGANISM: Zea mays

<400> SEQUENCE: 14

```
atgcgcaccg tgctgctggc catagccgtt gactcaccgg gattcactcc tctctcgcgt      60
gtgtgtgtgt ggcttccttg cagttgggta cgggccctac ttcggcaaga aggtggaccc     120
ggagcccggg cggtgccggc gtacggacgg caagaagtgg cggtgctcca aggaggccgc     180
cccggactcc aagtactgcg agcgccacat gcaccgcggc cgcaaccgtt caagaaagcc     240
tgtggaagcg cagctcgtgc ccccgccgca cgcccagcag cagcagcagc agcaggcccc     300
cgcgcccacc gctggcttcc agagccaccc catgtaccca tccatcctcg ccggcaacgg     360
cggcggcggc ggcggggtag gtggtggtgc tggtggcggt ggcacgttcg gcctggggcc     420
cacctctcag ctgcacatgg acagtgccgc tgcttacgcg actgctgctg gtggagggag     480
caaagatctc aggtactctg cctacggggt gaagtctctg tcggacgagc acagccagct     540
```

```
cttgtccggc ggcggcggca tggacgcgtc aatggacaac tcgtggcgcc tgttgccgtc      600
ccaaaccgcc gccacgttcc aggccacaag ctaccctctg ttcggcgcgc tgagcggtct      660
ggacgagagc accatcgcct cgctgcccaa gacgcagagg gagcccctct ccttcttcgg      720
gagcgacttc gtgaccccga agcaggagaa ccagacgctg cgccccttct tcgacgagtg      780
gcccaagtcg agggactcgt ggccggagct gaacgaggac aacagcctcg gctcctcggc      840
cacccagctc tccatctcca tccccatggc gccctccgac ttcaacacca gctccagatc      900
gccgaatgga ataccgtcaa gatgaacctg agtaaccatg cggaccccaa catctcagag      960
ctgacgactc tttgctgctg gcctggcctc atcgtacctt ga                       1002
```

<210> SEQ ID NO 15
<211> LENGTH: 381
<212> TYPE: PRT
<213> ORGANISM: Zea mays

<400> SEQUENCE: 15

Met Ala Met Pro Phe Ala Ser Leu Ser Pro Ala Asp His Arg Pro
1               5                   10                  15

Ser Ser Leu Leu Pro Tyr Cys Arg Ala Ala Pro Leu Ser Ala Val Gly
                20                  25                  30

Glu Asp Ala Ala Ala Gln Ala Gln Gln Gln Gln His Ala Met Ser
            35                  40                  45

Gly Arg Trp Ala Ala Arg Pro Pro Ala Leu Phe Thr Ala Ala Gln Tyr
        50                  55                  60

Glu Glu Leu Glu His Gln Ala Leu Ile Tyr Lys Tyr Leu Val Ala Gly
65                  70                  75                  80

Val Pro Val Pro Pro Asp Leu Leu Pro Leu Arg Arg Gly Phe Val
                85                  90                  95

Tyr His Gln Pro Ala Leu Gly Tyr Gly Pro Tyr Phe Gly Lys Lys Val
            100                 105                 110

Asp Pro Glu Pro Gly Arg Cys Arg Arg Thr Asp Gly Lys Lys Trp Arg
        115                 120                 125

Cys Ser Lys Glu Ala Ala Pro Asp Ser Lys Tyr Cys Glu Arg His Met
130                 135                 140

His Arg Gly Arg Asn Arg Ser Arg Lys Pro Val Glu Ala Gln Leu Val
145                 150                 155                 160

Pro Pro His Ala Gln Gln Gln Gln Gln Gln Ala Pro Ala Pro
                165                 170                 175

Thr Ala Gly Phe Gln Ser His Pro Met Tyr Pro Ser Ile Leu Ala Gly
            180                 185                 190

Asn Gly Gly Gly Gly Gly Val Gly Gly Ala Gly Gly Gly Gly
        195                 200                 205

Thr Phe Gly Leu Gly Pro Thr Ser Gln Leu His Met Asp Ser Ala Ala
210                 215                 220

Ala Tyr Ala Thr Ala Ala Gly Gly Gly Ser Lys Asp Leu Arg Tyr Ser
225                 230                 235                 240

Ala Tyr Gly Val Lys Ser Leu Ser Asp Glu His Ser Gln Leu Leu Ser
                245                 250                 255

Gly Gly Gly Gly Met Asp Ala Ser Met Asp Asn Ser Trp Arg Leu Leu
            260                 265                 270

Pro Ser Gln Thr Ala Ala Thr Phe Gln Ala Thr Ser Tyr Pro Leu Phe
        275                 280                 285

Gly Ala Leu Ser Gly Leu Asp Glu Ser Thr Ile Ala Ser Leu Pro Lys

```
            290                 295                 300
Thr Gln Arg Glu Pro Leu Ser Phe Phe Gly Ser Asp Phe Val Thr Pro
305                 310                 315                 320

Lys Gln Glu Asn Gln Thr Leu Arg Pro Phe Phe Asp Glu Trp Pro Lys
                325                 330                 335

Ser Arg Asp Ser Trp Pro Glu Leu Asn Glu Asp Asn Ser Leu Gly Ser
            340                 345                 350

Ser Ala Thr Gln Leu Ser Ile Ser Ile Pro Met Ala Pro Ser Asp Phe
        355                 360                 365

Asn Thr Ser Ser Arg Ser Pro Asn Gly Ile Pro Ser Arg
        370                 375                 380

<210> SEQ ID NO 16
<211> LENGTH: 2000
<212> TYPE: DNA
<213> ORGANISM: Triticum aestivum

<400> SEQUENCE: 16
```

| | | | | | |
|---|---|---|---|---|---|
| gatagtgtgg | gaagggagtg | gagtggagtg | gaatgcggct | agggttttag | ccggagtgcg | 60 |
| gcctatttag | gtggggtcgg | gtgagccaga | tccaacatgg | caggtaggtt | cgggcatccc | 120 |
| cgtactcgcc | ctaaatttgg | gctggactgg | ggagtgaccg | gaagtccgaa | cgtttgcgcg | 180 |
| tcaaaaatgc | ggcgctcggt | tgggcattga | ccatgcaact | tgctcggaca | tttggggcaa | 240 |
| gtatagggac | tccgattgta | gatgctccta | cgtctaattt | gatacttcat | tgagatgtgg | 300 |
| tgtccgatgc | gtgaaaatgc | ttcgagaagt | gagagcatct | acagccggac | ttagcaaatc | 360 |
| tggcatctat | aagtcagcgg | gcgcctccgc | ggacggcccc | tcacttgagt | tgccgcacat | 420 |
| tgacacaccg | caaatacgga | ttcttgaatt | catgcaatcc | attgacgtcc | atcaaacgat | 480 |
| acaaatcatc | ccaattcaac | agttcgaaac | aaaataagac | aaagcaaaac | aaatcataat | 540 |
| tcaacaatcc | ggacatgcta | aaataaaatc | aatgtccgag | cgtgatggtt | cactccttga | 600 |
| ccggctggat | cactcgcccg | acgccatcca | tattccgctt | gctccgtggc | catccttatg | 660 |
| ggcagcgagg | atgaggagca | aggatggcga | cgacaaggg | cttgaacacg | ggaataggtg | 720 |
| gagggagtcg | ggagggggaa | gggtttaggg | cctctttgat | tcacaggatt | gtcaaaataa | 780 |
| aggaatagaa | aaaatgcagg | aatagggtga | catgtcccat | agtatcctac | aggatttgaa | 840 |
| agaatgtttg | atagcatagg | aaaaacaaag | gaattctaca | aagaggtttg | agtggatgga | 900 |
| aatttttttt | caaatgtag | tacaaatgga | tcatatggaa | aaattcctaa | ggatgccaat | 960 |
| cctacgaatc | aaacgagcat | cacatgaaaa | atttctaagg | atttaaatcc | tccaaaaatc | 1020 |
| ctatataatt | cctttaaatc | aaaggagcgc | tagtgaattg | atgcaatttg | tgctgaagta | 1080 |
| agcctgtcgg | gttcgacgtg | acgggcgcgc | cgagacatcg | ctttcatatt | tggactgggt | 1140 |
| atatggagtg | ctagtcagct | caagtgtttg | agacgctcgt | ctcggttttt | tcatttgacc | 1200 |
| tgtaatcggg | ccgttcgtcc | ggacgttcga | tagaggtttg | tggtgcaggg | atgtagatgc | 1260 |
| acactgcttc | cgttatcagt | tatcaccacg | acacaagaag | caagcacata | gtactgtagt | 1320 |
| aaaaaaattg | acgagggaaa | agtggcgcaa | acggttgccc | cgcaccctct | cacgacgga | 1380 |
| ctttaaaagt | cggcattggt | aaccgcaaca | cagcacagag | agactcaccc | ccaaatctct | 1440 |
| ctcttctctc | tctattccta | tgcaatgcaa | tagttgtcac | cactcgctac | agtgccggca | 1500 |
| gcattgcatc | gcatcgcatc | catatccatt | cctcctcacg | agaaaaagag | agagagacga | 1560 |
| gcaatactag | tcgtcgtcgt | cgtcgtagcc | tggtacgtct | acgctagagc | gacagggaaa | 1620 |

| | | |
|---|---|---|
| gaggagggag ggggcgcttg tcatctactc ctcctcgcta ctaccctag ctgggatcca | 1680 | |
| cagcctcctc ctcctcctcg tgtcggcctc gtccacatcc accgtctcct ccgagcgagg | 1740 | |
| cggacagcga cgcggccacg gagcgaggga gggagagaga caaagccggt aataaaggcg | 1800 | |
| ggcgggcgcg cgcgcgcaca agccaagcaa agcacattaa cgacgccagc cagccagcca | 1860 | |
| gccagccagc ccgcggggaa ccccattaaa gacgcttccg ggggagcgcc gtgggcaagc | 1920 | |
| aagcacaggg gcttagctta gcttggcttg tgcatcgcgt gttgtgtgcg cgagagggag | 1980 | |
| acagcggccg agagagaaag | 2000 | |

<210> SEQ ID NO 17
<211> LENGTH: 1227
<212> TYPE: DNA
<213> ORGANISM: Triticum aestivum

<400> SEQUENCE: 17

| | | |
|---|---|---|
| atggcgatgc cgtatgcctc tctttccccg gcaggcgacc gccgctcctc cccggccgcc | 60 | |
| accgccaccg cctccctcct cccttctgc cgctcctccc ccttctccgc cggcggcaat | 120 | |
| ggcggcatgg gggaggaggc gccgatggac gggaggtgga tggcgaggcc ggtgcccttc | 180 | |
| acggcggcgc agtacgagga gctggagcac caggcgctca tatacaagta cctggtggcc | 240 | |
| ggcgtgcccg tcccgccgga tctcgtgctc cccatccgcc gcggcatcga gtccctcgcc | 300 | |
| gcccgcttct accacaaccc cctcgccatc gggtacggat cgtacctggg caagaaggtg | 360 | |
| gatccggagc cgggccggtg ccggcgcacg gacggcaaga agtggcggtg cgccaaggag | 420 | |
| gccgcctccg actccaagta ctgcgagcgc acatgcacc gcggccgcaa ccgttcaaga | 480 | |
| aagcctgtgg aaacgcagct cgtgccccac tcccagccgc cggccgcctc cgccgtgccg | 540 | |
| cccctcgcca ccggcttcca cggccactcc ctctaccccg ccgtcggcgg cggcaccaac | 600 | |
| ggtggtggag gcgggggaa caacggcatg tccatgcccg gcacgttctc ctccgcgctg | 660 | |
| gggccgcctc agcagcacat gggcaacaat gccgcctctc cctacgcggc tctcggcggc | 720 | |
| gccggaacat gcaaagattt caggtatacc gcatatggaa taagatcttt ggcagatgag | 780 | |
| cagagtcagc tcatgacaga agccatgaac acctccgtgg agaacccatg cgcctgccg | 840 | |
| ccatcttctc aaacgactac attcccgctc tcaagctact ctcctcagct tggagcaacg | 900 | |
| agtgacctgg gtcagaacaa cagcagcaac aacaacagcg gcgtcaaggc cgagcgacag | 960 | |
| cagcagcagc agccgctctc cttcccgggg tgcggcgact cggcggcgg cgactccgcg | 1020 | |
| aagcaggaga accagacgct gcggccgttc ttcgacgagt ggccgaagac gagggactcg | 1080 | |
| tggtcggacc tgaccgacga caactcgaac gtcgcctcct tctcggccac ccagctgtcg | 1140 | |
| atctcgatac ctatgacgtc ccccgacttc tccgccgcca gctcccagtc gcccaacggc | 1200 | |
| atgctgttcg ccggcgagat gtactag | 1227 | |

<210> SEQ ID NO 18
<211> LENGTH: 408
<212> TYPE: PRT
<213> ORGANISM: Triticum aestivum

<400> SEQUENCE: 18

Met Ala Met Pro Tyr Ala Ser Leu Ser Pro Ala Gly Asp Arg Arg Ser
1               5                   10                  15

Ser Pro Ala Ala Thr Ala Thr Ala Ser Leu Leu Pro Phe Cys Arg Ser
            20                  25                  30

Ser Pro Phe Ser Ala Gly Gly Asn Gly Gly Met Gly Glu Glu Ala Pro

```
            35                  40                  45
Met Asp Gly Arg Trp Met Ala Arg Pro Val Pro Phe Thr Ala Ala Gln
 50                  55                  60

Tyr Glu Glu Leu Glu His Gln Ala Leu Ile Tyr Lys Tyr Leu Val Ala
 65                  70                  75                  80

Gly Val Pro Val Pro Pro Asp Leu Val Leu Pro Ile Arg Arg Gly Ile
                 85                  90                  95

Glu Ser Leu Ala Ala Arg Phe Tyr His Asn Pro Leu Ala Ile Gly Tyr
                100                 105                 110

Gly Ser Tyr Leu Gly Lys Lys Val Asp Pro Glu Pro Gly Arg Cys Arg
            115                 120                 125

Arg Thr Asp Gly Lys Lys Trp Arg Cys Ala Lys Glu Ala Ala Ser Asp
            130                 135                 140

Ser Lys Tyr Cys Glu Arg His Met His Arg Gly Arg Asn Arg Ser Arg
145                 150                 155                 160

Lys Pro Val Glu Thr Gln Leu Val Pro His Ser Gln Pro Pro Ala Ala
                165                 170                 175

Ser Ala Val Pro Pro Leu Ala Thr Gly Phe His Gly His Ser Leu Tyr
                180                 185                 190

Pro Ala Val Gly Gly Gly Thr Asn Gly Gly Gly Gly Gly Asn Asn
            195                 200                 205

Gly Met Ser Met Pro Gly Thr Phe Ser Ser Ala Leu Gly Pro Pro Gln
    210                 215                 220

Gln His Met Gly Asn Asn Ala Ala Ser Pro Tyr Ala Ala Leu Gly Gly
225                 230                 235                 240

Ala Gly Thr Cys Lys Asp Phe Arg Tyr Thr Ala Tyr Gly Ile Arg Ser
                245                 250                 255

Leu Ala Asp Glu Gln Ser Gln Leu Met Thr Glu Ala Met Asn Thr Ser
                260                 265                 270

Val Glu Asn Pro Trp Arg Leu Pro Pro Ser Ser Gln Thr Thr Thr Phe
            275                 280                 285

Pro Leu Ser Ser Tyr Ser Pro Gln Leu Gly Ala Thr Ser Asp Leu Gly
    290                 295                 300

Gln Asn Asn Ser Ser Asn Asn Asn Ser Gly Val Lys Ala Glu Arg Gln
305                 310                 315                 320

Gln Gln Gln Gln Pro Leu Ser Phe Pro Gly Cys Gly Asp Phe Gly Gly
                325                 330                 335

Gly Asp Ser Ala Lys Gln Glu Asn Gln Thr Leu Arg Pro Phe Phe Asp
            340                 345                 350

Glu Trp Pro Lys Thr Arg Asp Ser Trp Ser Asp Leu Thr Asp Asp Asn
            355                 360                 365

Ser Asn Val Ala Ser Phe Ser Ala Thr Gln Leu Ser Ile Ser Ile Pro
    370                 375                 380

Met Thr Ser Pro Asp Phe Ser Ala Ser Ser Gln Ser Pro Asn Gly
385                 390                 395                 400

Met Leu Phe Ala Gly Glu Met Tyr
                405

<210> SEQ ID NO 19
<211> LENGTH: 2000
<212> TYPE: DNA
<213> ORGANISM: Triticum aestivum

<400> SEQUENCE: 19
```

```
ttttcgcacg caacgcccac ttgagttcct cctctctcaa gagagcatgt tggccttgct     60
cagcctcaga cttggttcga tgctcattaa cagaaagaag tgtggtttca gcctttacat    120
ctagtgtctc aatgagttga gttagacgtt ctttttttctg cttataaatc ccagtctcat    180
tcctggccca tcctctcaga aattgtcgga ggtttctaat cttattctgc catctctcga    240
catgtgtcct tcctgtaatt ggcttagccc attcgcatgc aatcatctcc ataaatcctt    300
ctcgctcaaa ccagctttac tcgaaagaga agatgttttt gtttgcaaca tgggtagcct    360
cacccgaatc taaaaagagt ggtgtatgat ctgagatccc tctatgcatt gcatggaccg    420
acaccaacgg atattttttgt tcccactcca cactagcaag taccctatcc agcttttcat    480
aagtcagaac aggtaacgag ttggcccatg taaactgtct accggtgagc tcaatttctc    540
tcaaattgag gctctcgata atcatgttaa acatcataga ccaacgtcca tcgaaattgt    600
cattattctt ttcttctctt ctccgaatga tattaaaatc accccgact agcagtggca    660
gattttcatc tccacaaatc cgcactagat gggcaagaaa atcgggttta aattgcttgg    720
aggagtgaga gcatctacaa ccggacttag cgaatctggg ctctataagc ccgcgggtgc    780
ctccgcggac ggccctccct tgagttgccg cacattcaca catctcaaat acggattctt    840
gaatccatgt atccatgcac gtccatcata cgatataaat catcccaatt caaatgtttg    900
aaaacaaaat acgacaatgc aaagcaaatc atagttcaat aattcagaca tgccaaatta    960
aaatcaatat ccgagcatga tagatcactc gttggacgcc atccatgccc gcttgctccg   1020
cggccatcct tgcgggcggc gaggatgggg agcaagggtg gcggacggca agggcttgga   1080
cacgaaaata ggtggatgaa ggcgggagag aggagggttt agtgaatttt atgcaattta   1140
tgtgggggt tggcctgtcg ggttctacgt aatggacgcg ccgaggcatg agggatgccg   1200
gtcagcttgg gtgttttaga tgcccgtccg gtcttttatt tttaagtccg taattgggcc   1260
gttcgccgga cgttccatag aggtttgggg tgccgggaag tagatgcaca gtacttccgt   1320
tatcaccacg acacaagaag caagcacata gtactgttgt aaaaaaatga cgagggaaaa   1380
gtggcgcaaa cggttgcccc gcaccctctc acggacggac tttaaaagtc ggcattggta   1440
accgcaacac aacacagaca gacgcacccc aaatctctct ctctctctct tcccatgcaa   1500
tagttgtcgc cactcgctcg ctacagtgac cgcatcgcat cgcatccatg tccattcctc   1560
cccacgagaa aaagagagag acagcagaaa taccagtcgt cgtcgtcgtc gtcgtagcct   1620
ggtacgtcta cgctagagcg acagggaaag aggagggcgc ttgtcatcta ctcctcctcc   1680
tcgcccgcta ctagctggga tccacagcct cctcctcctc ctcgtgtcgg cctcgtccac   1740
atccaccatc tcctccgagc gaggtggaca gcgacgcggc cacggagcga gtgagagaga   1800
caaagccggt aataaaggcg ggcgcgcgcg cgcgcacaag ccaagcaaag cacattaacg   1860
aggccagcca gcccgcaggg aaccccatta aagacgcttc cgtgggagcg ccgtggggaa   1920
gcaagcgagc gagcacaggg gcttggcttg cgcgtcgtgt gctgtgtgcg cgagagggag   1980
acagcggccg agagagaaag                                              2000
```

<210> SEQ ID NO 20  
<211> LENGTH: 1221  
<212> TYPE: DNA  
<213> ORGANISM: Triticum aestivum
<400> SEQUENCE: 20

```
atggcgatgc cgtatgcctc tctttccccg gcaggcgacc gccgctcctc cccggccgcc     60
accgcctccc tcctcccctt ctgccgctcc tccccgttct ccgccggcaa tggcggcatg    120
```

```
ggggaggagg cgcggatggc cggtaggtgg atggcgaggc cggcgccctt cacggcggcg      180
cagtacgagg agctggagca ccaggcgctg atatacaagt acctggtggc cggcgtgccc      240
gtcccgccgg atctcgtgct ccccatccgc cgcggcatcg agaccctcgc cgcccgcttc      300
taccacaacc ccctcgccat cgggtatgga tcgtacctgg gcaagaaggt ggatccggag      360
cccggccggt gccggcgcac ggacggcaag aagtggcggt gcgccaagga ggccgcctcc      420
gactccaagt attgcgagcg ccacatgcac cgcggccgca accgttcaag aaagcctgtg      480
gaaacgcagc tcgtctcgca ctcccagccg ccggccgcct ccgtcgtgcc gcccctcgcc      540
accggcttcc acaaccactc cctctacccc gccatcggcg caccaacgg tggtggaggc       600 gggggaaca acggcatgcc caacacgttc cctccgcgc tggggcctcc tcagcagcac        660
atgggcaaca atgcctcctc acctacgcg gctctcggtg gcgccggaac atgcaaagat       720
ttcaggtata ccgcatatgg aataagatct ttggcagacg agcacagtca gctcatgaca     780
gaagccatga atacctccgt ggagaaccca tggcgcctgc cgccatcgtc tcaaacgacc     840
acattcccgc tctcaagcta cgctcctcag cttggagcaa ctagtgacct gggtcagaac    900
aacaacagca gcagcagcaa cagtgccgtc aagtccgaac ggcagcagca gcagcagccc    960
ctctccttcc cggggtgcgg cgacttcggc ggcggcggcg ccatggactc cgcgaagcag   1020
gagaaccaga cgctgcggcc gttcttcgac gagtggccca agacgaggga ctcgtggtcg   1080
gacctgaccg acgacaactc cagcctcgcc tccttctcgg ccacccagct gtcgatctcg   1140
atacccatga cgtcctccga cttctcggcc gccagctccc agtcgcccaa cggtatgctg   1200
ttcgccggcg aaatgtacta g                                              1221

<210> SEQ ID NO 21
<211> LENGTH: 405
<212> TYPE: PRT
<213> ORGANISM: Triticum aestivum

<400> SEQUENCE: 21

Met Ala Met Pro Tyr Ala Ser Leu Ser Pro Ala Gly Asp Arg Arg Ser
1               5                   10                  15

Ser Pro Ala Ala Thr Ala Ser Leu Leu Pro Phe Cys Arg Ser Ser Pro
                20                  25                  30

Phe Ser Ala Gly Asn Gly Gly Met Gly Glu Glu Ala Arg Met Ala Gly
            35                  40                  45

Arg Trp Met Ala Arg Pro Ala Pro Phe Thr Ala Ala Gln Tyr Glu Glu
        50                  55                  60

Leu Glu His Gln Ala Leu Ile Tyr Lys Tyr Leu Val Ala Gly Val Pro
65                  70                  75                  80

Val Pro Pro Asp Leu Val Leu Pro Ile Arg Arg Gly Ile Glu Thr Leu
                85                  90                  95

Ala Ala Arg Phe Tyr His Asn Pro Leu Ala Ile Gly Tyr Gly Ser Tyr
            100                 105                 110

Leu Gly Lys Lys Val Asp Pro Glu Pro Gly Arg Cys Arg Arg Thr Asp
        115                 120                 125

Gly Lys Lys Trp Arg Cys Ala Lys Glu Ala Ala Ser Asp Ser Lys Tyr
    130                 135                 140

Cys Glu Arg His Met His Arg Gly Arg Asn Arg Ser Arg Lys Pro Val
145                 150                 155                 160

Glu Thr Gln Leu Val Ser His Ser Gln Pro Pro Ala Ala Ser Val Val
                165                 170                 175
```

```
Pro Leu Ala Thr Gly Phe His Asn His Ser Leu Tyr Pro Ala Ile Gly
            180                 185                 190

Gly Thr Asn Gly Gly Gly Gly Gly Asn Asn Gly Met Pro Asn Thr
        195                 200                 205

Phe Ser Ser Ala Leu Gly Pro Pro Gln Gln His Met Gly Asn Asn Ala
210                 215                 220

Ser Ser Pro Tyr Ala Ala Leu Gly Gly Ala Gly Thr Cys Lys Asp Phe
225                 230                 235                 240

Arg Tyr Thr Ala Tyr Gly Ile Arg Ser Leu Ala Asp Glu His Ser Gln
            245                 250                 255

Leu Met Thr Glu Ala Met Asn Thr Ser Val Glu Asn Pro Trp Arg Leu
            260                 265                 270

Pro Pro Ser Ser Gln Thr Thr Thr Phe Pro Leu Ser Ser Tyr Ala Pro
            275                 280                 285

Gln Leu Gly Ala Thr Ser Asp Leu Gly Gln Asn Asn Asn Ser Ser Ser
            290                 295                 300

Ser Asn Ser Ala Val Lys Ser Glu Arg Gln Gln Gln Gln Gln Pro Leu
305                 310                 315                 320

Ser Phe Pro Gly Cys Gly Asp Phe Gly Gly Gly Ala Met Asp Ser
                325                 330                 335

Ala Lys Gln Glu Asn Gln Thr Leu Arg Pro Phe Phe Asp Glu Trp Pro
            340                 345                 350

Lys Thr Arg Asp Ser Trp Ser Asp Leu Thr Asp Asp Asn Ser Ser Leu
            355                 360                 365

Ala Ser Phe Ser Ala Thr Gln Leu Ser Ile Ser Ile Pro Met Thr Ser
            370                 375                 380

Ser Asp Phe Ser Ala Ala Ser Ser Gln Ser Pro Asn Gly Met Leu Phe
385                 390                 395                 400

Ala Gly Glu Met Tyr
                405

<210> SEQ ID NO 22
<211> LENGTH: 2000
<212> TYPE: DNA
<213> ORGANISM: Triticum aestivum
<220> FEATURE:
<221> NAME/KEY: misc_feature
<222> LOCATION: (128)..(265)
<223> OTHER INFORMATION: n is a, c, g, or t

<400> SEQUENCE: 22
gtatgcgtta ccttgatttg ccacattagc tagctgaagt tggttgcccg tacatttgtc      60
agcgttagcg ccctgtgacg aaacttgcca tgctgccccc ctgattgtgg tttggtcata    120
agaacctnnn nnnnnnnnnn nnnnnnnnnn nnnnnnnnnn nnnnnnnnnn nnnnnnnnnn    180
nnnnnnnnnn nnnnnnnnnn nnnnnnnnnn nnnnnnnnnn nnnnnnnnnn nnnnnnnnnn    240
nnnnnnnnnn nnnnnnnnnn nnnnngcagc aatggccctg aagaaatgag ttgattgtac    300
tctgctgcat cccaaggtgg cgtttccggc ctttgagaaa gccaaggatc agtgccatct    360
tcgtgattca ttcttctgct ttttcttttc tgctactatg cttttagtca ctgcatgaac    420
aagaacgcat caacaatcca caaaaagcgt tcttgctgtt tgcacgtaga agataacacg    480
gcaatctcat aatattttt gcgtaggcaa ccaacacctc atggcaagta ggacatgcac    540
atccattttt cttttctgaa ttctggatgc catctatcat tttgaagcga tgcaacaga     600 aaataaaata ggatggcaag caataataca tggtggcaac tatggacaac gatagatggc    660
```

```
aactgacgtt agatacaagt ggcaattatt tttcctccct ccccatgcca aattcctcct    720
ttctctccct attttatagt gattactacg ctaccaacta ctcgcatcaa agccaaccca    780
gaagcttggc acaagtctag catagtatat ggcagatctg gcgtatgttg gtgggaaaat    840
gcaaagacac acaaattcgt ggggtgtttg ccctgatagc gtggatccag tcgccatctt    900
cgtgggcaaa ttttgcaaat tcagatttct ggacaaaaga agatcgggga tccacctgtt    960
ttagctcgtc gtcttgggag tgcggggagg ggggtagggt gggggtgggg tgggtggtta   1020
gctgtgggaa aggcgctagg gatttgctct ggttgccatg gcaaccagag aaggaaggcg   1080
acggaggtag gggatcggga gatgcgagac aatggcggca gggcggaccg gggatcggaa   1140
ggagcccggg acagctggcg tgctgagtcg tgcgggcagc gcggtcgttt ggcccggacg   1200
tgtgggcggt tttgccacac accggacgtg cgggttgtgg ctgcgcgcgc cggatgcgg    1260 ttttgcggc gagttcttct ccatgccaca cgaggcgtgc ggcacaacca cccgatacac    1320
cacacgtgtg gcagttatcg gtgttaaaaa aatgacgaga gaaagtggc gcaaacggtt     1380 gccccgcacc ctctcacgga cggactttaa aagtcggcat tggtaaccgc aacacaacac   1440
agacagacgc accccaagcc tctctctatc tctctcttcc catgcaatag ttgtcaccac   1500
tcgctcgcta cagtgcccgc attgcatcgc atccacatcc atatgaccat atccattcct   1560
ccccacgaga aaaggagaga gaggggagaa atactagtcg tcgtcgtcgt agtagctggt   1620
acgtctacgc tagagcgaca gggaaagagg agggaggggg cgcttgtcat ctactcctcc   1680
tcctcgcccc tagctgggat ccacagcctc ctcctcctcc tcgtgtcggc ctcgtccaca   1740
tccaccgtct cctccgagcg aggtggacag cgacgcggcc acggagcgag ggagggagag   1800
agacaaagcc ggtaataaag gcgggggcgc gcgcgcgcac aagccaagca aagcacatta   1860
acgacgccag ccagcccgcg gggaaccca ttaaagacgc ttccgggga gcgccgtggg     1920 caagcacagg ggcttagctt agcttggctt gtgtgttgtg tgcgcgagag ggagacagcg   1980
gccgagagag aaagatggcg                                              2000
```

<210> SEQ ID NO 23
<211> LENGTH: 1217
<212> TYPE: DNA
<213> ORGANISM: Triticum aestivum

<400> SEQUENCE: 23

```
atggcgatgc cgtatgcctc tctttccccg gcaggcgacc gccgctcctc cccggccgcc    60
accgcctccc tcctcccctt ctgccgctcc tcccccttct ccgccggcgg cggcaatggc   120
ggcatggggg aggaggcgcg gatggacggg aggtggatgg cgaggccggt gcccttcacg   180
gcggcgcagt acgaggagct ggagcaccag gcgctgatat acaagtacct ggtggccggc   240
gtgcccgtcc cgccggatct cgtgctcccc atccgccgcg gcatcgaatc cctcgccgcc   300
cgcttctacc acaacccccct cgccatcggg tacggatcgt acctaggcaa gaaggtggat   360
ccggagccgg gccggtgccg gcgcacggac ggcaagaagt ggcggtgcgc caaggaggcc   420
gcctccgatt ccaagtattg cgagcgccac atgcaccgcg gccgcaaccg ttcaagaaag   480
cctgtggaaa cgcagctcgt cccgcacacc cagccgccgg ccgcctccgc cgtgccgccc   540
ctcgccaccg gcttccacag ccactccctc taccccgcca tcggcggcag caccaacggt   600
ggtggaggcg gggggaacaa cggcatgtcc atgcccagca cgttctcctc cgcgctgggg   660
ccgcctcagc agcacatggg cagcaatgcc gcctctccct acgcggctct cggtggcgcc   720
```

```
ggttcaggta taccgcatat ggaataagat ctttggcaga cgagcacagt cagctcatga      780
cagaagccat gaatacctcc gtggagaacc catggcgcct gccgccgtcg tctcaaacga      840
cctcattccc gctttcaagc tacgctcctc agcttggagc aacgagtgac ctgggtcaga      900
acaacaacca caacaacagc agcagcaaca gtgccgtcaa gtccgagcgg cagcagccgc      960
tctccttccc ggggtgcggc gactttggcg gcggcggcat ggactccgcg aagcaggaga     1020
accagacgct gcggccgttc ttcgacgagt ggccgaagac gagggactcg tggtcggacc     1080
tgacggacga caactccagc ctcgcctcct tctcggccac ccagctgtcg atctcgatac     1140
ccatgacgtc ctccgacttc tccgccgcca gctcccagtc gcccaacggt atgctgttcg     1200
ccggcgagat gtactag                                                    1217
```

<210> SEQ ID NO 24
<211> LENGTH: 409
<212> TYPE: PRT
<213> ORGANISM: Triticum aestivum

<400> SEQUENCE: 24

```
Met Ala Met Pro Tyr Ala Ser Leu Ser Pro Ala Gly Asp Arg Arg Ser
1               5                   10                  15

Ser Pro Ala Ala Thr Ala Ser Leu Leu Pro Phe Cys Arg Ser Ser Pro
                20                  25                  30

Phe Ser Ala Gly Gly Asn Gly Gly Met Gly Glu Glu Ala Arg Met
            35                  40                  45

Asp Gly Arg Trp Met Ala Arg Pro Val Pro Phe Thr Ala Ala Gln Tyr
        50                  55                  60

Glu Glu Leu Glu His Gln Ala Leu Ile Tyr Lys Tyr Leu Val Ala Gly
65                  70                  75                  80

Val Pro Val Pro Pro Asp Leu Val Leu Pro Ile Arg Arg Gly Ile Glu
                85                  90                  95

Ser Leu Ala Ala Arg Phe Tyr His Asn Pro Leu Ala Ile Gly Tyr Gly
                100                 105                 110

Ser Tyr Leu Gly Lys Lys Val Asp Pro Glu Pro Gly Arg Cys Arg Arg
            115                 120                 125

Thr Asp Gly Lys Lys Trp Arg Cys Ala Lys Glu Ala Ala Ser Asp Ser
        130                 135                 140

Lys Tyr Cys Glu Arg His Met His Arg Gly Arg Asn Arg Ser Arg Lys
145                 150                 155                 160

Pro Val Glu Thr Gln Leu Val Pro His Thr Gln Pro Pro Ala Ala Ser
                165                 170                 175

Ala Val Pro Pro Leu Ala Thr Gly Phe His Ser His Ser Leu Tyr Pro
            180                 185                 190

Ala Ile Gly Gly Ser Thr Asn Gly Gly Gly Gly Gly Asn Asn Gly
        195                 200                 205

Met Ser Met Pro Ser Thr Phe Ser Ser Ala Leu Gly Pro Pro Gln Gln
    210                 215                 220

His Met Gly Ser Asn Ala Ala Ser Pro Tyr Ala Ala Leu Gly Gly Ala
225                 230                 235                 240

Gly Thr Cys Lys Asp Phe Arg Tyr Thr Ala Tyr Gly Ile Arg Ser Leu
                245                 250                 255

Ala Asp Glu His Ser Gln Leu Met Thr Glu Ala Met Asn Thr Ser Val
            260                 265                 270

Glu Asn Pro Trp Arg Leu Pro Pro Ser Ser Gln Thr Thr Ser Phe Pro
        275                 280                 285
```

```
Leu Ser Ser Tyr Ala Pro Gln Leu Gly Ala Thr Ser Asp Leu Gly Gln
    290                 295                 300

Asn Asn Asn His Asn Asn Ser Ser Ser Asn Ser Ala Val Lys Ser Glu
305                 310                 315                 320

Arg Gln Gln Pro Leu Ser Phe Pro Gly Cys Gly Asp Phe Gly Gly Gly
            325                 330                 335

Gly Met Asp Ser Ala Lys Gln Glu Asn Gln Thr Leu Arg Pro Phe Phe
            340                 345                 350

Asp Glu Trp Pro Lys Thr Arg Asp Ser Trp Ser Asp Leu Thr Asp Asp
            355                 360                 365

Asn Ser Ser Leu Ala Ser Phe Ser Ala Thr Gln Leu Ser Ile Ser Ile
    370                 375                 380

Pro Met Thr Ser Ser Asp Phe Ser Ala Ala Ser Ser Gln Ser Pro Asn
385                 390                 395                 400

Gly Met Leu Phe Ala Gly Glu Met Tyr
            405

<210> SEQ ID NO 25
<211> LENGTH: 2000
<212> TYPE: DNA
<213> ORGANISM: Hordeum vulgare

<400> SEQUENCE: 25
aaagttcaaa taagtttttc agaccctacc gtcatacacc ttgacggtag aatgtgaaac    60
cctaccatta tataaacgaa ttcccgttac aacaacttta cacacgaggt cagactccta   120
ccgccatagt tcctaatggt aaggtcttgc atcctatcgt cttatacttg gcggtacggc   180
cgttacgcca cgtgagccct tcggctggca gttgacggcc gctgttgtta ctcgactgtc   240
agatacctat aaacctatcg ccaacctgtg taacaatgaa aaacggtcaa atcccgaaaa   300
aatttcgaag caggatcgca tcctgctaaa cttttgacaa atggtcaaaa cacgaaattt   360
ttgccgctcg ttgtgcctct gtaagctgga agcctacggt gtcggcctca cccccacac   420 ggtgctgccg ctgctgcgcc atcgccagc gcttcacgct atatatccac cccgtcgtcg   480
tgtgagtctc accaggcaga tcgagccctg cgcagcgagg ggaaagagac acacacagcg   540
ccaccaggca agtagtagta aaaggcaaaa gcacggcaca ttaaaagaga ggccagccca   600
gccccggacc ggaccggagc caagcagcag ccgcagccgc agccgcagca gaggagagag   660
agagggaggg agaagcatat atggcgatgc cctttgcctc cctgtcgccg gcagccgacc   720
accaccgctc ctcccccatc ttcccccttct gccgctcctc ccctctctac tcgtaagccg   780
gccggccggc cggccaaccg cctcacttct ttcttcgtat ctgcttccat cttagctcga   840
ggggttcgct aatgcggtga ccgtctccgg cgcctgtgtt gtgttccgtg tgtgcagggt   900
agggagggag gcggcgcatc agcatcctca tcctcagcag cagcagcacg cgatgagcgg   960
cgcgcggtgg gcggcgaggc cggcgccctt cacggcggcg cagtacgagg agctggagca  1020
gcaggcgctc atctacaagt acctcgtcgc cggcgtcccc gtcccgcagg acctcctcct  1080
ccccatccgc cgcggcttcg agaccctcgc ctcgcgcttc taccaccacc acgcccgtac  1140
gtaccccatc ccttcctcct cctacccccgg ccaggagtag tacttgcttt tttgcattcg  1200
ccatgcgatt tgcccggttg tttattcgga tcgagcactt gcttttgcat tcgccatgcg  1260
atttgcccgg cttgtttatt gggatcgaga gattcaggtg tgctcgaccc ccatcccatg  1320
attcccatct ctttgttaat tgctccggtc atttgttaat ccctcccgg atttggccga  1380
```

```
gcaaaagtct cattattcta atccgagcaa gcctcgtgcc cctgttcaaa gatttgctcc    1440
taccatcacc acctaccacc atccagcaag catcccctgc ctcgccgggt cttttaattt    1500
acttgggatt tcattctcat gtcatgtcat gtgctatgat ttgattagat ggcgctagtc    1560
gagtcttggg ttagtttcca ttggtccttc cgtggcaagg gggttattcc tgtctggttg    1620
ttgggagcct cacccacgca ttcactcgct cgctcgctgg tcatgtcctg ccacggccga    1680
tctcaccgat ccatcctgca tcgcatcaca tggaccccg acgaaaaaga tcggcaatca    1740
accacgcaca gctcctcctt tccccggaaa ttatttcgca tacgtccttc cttccttcgt    1800
tccttccttc ttgcggggta aatgattggt ttggtgggt gggcacacag atagatccag    1860
gacgaggacg accgccttcg tccgtccctc cggccggccg gcgtcatgat tgattgctac    1920
ctgctacggc cttggactgg acgcgtctcc gttcttccga tctcgcgtct cctcctgagt    1980
tgatttcttg gtccctccgg                                              2000
```

```
<210> SEQ ID NO 26
<211> LENGTH: 489
<212> TYPE: DNA
<213> ORGANISM: Hordeum vulgare

<400> SEQUENCE: 26
atgagcaccg acacattcca agtgcgtaca gatgtatggg gtatttatca tgaaaaagca     60
ttcttgacgt gggtgttttt cgttgtttgc agttgggtac gggtcctact tcggaagaa    120 gctggatccg gagccggggc ggtgccggcg gacggacggc aagaagtggc ggtgctccaa    180
ggaggccgct caggactcca gtactgcga gcgccacatg caccgcggcc gcaaccgttc    240
aagaaagcct gtggaaacgc agctcgtcgc cagctcccac tcccagtccc agcagcacgc    300
caccgccgcc ttccacaacc actcgccgta tccggcgatc gccactggcg gtggctcctt    360
cgccctgggg tctgctcagc tgcacatgga cactgctgcg ccttacgcga cgaccgccgg    420
tgctgccgga aacaaagatt tcaggtgacc tcttctctgc atatactctg ctgccgtcgt    480
gttgattag                                                           489
```

```
<210> SEQ ID NO 27
<211> LENGTH: 162
<212> TYPE: PRT
<213> ORGANISM: Hordeum vulgare

<400> SEQUENCE: 27

Met Ser Thr Asp Thr Phe Gln Val Arg Thr Asp Val Trp Gly Ile Tyr
1               5                   10                  15

His Glu Lys Ala Phe Leu Thr Trp Val Phe Val Val Cys Ser Trp
            20                  25                  30

Val Arg Val Leu Leu Arg Glu Glu Ala Gly Ser Gly Ala Gly Ala Val
        35                  40                  45

Pro Ala Asp Gly Arg Gln Glu Val Ala Val Leu Gln Gly Gly Arg Ser
    50                  55                  60

Gly Leu Gln Val Leu Arg Ala Pro His Ala Pro Arg Gln Pro Phe
65                  70                  75                  80

Lys Lys Ala Cys Gly Asn Ala Ala Arg Arg Gln Leu Pro Leu Pro Val
                85                  90                  95

Pro Ala Ala Arg His Arg Arg Leu Pro Gln Pro Leu Ala Val Ser Gly
            100                 105                 110

Asp Arg His Trp Arg Trp Leu Leu Arg Pro Gly Val Cys Ser Ala Ala
        115                 120                 125
```

```
His Gly His Cys Cys Ala Leu Arg Asp Asp Arg Arg Cys Cys Arg Lys
    130                 135                 140

Gln Arg Phe Gln Val Thr Ser Ser Leu His Ile Leu Cys Cys Arg Arg
145                 150                 155                 160

Val Asp

<210> SEQ ID NO 28
<211> LENGTH: 2000
<212> TYPE: DNA
<213> ORGANISM: Sorghum bicolor

<400> SEQUENCE: 28
taaatattgt tttattataga ctaactaggc ttaaaaaatt cgtctcacaa attacaattg      60
aactgtctaa ttagtttata tttttgtcta tatttaatgc ttcatgcata agtataaaga     120
tttgacgtga cagagaatct aaaaaatttt acaaaattgt ttggaactaa acaaggccct     180
agaatacaag gctaaggcct tgtttagatg cacccaaaaa tccaaaactt tacaagattc     240
tccgtcacat cgaatcttac agcacatgca tgaagtatta aatatagata aaaataaaaa     300
ctaattacac agtttatctg taaatcgcga gacaaatctt ttaagcctag ttactccatg     360
attggacaat gtttgtcaaa taaaaacgaa agtgctacag tgtcaaaatc caaaaagttt     420
ttgcatctaa acaagcccta aatataaggc ctcgtttagt tcaccccaaa aatcaaaaac     480
ttttcaagat tctccgtcac atcgaatctt gcggcacatg cataaagcac taaataaaga     540
tgaaaataaa aactaattgt acagtttacg tgtaaatgaa tcttttaagc ctaattactc     600
catgattaga taatatttat caaataaaaa cgaaagtttt acggtttgga aaaccaaaaa     660
gttttcggaa ctagccctgt ttaaattgaa gttaaaattt ttttagatgt cacgttgtat     720
gtgtcggaag gatatcggga ggggttttaa gaaactaata aaagaacaaa ttacatagct     780
cgtctagaaa ctgcaagaca aatctattaa tcataattaa tatatcatta gcacatatga     840
gttattatag aacttaaggc taatcataga ctaactaggc ttaaagatt catctcgcaa      900 ttctaaacca aactgtgtaa ttagtttatt ttttatttac atttagtgat caatgtatgt     960
gtccaaagat ttgatatgat gaatctaaac acaaatctag gccttgttta gtttcaaaat    1020
attttgcaaa atggacacgg tagctctttc gtttgtattt gacaaatatt gtccaatcat    1080
ggactaaata ggctcaaaag attatctcg tcaattccga ccaaactgtg caattagttt    1140
ttattttgtt ctatatttag taattcatgc atgtgtctaa agattcgata tgacgtggaa    1200
tctgaaaaat tttgtaaaat tttttgggaa ctaaacaaga ccctaaccat caacaaatga    1260
ccggatgtac agtactagtt tccagtcggc tgtccaaacg cccccgctgc tcgctcgccg    1320
cctcgccggg agtctcgaca cgcctgacgc tccagcgcga ggcagacagc gacgcagaga    1380
gagacaaagg gggcaataaa ggcagcgcgc gcgagcacca gcgagggagc gaagcaaagc    1440
acatcacgag cccggaagct cattaagagc aactccagca ttagacccta aaactaaacc    1500
cctactttta atttgggtgc tcttcctact tcgtggggct caatttttt gcttcaactc    1560 caacagtagc acccaaattt aggccccaa acttattcca gagagaatga cacaagggac    1620
ccactcgtca gtgtcctttt cttcttcctc tttcttcttc ctttggacat ggacacaatt    1680
agagcatcga gccggttacc gtagggtgtc atgcacatac aagggtagag agagaaggag    1740
catgagctga ggctaggaca cgcgatggag gatgggggct gccctgttgg gccaacagga    1800
atggggtcta ggagagaaat atgggtgccc agccaaatat ggggtctgga gtagggaccg    1860
```

```
tgctggagta atgttttag tctgagcacc catatttagc tattggggct tgagtagaag    1920
ctctgctgga gttgctctaa agaggggtgc cgtccggccg ccgcgggga gcaagcagcg    1980 cgcgcgagag acaggttgag                                                2000
```

<210> SEQ ID NO 29
<211> LENGTH: 1221
<212> TYPE: DNA
<213> ORGANISM: Sorghum bicolor

<400> SEQUENCE: 29

```
atggcgatgc cgtatgcctc tctttccccg gcaggcgccg accaccgctc ctccacggcc     60
acggcggcgt cgctcctccc cttctgccgc tccaccccgc tctccgcggg cggcggcggc    120
ggcctggggg aggacgccca gttgagctcg cggtggccgg ccgcgaggcc ggtggtgccg    180
ttcacgccgg cgcagtacga ggagctggag cagcaggcgc tcatatacaa gtacctggtg    240
gccggcgtgc ccgtcccgcc ggatctcgtg gttccaatcc gccgcggtct cgactccctc    300
gcaacccgct tctacggcca tcccacactt ggtgggtacg gacgtacta cttaggcaag    360 aaactggatc cggagccggg gcggtgccgg cgtacggacg gcaagaagtg gcggtgctcc    420
aaggaggccg ccccagactc caagtactgc gagcgccaca tgcaccgcgg ccgcaaccgt    480
tcaagaaagc ctgtggaaac gcagctcgtg ccccagtccc aaccgcccgc caccgccgct    540
gccgtctccg ccgctccgcc cttggccttg gccgccgcca ccaccaccac caacggcagc    600
tgcttccaga tcactctct ttacccggcc attgcaggca gcaccggtgg aggtggcggg    660
gccagcaata tctctacccc gttctcctcg tcgatggggt cgtctcagct gcacatggac    720
aatgctgcca gctacgcagc tcttggtggt ggaactgcaa aggatctcag gtacaacgcc    780
tacggaataa gatctttggc ggaggagcac aaccagctga ttgcagaagc cattgactca    840
tcaatggaga accagtggcg cctccgcca tcccaaacct cttcgtttcc gctctcgagc    900 taccccccagc ttgggcgct gagcaacctg gtcagagca cagtcacctc gctgtcgaag    960
atggagcggc agcagccact ctccttccta gggaactccg agttcggggc catggaatcc   1020
gccgccaagc agcaggagaa ccagacgctg cggcccttct tcgacgagtg cccaaggcg   1080 agggactcct ggccgggcct ctccgacgac aacgccgcaa gcctcgctcc gtcgttcccg   1140
gcgacccagc tgtcgatgtc cataccgatg gcgtcctcgg acttctccgt ggccagctcc   1200
cagtcgccca acgatgacta a                                             1221
```

<210> SEQ ID NO 30
<211> LENGTH: 406
<212> TYPE: PRT
<213> ORGANISM: Sorghum bicolor

<400> SEQUENCE: 30

```
Met Ala Met Pro Tyr Ala Ser Leu Ser Pro Ala Gly Ala Asp His Arg
1               5                   10                  15

Ser Ser Thr Ala Thr Ala Ala Ser Leu Leu Pro Phe Cys Arg Ser Thr
            20                  25                  30

Pro Leu Ser Ala Gly Gly Gly Gly Leu Gly Glu Asp Ala Gln Leu
        35                  40                  45

Ser Ser Arg Trp Pro Ala Ala Arg Pro Val Val Pro Phe Thr Pro Ala
    50                  55                  60

Gln Tyr Glu Glu Leu Glu Gln Gln Ala Leu Ile Tyr Lys Tyr Leu Val
65                  70                  75                  80
```

```
Ala Gly Val Pro Val Pro Asp Leu Val Pro Ile Arg Arg Gly
             85                  90                  95
Leu Asp Ser Leu Ala Thr Arg Phe Tyr Gly His Pro Thr Leu Gly Gly
            100                 105                 110
Tyr Gly Thr Tyr Tyr Leu Gly Lys Lys Leu Asp Pro Glu Pro Gly Arg
            115                 120                 125
Cys Arg Arg Thr Asp Gly Lys Lys Trp Arg Cys Ser Lys Glu Ala Ala
            130                 135                 140
Pro Asp Ser Lys Tyr Cys Glu Arg His Met His Arg Gly Arg Asn Arg
145                 150                 155                 160
Ser Arg Lys Pro Val Glu Thr Gln Leu Val Pro Gln Ser Gln Pro Pro
                165                 170                 175
Ala Thr Ala Ala Ala Val Ser Ala Ala Pro Leu Ala Leu Ala Ala
            180                 185                 190
Ala Thr Thr Thr Thr Asn Gly Ser Cys Phe Gln Asn His Ser Leu Tyr
            195                 200                 205
Pro Ala Ile Ala Gly Ser Thr Gly Gly Gly Gly Ala Ser Asn Ile
            210                 215                 220
Ser Thr Pro Phe Ser Ser Ser Met Gly Ser Ser Gln Leu His Met Asp
225                 230                 235                 240
Asn Ala Ala Ser Tyr Ala Ala Leu Gly Gly Gly Thr Ala Lys Asp Leu
                245                 250                 255
Arg Tyr Asn Ala Tyr Gly Ile Arg Ser Leu Ala Glu Glu His Asn Gln
            260                 265                 270
Leu Ile Ala Glu Ala Ile Asp Ser Ser Met Glu Asn Gln Trp Arg Leu
            275                 280                 285
Pro Pro Ser Gln Thr Ser Ser Phe Pro Leu Ser Ser Tyr Pro Gln Leu
            290                 295                 300
Gly Ala Leu Ser Asn Leu Gly Gln Ser Thr Val Thr Ser Leu Ser Lys
305                 310                 315                 320
Met Glu Arg Gln Gln Pro Leu Ser Phe Leu Gly Asn Ser Glu Phe Gly
            325                 330                 335
Ala Met Glu Ser Ala Ala Lys Gln Gln Glu Asn Gln Thr Leu Arg Pro
            340                 345                 350
Phe Phe Asp Glu Trp Pro Lys Ala Arg Asp Ser Trp Pro Gly Leu Ser
            355                 360                 365
Asp Asp Asn Ala Ala Ser Leu Ala Pro Ser Phe Pro Ala Thr Gln Leu
            370                 375                 380
Ser Met Ser Ile Pro Met Ala Ser Ser Asp Phe Ser Val Ala Ser Ser
385                 390                 395                 400
Gln Ser Pro Asn Asp Asp
                405

<210> SEQ ID NO 31
<211> LENGTH: 2000
<212> TYPE: DNA
<213> ORGANISM: Glycine max

<400> SEQUENCE: 31
acatacactc tttctctcca aaaataaata aattaatata cactagtttg gcttttaatt     60
cccaaattac accatttttt tgtgacattg agatgtaggg atttgacaac ccgacttctc    120
agtgattttt attttttttt aatttaaatt ttatttttat tctaaattta tgttttagtt    180
taaattatta tacacaaaag ttaagaagtt aaaaagttgg gattcatccc tatttttat    240
```

```
ctatggtttt actccaattt actctaatca agaattaaga gaatctaact tacttgaatg      300
ttataaatcc ttcatacctt atttaattct tacctataaa aaatcccaat caagaaaaaa      360
atcccaatta agagaatcta acttacttta attataaccg aaacaaagct acgtaacttg      420
attacaaaat gtacgagaaa ccaaaattag tgatggtgaa aaaaatcacc gacaaaagta      480
agaatctaca cgtgatctga gatcagagac atactttaag aagcaacaat caacagccga      540
aaaccaaaat taaaggtata tattccttaa attgctttgt ccctttgact tttgccatcg      600
tgatgattaa ttaaaggttt agcaaacccc ttcgaacttc atacaattga ctgaattgag      660
aattttattt tcacattcga ggaagcgatg ctacaacatc actttttttg ttctgtattg      720
tgctttttaa ctgcctttt tcttcttctt tttttgcctc cctaacaaag acatgtaaaa       780
gtaattgtaa taatattcgt ttcttatgga atgcaatcag ttgattgatg taactataaa      840
ctattatctc cttaatatcg aaagacaagt gaagccaaac acaaacaaga tagggcctag      900
ggagaggtgt ggtccatgaa tgatgaggta tgggtgacca acaatgaat gaataattga      960 agcatccttg accgttgctt gagtttgtgt catcctcaat aatatactag tcccttggct     1020
acagaaaccg ataagcctaa aactggaatt gcacacattt acgttttga ttttgatttt     1080 gttttttggca atctcgcccc acatcaaatg tcacccgcat tccggcaagt agtggatggt     1140
ttcctctagc ggtgctttgc ctttgggcca ctgggcccgc aattactcca gcccatcatg     1200
ccttgttgct gtccgttaaa gggtagcata taaaataaa agtagatcaa caaatgaga      1260 gcaagtattt caaaaaaaa aaaacatagt aaaaaaacac ttcctctatt tatattatca     1320
agatttattt atcttaaaac attcattatc tcaaaaatac ctatattact taatagtatt     1380
tcatgaattt aaatctaagt ttactatcaa actcaccttt taaaacaatt attacacaac     1440
aagttataat tgaatgtcat aaaaaaaatt gattattgtg ctaacacgtg aaaaaaattt     1500
atatttaatt tttttatgta taatttgttt ggaccaatga tagagattaa ttgtgatcta     1560
atgagttata agaaatacgt ggcacatgat cctagacaaa aataaataag aattgtaaaa     1620
taatgtattt tatagctttt ctgaaagatt ttttttttta atttcttctc atgcccatac     1680
atgaatacat gaatgagaat ttttatttt atttttttgt ctgaaataaa gttaaaaatt     1740
gggagcagtg aatgttaagg atgacttttg acttgaatgc aacaagaagt aaagttcact     1800
ttaagttgga ggcttggagc atcgccatcc ataacacaac acaatcgaca atcctaatgg     1860
ttccgacaaa gctcgacctg agtgtgatct catgatgttt ctgctctaac tatgtttgat     1920
ttggataccc aacaacaaaa agagtgttgt cgtgttgttg tagttaatag taataggact     1980
aagtaagagt agtggaaaac                                                2000
```

<210> SEQ ID NO 32
<211> LENGTH: 1026
<212> TYPE: DNA
<213> ORGANISM: Glycine max

<400> SEQUENCE: 32

```
atgaacaaca gcagtggcgg aggaggacga ggaactttga tgggtttgag taatgggtat       60
tgtgggaggt cgccattcac agtgtctcag tggcaggaac tggagcacca agctttgatc      120
ttcaagtaca tgcttgcggg tcttcctgtt cctctcgatc tcgtgttccc cattcagaac      180
agcttccact ctactatctc gctctcgcac gctttctttc accatcccac gttgagttac      240
tgttccttct atgggaagaa ggtggaccct gagccaggac gatgcaggag gactgatgga      300
aaaaagtgga ggtgctccaa ggaagcatac ccagactcca agtactgcga gcgccacatg      360
```

```
caccgtggcc gcaaccgttc aagaaagcct gtggaatcac aaactatgac tcactcatct    420
tcaactgtca catcactcac tgtcactggg ggtagtggtg ccagcaaagg aactgtaaat    480
ttccaaaacc tttctacaaa tacctttggt aatctccagg gtaccgattc tggaactgac    540
cacaccaatt atcatctaga ttccattccc tatgcgattc aagtaaaga atacaggtat     600
gttcaaggac ttaaatctga gggtggtgag cactgctttt tttctgaagc ttctggaagc    660
aacaaggttc tccaaatgga gtcacagctg aaaacacat ggcctttgat gtcaaccaga     720
gttgcctctt tttctacgtc aaaatcaagt aatgattccc tgttgcatag tgattatccc    780
cggcattcgt ttttatctgg tgaatatgtg tcgggagaac acgtaaagga ggagggccag    840
cctcttcgac ctttttttaa tgaatggcct aaaagcaggg agtcatggtc tggtctagaa    900
gatgagagat ccaaccaaac agccttctcc acaactcaac tctcaatatc cattcctatg    960
tcttccaatt tctctgcaac gagctctcag tccccacatg gtgaagatga gattcaattt   1020
aggtaa                                                              1026

<210> SEQ ID NO 33
<211> LENGTH: 341
<212> TYPE: PRT
<213> ORGANISM: Glycine max

<400> SEQUENCE: 33

Met Asn Asn Ser Ser Gly Gly Gly Gly Arg Gly Thr Leu Met Gly Leu
  1               5                  10                  15

Ser Asn Gly Tyr Cys Gly Arg Ser Pro Phe Thr Val Ser Gln Trp Gln
                 20                  25                  30

Glu Leu Glu His Gln Ala Leu Ile Phe Lys Tyr Met Leu Ala Gly Leu
             35                  40                  45

Pro Val Pro Leu Asp Leu Val Phe Pro Ile Gln Asn Ser Phe His Ser
         50                  55                  60

Thr Ile Ser Leu Ser His Ala Phe Phe His Pro Thr Leu Ser Tyr
 65                  70                  75                  80

Cys Ser Phe Tyr Gly Lys Lys Val Asp Pro Glu Pro Gly Arg Cys Arg
                 85                  90                  95

Arg Thr Asp Gly Lys Lys Trp Arg Cys Ser Lys Glu Ala Tyr Pro Asp
            100                 105                 110

Ser Lys Tyr Cys Glu Arg His Met His Arg Gly Arg Asn Arg Ser Arg
        115                 120                 125

Lys Pro Val Glu Ser Gln Thr Met Thr His Ser Ser Thr Val Thr
    130                 135                 140

Ser Leu Thr Val Thr Gly Gly Ser Gly Ala Ser Lys Gly Thr Val Asn
145                 150                 155                 160

Phe Gln Asn Leu Ser Thr Asn Thr Phe Gly Asn Leu Gln Gly Thr Asp
                165                 170                 175

Ser Gly Thr Asp His Thr Asn Tyr His Leu Asp Ser Ile Pro Tyr Ala
            180                 185                 190

Ile Pro Ser Lys Glu Tyr Arg Tyr Val Gln Gly Leu Lys Ser Glu Gly
        195                 200                 205

Gly Glu His Cys Phe Phe Ser Glu Ala Ser Gly Ser Asn Lys Val Leu
    210                 215                 220

Gln Met Glu Ser Gln Leu Glu Asn Thr Trp Pro Leu Met Ser Thr Arg
225                 230                 235                 240

Val Ala Ser Phe Ser Thr Ser Lys Ser Ser Asn Asp Ser Leu Leu His
```

```
                    245                 250                 255
Ser Asp Tyr Pro Arg His Ser Phe Leu Ser Gly Glu Tyr Val Ser Gly
            260                 265                 270

Glu His Val Lys Glu Glu Gly Gln Pro Leu Arg Pro Phe Phe Asn Glu
        275                 280                 285

Trp Pro Lys Ser Arg Glu Ser Trp Ser Gly Leu Glu Asp Glu Arg Ser
    290                 295                 300

Asn Gln Thr Ala Phe Ser Thr Thr Gln Leu Ser Ile Ser Ile Pro Met
305                 310                 315                 320

Ser Ser Asn Phe Ser Ala Thr Ser Ser Gln Ser Pro His Gly Glu Asp
                325                 330                 335

Glu Ile Gln Phe Arg
            340

<210> SEQ ID NO 34
<211> LENGTH: 2000
<212> TYPE: DNA
<213> ORGANISM: Brassica napus

<400> SEQUENCE: 34
cataccttca ggatgtgtga agcattccta ttgaattttg tcgataaaat agaaattgca    60
agttgaacaa attgcaatat atatggaaag atgctagcta gtgccaataa tatattaacg   120
gaacaattca tatttcattt tatattatat aatgattatt ttagttttta gttaatacta   180
ataaataata agaaatataa ctacatagtt taaaatgata gtgtgttcta aatttgttaa   240
atggatatct aaatcagttt aggtggcttt taaatgttat tttatgttca tgtaaattaa   300
ttattgtttt acatttaaca ttgtattact ttttatcata ttagttaatt aatgacactc   360
gttttcattc taaaatcaaa atatcagaca tattcatctt tataacaata tgaaaattaa   420
ttttcagtat taatctaaaa aatctattta aattttgatg cgtctgactt ataaaaacac   480
acacacatat atatatatat atatgtatat atttattaat tagtaaaatt tattttaaga   540
aaaattgaaa ctaattaaat tttgggaaag tagtgattat ataatagttt tgttatttta   600
tatgctaaaa tttattaagt acttttttttt taatttgag acttaccaaa ttacggatcc   660
taaatatatt gatcttgaat tatgatatat taattaaatt ttaaagttat cataaatttg   720
ttgtgaattc agtttaggta attgtctatt aaattagaaa aaagataaat aatgataaag   780
ttatgttagt tattagttta atagtattga ggtgtaaata aattaaagtt gtaatggtta   840
atttataagt gtatttgtgt tttaattata ttagatttca attgattcca cagataattc   900
aacatgttcc atgtaattaa tgttacagca gaaatctaga taaatttttt ttttaacact   960
ggataatgcg attataaacg ataagacgat tctatatgcg acatgtctta taatgattca  1020
tgtctgaata catcatttga accgttttat aagatctacg tttggtggta ttttttgtgc  1080
tatgctgcag attttttata agtatttatt tcattaattc gcataatttt attttttttc  1140
taaagatcga aactccgatt ttatggtgtt gaacatctag atagagatct atggataaaa  1200
caaatataga ggaagctaca caatttaaag ggtcaaaata gaaacacaga actgaaaagt  1260
atactcagtg ccatatgatt taatagtatg aatttaactt gaacttaatg tcgtttggtt  1320
tgtcatcaaa tgcaactgca aatcatatcg aagtaacgcc cgtgtcataa tatatctgat  1380
taaggactat tattttctgt ttgacaaaaa aaaaaggact attattttct cactaatcag  1440
gctattgttt ttttctcaat aaactaattt aaagaaatac agattattca agtgctattt  1500
ccaaggcaga tgcaggttac tatctctcga tcttcatctc ggagtgtggt tctttatgtg  1560
```

```
tttctgact tgctttatta tactaatatt attaatagat taatgaagat taatagttta      1620
atagattaat gaagacataa actataattt aataatcata gattaatgaa gatttgtgaa      1680
ccccattaat aaagtttaat agttgttgtt cttatagtct tttaccgtat agttttctcc      1740
ccccatctgt ctcgtctcac tgtctttttcc tctcaagttt caagtgccct aaataaaaac     1800
ctctttcccc ttctctctct ctgcagaaga aggtcagata cagaaactga ctgcaaagaa      1860
caaagctgca aggtgcagct attccttagt aaaaagcttt gttctctttc ttcttttgct      1920
cttcacatcc cccccaacag agacttttct gctatttaaa accagaccct ggaaaaagta      1980
gccaacactc tctctttccc                                                  2000

<210> SEQ ID NO 35
<211> LENGTH: 1107
<212> TYPE: DNA
<213> ORGANISM: Brassica napus

<400> SEQUENCE: 35
atggatttgc aactgaaaca atggaggagc aagcaggtgc agacagagtc agaaccacaa       60
ccttctgcag ctaagatacc aagacatgcc tttgatccga ttcagtccca aactgcaact      120
tctactgttc ttccactctt tgcccctgaa cctgcgtctt ctaaactctc ctccttatgt      180
cctgattctt cttccaggtt ctccaagatg gggagtttct ttagctcggc acagtggcaa      240
gagcttgaac tacaggcact gatctacagg tacatgctgg ctggagctgc tgttccacaa      300
gagctccttc taccaatcaa gaaaagtctt ctccatctat ctccttccta ctttcttcac      360
cacctacctc attaccagcc tgcttggtat ttggggaggg gggcgatgga tcctgagcca      420
gggagatgca ggagaacgga tggtaagaag tggagatgtt caagggacgt cttcgctggc      480
cacaagtact gcgagcgcca catgcaccga ggccgcaacc gttcaagaaa gcctgtggaa      540
actcccatag tcaatgctac caccaccact tccatggctt ccccagccac agcggcaccg      600
tcatcaacac catcctcctt tgcttttggc ggtggtgaga agtgggtca aggtggatca       660 tctagcttct tcttctcaag tcaaagttgt tcagagatga acaagaaag caacaacaac       720 aagaggccat acgagtccca taatggattt gggagcaatg gatcagacgg aggccacatc      780
ttgaggcact ctttgatga ttggcctcgt tctgaagccg acaatagttc aagcccatg       840 agctcagcca cttgtctctc catctctatg cctggaaact cttcctcaga cgtctctctg      900
aagctgtcca ctggtaatga agaggaagct aggagcaaca acattgggag ggaccagcaa      960
aacatgagct ggtggagcgg tggaggtacc aaccacaacc accatcacat gggaggacca     1020
ttggctgaag ccctgagatc ttcctcatca tcttccccga ccagtgttct ccatcagctc     1080
ggtgtttcaa cgcaagcctt tcattga                                        1107

<210> SEQ ID NO 36
<211> LENGTH: 368
<212> TYPE: PRT
<213> ORGANISM: Brassica napus

<400> SEQUENCE: 36

Met Asp Leu Gln Leu Lys Gln Trp Arg Ser Lys Gln Val Gln Thr Glu
1               5                   10                  15

Ser Glu Pro Gln Pro Ser Ala Ala Lys Ile Pro Arg His Ala Phe Asp
            20                  25                  30

Pro Ile Gln Ser Gln Thr Ala Thr Ser Thr Val Leu Pro Leu Phe Ala
        35                  40                  45
```

```
Pro Glu Pro Ala Ser Ser Lys Leu Ser Ser Leu Cys Pro Asp Ser Ser
    50                  55                  60

Ser Arg Phe Ser Lys Met Gly Ser Phe Phe Ser Ala Gln Trp Gln
65                  70                  75                  80

Glu Leu Glu Leu Gln Ala Leu Ile Tyr Arg Tyr Met Leu Ala Gly Ala
                85                  90                  95

Ala Val Pro Gln Glu Leu Leu Pro Ile Lys Lys Ser Leu Leu His
            100                 105                 110

Leu Ser Pro Ser Tyr Phe Leu His His Leu Pro His Tyr Gln Pro Ala
            115                 120                 125

Trp Tyr Leu Gly Arg Gly Ala Met Asp Pro Glu Pro Gly Arg Cys Arg
            130                 135                 140

Arg Thr Asp Gly Lys Lys Trp Arg Cys Ser Arg Asp Val Phe Ala Gly
145                 150                 155                 160

His Lys Tyr Cys Glu Arg His Met His Arg Gly Arg Asn Arg Ser Arg
                165                 170                 175

Lys Pro Val Glu Thr Pro Ile Val Asn Ala Thr Thr Thr Ser Met
            180                 185                 190

Ala Ser Pro Ala Thr Ala Ala Pro Ser Ser Thr Pro Ser Ser Phe Ala
            195                 200                 205

Phe Gly Gly Gly Glu Lys Val Gly Gln Gly Gly Ser Ser Ser Phe Phe
210                 215                 220

Phe Ser Ser Gln Ser Cys Ser Glu Met Lys Gln Glu Ser Asn Asn Asn
225                 230                 235                 240

Lys Arg Pro Tyr Glu Ser His Asn Gly Phe Gly Ser Asn Gly Ser Asp
                245                 250                 255

Gly Gly His Ile Leu Arg His Phe Phe Asp Asp Trp Pro Arg Ser Glu
            260                 265                 270

Ala Asp Asn Ser Ser Ser Pro Met Ser Ser Ala Thr Cys Leu Ser Ile
            275                 280                 285

Ser Met Pro Gly Asn Ser Ser Ser Asp Val Ser Leu Lys Leu Ser Thr
    290                 295                 300

Gly Asn Glu Glu Glu Ala Arg Ser Asn Asn Ile Gly Arg Asp Gln Gln
305                 310                 315                 320

Asn Met Ser Trp Trp Ser Gly Gly Thr Asn His Asn His His His
                325                 330                 335

Met Gly Gly Pro Leu Ala Glu Ala Leu Arg Ser Ser Ser Ser Ser
            340                 345                 350

Pro Thr Ser Val Leu His Gln Leu Gly Val Ser Thr Gln Ala Phe His
            355                 360                 365
```

<210> SEQ ID NO 37
<211> LENGTH: 2000
<212> TYPE: DNA
<213> ORGANISM: Lycopersicon esculentum

<400> SEQUENCE: 37

| | | | | | |
|---|---|---|---|---|---|
| catttaatta | gttaaatcaa | atacatacat | atataattgt | tattaatttt | taggtatgat | 60 |
| gtaccattaa | gactaagaag | atcagtgatg | acgcaacgta | tttcaatttt | tttgtgggtt | 120 |
| aagtatatgt | cttaaactta | acatagattt | aaaattattt | aaattgttaa | tacctaaagt | 180 |
| ttatttttat | tttcattttt | gaaagaacaa | taattcaagt | gggtaattga | caaattattt | 240 |
| tgaatataaa | aaaatgaaa | aacagagaaa | aaaaacatta | gtaaaatcat | taaattacac | 300 |

| | |
|---|---|
| caaacaaatt tggagaattg aaaaagaaca tttataacaa ctctaatata aataaaaaga | 360 |
| aaattaaatt acaaaagttt tttttaaaaa aaataaaggg ttagtttagt catttaggaa | 420 |
| tcttatccga ggtttaacaa attttgaatt agttatccct ccattcgaa gggataagat | 480 |
| aatactagat atgatggata agcaatccat gagttaaatt aaatgaagta accaaaacaa | 540 |
| tgtattagtt gaattaaatt ttaatccata aattattcta cctaatattg tctatcaaac | 600 |
| gggtccttag tattagttaa ctggtgacga ggatcatata atttaaagag ttgggtccag | 660 |
| ttttaaagcg tgattatagc gaaatgaaat gtttcttatc ccaccaaaaa tttgattata | 720 |
| aaacgaaaat gactctcgtt gagaaaagaa aatttacaaa tgatattcat cctcccgtaa | 780 |
| ttctcatata atttgttttt gatgtacatg aatattttt aaaatagttt ttttagtttt | 840 |
| tacaaaaata tataatctca ctcaacacaa actcgttagg aattaaatta aacttttgtg | 900 |
| ttgatcaaca taagtcgcat aacttatgag ttttgatatc gaactttgtc ggactggata | 960 |
| taaattagaa aacagagtca tgaaatactt aatataagtc acataattta tgaattttga | 1020 |
| tattagactt tgtcttgctc gaaacaagtt ttgaataaaa aaattatgc aatacgacat | 1080 |
| aactaatgag attaatcaca tttgcattat tcaagactca taaatacaaa atttctaaat | 1140 |
| tgagtaatct catctatgtc atctgttcac atacaaaact aaaaactatc tatgccacca | 1200 |
| cacttcttga tgatgtgttg gagcttattt ctcaagatat ttcacattct tgctcaaaca | 1260 |
| aaaagcacaa agtttcaaaa agtaaaaaaa aaaagagaga aaaacaatca tatatatata | 1320 |
| tatatatcaa actagaataa gatcttttgt aggtcatctt aattattgtt gaaccttaaa | 1380 |
| ggacaaagtt tacatcttta gggtcatgat acattcacat gactaaattt tgaaagatat | 1440 |
| aaaaagaggt gttacatcat ttggaccaca ataagacatt atccattcta ccccactcca | 1500 |
| taaggtcccc cttctttcaa tcccctttc tccccccat gccccaatgc ttccttaaac | 1560 |
| ccttcattat ctttcacaaa acttatacta taatgtcatc attcatattg ttattgtcat | 1620 |
| ttattcttct caccataaag ttcaatgtaa gtttgttaat tttgtcttgt acattaataa | 1680 |
| gtactagtgt tatgaatgtt tcttgatttc actctaatta aatctcactc tctttcttca | 1740 |
| gcttttatct ctctgctctt tcttccatgc ttgtccaaac cctagatctg tcccctctt | 1800 |
| aggtaacctc aacaaacttt gctctctata actcacacac aacacacaaa aacacattct | 1860 |
| ttttctcttt ctctgtgtat atgtttgtat attaactgat attgtgttga tttctaggtg | 1920 |
| cagcttttg agtgaagtga aaaaggggaa aggggggtgg gtaaaattg gaaagattag | 1980 |
| tttttttagtg aagggagaag | 2000 |

<210> SEQ ID NO 38
<211> LENGTH: 1086
<212> TYPE: DNA
<213> ORGANISM: Lycopersicon esculentum

<400> SEQUENCE: 38

| | |
|---|---|
| atgagtggca cctctacatc agtagtgggg ggtgggggtg gaggggaggg gggaatgggg | 60 |
| tatgggtatg gttaccggcc gccatttacg gcggtgcaat ggcaggagct ggagcatcaa | 120 |
| gcaatgatat acaagtactt ggtggcaggt cttcctgtgc cacctgatct tgttgtccct | 180 |
| attcgtcgta gctttgaagc catctcagct aggttctttc atcatccaag cttgggctat | 240 |
| tgttcctatt atgggaagaa gtttgatcct gagccaggaa ggtgtagaag gactgacgga | 300 |
| aaaaagtgga gatgctcaaa agatgcatat cctgactcca atattgcga gcggcacatg | 360 |
| catcgaggcc gcaaccgttc aagaaagcct gtggaatctc aatctactcc ccagtccttg | 420 |

```
tcgactagta tgtcacaaat tacagctggg agcagcaata caagaggaag tttccaaaat      480
agcagcagcg gaagcttcca aaacatgcca ttgtattctg ttgctaattc gggaacgctg      540
aattatggaa gcactggaac aaagctgcag atggagcctg tctcctatgg aatagataac      600
aaggactata ggtatctcca tggaattact cctgatgctg atgagcacaa tttatcttca      660
gaggcttctg ctactgtcag aagtttaggg atgaggacca acacagacag tacctgggta      720
ttgccttctc aaatttcttc aagccccatg caagatcaa aaaatgattc tcagctgcta      780
ggtagctcaa cagagatgca tctacctaat ctacttgagc ctatgattga tgcaacaatt      840
tcaaaacgac gacaccagca ttgcttcttt ggcagtgaca tcgattcacc tggaacagta      900
aaggaggagc agcattcaat gcgccctttc tttaacgaat ggcccactgc taaagaatcg      960
tggtccaacc tcgacgatga gggatccaac aaaaacaatt tctccacaac acagctctcc     1020
atgtccattc caatcgctcc ttccaacttc tcttcaagga gtgcttgctc tccaaatgat     1080
acttga                                                                1086

<210> SEQ ID NO 39
<211> LENGTH: 361
<212> TYPE: PRT
<213> ORGANISM: Lycopersicon esculentum

<400> SEQUENCE: 39

Met Ser Gly Thr Ser Thr Ser Val Val Gly Gly Gly Gly Gly Gly Glu
1               5                   10                  15

Gly Gly Met Gly Tyr Gly Tyr Gly Tyr Arg Pro Pro Phe Thr Ala Val
            20                  25                  30

Gln Trp Gln Glu Leu Glu His Gln Ala Met Ile Tyr Lys Tyr Leu Val
        35                  40                  45

Ala Gly Leu Pro Val Pro Pro Asp Leu Val Val Pro Ile Arg Arg Ser
    50                  55                  60

Phe Glu Ala Ile Ser Ala Arg Phe Phe His His Pro Ser Leu Gly Tyr
65                  70                  75                  80

Cys Ser Tyr Tyr Gly Lys Lys Phe Asp Pro Glu Pro Gly Arg Cys Arg
                85                  90                  95

Arg Thr Asp Gly Lys Lys Trp Arg Cys Ser Lys Asp Ala Tyr Pro Asp
            100                 105                 110

Ser Lys Tyr Cys Glu Arg His Met His Arg Gly Arg Asn Arg Ser Arg
        115                 120                 125

Lys Pro Val Glu Ser Gln Ser Thr Pro Gln Ser Leu Ser Thr Ser Met
    130                 135                 140

Ser Gln Ile Thr Ala Gly Ser Ser Asn Thr Arg Gly Ser Phe Gln Asn
145                 150                 155                 160

Ser Ser Ser Gly Ser Phe Gln Asn Met Pro Leu Tyr Ser Val Ala Asn
                165                 170                 175

Ser Gly Thr Leu Asn Tyr Gly Ser Thr Gly Thr Lys Leu Gln Met Glu
            180                 185                 190

Pro Val Ser Tyr Gly Ile Asp Asn Lys Asp Tyr Arg Tyr Leu His Gly
        195                 200                 205

Ile Thr Pro Asp Ala Asp Glu His Asn Leu Ser Ser Glu Ala Ser Ala
    210                 215                 220

Thr Val Arg Ser Leu Gly Met Arg Thr Asn Thr Asp Ser Thr Trp Val
225                 230                 235                 240

Leu Pro Ser Gln Ile Ser Ser Ser Pro Met Ala Arg Ser Lys Asn Asp
```

```
                245                 250                 255
Ser Gln Leu Leu Gly Ser Ser Thr Glu Met His Leu Pro Asn Leu Leu
            260                 265                 270

Glu Pro Met Ile Asp Ala Thr Ile Ser Lys Arg Arg His Gln His Cys
        275                 280                 285

Phe Phe Gly Ser Asp Ile Asp Ser Pro Gly Thr Val Lys Glu Glu Gln
    290                 295                 300

His Ser Met Arg Pro Phe Phe Asn Glu Trp Pro Thr Ala Lys Glu Ser
305                 310                 315                 320

Trp Ser Asn Leu Asp Asp Glu Gly Ser Asn Lys Asn Asn Phe Ser Thr
                325                 330                 335

Thr Gln Leu Ser Met Ser Ile Pro Ile Ala Pro Ser Asn Phe Ser Ser
            340                 345                 350

Arg Ser Ala Cys Ser Pro Asn Asp Thr
            355                 360

<210> SEQ ID NO 40
<211> LENGTH: 541
<212> TYPE: DNA
<213> ORGANISM: Artificial Sequence
<220> FEATURE:
<223> OTHER INFORMATION: synthesized - p35S promoter

<400> SEQUENCE: 40
aattcccatg gagtcaaaga ttcaaataga ggacctaaca gaactcgccg taaagactgg      60
cgaacagttc atacagagtc tcttacgact caatgacaag aagaaaatct tcgtcaacat     120
ggtggagcac gacacgcttg tctactccaa aaatatcaaa gatacagtct cagaagacca     180
aagggcaatt gagactttc aacaaagggt aatatccgga acctcctcg gattccattg       240 cccagctatc tgtcacttta ttgtgaagat agtggaaaag gaaggtggct cctacaaatg     300
ccatcattgc gataaaggaa aggccatcgt tgaagatgcc tctgccgaca gtggtcccaa     360
agatggaccc ccacccacga ggagcatcgt ggaaaaagaa gacgttccaa ccacgtcttc     420
aaagcaagtg gattgatgtg atatctccac tgacgtaagg gatgacgcac aatcccacta     480
tccttcgcaa gacccttcct ctataaagg aagttcattt catttggaga ggacagggta     540
c                                                                    541

<210> SEQ ID NO 41
<211> LENGTH: 1991
<212> TYPE: DNA
<213> ORGANISM: Artificial Sequence
<220> FEATURE:
<223> OTHER INFORMATION: synthesized - pUbi promoter

<400> SEQUENCE: 41
ctgcagtgca gcgtgacccg gtcgtgcccc tctctagaga taatgagcat tgcatgtcta      60
agttataaaa aattaccaca tattttttt gtcacacttg tttgaagtgc agtttatcta     120
tctttataca tatatttaaa ctttactcta cgaataatat aatctatagt actacaataa     180
tatcagtgtt ttagagaatc atataaatga acagttagac atggtctaaa ggacaattga     240
gtattttgac aacaggactc tacagtttta tcttttagt gtgcatgtgt tctcctttt     300 ttttgcaaat agcttcacct atataatact tcatccattt tattagtaca tccatttagg    360
gtttagggtt aatggttttt atagactaat tttttagta catctatttt attctatttt    420
agcctctaaa ttaagaaaac taaaactcta tttagttttt ttatttaat aatttagata     480
```

```
taaaatagaa taaaataaag tgactaaaaa ttaaacaaat acccctttaag aaattaaaaa    540 aactaaggaa acatttttct tgtttcgagt agataatgcc agcctgttaa acgccgtcga    600
cgagtctaac ggacaccaac cagcgaacca gcagcgtcgc gtcgggccaa gcgaagcaga    660
cggcacggca tctctgtcgc tgcctctgga cccctctcga gagttccgct ccaccgttgg    720
acttgctccg ctgtcggcat ccagaaatgc gtggcggagc ggcagacgtg agccggcacg    780
gcaggcggcc tcctcctcct ctcacggcac ggcagctacg ggggattcct ttcccaccgc    840
tccttcgctt tcccttcctc gcccgccgta ataaatagac ccccctcca caccctcttt    900 ccccaacctc gtgttgttcg gagcgcacac acacacaacc agatctcccc caaatccacc    960
cgtcggcacc tccgcttcaa ggtacgccgc tcgtcctccc ccccccccc tctctacctt    1020 ctctagatcg gcgttccggt ccatggttag ggcccggtag ttctacttct gttcatgttt    1080
gtgttagatc cgtgtttgtg ttagatccgt gctgctagcg ttcgtacacg gatgcgacct    1140
gtacgtcaga cacgtctga ttgctaactt gccagtgttt ctctttgggg aatcctggga    1200
tggctctagc cgttccgcag acgggatcga tttcatgatt tttttttgttt cgttgcatag    1260 ggtttggttt gcccttttcc tttatttcaa tatatgccgt gcacttgttt gtcgggtcat    1320
cttttcatgc ttttttttgt cttggttgtg atgatgtggt ctggttgggc ggtcgttcta    1380
gatcggagta gaattctgtt tcaaactacc tggtggattt attaattttg gatctgtatg    1440
tgtgtgccat acatattcat agttacgaat tgaagatgat ggatgaaat atcgatctag    1500 gataggtata catgttgatg cgggttttac tgatgcatat acagagatgc ttttttgttcg    1560 cttggttgtg atgatgtggt gtggttgggc ggtcgttcat tcgttctaga tcggagtaga    1620
atactgtttc aaactacctg gtgtatttat taattttgga actgtatgtg tgtgtcatac    1680
atcttcatag ttacgagttt aagatggatg gaaatatcga tctaggatag gtatacatgt    1740
tgatgtgggt tttactgatg catatacatg atggcatatg cagcatctat tcatatgctc    1800
taaccttgag tacctatcta ttataataaa caagtatgtt ttataattat ttgatcttg    1860 atatacttgg atgatggcat atgcagcagc tatatgtgga ttttttagc cctgccttca    1920 tacgctattt atttgcttgg tactgttttct tttgtcgatg ctcaccctgt tgtttggtgt    1980
tacttctgca g                                                        1991
```

<210> SEQ ID NO 42
<211> LENGTH: 4101
<212> TYPE: DNA
<213> ORGANISM: Artificial Sequence
<220> FEATURE:
<223> OTHER INFORMATION: synthesized - Cas 9 nucleic acid

<400> SEQUENCE: 42

```
gtcaccccca agctgtgaca aatctatccg agtttcatat aatcccgtga tggattggtg     60
aatcagtgtc gcgtctagca cctccttggt agaagtgtat cgtttgcgat ctatcgttgt    120
gtcaaaatac ttgaatgcgg ctggagcgcc gaggttggta agagtaaaca aatggataat    180
attttccgcc tgctcacgta tgggtttatc cctgtgcttg ttgtatgcgc ttaatacttt    240
gtccagattg gcatcagcta ggatgactct cttactgaat tccgaaattt gctctatgat    300
ttcgtcgaga taatgtttgt gctgctcaac aaaaagttgc ttctgttcgt tatcttcagg    360
tgaacctttc aacttctcgt aatgggacgc taaatacagg aaattcacgt atttagacgg    420
tagtgcgagt tcgttcccct tttgaagctc tccggcgcta gccaacatcc gttttcggcc    480
attttctaac tcaaacagac tatactttgg tagtttaatt atgagatcct ttttttacttc    540
```

```
cttgtaacct ttcgcctcaa ggaagtcgat ggggttcttt tcaaaagacg agcgctccat    600
aatcgttatc cccaataatt ctttgactga cttcagtttc ttggatttc ccttctcaac    660 ttttgccact actaggacag aataggcaac tgtagggcta tcgaagccac cgtactttt    720 cgggtcccag tccttttac gagcgatgag cttatcacta ttccttttg gaagaatcga    780 ttcctttgaa aaccctccgg tctgcacctc agttttcttt actatgttga cttggggcat    840
ggacaaaact tttctcaccg tcgcgaagtc ccggcccta tcccatacga tttcacctgt    900
ctccccattg gtttcaatta aaggtcgttt gcgtatctct ccgtttgcca gagtgatttc    960
cgtcttaaag aaattcataa tgttagaata aagaagtat ttggctgtag ccttgcctat   1020
ctcctgttcg cttttcgcga tcatcttacg gacgtcataa actttgtaat caccatacac   1080
aaactcactt tctagcttcg ggtatttctt aatgagtgcg gtccctacga cggcattaag   1140
ataagcgtcg tgcgcatggt ggtagttatt tatctcccta actttataga attgaaaatc   1200
ctttctgaag tccgacacca attttgactt taaagtgatt actttgactt cccgaatcag   1260
cttatcgttc tcgtcgtatt tcgtattcat tcgggaatct agtatctgtg caacatgctt   1320
tgtgatttgg cgggttttcca cgagctgacg tttaataaat ccggccttgt caagttcaga   1380
caagccaccc ctctcagctt tagttaagtt atcgaacttt ctttgcgtta tcagtttcgc   1440
atttaggagc tgccgccaat agttcttcat tttctttacg acttcctcgc ttggaacatt   1500 gtcactttc cctcggttct tatccgagcg tgtaagcact ttattgtcga ttgaatcgtc   1560
cttcaaaaag gattgggta caatgtgatc gacgtcgtaa tcagataaac ggtttatgtc   1620
cagttcctga tcaacataca tgtcccttcc attttgtagg taatagaggt aaagtttctc   1680
gttctgcaat tgggtatttt ccacaggatg ctccttaag atctggctgc ccagttcttt   1740 aatacctct tctattctct tcatccgctc tcgactgttt ttttgcccct tctgagtcgt   1800
ttgattttcg cgtgccatct cgattacaat gttttccggt ttgtgacgtc ccatgacctt   1860
aactagctca tccactactt tgactgtctg gagtatgccc tttttgatgg ctggcgaacc   1920
agcaagattc gcaatatgtt cgtgcaatga gtccccttgt ccggaaacct gtgccttttg   1980
tatatcctct ttgaaggtta aagagtcatc atggatcagc tgcataaagt tcctattggc   2040
gaagccgtcg ctctttagaa aatcgagaat agttttacca ctttgcttgt ctcttatccc   2100
gttgataagt ttccgcgaca atcgtcccca gcccgtatag cgacgcctct ttaactgttt   2160 cataaccta tcgtcgaaca ggtgagcgta tgtttttagt cttctcctcaa tcatttcccg   2220 atcttcaaag agggtaagag tcaacactat atccttctaag atatcttcat tctcttcgtt   2280
atccaggaag tccttatctt taattatctt taggaggtca tgatacgtac caagtgacgc   2340
attaaatcga tcttctaccc cggagatctc gacagaatcg aagcattcaa tttttcttaaa   2400 gtagtcctct ttcaattgct taactgtcac tttgcggttg gtcttgaata acagatctac   2460
tattgctttc ttctgttctc cgcttagaaa ggcgggttta cgcatgccct cagtgacata   2520
cttaactttc gtgagttcat tgtacactgt gaaatactcg taaagtaaac tgtgcttagg   2580
caatactttt tcgttcggta aattcttgtc aaagttggtc atcctctcga tgaacgattg   2640
agctgacgca cctttatcga caacttcctc aaaattccat ggagtaatcg tttcttcgga   2700
ctttcttgtc atccatgcga accgagagtt ccctcgggcc aggggtccca catagtaagg   2760
tatgcgaaag gttaggattt tctcaatctt ttcacgattg tctttgagga acggataaaa   2820
atcctcctgc cttctaagta tagcatgcaa ttcgcctaag tggatttgat gtggaatgct   2880
```

```
accgttgtcg aaagtccgct gctttcgcag tagatcttcg cgattgagtt ttacaagcaa   2940
ctcttccgtc ccatccatct tctctaatat gggtttgata aacttgtaga attcctcttg   3000
actcgctccg ccgtcaatat aacctgcgta cccgttttc gactgatcaa agaatatttc   3060
cttatatttc tcaggcagtt gctgacggac tagggccttg agaagtgtca agtcttggtg   3120
atgttcatcg taccttttga tcattgaagc ggataacggc gccttggtaa tctcagtatt   3180
aactctcagt atgtcagata ggaggattgc atcgctaagg ttttggcag ccaaaaataa    3240 gtccgcatac tgatctccaa tttgtgccag tagattgtcg agatcgtcat cgtacgtgtc   3300
cttactaagc tgcaatttgg catcttcagc taagtcgaag ttcgacttaa aatttggtgt   3360
caggcctagt gagagcgcta aaggttacc gaacaaccca tttttcttct ctccgggtaa    3420
ttgtgcgatc aggttttcta gccgtcggga tttagagagg cgggcgctaa gaatagcctt   3480
cgcatccacg ccacttgcat ttatagggtt ctcttcaaac aactgattat aggtttgtac   3540
taactggatg aacagtttgt cgacatccga gttgtccgga tttagatcac cctcaatgag   3600
aaagtgccca cggaacttta tcatatgggc aagagccaag tagattaacc tcaggtccgc   3660
tttatcagtt gagtcaacta gcttttttct gaggtgataa atcgttgggt acttttcatg   3720
atatgccacc tcatctacta tgtttccaaa gatggggtgc cgttcatgtt tcttgtcctc   3780
ttcgacaagg aaggactctt ccaaacggtg aaagaaagaa tcgtcaactt tggccatctc   3840
attgctaaaa atttcttgta agtaacatat tcggttcttg cgacgtgtat accttctccg   3900
agcggttcgt ttcaggcgag tcgcctctgc cgtttcgcca ctatcgaata ggagggcacc   3960
gataagattc ttttaatcg aatgacggtc tgtgttcccc aacaccttaa atttctttga    4020
aggtactttg tattcatcgg ttatgacagc ccatccaacg gaattagtgc cgatggctaa   4080
accaatagaa tactttttat c                                             4101
```

<210> SEQ ID NO 43
<211> LENGTH: 561
<212> TYPE: DNA
<213> ORGANISM: Artificial Sequence
<220> FEATURE:
<223> OTHER INFORMATION: synthesized - Cys 4 endoribonuclease nucleic
      acid sequence

<400> SEQUENCE: 43

```
atggaccact acctcgacat caggctcagg ccagacccag agttcccacc agcccagctc     60
atgtccgtcc tcttcggcaa gctccaccag gccctcgtgg cccagggcgg cgacaggatc   120
ggcgtgtcct tcccagacct cgacgagtcc aggtccaggc tcggcgagag gctccgcatc   180
cacgcctccg ccgacgacct cagggccctc ctcgccaggc cgtggctgga gggcctcagg   240
gaccacctcc agttcggcga gccagccgtg gtgccacacc caaccccata caggcaagtg   300
tccagggtgc aagccaagtc caacccagag aggctcagga ggaggctcat gaggaggcac   360
gacctctccg aggaagaggc caggaagcgc atccagaca ccgtggccag ggccctcgac    420
ctcccattcg tgaccctcag gtcccagtcc accggccagc acttccgcct cttcatcagg   480
cacggcccac tccaggtgac cgccgaggag ggcggcttta cctgctacgg cctctccaag   540
ggcggcttcg tgccgtggtt c                                             561
```

<210> SEQ ID NO 44
<211> LENGTH: 405
<212> TYPE: PRT
<213> ORGANISM: Triticum aestivum

```
<400> SEQUENCE: 44

Met Ala Met Pro Tyr Ala Ser Leu Ser Pro Ala Gly Asp Arg Arg Ser
1               5                   10                  15

Ser Pro Ala Ala Thr Ala Ser Leu Leu Pro Phe Cys Arg Ser Ser Pro
            20                  25                  30

Phe Ser Ala Gly Asn Gly Gly Met Gly Glu Ala Arg Met Ala Gly
        35                  40                  45

Arg Trp Met Ala Arg Pro Ala Pro Phe Thr Ala Ala Gln Tyr Glu Glu
    50                  55                  60

Leu Glu His Gln Ala Leu Ile Tyr Lys Tyr Leu Val Ala Gly Val Pro
65                  70                  75                  80

Val Pro Pro Asp Leu Val Leu Pro Ile Arg Arg Gly Ile Glu Thr Leu
                85                  90                  95

Ala Ala Arg Phe Tyr His Asn Pro Leu Ala Ile Gly Tyr Gly Ser Tyr
            100                 105                 110

Leu Gly Lys Lys Val Asp Pro Glu Pro Gly Arg Cys Arg Arg Thr Asp
        115                 120                 125

Gly Lys Lys Trp Arg Cys Ala Lys Glu Ala Ser Asp Ser Lys Tyr
    130                 135                 140

Cys Glu Arg His Met His Arg Gly Arg Asn Arg Ser Arg Lys Pro Val
145                 150                 155                 160

Glu Thr Gln Leu Val Ser His Ser Gln Pro Ala Ala Ser Val Val
                165                 170                 175

Pro Leu Ala Thr Gly Phe His Asn His Ser Leu Tyr Pro Ala Ile Gly
            180                 185                 190

Gly Thr Asn Gly Gly Gly Gly Gly Asn Asn Gly Met Pro Asn Thr
        195                 200                 205

Phe Ser Ser Ala Leu Gly Pro Pro Gln Gln His Met Gly Asn Asn Ala
210                 215                 220

Ser Ser Pro Tyr Ala Ala Leu Gly Gly Ala Gly Thr Cys Lys Asp Phe
225                 230                 235                 240

Arg Tyr Thr Ala Tyr Gly Ile Arg Ser Leu Ala Asp Glu His Ser Gln
            245                 250                 255

Leu Met Thr Glu Ala Met Asn Thr Ser Val Glu Asn Pro Trp Arg Leu
        260                 265                 270

Pro Pro Ser Ser Gln Thr Thr Thr Phe Pro Leu Ser Ser Tyr Ala Pro
    275                 280                 285

Gln Leu Gly Ala Thr Ser Asp Leu Gly Gln Asn Asn Asn Ser Ser Ser
290                 295                 300

Ser Asn Ser Ala Val Lys Ser Glu Arg Gln Gln Gln Gln Pro Leu
305                 310                 315                 320

Ser Phe Pro Gly Cys Gly Asp Phe Gly Gly Gly Ala Met Asp Ser
            325                 330                 335

Ala Lys Gln Glu Asn Gln Thr Leu Arg Pro Phe Phe Asp Glu Trp Pro
        340                 345                 350

Lys Thr Arg Asp Ser Trp Ser Asp Leu Thr Asp Asp Asn Ser Ser Leu
    355                 360                 365

Ala Ser Phe Ser Ala Thr Gln Leu Ser Ile Ser Ile Pro Met Thr Ser
370                 375                 380

Ser Asp Phe Ser Ala Ala Ser Ser Gln Ser Pro Asn Gly Met Leu Phe
385                 390                 395                 400

Ala Gly Glu Met Tyr
            405
```

<210> SEQ ID NO 45
<211> LENGTH: 22
<212> TYPE: DNA
<213> ORGANISM: Artificial Sequence
<220> FEATURE:
<223> OTHER INFORMATION: synthesized - mR396 binding site

<400> SEQUENCE: 45
ccgttcaaga aagcctgtgg aa                                          22

<210> SEQ ID NO 46
<211> LENGTH: 83
<212> TYPE: DNA
<213> ORGANISM: Artificial Sequence
<220> FEATURE:
<223> OTHER INFORMATION: synthesized - tracrRNA

<400> SEQUENCE: 46
gttttagagc tagaaatagc aagttaaaat aaggctagtc cgttatcaac ttgaaaaagt    60
ggcaccgagt cggtgctttt ttt                                           83

<210> SEQ ID NO 47
<211> LENGTH: 103
<212> TYPE: DNA
<213> ORGANISM: Artificial Sequence
<220> FEATURE:
<223> OTHER INFORMATION: synthesized - a repair template sequence for
      introduction of the correct SNP

<400> SEQUENCE: 47
ccgcgccgga ttccaagtac tgcgagcgcc acatgcaccg cggccgcaac cgtaaaagaa    60
agcctgtgga aacgcagctg gtcgcccagt cccaaccgcc ctc                    103

<210> SEQ ID NO 48
<211> LENGTH: 397
<212> TYPE: DNA
<213> ORGANISM: Artificial Sequence
<220> FEATURE:
<223> OTHER INFORMATION: synthesized - donor DNA sequence for
      introduction of the correct SNP

<400> SEQUENCE: 48
gaaatggcgg tgctcgaagg aggacggttg ctacgatgtg cctgtttttg tacagttgga    60
tatggtccgt acttcggcaa gaagctggac ccagagccag gcggtgccg gcgtacggac    120 ggcaagaaat ggcggtgctc gaaggaagcc gcgccggatt ccaagtactg cgagcgccac   180
atgcaccgcg gccgcaaccg taaaagaaag cctgtggaaa cgcagctggt cgcccagtcc   240
caaccgccct catctgttgt cggttctgcg gcagcgcccc ttgctgctgc ctccaatggc   300
agcagcttcc aaaaccactc tctttaccct gctattgccg gcagcaatgg cggggcggg    360 gggaggaaca tgccatctgt tgtcggttct gcggcgg                           397

<210> SEQ ID NO 49
<211> LENGTH: 23
<212> TYPE: DNA
<213> ORGANISM: Artificial Sequence
<220> FEATURE:
<223> OTHER INFORMATION: synthesized - target 1 target sequence

<400> SEQUENCE: 49
gaaatggcgg tgctcgaagg agg                                          23

```
<210> SEQ ID NO 50
<211> LENGTH: 20
<212> TYPE: DNA
<213> ORGANISM: Artificial Sequence
<220> FEATURE:
<223> OTHER INFORMATION: synthesized - target 1 protospacer sequence

<400> SEQUENCE: 50
gaaatggcgg tgctcgaagg                                              20

<210> SEQ ID NO 51
<211> LENGTH: 103
<212> TYPE: DNA
<213> ORGANISM: Artificial Sequence
<220> FEATURE:
<223> OTHER INFORMATION: synthesized - target 1 complete sgRNA nucleic
      acid sequence

<400> SEQUENCE: 51
gaaatggcgg tgctcgaagg gttttagagc tagaaatagc aagttaaaat aaggctagtc    60
cgttatcaac ttgaaaaagt ggcaccgagt cggtgctttt ttt                     103

<210> SEQ ID NO 52
<211> LENGTH: 23
<212> TYPE: DNA
<213> ORGANISM: Artificial Sequence
<220> FEATURE:
<223> OTHER INFORMATION: synthesized - target 2 target sequence

<400> SEQUENCE: 52
atctgttgtc ggttctgcgg cgg                                           23

<210> SEQ ID NO 53
<211> LENGTH: 20
<212> TYPE: DNA
<213> ORGANISM: Artificial Sequence
<220> FEATURE:
<223> OTHER INFORMATION: synthesized - target 2 protospacer sequence

<400> SEQUENCE: 53
atctgttgtc ggttctgcgg                                               20

<210> SEQ ID NO 54
<211> LENGTH: 103
<212> TYPE: DNA
<213> ORGANISM: Artificial Sequence
<220> FEATURE:
<223> OTHER INFORMATION: synthesized - target 2 complete sgRNA nucleic
      acid sequence

<400> SEQUENCE: 54
atctgttgtc ggttctgcgg gttttagagc tagaaatagc aagttaaaat aaggctagtc    60
cgttatcaac ttgaaaaagt ggcaccgagt cggtgctttt ttt                     103

<210> SEQ ID NO 55
<211> LENGTH: 194
<212> TYPE: DNA
<213> ORGANISM: Artificial Sequence
<220> FEATURE:
<223> OTHER INFORMATION: synthesized - a repair template sequence for
      introduction of the correct SNP

<400> SEQUENCE: 55
ctaagtttag tttcaaactt ttccttcaaa catacagctt ttttatcaca ttaaaacttt    60
```

```
cctacataca aactttcaac ttttccatca catcttttaa tttcaaccaa acttctaatt    120
ttaacgtgaa ctaaaaacac cctgaattca aaactctttt tattttcctt caagatgtcc    180
gatgcacacg ctct                                                      194

<210> SEQ ID NO 56
<211> LENGTH: 486
<212> TYPE: DNA
<213> ORGANISM: Artificial Sequence
<220> FEATURE:
<223> OTHER INFORMATION: synthesized - donor DNA sequence for
      introduction of the correct SNP

<400> SEQUENCE: 56
atctctatgg agtagtaccg aggccatgga taaaatgtaa tttctatgca tacaactaaa     60
ttatcgatgg caacagtgca tgagcatata tttatttcat tgacctacgg ttgcatgtct    120
tcgatctcta tggagtagta ccgattctaa gtttagtttc aaacttttcc ttcaaacata    180 cagcttttt atcacattaa aactttccta catacaaact ttcaacttttt ccatcacatc    240 ttttaatttc aaccaaactt ctaattttaa cgtgaactaa aaacaccctg aattcaaaac    300 tcttttatt ttccttcaag atgtccgatg cacacgctct atgtagacgc aagaagatgt    360
taaagcagca gactaacagt agcaaaaaaa tggcaggtcg aaaagcaact gcgacggttg    420
ctccgtcatc ctctcatcgc cttttattg ctccggcgtt gggatgtaga cgcaagaaga    480
tgttgg                                                              486

<210> SEQ ID NO 57
<211> LENGTH: 23
<212> TYPE: DNA
<213> ORGANISM: Artificial Sequence
<220> FEATURE:
<223> OTHER INFORMATION: synthesized - target 1 target sequence

<400> SEQUENCE: 57
atctctatgg agtagtaccg agg                                             23

<210> SEQ ID NO 58
<211> LENGTH: 20
<212> TYPE: DNA
<213> ORGANISM: Artificial Sequence
<220> FEATURE:
<223> OTHER INFORMATION: synthesized - target 1 protospacer sequence

<400> SEQUENCE: 58
atctctatgg agtagtaccg                                                 20

<210> SEQ ID NO 59
<211> LENGTH: 103
<212> TYPE: DNA
<213> ORGANISM: Artificial Sequence
<220> FEATURE:
<223> OTHER INFORMATION: synthesized - target 1 complete sgRNA nucleic
      acid sequence

<400> SEQUENCE: 59
atctctatgg agtagtaccg gttttagagc tagaaatagc aagttaaaat aaggctagtc     60
cgttatcaac ttgaaaaagt ggcaccgagt cggtgctttt ttt                      103

<210> SEQ ID NO 60
<211> LENGTH: 23
<212> TYPE: DNA
<213> ORGANISM: Artificial Sequence
```

```
<220> FEATURE:
<223> OTHER INFORMATION: synthesized - target 2 target sequence

<400> SEQUENCE: 60
atgtagacgc aagaagatgt tgg                                            23

<210> SEQ ID NO 61
<211> LENGTH: 20
<212> TYPE: DNA
<213> ORGANISM: Artificial Sequence
<220> FEATURE:
<223> OTHER INFORMATION: synthesized - target 2 protospacer sequence

<400> SEQUENCE: 61
atgtagacgc aagaagatgt                                                20

<210> SEQ ID NO 62
<211> LENGTH: 103
<212> TYPE: DNA
<213> ORGANISM: Artificial Sequence
<220> FEATURE:
<223> OTHER INFORMATION: synthesized - target 2 complete sgRNA nucleic
      acid sequence

<400> SEQUENCE: 62
atgtagacgc aagaagatgt gttttagagc tagaaatagc aagttaaaat aaggctagtc    60
cgttatcaac ttgaaaaagt ggcaccgagt cggtgctttt ttt                      103

<210> SEQ ID NO 63
<211> LENGTH: 194
<212> TYPE: DNA
<213> ORGANISM: Artificial Sequence
<220> FEATURE:
<223> OTHER INFORMATION: synthesized - a repair template sequence for
      introduction of the correct SNP

<400> SEQUENCE: 63
ctaagtttag tttcaaactt ttccttcaaa cttacagctt ttttatcaca ttaaaacttt    60
cctacatata aactttcaac ttttccatca catcttttaa tttcaaccaa acttctaatt    120
ttaacgtgaa ctaaaaacac cctgaattca aaactctttt tattttcctt caagatgtcc   180
gatgcacacg ctct                                                     194

<210> SEQ ID NO 64
<211> LENGTH: 486
<212> TYPE: DNA
<213> ORGANISM: Artificial Sequence
<220> FEATURE:
<223> OTHER INFORMATION: synthesized - donor DNA sequence for
      introduction of the correct SNP

<400> SEQUENCE: 64
atctctatgg agtagtaccg aggccatgga taaaatgtaa tttctatgca tacaactaaa    60
ttatcgatgg caacagtgca tgagcatata tttatttcat tgacctacgg ttgcatgtct   120
tcgatctcta tggagtagta ccgattctaa gtttagtttc aaactttcc ttcaaactta    180 cagctttttt atcacattaa aactttccta catataaact ttcaactttt ccatcacatc   240
ttttaatttc aaccaaactt ctaattttaa cgtgaactaa aaacaccctg aattcaaaac   300 tcttttatt ttccttcaag atgtccgatg cacacgctct atgtagacgc aagaagatgt   360
taaagcagca gactaacagt agcaaaaaaa tggcaggtcg aaaagcaact gcgacggttg   420
ctccgtcatc ctctcatcgc ctttttattg ctccggcgtt gggatgtaga cgcaagaaga   480
```

```
tgttgg                                                             486

<210> SEQ ID NO 65
<211> LENGTH: 23
<212> TYPE: DNA
<213> ORGANISM: Artificial Sequence
<220> FEATURE:
<223> OTHER INFORMATION: synthesized - target 1 target sequence

<400> SEQUENCE: 65
atctctatgg agtagtaccg agg                                           23

<210> SEQ ID NO 66
<211> LENGTH: 20
<212> TYPE: DNA
<213> ORGANISM: Artificial Sequence
<220> FEATURE:
<223> OTHER INFORMATION: synthesized - target 1 protospacer sequence

<400> SEQUENCE: 66
atctctatgg agtagtaccg                                               20

<210> SEQ ID NO 67
<211> LENGTH: 103
<212> TYPE: DNA
<213> ORGANISM: Artificial Sequence
<220> FEATURE:
<223> OTHER INFORMATION: synthesized - target 1 complete sgRNA nucleic
      acid sequence

<400> SEQUENCE: 67
atctctatgg agtagtaccg gttttagagc tagaaatagc aagttaaaat aaggctagtc    60
cgttatcaac ttgaaaaagt ggcaccgagt cggtgctttt ttt                     103

<210> SEQ ID NO 68
<211> LENGTH: 23
<212> TYPE: DNA
<213> ORGANISM: Artificial Sequence
<220> FEATURE:
<223> OTHER INFORMATION: synthesized - target 2 target sequence

<400> SEQUENCE: 68
atgtagacgc aagaagatgt tgg                                           23

<210> SEQ ID NO 69
<211> LENGTH: 20
<212> TYPE: DNA
<213> ORGANISM: Artificial Sequence
<220> FEATURE:
<223> OTHER INFORMATION: synthesized - target 2 protospacer sequence

<400> SEQUENCE: 69
atgtagacgc aagaagatgt                                               20

<210> SEQ ID NO 70
<211> LENGTH: 103
<212> TYPE: DNA
<213> ORGANISM: Artificial Sequence
<220> FEATURE:
<223> OTHER INFORMATION: synthesized - target 2 complete sgRNA nucleic
      acid sequence

<400> SEQUENCE: 70
atgtagacgc aagaagatgt gttttagagc tagaaatagc aagttaaaat aaggctagtc    60
```
cgttatcaac ttgaaaaagt ggcaccgagt cggtgctttt ttt        103

<210> SEQ ID NO 71
<211> LENGTH: 194
<212> TYPE: DNA
<213> ORGANISM: Artificial Sequence
<220> FEATURE:
<223> OTHER INFORMATION: synthesized - a repair template sequence for
      introduction of the correct SNP

<400> SEQUENCE: 71
ctaagtttag tttcaaactt ttccttcaaa cttacagctt ttttatcaca ttaaaacttt        60
cctacataca aactttcaac ttttccatca catcttttaa tttcaaccaa acttttaatt       120
ttaacgtgaa ctaaaaacac cctgaattca aaactctttt tattttcctt caagatgtcc      180
gatgcacacg ctct        194

<210> SEQ ID NO 72
<211> LENGTH: 486
<212> TYPE: DNA
<213> ORGANISM: Artificial Sequence
<220> FEATURE:
<223> OTHER INFORMATION: synthesized - donor DNA sequence for
      introduction of the correct SNP

<400> SEQUENCE: 72
atctctatgg agtagtaccg aggccatgga taaaatgtaa tttctatgca tacaactaaa        60
ttatcgatgg caacagtgca tgagcatata tttatttcat tgacctacgg ttgcatgtct      120
tcgatctcta tggagtagta ccgattctaa gtttagtttc aaacttttcc ttcaaactta      180 cagcttttt atcacattaa aactttccta catacaaact ttcaacttttt ccatcacatc      240 ttttaatttc aaccaaactt ttaattttaa cgtgaactaa aaacaccctg aattcaaaac      300 tcttttatt ttccttcaag atgtccgatg cacacgctct atgtagacgc aagaagatgt      360
taaagcagca gactaacagt agcaaaaaaa tggcaggtcg aaaagcaact gcgacggttg      420
ctccgtcatc ctctcatcgc cttttattg ctccggcgtt gggatgtaga cgcaagaaga      480
tgttgg        486

<210> SEQ ID NO 73
<211> LENGTH: 23
<212> TYPE: DNA
<213> ORGANISM: Artificial Sequence
<220> FEATURE:
<223> OTHER INFORMATION: synthesized - target 1 target sequence

<400> SEQUENCE: 73
atctctatgg agtagtaccg agg        23

<210> SEQ ID NO 74
<211> LENGTH: 20
<212> TYPE: DNA
<213> ORGANISM: Artificial Sequence
<220> FEATURE:
<223> OTHER INFORMATION: synthesized - target 1 protospacer sequence

<400> SEQUENCE: 74
atctctatgg agtagtaccg        20

<210> SEQ ID NO 75
<211> LENGTH: 103
<212> TYPE: DNA
<213> ORGANISM: Artificial Sequence

```
<220> FEATURE:
<223> OTHER INFORMATION: synthesized - target 1 complete sgRNA nucleic
      acid sequence

<400> SEQUENCE: 75
atctctatgg agtagtaccg gttttagagc tagaaatagc aagttaaaat aaggctagtc        60
cgttatcaac ttgaaaaagt ggcaccgagt cggtgctttt ttt                         103

<210> SEQ ID NO 76
<211> LENGTH: 23
<212> TYPE: DNA
<213> ORGANISM: Artificial Sequence
<220> FEATURE:
<223> OTHER INFORMATION: synthesized - target 2 target sequence

<400> SEQUENCE: 76
atgtagacgc aagaagatgt tgg                                                23

<210> SEQ ID NO 77
<211> LENGTH: 20
<212> TYPE: DNA
<213> ORGANISM: Artificial Sequence
<220> FEATURE:
<223> OTHER INFORMATION: synthesized - target 2 protospacer sequence

<400> SEQUENCE: 77
atgtagacgc aagaagatgt                                                    20

<210> SEQ ID NO 78
<211> LENGTH: 103
<212> TYPE: DNA
<213> ORGANISM: Artificial Sequence
<220> FEATURE:
<223> OTHER INFORMATION: synthesized - target 2 complete sgRNA nucleic
      acid sequence

<400> SEQUENCE: 78
atgtagacgc aagaagatgt gttttagagc tagaaatagc aagttaaaat aaggctagtc        60
cgttatcaac ttgaaaaagt ggcaccgagt cggtgctttt ttt                         103

<210> SEQ ID NO 79
<211> LENGTH: 194
<212> TYPE: DNA
<213> ORGANISM: Artificial Sequence
<220> FEATURE:
<223> OTHER INFORMATION: synthesized - a repair template sequence for
      introduction of the correct SNP

<400> SEQUENCE: 79
ctaagtttag tttcaaactt ttccttcaaa catacagctt ttttatcaca ttaaaacttt        60
cctacatata aactttcaac ttttccatca catcttttaa tttcaaccaa acttctaatt      120
ttaacgtgaa ctaaaaacac cctgaattca aaactctttt tatttccctt caagatgtcc      180
gatgcacacg ctct                                                        194

<210> SEQ ID NO 80
<211> LENGTH: 486
<212> TYPE: DNA
<213> ORGANISM: Artificial Sequence
<220> FEATURE:
<223> OTHER INFORMATION: synthesized - donor DNA sequence for
      introduction of the correct SNP

<400> SEQUENCE: 80
```

```
atctctatgg agtagtaccg aggccatgga taaaatgtaa tttctatgca tacaactaaa      60
ttatcgatgg caacagtgca tgagcatata tttatttcat tgacctacgg ttgcatgtct     120
tcgatctcta tggagtagta ccgattctaa gtttagtttc aaacttttcc ttcaaacata     180
cagctttttt atcacattaa aactttccta catataaact ttcaacttt ccatcacatc      240 ttttaatttc aaccaaactt ctaattttaa cgtgaactaa aaacaccctg aattcaaaac     300
tcttttattt ttccttcaag atgtccgatg cacacgctct atgtagacgc aagaagatgt     360
taaagcagca gactaacagt agcaaaaaaa tggcaggtcg aaaagcaact gcgacggttg     420
ctccgtcatc ctctcatcgc cttttattg ctccggcgtt gggatgtaga cgcaagaaga     480
tgttgg                                                                486
```

<210> SEQ ID NO 81
<211> LENGTH: 23
<212> TYPE: DNA
<213> ORGANISM: Artificial Sequence
<220> FEATURE:
<223> OTHER INFORMATION: synthesized - target 1 target sequence

<400> SEQUENCE: 81

```
atctctatgg agtagtaccg agg                                              23
```

<210> SEQ ID NO 82
<211> LENGTH: 20
<212> TYPE: DNA
<213> ORGANISM: Artificial Sequence
<220> FEATURE:
<223> OTHER INFORMATION: synthesized - target 1 protospacer sequence

<400> SEQUENCE: 82

```
atctctatgg agtagtaccg                                                  20
```

<210> SEQ ID NO 83
<211> LENGTH: 103
<212> TYPE: DNA
<213> ORGANISM: Artificial Sequence
<220> FEATURE:
<223> OTHER INFORMATION: synthesized - target 1 complete sgRNA nucleic
      acid sequence

<400> SEQUENCE: 83

```
atctctatgg agtagtaccg gttttagagc tagaaatagc aagttaaaat aaggctagtc      60
cgttatcaac ttgaaaaagt ggcaccgagt cggtgctttt ttt                       103
```

<210> SEQ ID NO 84
<211> LENGTH: 103
<212> TYPE: DNA
<213> ORGANISM: Artificial Sequence
<220> FEATURE:
<223> OTHER INFORMATION: synthesized - target 1 complete sgRNA nucleic
      acid sequence

<400> SEQUENCE: 84

```
atctctatgg agtagtaccg gttttagagc tagaaatagc aagttaaaat aaggctagtc      60
cgttatcaac ttgaaaaagt ggcaccgagt cggtgctttt ttt                       103
```

<210> SEQ ID NO 85
<211> LENGTH: 23
<212> TYPE: DNA
<213> ORGANISM: Artificial Sequence
<220> FEATURE:
<223> OTHER INFORMATION: synthesized - target 2 target sequence

<400> SEQUENCE: 85
atgtagacgc aagaagatgt tgg                                             23

<210> SEQ ID NO 86
<211> LENGTH: 20
<212> TYPE: DNA
<213> ORGANISM: Artificial Sequence
<220> FEATURE:
<223> OTHER INFORMATION: synthesized - target 2 protospacer sequence

<400> SEQUENCE: 86
atgtagacgc aagaagatgt                                                 20

<210> SEQ ID NO 87
<211> LENGTH: 103
<212> TYPE: DNA
<213> ORGANISM: Artificial Sequence
<220> FEATURE:
<223> OTHER INFORMATION: synthesized - target 2 complete sgRNA nucleic
       acid sequence

<400> SEQUENCE: 87
atgtagacgc aagaagatgt gttttagagc tagaaatagc aagttaaaat aaggctagtc     60
cgttatcaac ttgaaaaagt ggcaccgagt cggtgctttt ttt                      103

<210> SEQ ID NO 88
<211> LENGTH: 194
<212> TYPE: DNA
<213> ORGANISM: Artificial Sequence
<220> FEATURE:
<223> OTHER INFORMATION: synthesized - a repair template sequence for
       introduction of the correct SNP

<400> SEQUENCE: 88
ctaagtttag tttcaaactt ttccttcaaa catacagctt ttttatcaca ttaaaacttt     60
cctacataca aactttcaac ttttccatca catcttttaa tttcaaccaa acttttaatt   120
ttaacgtgaa ctaaaaacac cctgaattca aaactctttt tatttteett caagatgtcc   180 gatgcacacg ctct                                                     194

<210> SEQ ID NO 89
<211> LENGTH: 486
<212> TYPE: DNA
<213> ORGANISM: Artificial Sequence
<220> FEATURE:
<223> OTHER INFORMATION: synthesized - donor DNA sequence for
       introduction of the correct SNP

<400> SEQUENCE: 89
atctctatgg agtagtaccg aggccatgga taaaatgtaa tttctatgca tacaactaaa     60
ttatcgatgg caacagtgca tgagcatata tttatttcat tgacctacgg ttgcatgtct   120
tcgatctcta tggagtagta ccgattctaa gtttagtttc aaacttttcc ttcaaacata   180
cagctttttt atcacattaa aactttccta catacaaact ttcaactttt ccatcacatc   240
ttttaatttc aaccaaactt ttaattttaa cgtgaactaa aaacacctg aattcaaaac    300 tcttttatt ttccttcaag atgtccgatg cacacgctct atgtagacgc aagaagatgt    360
taaagcagca gactaacagt agcaaaaaaa tggcaggtcg aaaagcaact gcgacggttg   420
ctccgtcatc ctctcatcgc ctttttattg ctccggcgtt gggatgtaga cgcaagaaga   480
tgttgg                                                              486

<210> SEQ ID NO 90
<211> LENGTH: 23
<212> TYPE: DNA
<213> ORGANISM: Artificial Sequence
<220> FEATURE:
<223> OTHER INFORMATION: synthesized - target 1 target sequence

<400> SEQUENCE: 90
atctctatgg agtagtaccg agg                                            23

<210> SEQ ID NO 91
<211> LENGTH: 20
<212> TYPE: DNA
<213> ORGANISM: Artificial Sequence
<220> FEATURE:
<223> OTHER INFORMATION: synthesized - target 1 protospacer sequence

<400> SEQUENCE: 91
atctctatgg agtagtaccg                                                20

<210> SEQ ID NO 92
<211> LENGTH: 103
<212> TYPE: DNA
<213> ORGANISM: Artificial Sequence
<220> FEATURE:
<223> OTHER INFORMATION: synthesized - target 1 complete sgRNA nucleic
      acid sequence

<400> SEQUENCE: 92
atctctatgg agtagtaccg gttttagagc tagaaatagc aagttaaaat aaggctagtc    60
cgttatcaac ttgaaaaagt ggcaccgagt cggtgctttt ttt                     103

<210> SEQ ID NO 93
<211> LENGTH: 23
<212> TYPE: DNA
<213> ORGANISM: Artificial Sequence
<220> FEATURE:
<223> OTHER INFORMATION: synthesized - target 2 target sequence

<400> SEQUENCE: 93
atgtagacgc aagaagatgt tgg                                            23

<210> SEQ ID NO 94
<211> LENGTH: 20
<212> TYPE: DNA
<213> ORGANISM: Artificial Sequence
<220> FEATURE:
<223> OTHER INFORMATION: synthesized - target 2 protospacer sequence

<400> SEQUENCE: 94
atgtagacgc aagaagatgt                                                20

<210> SEQ ID NO 95
<211> LENGTH: 103
<212> TYPE: DNA
<213> ORGANISM: Artificial Sequence
<220> FEATURE:
<223> OTHER INFORMATION: synthesized - target 2 complete sgRNA nucleic
      acid sequence

<400> SEQUENCE: 95
atgtagacgc aagaagatgt gttttagagc tagaaatagc aagttaaaat aaggctagtc    60
cgttatcaac ttgaaaaagt ggcaccgagt cggtgctttt ttt                     103

<210> SEQ ID NO 96
<211> LENGTH: 194
<212> TYPE: DNA
<213> ORGANISM: Artificial Sequence
<220> FEATURE:
<223> OTHER INFORMATION: synthesized - a repair template sequence for
      introduction of the correct SNP

<400> SEQUENCE: 96
ctaagtttag tttcaaactt ttccttcaaa catacagctt ttttatcaca ttaaaacttt    60
cctacatata aactttcaac ttttccatca catcttttaa tttcaaccaa actttaatt    120 ttaacgtgaa ctaaaaacac cctgaattca aaactctttt tatttccctt caagatgtcc   180
gatgcacacg ctct                                                     194

<210> SEQ ID NO 97
<211> LENGTH: 486
<212> TYPE: DNA
<213> ORGANISM: Artificial Sequence
<220> FEATURE:
<223> OTHER INFORMATION: synthesized - donor DNA sequence for
      introduction of the correct SNP

<400> SEQUENCE: 97
atctctatgg agtagtaccg aggccatgga taaaatgtaa tttctatgca tacaactaaa    60
ttatcgatgg caacagtgca tgagcatata tttatttcat tgacctacgg ttgcatgtct   120
tcgatctcta tggagtagta ccgattctaa gtttagtttc aaacttttcc ttcaaacata   180
cagctttttt atcacattaa aactttccta catataaact ttcaactttt ccatcacatc   240
ttttaatttc aaccaaactt taattttaa cgtgaactaa aaacaccctg aattcaaaac    300 tcttttatt ttccttcaag atgtccgatg cacacgctct atgtagacgc aagaagatgt    360
taaagcagca gactaacagt agcaaaaaaa tggcaggtcg aaaagcaact gcgacggttg   420
ctccgtcatc ctctcatcgc cttttattg ctccggcgtt gggatgtaga cgcaagaaga   480
tgttgg                                                              486

<210> SEQ ID NO 98
<211> LENGTH: 23
<212> TYPE: DNA
<213> ORGANISM: Artificial Sequence
<220> FEATURE:
<223> OTHER INFORMATION: synthesized - target 1 target sequence

<400> SEQUENCE: 98
atctctatgg agtagtaccg agg                                            23

<210> SEQ ID NO 99
<211> LENGTH: 20
<212> TYPE: DNA
<213> ORGANISM: Artificial Sequence
<220> FEATURE:
<223> OTHER INFORMATION: synthesized - target 1 protospacer sequence

<400> SEQUENCE: 99
atctctatgg agtagtaccg                                                20

<210> SEQ ID NO 100
<211> LENGTH: 103
<212> TYPE: DNA
<213> ORGANISM: Artificial Sequence
<220> FEATURE:
<223> OTHER INFORMATION: synthesized - target 1 complete sgRNA nucleic acid sequence

<400> SEQUENCE: 100
atctctatgg agtagtaccg gttttagagc tagaaatagc aagttaaaat aaggctagtc    60
cgttatcaac ttgaaaaagt ggcaccgagt cggtgctttt ttt    103

<210> SEQ ID NO 101
<211> LENGTH: 23
<212> TYPE: DNA
<213> ORGANISM: Artificial Sequence
<220> FEATURE:
<223> OTHER INFORMATION: synthesized - target 2 target sequence

<400> SEQUENCE: 101
atgtagacgc aagaagatgt tgg    23

<210> SEQ ID NO 102
<211> LENGTH: 20
<212> TYPE: DNA
<213> ORGANISM: Artificial Sequence
<220> FEATURE:
<223> OTHER INFORMATION: synthesized - target 2 protospacer sequence

<400> SEQUENCE: 102
atgtagacgc aagaagatgt    20

<210> SEQ ID NO 103
<211> LENGTH: 103
<212> TYPE: DNA
<213> ORGANISM: Artificial Sequence
<220> FEATURE:
<223> OTHER INFORMATION: synthesized - target 2 complete sgRNA nucleic
      acid sequence

<400> SEQUENCE: 103
atgtagacgc aagaagatgt gttttagagc tagaaatagc aagttaaaat aaggctagtc    60
cgttatcaac ttgaaaaagt ggcaccgagt cggtgctttt ttt    103

<210> SEQ ID NO 104
<211> LENGTH: 194
<212> TYPE: DNA
<213> ORGANISM: Artificial Sequence
<220> FEATURE:
<223> OTHER INFORMATION: synthesized - a repair template sequence for
      introduction of the correct SNP

<400> SEQUENCE: 104
ctaagtttag tttcaaactt ttccttcaaa cttacagctt ttttatcaca ttaaaacttt    60
cctacatata aactttcaac ttttccatca catcttttaa tttcaaccaa acttttaatt    120
ttaacgtgaa ctaaaaacac cctgaattca aaactctttt tattttcctt caagatgtcc    180
gatgcacacg ctct    194

<210> SEQ ID NO 105
<211> LENGTH: 486
<212> TYPE: DNA
<213> ORGANISM: Artificial Sequence
<220> FEATURE:
<223> OTHER INFORMATION: synthesized - donor DNA sequence for
      introduction of the correct SNP

<400> SEQUENCE: 105
atctctatgg agtagtaccg aggccatgga taaaatgtaa tttctatgca tacaactaaa    60

```
ttatcgatgg caacagtgca tgagcatata tttatttcat tgacctacgg ttgcatgtct    120
tcgatctcta tggagtagta ccgattctaa gtttagtttc aaacttttcc ttcaaactta    180 cagcttttt atcacattaa aactttccta catataaact ttcaactttt ccatcacatc     240
ttttaatttc aaccaaactt ttaattttaa cgtgaactaa aaacaccctg aattcaaaac    300 tcttttatt ttccttcaag atgtccgatg cacacgctct atgtagacgc aagaagatgt     360
taaagcagca gactaacagt agcaaaaaaa tggcaggtcg aaaagcaact gcgacggttg    420
ctccgtcatc ctctcatcgc cttttattg ctccggcgtt gggatgtaga cgcaagaaga    480
tgttgg                                                              486

<210> SEQ ID NO 106
<211> LENGTH: 23
<212> TYPE: DNA
<213> ORGANISM: Artificial Sequence
<220> FEATURE:
<223> OTHER INFORMATION: synthesized - target 1 target sequence

<400> SEQUENCE: 106
atctctatgg agtagtaccg agg                                            23

<210> SEQ ID NO 107
<211> LENGTH: 20
<212> TYPE: DNA
<213> ORGANISM: Artificial Sequence
<220> FEATURE:
<223> OTHER INFORMATION: synthesized - target 1 protospacer sequence

<400> SEQUENCE: 107
atctctatgg agtagtaccg                                                20

<210> SEQ ID NO 108
<211> LENGTH: 103
<212> TYPE: DNA
<213> ORGANISM: Artificial Sequence
<220> FEATURE:
<223> OTHER INFORMATION: synthesized - target 1 complete sgRNA nucleic
      acid sequence

<400> SEQUENCE: 108
atctctatgg agtagtaccg gttttagagc tagaaatagc aagttaaaat aaggctagtc    60
cgttatcaac ttgaaaaagt ggcaccgagt cggtgctttt ttt                     103

<210> SEQ ID NO 109
<211> LENGTH: 23
<212> TYPE: DNA
<213> ORGANISM: Artificial Sequence
<220> FEATURE:
<223> OTHER INFORMATION: synthesized - target 2 target sequence

<400> SEQUENCE: 109
atgtagacgc aagaagatgt tgg                                            23

<210> SEQ ID NO 110
<211> LENGTH: 20
<212> TYPE: DNA
<213> ORGANISM: Artificial Sequence
<220> FEATURE:
<223> OTHER INFORMATION: synthesized - target 2 protospacer sequence

<400> SEQUENCE: 110
atgtagacgc aagaagatgt                                                20
```

<210> SEQ ID NO 111
<211> LENGTH: 103
<212> TYPE: DNA
<213> ORGANISM: Artificial Sequence
<220> FEATURE:
<223> OTHER INFORMATION: synthesized - target 2 complete sgRNA nucleic
      acid sequence

<400> SEQUENCE: 111
atgtagacgc aagaagatgt gttttagagc tagaaatagc aagttaaaat aaggctagtc         60
cgttatcaac ttgaaaaagt ggcaccgagt cggtgctttt ttt                          103

<210> SEQ ID NO 112
<211> LENGTH: 128
<212> TYPE: DNA
<213> ORGANISM: Artificial Sequence
<220> FEATURE:
<223> OTHER INFORMATION: synthesized - a repair template sequence for
      introduction of the correct SNP

<400> SEQUENCE: 112
cggtgctcca aggaggccgc cccggactcc aagtactgcg agcgccacat gcaccgcggc         60
cgcaaccgta aaagaaagcc tgtggaaacg cagctcgcgc cccagtccca accgcccgcc        120
gccgcagc                                                                 128

<210> SEQ ID NO 113
<211> LENGTH: 420
<212> TYPE: DNA
<213> ORGANISM: Artificial Sequence
<220> FEATURE:
<223> OTHER INFORMATION: synthesized - donor DNA sequence for
      introduction of the correct SNP

<400> SEQUENCE: 113
ggcgaacgga cggcaagaag tggcgcggcc tcgactccct cgcaacccgc ttctacggcc         60
aacccacact cgggtacgga ccgtacctgg ggaggaaact ggatccggag cccggccggt        120
gccggcgaac ggacggcaag aagtgccggt gctccaagga ggccgcccg gactccaagt         180 actgcgagcg ccacatgcac cgcggccgca accgtaaaag aaagcctgtg gaaacgcagc        240
tcgcgcccca gtcccaaccg cccgccgccg cagccgtctc cgccgctccg ccctagcag         300 ccgccgccgc cgccaccacc aacggcagcg gcttccagaa ccactctctc tacccggcca        360
tcgccggcag cactggtggt ggaggaggag ttggcggcgt ctccgccgct ccgcccctgg        420

<210> SEQ ID NO 114
<211> LENGTH: 23
<212> TYPE: DNA
<213> ORGANISM: Artificial Sequence
<220> FEATURE:
<223> OTHER INFORMATION: synthesized - target 1 target sequence

<400> SEQUENCE: 114
ggcgaacgga cggcaagaag tgg                                                 23

<210> SEQ ID NO 115
<211> LENGTH: 20
<212> TYPE: DNA
<213> ORGANISM: Artificial Sequence
<220> FEATURE:
<223> OTHER INFORMATION: synthesized - target 1 protospacer sequence

<400> SEQUENCE: 115
ggcgaacgga cggcaagaag                                                  20

<210> SEQ ID NO 116
<211> LENGTH: 103
<212> TYPE: DNA
<213> ORGANISM: Artificial Sequence
<220> FEATURE:
<223> OTHER INFORMATION: synthesized - target 1 complete sgRNA nucleic
      acid sequence

<400> SEQUENCE: 116
ggcgaacgga cggcaagaag gttttagagc tagaaatagc aagttaaaat aaggctagtc      60
cgttatcaac ttgaaaaagt ggcaccgagt cggtgctttt ttt                       103

<210> SEQ ID NO 117
<211> LENGTH: 23
<212> TYPE: DNA
<213> ORGANISM: Artificial Sequence
<220> FEATURE:
<223> OTHER INFORMATION: synthesized - target 2 target sequence

<400> SEQUENCE: 117
cgtctccgcc gctccgcccc tgg                                              23

<210> SEQ ID NO 118
<211> LENGTH: 20
<212> TYPE: DNA
<213> ORGANISM: Artificial Sequence
<220> FEATURE:
<223> OTHER INFORMATION: synthesized - target 2 protospacer sequence

<400> SEQUENCE: 118
cgtctccgcc gctccgcccc                                                  20

<210> SEQ ID NO 119
<211> LENGTH: 103
<212> TYPE: DNA
<213> ORGANISM: Artificial Sequence
<220> FEATURE:
<223> OTHER INFORMATION: synthesized - target 2 complete sgRNA nucleic
      acid sequence

<400> SEQUENCE: 119
cgtctccgcc gctccgcccc gttttagagc tagaaatagc aagttaaaat aaggctagtc      60
cgttatcaac ttgaaaaagt ggcaccgagt cggtgctttt ttt                       103

<210> SEQ ID NO 120
<211> LENGTH: 116
<212> TYPE: DNA
<213> ORGANISM: Artificial Sequence
<220> FEATURE:
<223> OTHER INFORMATION: synthesized - a repair template sequence for
      introduction of the correct SNP

<400> SEQUENCE: 120
ccgccccgga ctccaagtac tgcgagcgcc acatgcaccg cggccgcaac cgtaaaagaa      60
agcctgtgga agcgcagctc gtgccccgc cgcacgccca gcagcagcag cagcag         116

<210> SEQ ID NO 121
<211> LENGTH: 420
<212> TYPE: DNA
<213> ORGANISM: Artificial Sequence
<220> FEATURE:
<223> OTHER INFORMATION: synthesized - donor DNA sequence for
      introduction of the correct SNP

<400> SEQUENCE: 121

```
aagtggcggt gctccaaggg aggtcctctc tcgcgtgtgt gtgtgtggct tccttgcagt      60
tgggtacggg ccctacttcg gcaagaaggt ggacccggag cccggcggt gccggcgtac      120
ggacggcaag aagtggcggt gctccaagga agccgccccg gactccaagt actgcgagcg     180
ccacatgcac cgcggccgca accgtaaaag aaagcctgtg gaagcgcagc tcgtgccccc     240
gccgcacgcc cagcagcagc agcagcagca ggccccgcg cccaccgcta gcttccagag      300
ccaccccatg tacccatcca tcctcgccgg caacggcggc ggcggcggcg gggtaggtgg     360
tggtgctggt ggcggtggca cgttcggcct ggggccccag gccccgcgc ccaccgctgg      420
```

<210> SEQ ID NO 122
<211> LENGTH: 23
<212> TYPE: DNA
<213> ORGANISM: Artificial Sequence
<220> FEATURE:
<223> OTHER INFORMATION: synthesized - target 1 target sequence

<400> SEQUENCE: 122

```
aagtggcggt gctccaaggg agg                                              23
```

<210> SEQ ID NO 123
<211> LENGTH: 20
<212> TYPE: DNA
<213> ORGANISM: Artificial Sequence
<220> FEATURE:
<223> OTHER INFORMATION: synthesized - target 1 protospacer sequence

<400> SEQUENCE: 123

```
aagtggcggt gctccaaggg                                                  20
```

<210> SEQ ID NO 124
<211> LENGTH: 103
<212> TYPE: DNA
<213> ORGANISM: Artificial Sequence
<220> FEATURE:
<223> OTHER INFORMATION: synthesized - target 1 complete sgRNA nucleic
      acid sequence

<400> SEQUENCE: 124

```
aagtggcggt gctccaaggg gttttagagc tagaaatagc aagttaaaat aaggctagtc      60
cgttatcaac ttgaaaaagt ggcaccgagt cggtgctttt ttt                        103
```

<210> SEQ ID NO 125
<211> LENGTH: 23
<212> TYPE: DNA
<213> ORGANISM: Artificial Sequence
<220> FEATURE:
<223> OTHER INFORMATION: synthesized - target 2 target sequence

<400> SEQUENCE: 125

```
caggcccccg cgcccaccgc tgg                                              23
```

<210> SEQ ID NO 126
<211> LENGTH: 20
<212> TYPE: DNA
<213> ORGANISM: Artificial Sequence
<220> FEATURE:
<223> OTHER INFORMATION: synthesized - target 2 protospacer sequence

<400> SEQUENCE: 126

```
caggcccccg cgcccaccgc                                                  20
```

<210> SEQ ID NO 127
<211> LENGTH: 103
<212> TYPE: DNA
<213> ORGANISM: Artificial Sequence
<220> FEATURE:
<223> OTHER INFORMATION: synthesized - target 2 complete sgRNA nucleic
      acid sequence

<400> SEQUENCE: 127
caggcccccg cgcccaccgc gttttagagc tagaaatagc aagttaaaat aaggctagtc      60
cgttatcaac ttgaaaaagt ggcaccgagt cggtgctttt ttt                      103

<210> SEQ ID NO 128
<211> LENGTH: 171
<212> TYPE: DNA
<213> ORGANISM: Artificial Sequence
<220> FEATURE:
<223> OTHER INFORMATION: synthesized - a repair template sequence for
      introduction of the correct SNP

<400> SEQUENCE: 128
ccgcctccga ctccaagtac tgcgagcgcc acatgcaccg cggccgcaac cgtaaaagaa      60
agcctgtgga aacgcagctc gtgccccact cccagccgcc ggccgcctcc gccgtgccgc     120
ccctcgccac cggcttccac ggccactccc tctaccccgc cgtcggcggc g             171

<210> SEQ ID NO 129
<211> LENGTH: 475
<212> TYPE: DNA
<213> ORGANISM: Artificial Sequence
<220> FEATURE:
<223> OTHER INFORMATION: synthesized - donor DNA sequence for
      introduction of the correct SNP

<400> SEQUENCE: 129
gaagtggcgg tgcgccaagg aggccctcgc cgcccgcttc taccacaacc ccctcgccat      60
cgggtacgga tcgtacctgg gcaagaaggt ggatccggag ccgggccggt gccggcgcac     120
ggacggcaag aagtggcggt gcgccaagga agccgcctcc gactccaagt actgcgagcg     180
ccacatgcac cgcggccgca accgtaaaag aaagcctgtg gaaacgcagc tcgtgcccca     240
ctcccagccg ccggccgcct ccgccgtgcc gcccctcgcc accggcttcc acggccactc     300
cctctacccc gccgtcggcg gcggcaccaa cggtggtgga ggcggaggga acaacggcat     360
gtccatgccc ggcacgttct cctccgcgct ggggccgcct cagcagcaca tgggcaacaa     420
tgccgcctct ccctacgcgg ctctcggcgg cggcaccaac ggtggtggag gcggg         475

<210> SEQ ID NO 130
<211> LENGTH: 23
<212> TYPE: DNA
<213> ORGANISM: Artificial Sequence
<220> FEATURE:
<223> OTHER INFORMATION: synthesized - target 1 target sequence

<400> SEQUENCE: 130
gaagtggcgg tgcgccaagg agg                                              23

<210> SEQ ID NO 131
<211> LENGTH: 20
<212> TYPE: DNA
<213> ORGANISM: Artificial Sequence
<220> FEATURE:
<223> OTHER INFORMATION: synthesized - target 1 protospacer sequence -continued

<400> SEQUENCE: 131
gaagtggcgg tgcgccaagg                                                    20

<210> SEQ ID NO 132
<211> LENGTH: 103
<212> TYPE: DNA
<213> ORGANISM: Artificial Sequence
<220> FEATURE:
<223> OTHER INFORMATION: synthesized - target 1 complete sgRNA nucleic
      acid sequence

<400> SEQUENCE: 132
gaagtggcgg tgcgccaagg gttttagagc tagaaatagc aagttaaaat aaggctagtc        60
cgttatcaac ttgaaaaagt ggcaccgagt cggtgctttt ttt                         103

<210> SEQ ID NO 133
<211> LENGTH: 23
<212> TYPE: DNA
<213> ORGANISM: Artificial Sequence
<220> FEATURE:
<223> OTHER INFORMATION: synthesized - target 2 target sequence

<400> SEQUENCE: 133
gcaccaacgg tggtggaggc ggg                                                23

<210> SEQ ID NO 134
<211> LENGTH: 20
<212> TYPE: DNA
<213> ORGANISM: Artificial Sequence
<220> FEATURE:
<223> OTHER INFORMATION: synthesized - target 2 protospacer sequence

<400> SEQUENCE: 134
gcaccaacgg tggtggaggc                                                    20

<210> SEQ ID NO 135
<211> LENGTH: 103
<212> TYPE: DNA
<213> ORGANISM: Artificial Sequence
<220> FEATURE:
<223> OTHER INFORMATION: synthesized - target 2 complete sgRNA nucleic
      acid sequence

<400> SEQUENCE: 135
gcaccaacgg tggtggaggc gttttagagc tagaaatagc aagttaaaat aaggctagtc        60
cgttatcaac ttgaaaaagt ggcaccgagt cggtgctttt ttt                         103

<210> SEQ ID NO 136
<211> LENGTH: 174
<212> TYPE: DNA
<213> ORGANISM: Artificial Sequence
<220> FEATURE:
<223> OTHER INFORMATION: synthesized - a repair template sequence for
      introduction of the correct SNP

<400> SEQUENCE: 136
aggaggccgc ctccgactcc aagtattgcg agcgccacat gcaccgcggc cgcaaccgta        60
aaagaaagcc tgtggaaacg cagctcgtct cgcactccca gccgccggcc gcctccgtcg       120
tgccgcccct cgccaccggc ttccacaacc actccctcta ccccgccatc ggcg             174

<210> SEQ ID NO 137
<211> LENGTH: 466

```
<212> TYPE: DNA
<213> ORGANISM: Artificial Sequence
<220> FEATURE:
<223> OTHER INFORMATION: synthesized - donor DNA sequence for
      introduction of the correct SNP

<400> SEQUENCE: 137
caagaagtgg cggtgcgcca agggccgccc gcttctacca caaccccctc gccatcgggt    60
atggatcgta cctgggcaag aaggtggatc cggagcccgg ccggtgccgg cgcacggacg    120
gcaagaagtg gcggtgcgcc aaagaggccg cctccgactc caagtattgc gagcgccaca    180
tgcaccgcgg ccgcaaccgt aaaagaaagc ctgtggaaac gcagctcgtc tcgcactccc    240
agccgccggc cgcctccgtc gtgccgcccc tcgccaccgg cttccacaac cactccctct    300 acccccgccat cggcggcacc aacggtggtg gaggcggagg gaacaacggc atgcccaaca    360
cgttctcctc cgcgctgggg cctcctcagc agcacatggg caacaatgcc tcctcaccct    420
acgcggctct cggtggcgcc ggagcaccaa cggtggtgga ggcggg              466

<210> SEQ ID NO 138
<211> LENGTH: 23
<212> TYPE: DNA
<213> ORGANISM: Artificial Sequence
<220> FEATURE:
<223> OTHER INFORMATION: synthesized - target 1 target sequence

<400> SEQUENCE: 138
caagaagtgg cggtgcgcca agg                                            23

<210> SEQ ID NO 139
<211> LENGTH: 20
<212> TYPE: DNA
<213> ORGANISM: Artificial Sequence
<220> FEATURE:
<223> OTHER INFORMATION: synthesized - target 1 protospacer sequence

<400> SEQUENCE: 139
caagaagtgg cggtgcgcca                                                20

<210> SEQ ID NO 140
<211> LENGTH: 103
<212> TYPE: DNA
<213> ORGANISM: Artificial Sequence
<220> FEATURE:
<223> OTHER INFORMATION: synthesized - target 1 complete sgRNA nucleic
      acid sequence

<400> SEQUENCE: 140
caagaagtgg cggtgcgcca gttttagagc tagaaatagc aagttaaaat aaggctagtc    60
cgttatcaac ttgaaaaagt ggcaccgagt cggtgctttt ttt                     103

<210> SEQ ID NO 141
<211> LENGTH: 23
<212> TYPE: DNA
<213> ORGANISM: Artificial Sequence
<220> FEATURE:
<223> OTHER INFORMATION: synthesized - target 2 target sequence

<400> SEQUENCE: 141
gcaccaacgg tggtggaggc ggg                                            23

<210> SEQ ID NO 142
<211> LENGTH: 20
<212> TYPE: DNA
```

```
<213> ORGANISM: Artificial Sequence
<220> FEATURE:
<223> OTHER INFORMATION: synthesized - target 2 protospacer sequence

<400> SEQUENCE: 142
gcaccaacgg tggtggaggc                                                  20

<210> SEQ ID NO 143
<211> LENGTH: 103
<212> TYPE: DNA
<213> ORGANISM: Artificial Sequence
<220> FEATURE:
<223> OTHER INFORMATION: synthesized - target 2 complete sgRNA nucleic
      acid sequence

<400> SEQUENCE: 143
gcaccaacgg tggtggaggc gttttagagc tagaaatagc aagttaaaat aaggctagtc      60
cgttatcaac ttgaaaaagt ggcaccgagt cggtgctttt ttt                       103

<210> SEQ ID NO 144
<211> LENGTH: 174
<212> TYPE: DNA
<213> ORGANISM: Artificial Sequence
<220> FEATURE:
<223> OTHER INFORMATION: synthesized - a repair template sequence for
      introduction of the correct SNP

<400> SEQUENCE: 144
aggccgcctc cgattccaag tattgcgagc gccacatgca ccgcggccgc aaccgtaaaa      60
gaaagcctgt ggaaacgcag ctcgtcccgc acacccagcc gccggccgcc tccgccgtgc    120 cgccctcgc caccggcttc cacagccact ccctctaccc cgccatcggc ggca            174

<210> SEQ ID NO 145
<211> LENGTH: 468
<212> TYPE: DNA
<213> ORGANISM: Artificial Sequence
<220> FEATURE:
<223> OTHER INFORMATION: synthesized - donor DNA sequence for
      introduction of the correct SNP

<400> SEQUENCE: 145
caagaagtgg cggtgcgcca aggtcgccgc ccgcttctac cacaaccccc tcgccatcgg      60
gtacggatcg tacctaggca agaaggtgga tccggagccg gccggtgcc ggcgcacgga     120 cggcaagaag tggcggtgcg ccaaagaggc cgcctccgat tccaagtatt gcgagcgcca    180
catgcaccgc ggccgcaacc gtaaaagaaa gcctgtggaa acgcagctcg tcccgcacac    240
ccagccgccg ccgcctccg ccgtgccgcc cctcgccacc ggcttccaca gccactccct    300
ctaccccgcc atcggcggca gcaccaacgg tggtggaggc ggagggaaca acggcatgtc    360
catgcccagc acgttctcct ccgcgctggg gccgcctcag cagcacatgg cagcaatgc    420 cgcctctccc tacgcggctc tcggtgcacc aacggtggtg gaggcggg                468

<210> SEQ ID NO 146
<211> LENGTH: 23
<212> TYPE: DNA
<213> ORGANISM: Artificial Sequence
<220> FEATURE:
<223> OTHER INFORMATION: synthesized - target 1 target sequence

<400> SEQUENCE: 146
caagaagtgg cggtgcgcca agg                                              23
```

<210> SEQ ID NO 147
<211> LENGTH: 20
<212> TYPE: DNA
<213> ORGANISM: Artificial Sequence
<220> FEATURE:
<223> OTHER INFORMATION: synthesized - target 1 protospacer sequence

<400> SEQUENCE: 147
caagaagtgg cggtgcgcca                                                    20

<210> SEQ ID NO 148
<211> LENGTH: 103
<212> TYPE: DNA
<213> ORGANISM: Artificial Sequence
<220> FEATURE:
<223> OTHER INFORMATION: synthesized - target 1 complete sgRNA nucleic
      acid sequence

<400> SEQUENCE: 148
caagaagtgg cggtgcgcca gttttagagc tagaaatagc aagttaaaat aaggctagtc        60
cgttatcaac ttgaaaaagt ggcaccgagt cggtgctttt ttt                         103

<210> SEQ ID NO 149
<211> LENGTH: 23
<212> TYPE: DNA
<213> ORGANISM: Artificial Sequence
<220> FEATURE:
<223> OTHER INFORMATION: synthesized - target 2 target sequence

<400> SEQUENCE: 149
gcaccaacgg tggtggaggc ggg                                                23

<210> SEQ ID NO 150
<211> LENGTH: 20
<212> TYPE: DNA
<213> ORGANISM: Artificial Sequence
<220> FEATURE:
<223> OTHER INFORMATION: synthesized - target 2 protospacer sequence

<400> SEQUENCE: 150
gcaccaacgg tggtggaggc                                                    20

<210> SEQ ID NO 151
<211> LENGTH: 103
<212> TYPE: DNA
<213> ORGANISM: Artificial Sequence
<220> FEATURE:
<223> OTHER INFORMATION: synthesized - target 2 complete sgRNA nucleic
      acid sequence

<400> SEQUENCE: 151
gcaccaacgg tggtggaggc gttttagagc tagaaatagc aagttaaaat aaggctagtc        60
cgttatcaac ttgaaaaagt ggcaccgagt cggtgctttt ttt                         103

<210> SEQ ID NO 152
<211> LENGTH: 168
<212> TYPE: DNA
<213> ORGANISM: Artificial Sequence
<220> FEATURE:
<223> OTHER INFORMATION: synthesized - a repair template sequence for
      introduction of the correct SNP

<400> SEQUENCE: 152
caagaagtgg cggtgctcca aggaggccgc tcaggactcc aagtactgcg agcgccacat        60

```
gcacgcggcc gcaaccgtaa aagaaagcct gtggaaacgc agctcgtcgc cagctcccac    120
tcccagtccc agcagcacgc caccgccgcc ttccacaacc actcgccg                 168
```

<210> SEQ ID NO 153
<211> LENGTH: 474
<212> TYPE: DNA
<213> ORGANISM: Artificial Sequence
<220> FEATURE:
<223> OTHER INFORMATION: synthesized - donor DNA sequence for
      introduction of the correct SNP

<400> SEQUENCE: 153

```
gggcggtgcc ggcggacgga cggacagatg tatggggtat ttatcatgaa aaagcattct    60
tgacgtgggt gttttcgtt gtttgcagtt gggtacgggt cctacttcgg gaagaagctg    120
gatccggagc cggggcggtg ccggcggacg gacgacaaga agtggcggtg ctccaaggag    180
gccgctcagg actccaagta ctgcgagcgc cacatgcacg cggccgcaac cgtaaaagaa    240
agcctgtgga aacgcagctc gtcgccagct cccactccca gtcccagcag cacgccaccg    300
ccgccttcca caaccactcg ccgtatccgg cgatcgccac tggcgatggc ccttcgccc    360 tggggtctgc tcagctgcac atggacactg ctgcgcctta cgcgacgacc gccggtgctg    420
ccggaaacaa agatttcagg tgacctcttc ttatccggcg atcgccactg gcgg         474
```

<210> SEQ ID NO 154
<211> LENGTH: 23
<212> TYPE: DNA
<213> ORGANISM: Artificial Sequence
<220> FEATURE:
<223> OTHER INFORMATION: synthesized - target 1 target sequence

<400> SEQUENCE: 154

```
gggcggtgcc ggcggacgga cgg                                            23
```

<210> SEQ ID NO 155
<211> LENGTH: 20
<212> TYPE: DNA
<213> ORGANISM: Artificial Sequence
<220> FEATURE:
<223> OTHER INFORMATION: synthesized - target 1 protospacer sequence

<400> SEQUENCE: 155

```
gggcggtgcc ggcggacgga                                                20
```

<210> SEQ ID NO 156
<211> LENGTH: 103
<212> TYPE: DNA
<213> ORGANISM: Artificial Sequence
<220> FEATURE:
<223> OTHER INFORMATION: synthesized - target 1 complete sgRNA nucleic
      acid sequence

<400> SEQUENCE: 156

```
gggcggtgcc ggcggacgga gttttagagc tagaaatagc aagttaaaat aaggctagtc    60
cgttatcaac ttgaaaaagt ggcaccgagt cggtgctttt ttt                      103
```

<210> SEQ ID NO 157
<211> LENGTH: 23
<212> TYPE: DNA
<213> ORGANISM: Artificial Sequence
<220> FEATURE:
<223> OTHER INFORMATION: synthesized - target 2 target sequence

<400> SEQUENCE: 157
tatccggcga tcgccactgg cgg                                              23

<210> SEQ ID NO 158
<211> LENGTH: 20
<212> TYPE: DNA
<213> ORGANISM: Artificial Sequence
<220> FEATURE:
<223> OTHER INFORMATION: synthesized - target 2 protospacer sequence

<400> SEQUENCE: 158
tatccggcga tcgccactgg                                                  20

<210> SEQ ID NO 159
<211> LENGTH: 103
<212> TYPE: DNA
<213> ORGANISM: Artificial Sequence
<220> FEATURE:
<223> OTHER INFORMATION: synthesized - target 2 complete sgRNA nucleic
      acid sequence

<400> SEQUENCE: 159
tatccggcga tcgccactgg gttttagagc tagaaatagc aagttaaaat aaggctagtc      60
cgttatcaac ttgaaaaagt ggcaccgagt cggtgctttt ttt                       103

<210> SEQ ID NO 160
<211> LENGTH: 158
<212> TYPE: DNA
<213> ORGANISM: Artificial Sequence
<220> FEATURE:
<223> OTHER INFORMATION: synthesized - a repair template sequence for
      introduction of the correct SNP

<400> SEQUENCE: 160
tgccggcgta cggacggcaa gaagtggcgg tgctccaagg aggccgcccc agactccaag      60
tactgcgagc gccacatgca ccgcggccgc aaccgtaaaa gaaagcctgt ggaaacgcag     120
ctcgtgcccc agtcccaacc gcccgccacc gccgctgc                             158

<210> SEQ ID NO 161
<211> LENGTH: 454
<212> TYPE: DNA
<213> ORGANISM: Artificial Sequence
<220> FEATURE:
<223> OTHER INFORMATION: synthesized - donor DNA sequence for
      introduction of the correct SNP

<400> SEQUENCE: 161
aactggatcc ggagccgggg cgggatctcg tggttccaat ccgccgcggt ctcgactccc      60
tcgcaacccg cttctacggc catcccacac ttggtgggta cggacgtac tacttaggca     120 agaaactgga tccggagccg gggcgatgcc ggcgtacgga cggcaagaag tggcggtgct    180
ccaaggaggc cgccccagac tccaagtact gcgagcgcca catgcaccgc ggccgcaacc    240
gtaaaagaaa gcctgtggaa acgcagctcg tgccccagtc ccaaccgccc gccaccgccg    300
ctgccgtctc cgccgctccg cccttagcct tggccgccgc caccaccacc accaacggca    360
gctgcttcca gaatcactct ctttacccgg ccattgcagg cagcaccggt ggaggtggcg    420
gggccagcaa tcgtctccgc cgctccgccc ttgg                                454

<210> SEQ ID NO 162
<211> LENGTH: 23
<212> TYPE: DNA
<213> ORGANISM: Artificial Sequence

```
<220> FEATURE:
<223> OTHER INFORMATION: synthesized - target 1 target sequence

<400> SEQUENCE: 162
aactggatcc ggagccgggg cgg                                              23

<210> SEQ ID NO 163
<211> LENGTH: 20
<212> TYPE: DNA
<213> ORGANISM: Artificial Sequence
<220> FEATURE:
<223> OTHER INFORMATION: synthesized - target 1 protospacer sequence

<400> SEQUENCE: 163
aactggatcc ggagccgggg                                                  20

<210> SEQ ID NO 164
<211> LENGTH: 103
<212> TYPE: DNA
<213> ORGANISM: Artificial Sequence
<220> FEATURE:
<223> OTHER INFORMATION: synthesized - target 1 complete sgRNA nucleic
      acid sequence

<400> SEQUENCE: 164
aactggatcc ggagccgggg gttttagagc tagaaatagc aagttaaaat aaggctagtc      60
cgttatcaac ttgaaaaagt ggcaccgagt cggtgctttt ttt                        103

<210> SEQ ID NO 165
<211> LENGTH: 23
<212> TYPE: DNA
<213> ORGANISM: Artificial Sequence
<220> FEATURE:
<223> OTHER INFORMATION: synthesized - target 2 target sequence

<400> SEQUENCE: 165
cgtctccgcc gctccgccct tgg                                              23

<210> SEQ ID NO 166
<211> LENGTH: 20
<212> TYPE: DNA
<213> ORGANISM: Artificial Sequence
<220> FEATURE:
<223> OTHER INFORMATION: synthesized - target 2 protospacer sequence

<400> SEQUENCE: 166
cgtctccgcc gctccgccct                                                  20

<210> SEQ ID NO 167
<211> LENGTH: 103
<212> TYPE: DNA
<213> ORGANISM: Artificial Sequence
<220> FEATURE:
<223> OTHER INFORMATION: synthesized - target 2 complete sgRNA nucleic
      acid sequence

<400> SEQUENCE: 167
cgtctccgcc gctccgccct gttttagagc tagaaatagc aagttaaaat aaggctagtc      60
cgttatcaac ttgaaaaagt ggcaccgagt cggtgctttt ttt                        103

<210> SEQ ID NO 168
<211> LENGTH: 107
<212> TYPE: DNA
<213> ORGANISM: Artificial Sequence
<220> FEATURE:
```

```
<223> OTHER INFORMATION: synthesized - a repair template sequence for
      introduction of the correct SNP

<400> SEQUENCE: 168
aagcataccc agactccaag tactgcgagc gccacatgca ccgtggccgc aaccgtaaaa    60
gaaagcctgt ggaatcacaa actatgactc actcatcttc aactgtc                107

<210> SEQ ID NO 169
<211> LENGTH: 402
<212> TYPE: DNA
<213> ORGANISM: Artificial Sequence
<220> FEATURE:
<223> OTHER INFORMATION: synthesized - donor DNA sequence for
      introduction of the correct SNP

<400> SEQUENCE: 169
aaaaaagtgg aggtgctcca aggtctcgca cgctttcttt caccatccca cgttgagtta    60
ctgttccttc tatgggaaga aggtggaccc tgagccagga cgatgcagga ggactgatgg   120
aaaaaagtgg aggtgctcca aagaagcata cccagactcc aagtactgcg agcgccacat   180
gcaccgtggc cgcaaccgta aagaaagcc tgtggaatca caaactatga ctcactcatc   240
ttcaactgtc acatcactca ctgtcactgg gagtagtggt gccagcaaag gaactgtaaa   300
tttccaaaac ctttctacaa ataccttttgg taatctccag ggtaccgatt ctggaactga   360
ccacaccaat tatcatctag acatcactca ctgtcactgg gg                      402

<210> SEQ ID NO 170
<211> LENGTH: 23
<212> TYPE: DNA
<213> ORGANISM: Artificial Sequence
<220> FEATURE:
<223> OTHER INFORMATION: synthesized - target 1 target sequence

<400> SEQUENCE: 170
aaaaaagtgg aggtgctcca agg                                           23

<210> SEQ ID NO 171
<211> LENGTH: 20
<212> TYPE: DNA
<213> ORGANISM: Artificial Sequence
<220> FEATURE:
<223> OTHER INFORMATION: synthesized - target 1 protospacer sequence

<400> SEQUENCE: 171
aaaaaagtgg aggtgctcca                                               20

<210> SEQ ID NO 172
<211> LENGTH: 103
<212> TYPE: DNA
<213> ORGANISM: Artificial Sequence
<220> FEATURE:
<223> OTHER INFORMATION: synthesized - target 1 complete sgRNA nucleic
      acid sequence

<400> SEQUENCE: 172
aaaaaagtgg aggtgctcca gttttagagc tagaaatagc aagttaaaat aaggctagtc    60
cgttatcaac ttgaaaaagt ggcaccgagt cggtgctttt ttt                     103

<210> SEQ ID NO 173
<211> LENGTH: 23
<212> TYPE: DNA
<213> ORGANISM: Artificial Sequence
<220> FEATURE:
```

<223> OTHER INFORMATION: synthesized - target 2 target sequence

<400> SEQUENCE: 173
gacatcactc actgtcactg ggg                                         23

<210> SEQ ID NO 174
<211> LENGTH: 20
<212> TYPE: DNA
<213> ORGANISM: Artificial Sequence
<220> FEATURE:
<223> OTHER INFORMATION: synthesized - target 2 protospacer sequence

<400> SEQUENCE: 174
gacatcactc actgtcactg                                             20

<210> SEQ ID NO 175
<211> LENGTH: 103
<212> TYPE: DNA
<213> ORGANISM: Artificial Sequence
<220> FEATURE:
<223> OTHER INFORMATION: synthesized - target 2 complete sgRNA nucleic
      acid sequence

<400> SEQUENCE: 175
gacatcactc actgtcactg gttttagagc tagaaatagc aagttaaaat aaggctagtc    60
cgttatcaac ttgaaaaagt ggcaccgagt cggtgctttt ttt                     103

<210> SEQ ID NO 176
<211> LENGTH: 107
<212> TYPE: DNA
<213> ORGANISM: Artificial Sequence
<220> FEATURE:
<223> OTHER INFORMATION: synthesized - a repair template sequence for
      introduction of the correct SNP

<400> SEQUENCE: 176
gacgtcttcg ctggccacaa gtactgcgag cgccacatgc accgaggccg caaccgtaaa    60
agaaagcctg tggaaactcc catagtcaat gctaccacca ccacttc                 107

<210> SEQ ID NO 177
<211> LENGTH: 418
<212> TYPE: DNA
<213> ORGANISM: Artificial Sequence
<220> FEATURE:
<223> OTHER INFORMATION: synthesized - donor DNA sequence for
      introduction of the correct SNP

<400> SEQUENCE: 177
gtaagaagta aagatgttca aggcttctcc atctatctcc ttcctacttt cttcaccacc    60
tacctcatta ccagcctgct tggtatttgg ggaggggggc gatggatcct gagccaggga   120
gatgcaggag aacggatggt aagaagtaaa gatgttcaag agacgtcttc gctggccaca   180
agtactgcga gcgccacatg caccgaggcc gcaaccgtaa agaaagcct gtggaaactc    240 ccatagtcaa tgctaccacc accacttcca tggcttcccc agccacagca gcaccgtcat   300
caacaccatc ctccttttgct tttggcggtg gtgagaaagt gggtcaaggt ggatcatcta   360
gcttcttctt ctcaagtcaa agttgttcag agatgcatgg cttccccagc cacagcgg    418

<210> SEQ ID NO 178
<211> LENGTH: 23
<212> TYPE: DNA
<213> ORGANISM: Artificial Sequence
<220> FEATURE:

```
<223> OTHER INFORMATION: synthesized - target 1 target sequence

<400> SEQUENCE: 178
gtaagaagta aagatgttca agg                                           23

<210> SEQ ID NO 179
<211> LENGTH: 20
<212> TYPE: DNA
<213> ORGANISM: Artificial Sequence
<220> FEATURE:
<223> OTHER INFORMATION: synthesized - target 1 protospacer sequence

<400> SEQUENCE: 179
gtaagaagta aagatgttca                                               20

<210> SEQ ID NO 180
<211> LENGTH: 103
<212> TYPE: DNA
<213> ORGANISM: Artificial Sequence
<220> FEATURE:
<223> OTHER INFORMATION: synthesized - target 1 complete sgRNA nucleic
      acid sequence

<400> SEQUENCE: 180
gtaagaagta aagatgttca gttttagagc tagaaatagc aagttaaaat aaggctagtc   60
cgttatcaac ttgaaaaagt ggcaccgagt cggtgctttt ttt                    103

<210> SEQ ID NO 181
<211> LENGTH: 23
<212> TYPE: DNA
<213> ORGANISM: Artificial Sequence
<220> FEATURE:
<223> OTHER INFORMATION: synthesized - target 2 target sequence

<400> SEQUENCE: 181
catggcttcc ccagccacag cgg                                           23

<210> SEQ ID NO 182
<211> LENGTH: 20
<212> TYPE: DNA
<213> ORGANISM: Artificial Sequence
<220> FEATURE:
<223> OTHER INFORMATION: synthesized - target 2 protospacer sequence

<400> SEQUENCE: 182
catggcttcc ccagccacag                                               20

<210> SEQ ID NO 183
<211> LENGTH: 103
<212> TYPE: DNA
<213> ORGANISM: Artificial Sequence
<220> FEATURE:
<223> OTHER INFORMATION: synthesized - target 2 complete sgRNA nucleic
      acid sequence

<400> SEQUENCE: 183
catggcttcc ccagccacag gttttagagc tagaaatagc aagttaaaat aaggctagtc   60
cgttatcaac ttgaaaaagt ggcaccgagt cggtgctttt ttt                    103

<210> SEQ ID NO 184
<211> LENGTH: 136
<212> TYPE: DNA
<213> ORGANISM: Artificial Sequence
<220> FEATURE:
<223> OTHER INFORMATION: synthesized - a repair template sequence for
``` introduction of the correct SNP

<400> SEQUENCE: 184

```
actgacggaa aaaagtggag atgctcaaaa gatgcatatc ctgactccaa atattgcgag    60
cggcacatgc atcgaggccg caaccgttca agaaagcctg tggaatctca atctactccc   120
cagtccttgt cgacta                                                   136
```

<210> SEQ ID NO 185
<211> LENGTH: 429
<212> TYPE: DNA
<213> ORGANISM: Artificial Sequence
<220> FEATURE:
<223> OTHER INFORMATION: synthesized - donor DNA sequence for
      introduction of the correct SNP

<400> SEQUENCE: 185

```
ctgagccagg aaggtgtaga aggtggtggt ttcagctata tgcattagct catgatggag    60
cttaatgatt tgtttcttct ttgtacagtg ggctattgtt cctattatgg gaagaagttt   120
gatcctgagc caggaaggtg tagaagaact gacggaaaaa agtggagatg ctcaaaagat   180
gcatatcctg actccaaata ttgcgagcgg cacatgcatc gaggccgcaa ccgttcaaga   240
aagcctgtgg aatctcaatc tactccccag tccttgtcga ctagtatgtc acaaattaca   300
gctggaagca gcaatacaag aggaagtttc caaatagca gcagcggaag cttccaaaac   360
atgccattgt attctgttgc taattcggga acgctgaatt atggaagtat gtcacaaatt   420
acagctggg                                                          429
```

<210> SEQ ID NO 186
<211> LENGTH: 23
<212> TYPE: DNA
<213> ORGANISM: Artificial Sequence
<220> FEATURE:
<223> OTHER INFORMATION: synthesized - target 1 target sequence

<400> SEQUENCE: 186

```
ctgagccagg aaggtgtaga agg                                            23
```

<210> SEQ ID NO 187
<211> LENGTH: 20
<212> TYPE: DNA
<213> ORGANISM: Artificial Sequence
<220> FEATURE:
<223> OTHER INFORMATION: synthesized - target 1 protospacer sequence

<400> SEQUENCE: 187

```
ctgagccagg aaggtgtaga                                                20
```

<210> SEQ ID NO 188
<211> LENGTH: 103
<212> TYPE: DNA
<213> ORGANISM: Artificial Sequence
<220> FEATURE:
<223> OTHER INFORMATION: synthesized - target 1 complete sgRNA nucleic
      acid sequence

<400> SEQUENCE: 188

```
ctgagccagg aaggtgtaga gttttagagc tagaaatagc aagttaaaat aaggctagtc    60
cgttatcaac ttgaaaaagt ggcaccgagt cggtgctttt ttt                     103
```

<210> SEQ ID NO 189
<211> LENGTH: 23

```
<212> TYPE: DNA
<213> ORGANISM: Artificial Sequence
<220> FEATURE:
<223> OTHER INFORMATION: synthesized - target 2 target sequence

<400> SEQUENCE: 189
gtatgtcaca aattacagct ggg                                            23

<210> SEQ ID NO 190
<211> LENGTH: 20
<212> TYPE: DNA
<213> ORGANISM: Artificial Sequence
<220> FEATURE:
<223> OTHER INFORMATION: synthesized - target 2 protospacer sequence

<400> SEQUENCE: 190
gtatgtcaca aattacagct                                                20

<210> SEQ ID NO 191
<211> LENGTH: 103
<212> TYPE: DNA
<213> ORGANISM: Artificial Sequence
<220> FEATURE:
<223> OTHER INFORMATION: synthesized - target 2 complete sgRNA nucleic
      acid sequence

<400> SEQUENCE: 191
gtatgtcaca aattacagct gttttagagc tagaaatagc aagttaaaat aaggctagtc    60
cgttatcaac ttgaaaaagt ggcaccgagt cggtgctttt ttt                     103

<210> SEQ ID NO 192
<211> LENGTH: 2000
<212> TYPE: DNA
<213> ORGANISM: Zea mays

<400> SEQUENCE: 192
ttctagtgtt tcaacggaag cctaagtttc gatgggaaga aggacatgt  actagcaagg    60 aaccaaactc cacgcatcat tcttgcctag ccttgcttta tcgtggctac cttggaccaa   120
caaaagaacc aagcagcccc aatgtatctg atatggagct aaaaatacaa ccaactcata   180
ttatacgttg gatgttttga ctgcacttga gatgttgtaa gactttcggt acgctataca   240
tatagagttg aatatacagt tgaagactgc tgcagcggtc aactgtctga tctactgtaa   300
actctatgag gaaatcggaa acgctacttc cagagtagtg taactccgac tggaaaactg   360
ttgcagaata cggatagcct gatcagttag actgtcggct gcggagttca actgttgcag   420
agttagaaag aaatgataaa atatatagta gttagtatag agttgatata tagagtaaac   480
atgactgtag aggattgtag tatagggtag atagttttgc tgaccaggac aagatattcc   540
ttttagagta tgaatttaga gtagtatgag tgcggatagc ctaactttgt aagtattttt   600
aaagcttact ttgcatacgg tctttgtgat ctacatcttt actatggcta tttcatgata   660
ataactagat gagatatatg accaatcgag ttgtacatat atgtttgggt tttaattaag   720
ggcatagtta aaagcactga gcttttaaga aaacgatgtg gttctaaata tggcagttta   780
tgctttggtt tctagaaact gaatttctag catatttccg tactattctt agttggtttg   840
gatagaaact acgacgatta tcaccgctct gaggcctaat ggcctatgca cttgattctc   900
tccatgccca ctctgccctg ttcaaatgtt aattaatat ttaatttaat aattttgaat    960
tcaagaatac gagttcaagg tatatttaaa attgacatca aagagaaatg aaattaaagc   1020
aatgatagac ttgtctttgg gtgtgaaaaa aagctagaaa cttatttata aaaacccaat   1080
```

```
tctaaacatg tatacctaat ttttattata aatcggtttt tagatagaat cgtaaagccc      1140
ttgatcagag catccaacga gccatgaggc catgacggaa gagcggaagt gcagacggca      1200
acggcgttcc gcttcatgcc gcaccctcca gtgtcctgtg gcctttaagt gccggccttg      1260
ggaaccgcga cgcagacaca gcccaaatcc gcagtcactc ctccaacacg atgcttgtca      1320
ccacccttgc tacagtgcct gcatccatat ccactccgct cgcgcaaaaa atatccgagt      1380
cggaaacaaa caaagcagca taggaaacag aagaaagctg tactagtacg tgaggacgag      1440
gagggagaga gagcaataca cagaagcctg ctaccgtgct acggactacc acaacgccag      1500
agggacaacc ggacagaggg ggaggcaggc ctcgcttgtc atctagctag gtcagccggg      1560
gacggggtcg gagcagtaga gctaaagcca gaggccaggc tcgtagtagt acgtagtagt      1620
agtgccctcc tcgtgtcatt tggccagcct tgtccagacg accacacaca ccagattacg      1680
cttaacattc tgtttgacat ctaaaaccag ccggcttgat ccaaatgcct ccctaggtag      1740
tagcttagtc ttgctcgccg cctctccggg agacgacgac acgcctgatg agtgcctgac      1800
gttccagcgc gaggcagaca gcgacgcaga gagagacaaa gcgggcaata aaggcagccg      1860
cgcgcgagcg agggaaggga gcgaagcaaa gcacatcacg agcccagcct gcgcctgcgg      1920 agggagggg ctcattaaag aggggcgcg agcgcgaccg gccgcgggga gcaagcagcg      1980
cgcgagagag acaggttgag                                                  2000

<210> SEQ ID NO 193
<211> LENGTH: 2000
<212> TYPE: DNA
<213> ORGANISM: Zea mays

<400> SEQUENCE: 193
aaacaaatac ttatcgttaa taaacatgac atatgatctg atgcataaat tgtattttt      60 attttaaca ttgattttt aaagattccc aaaagataaa catcaaattt atcatataat      120
tcctcaaatg atacatataa aatttgaata cgaatatatt tttactttgt ttattactgg      180
gagtaaatat tgtataaaaa atatgcaaaa tttattctta tttatagtaa tatgcaaata      240
atgtataaat agtccatgct cataaatttt ttagtagccc gcaacccaag gcgaccgcga      300
acagtgccaa gccgagcggg ggtgtgcatg ttggagatgg agagagagag agagagcccg      360
aaaaatatcg ctgatgactc gacgagatag aggaggagg gagggaggga ggcgcagtag      420
gacagggctg caggcaggtg cttgtcctta gctggaaccc tcccgtgtcg gcctcatccc      480
accgccccgc cctgccgtcc tgccctgcgc ggctgcggtc gcctataagg ctagcccagg      540
ccatttgccc tttgccccg tccgtccgtc cctcacctca cctcacctca cctcggcccg      600
cctccctcat caggtagccg tagcgagcag tatagcacgc acagccgccg ccctgccctg      660
ccctgccctg ctcggcgtag gcacaggcac agcccagagc gagcgagaca gagggaaaga      720
gacagagcca gccaggtaaa aggcaaaagc acagcacatt aaaagagagg ccggaagcag      780
cggcagagcg gagagagaga gagaactaga agcatatatg gcgatgccct ttgcctccct      840
gtctccggca gccgaccacc gccctcctc cctcctcccc tactgccgcg ccgcccctct      900
ctccgcgtaa gccacctccc tttcgcccgt ccgggaaaaa accctcttct tcgctcggtt      960
tatgccaccc ggagccgtgc tgcagcctgc aggtatctga tgccgcgagc tttgccttgc      1020
agggtgggag aggacgccgc cgcgcaggcg caacagcagc agcagcacgc tatgagcggc      1080
aggtgggcag cgaggccgcc ggcgctcttc accgcggcgc agtacgagga gctggagcac      1140
```

```
caggcgctta tatacaagta cctcgtcgcc ggcgtgcccg tcccgccgga cctcctcctc   1200
cccctacgcc gaggcttcgt ctaccaccaa cccgcccgta agcaagcacg gccccgcgc    1260 cgcctccgca ccccttcaca ctcacacgca cgtttaaccg cttttgcact gcacaacccc   1320
ggccgcccgg cggcggcgtc cgtgccttga tctggttgtt tactcggatc gagggattca   1380
gatgtcctct ccgtccgttt gttaatcggc tccggtcatt tcttaatctc gtcctggatt   1440
cggtcacgaa aagctagagg tcaagatttt gctctcgatt actatatcct tgcctcatgt   1500
tctaatggag tttattttat tggtctgatg tgattagata ggatgctagc caggcttgtc   1560
tccggccaaa agcggcggtt tagtttattg atgattgctt ctttccttgg gggatttatt   1620
cctgtctggt tgttgggagc ctaaccacgc tcctattgct gctgcggttt actaaccatc   1680
tgcgccagta cacctactcc atggacccca aaatacagtt cttccaacca ttccccccct   1740
ccatctgctt tctcgcgggc aaataaaaac gtgtagaacg acggtgtagt aggcagatct   1800
actccttgtg ccgctacgct agcccgctac cgaagatcgg gccgtttca accggttcgt    1860 tggtctgagc ggagctaaga tggggcgcat ttcattttt ggtcctttcg tctgattgga    1920
gaagtgccca ttccggtatc gctccccggc ctccaaatac gcaccgacac agaacgtgtt   1980
cgtacgcacg tacacatggt                                              2000

<210> SEQ ID NO 194
<211> LENGTH: 2000
<212> TYPE: DNA
<213> ORGANISM: Triticum aestivum

<400> SEQUENCE: 194
gatagtgtgg gaagggagtg gagtggagtg gaatgcggct agggttttag ccggagtgcg     60
gcctatttag gtggggtcgg gtgagccaga tccaacatgg caggtaggtt cgggcatccc    120
cgtactcgcc ctaaatttgg gctggactgg ggagtgaccg gaagtccgaa cgtttgcgcg    180
tcaaaaatgc ggcgctcggt tgggcattga ccatgcaact tgctcggaca tttggggcaa    240
gtatagggac tccgattgta gatgctccta cgtctaattt gatacttcat tgagatgtgg    300
tgtccgatgc gtgaaaatgc ttcgagaagt gagagcatct acagccggac ttagcaaatc    360
tggcatctat aagtcagcgg gcgcctccgc ggacggcccc tcacttgagt tgccgcacat    420
tgacacaccg caaatacgga ttcttgaatt catgcaatcc attgacgtcc atcaaacgat    480
acaaatcatc ccaattcaac agttcgaaac aaaataagac aaagcaaaac aaatcataat    540
tcaacaatcc ggacatgcta aaataaaatc aatgtccgag cgtgatggtt cactccttga    600
ccggctggat cactcgcccg acgccatcca tattccgctt gctccgtggc catccttatg    660
ggcagcgagg atgaggagca aggatggcgg acgacaaggg cttgaacacg gaataggtg     720 gagggagtcg ggaggggaa gggtttaggg cctctttgat tcacaggatt gtcaaaataa    780
aggaatagaa aaaatgcagg aatagggtga catgtcccat agtatcctac aggatttgaa   840
agaatgtttg atagcatagg aaaaacaaag gaattctaca aagaggtttg agtggatgga   900
aatttttttt caaatgtag tacaaatgga tcatatggaa aaattcctaa ggatgccaat    960
cctacgaatc aaacgagcat cacatgaaaa atttctaagg atttaaatcc tccaaaaatc  1020
ctatataatt cctttaaatc aaaggagcgc tagtgaattg atgcaatttg tgctgaagta   1080
agcctgtcgg gttcgacgtg acgggcgcgc cgagacatcg ctttcatatt tggactgggt   1140
atatggagtc ctagtcagct caagtgtttg agacgctcgt ctcggttttt tcatttgacc   1200
tgtaatcggg ccgttcgtcc ggacgttcga tagaggtttg tggtgcaggg atgtagatgc   1260
```

```
acactgcttc cgttatcagt tatcaccacg acacaagaag caagcacata gtactgtagt    1320
aaaaaaattg acgagggaaa agtggcgcaa acggttgccc cgcaccctct cacggacgga    1380
ctttaaaagt cggcattggt aaccgcaaca cagcacagag agactcaccc ccaaatctct    1440
ctcttctctc tctattccta tgcaatgcaa tagttgtcac cactcgctac agtgccggca    1500
gcattgcatc gcatcgcatc catatccatt cctcctcacg agaaaagag agagagacga     1560 gcaatactag tcgtcgtcgt cgtcgtagcc tggtacgtct acgctagagc gacagggaaa    1620
gaggagggag ggggcgcttg tcatctactc ctcctcgcta ctaccccctag ctgggatcca   1680 cagcctcctc ctcctcctcg tgtcggcctc gtccacatcc accgtctcct ccgagcgagg    1740
cggacagcga cgcggccacg gagcgaggga gggagagaga caaagccggt aataaaggcg    1800
ggcgggcgcg cgcgcgcaca agccaagcaa agcacattaa cgacgccagc cagccagcca    1860
gccagccagc ccgcggggaa ccccattaaa gacgcttccg ggggagcgcc gtgggcaagc    1920
aagcacaggg gcttagctta gcttggcttg tgcatcgcgt gttgtgtgcg cgagagggag    1980
acagcggccg agagagaaag                                                2000

<210> SEQ ID NO 195
<211> LENGTH: 2000
<212> TYPE: DNA
<213> ORGANISM: Triticum aestivum

<400> SEQUENCE: 195
ttttcgcacg caacgcccac ttgagttcct cctctctcaa gagagcatgt tggccttgct     60
cagcctcaga cttggttcga tgctcattaa cagaaagaag tgtggtttca gcctttacat    120
ctagtgtctc aatgagttga gttagacgtt cttttttctg cttataaatc ccagtctcat    180
tcctggccca tcctctcaga aattgtcgga ggtttctaat cttattctgc catctctcga    240
catgtgtcct tcctgtaatt ggcttagccc attcgcatgc aatcatctcc ataaatcctt    300
ctcgctcaaa ccagctttac tcgaaagaga agatgttttt gtttgcaaca tgggtagcct    360
cacccgaatc taaaaagagt ggtgtatgat ctgagatccc tctatgcatt gcatggaccg    420
acaccaacgg atattttgt tcccactcca cactagcaag taccctatcc agcttttcat     480
aagtcagaac aggtaacgag ttggcccatg taaactgtct accggtgagc tcaatttctc    540
tcaaattgag gctctcgata atcatgttaa acatcataga ccaacgtcca tcgaaattgt    600
cattattctt ttcttctctt ctccgaatga tattaaaatc accccgact agcagtggca     660 gattttcatc tccacaaatc cgcactagat gggcaagaaa atcgggttta aattgcttgg    720
aggagtgaga gcatctacaa ccggacttag cgaatctggg ctctataagc ccgcgggtgc    780
ctccgcggac ggcctccct tgagttgccg cacattcaca catctcaaat acggattctt     840
gaatccatgt atccatgcac gtccatcata cgatataaat catcccaatt caaatgtttg    900
aaaacaaaat acgacaatgc aaagcaaatc atagttcaat aattcagaca tgccaaatta    960
aaatcaatat ccgagcatga tagatcactc gttggacgcc atccatgccc gcttgctccg   1020
cggccatcct tgcgggcggc gaggatgggg agcaagggtg gcggacggca agggcttgga   1080
cacgaaaata ggtggatgaa ggcggagag aggagggttt agtgaatttt atgcaattta    1140 tgtgggggt tggcctgtcg ggttctacgt aatggacgcg ccgaggcatg agggatgccg    1200
gtcagcttgg gtgttttaga tgcccgtccg gtcttttatt tttaagtccg taattgggcc   1260
gttcgccgga cgttccatag aggtttgggg tgccgggaag tagatgcaca gtacttccgt   1320
```

| | | | | |
|---|---|---|---|---|
| tatcaccacg | acacaagaag | caagcacata | gtactgttgt | aaaaaaatga cgagggaaaa | 1380 |
| gtggcgcaaa | cggttgcccc | gcaccctctc | acggacggac | tttaaaagtc ggcattggta | 1440 |
| accgcaacac | aacacagaca | gacgcacccc | aaatctctct | ctctctctct tcccatgcaa | 1500 |
| tagttgtcgc | cactcgctcg | ctacagtgac | cgcatcgcat | cgcatccatg tccattcctc | 1560 |
| cccacgagaa | aaagagagag | acagcagaaa | taccagtcgt | cgtcgtcgtc gtcgtagcct | 1620 |
| ggtacgtcta | cgctagagcg | acagggaaag | aggagggcgc | ttgtcatcta ctcctcctcc | 1680 |
| tcgcccgcta | ctagctggga | tccacagcct | cctcctcctc | ctcgtgtcgg cctcgtccac | 1740 |
| atccaccatc | tcctccgagc | gaggtggaca | gcgacgcggc | cacggagcga gtgagagaga | 1800 |
| caaagccggt | aataaaggcg | ggcgcgcgcg | cgcgcacaag | ccaagcaaag cacattaacg | 1860 |
| aggccagcca | gcccgcaggg | aaccccatta | aagacgcttc | cgtgggagcg ccgtggggaa | 1920 |
| gcaagcgagc | gagcacaggg | gcttggcttg | cgcgtcgtgt | gctgtgtgcg cgagagggag | 1980 |
| acagcggccg | agagagaaag | | | | 2000 |

<210> SEQ ID NO 196
<211> LENGTH: 2000
<212> TYPE: DNA
<213> ORGANISM: Triticum aestivum
<220> FEATURE:
<221> NAME/KEY: misc_feature
<222> LOCATION: (128)..(265)
<223> OTHER INFORMATION: n is a, c, g, or t

<400> SEQUENCE: 196

| | | | | |
|---|---|---|---|---|
| gtatgcgtta | ccttgatttg | ccacattagc | tagctgaagt | tggttgcccg tacatttgtc | 60 |
| agcgttagcg | ccctgtgacg | aaacttgcca | tgctgccccc | ctgattgtgg tttggtcata | 120 |
| agaacctnnn | nnnnnnnnnn | nnnnnnnnnn | nnnnnnnnnn | nnnnnnnnnn nnnnnnnnnn | 180 |
| nnnnnnnnnn | nnnnnnnnnn | nnnnnnnnnn | nnnnnnnnnn | nnnnnnnnnn nnnnnnnnnn | 240 |
| nnnnnnnnnn | nnnnnnnnnn | nnnnngcagc | aatggccctg | aagaaatgag ttgattgtac | 300 |
| tctgctgcat | cccaaggtgg | cgtttccggc | ctttgagaaa | gccaaggatc agtgccatct | 360 |
| tcgtgattca | ttcttctgct | ttttcttttc | tgctactatg | cttttagtca ctgcatgaac | 420 |
| aagaacgcat | caacaatcca | caaaaagcgt | tcttgctgtt | tgcacgtaga agataacacg | 480 |
| gcaatctcat | aatatttttt | gcgtaggcaa | ccaacacctc | atggcaagta ggacatgcac | 540 |
| atccattttt | cttttctgaa | ttctggatgc | catctatcat | tttgaagcga tggcaacaga | 600 |
| aaataaaata | ggatggcaag | caataataca | tggtggcaac | tatggacaac gatagatggc | 660 |
| aactgacgtt | agatacaagt | ggcaattatt | tttcctccct | ccccatgcca aattcctcct | 720 |
| ttctctccct | attttatagt | gattactacg | ctaccaacta | ctcgcatcaa agccaaccca | 780 |
| gaagcttggc | acaagtctag | catagtatat | ggcagatctg | gcgtatgttg gtgggaaaat | 840 |
| gcaaagacac | acaaattcgt | ggggtgtttg | ccctgatagc | gtggatccag tcgccatctt | 900 |
| cgtgggcaaa | tttgcaaat | tcagatttct | ggacaaaaga | agatcgggga tccacctgtt | 960 |
| ttagctcgtc | gtcttgggag | tgcggggagg | ggggtagggt | ggggtgggg tgggtggtta | 1020 |
| gctgtgggaa | aggcgctagg | gatttgctct | ggttgccatg | gcaaccagag aaggaaggcg | 1080 |
| acggaggtag | gggatcggga | gatgcgagac | aatggcggca | gggcggaccg gggatcggaa | 1140 |
| ggagcccggg | acagctggcg | tgctgagtcg | tgcgggcagc | gcggtcgttt ggcccggacg | 1200 |
| tgtgggcggt | tttgccacac | accggacgtg | cgggttgtgg ctgcgcgcgc ccggatgcgg | 1260 |
| ttttgcgggc | gagttcttct | ccatgccaca | cgaggcgtgc | ggcacaacca cccgatacac | 1320 |

```
cacacgtgtg gcagttatcg gtgttaaaaa aatgacgaga gaaaagtggc gcaaacggtt    1380
gccccgcacc ctctcacgga cggactttaa aagtcggcat tggtaaccgc aacacaacac    1440
agacagacgc accccaagcc tctctctatc tctctcttcc catgcaatag ttgtcaccac    1500
tcgctcgcta cagtgcccgc attgcatcgc atccacatcc atatgaccat atccattcct    1560
ccccacgaga aaggagaga gaggggagaa atactagtcg tcgtcgtcgt agtagctggt    1620
acgtctacgc tagagcgaca gggaaagagg agggaggggg cgcttgtcat ctactcctcc    1680
tcctcgcccc tagctgggat ccacagcctc ctcctcctcc tcgtgtcggc ctcgtccaca    1740
tccaccgtct cctccgagcg aggtggacag cgacgcggcc acggagcgag ggagggagag    1800
agacaaagcc ggtaataaag gcgggggcgc gcgcgcgcac aagccaagca aagcacatta    1860
acgacgccag ccagcccgcg gggaaccccca ttaaagacgc ttccggggga gcgccgtggg    1920
caagcacagg ggcttagctt agcttggctt gtgtgttgtg tgcgcgagag ggagacagcg    1980
gccgagagag aaagatggcg                                               2000

<210> SEQ ID NO 197
<211> LENGTH: 2000
<212> TYPE: DNA
<213> ORGANISM: Hordeum vulgare

<400> SEQUENCE: 197
aaagttcaaa taagttttttc agaccctacc gtcatacacc ttgacggtag aatgtgaaac      60
cctaccatta tataaacgaa ttcccgttac aacaactta cacacgaggt cagactccta     120
ccgccatagt tcctaatggt aaggtcttgc atcctatcgt cttatacttg gcggtacggc     180
cgttacgcca cgtgagccct tcggctggca gttgacggcc gctgttgtta ctcgactgtc     240
agatacctat aaacctatcg ccaacctgtg taacaatgaa aaacggtcaa atcccgaaaa     300
aatttcgaag caggatcgca tcctgctaaa cttttgacaa atggtcaaaa cacgaaattt     360
ttgccgctcg ttgtgcctct gtaagctgga agcctacggt gtcggcctca ccccccacac     420
ggtgctgccg ctgctgcgcc catcgccagc gcttcacgct atatatccac cccgtcgtcg     480
tgtgagtctc accaggcaga tcgagccctg cgcagcgagg ggaaagagac acacacagcg     540
ccaccaggca agtagtagta aaaggcaaaa gcacggcaca ttaaaagaga ggccagccca     600
gccccggacc ggaccggagc caagcagcag ccgcagccgc agccgcagca gaggagagag     660
agagggaggg agaagcatat atggcgatgc ccctttgcctc cctgtcgccg gcagccgacc     720
accaccgctc ctccccatc ttccccttct gccgctcctc ccctctctac tcgtaagccg     780
gccggccggc cggccaaccg cctcacttct ttcttcgtat ctgcttccat cttagctcga     840
ggggttcgct aatgcggtga ccgtctccgg cgcctgtgtt gtgttccgtg tgtgcagggt     900
aggggaggag gcggcgcatc agcatcctca tcctcagcag cagcagcacg cgatgagcgg     960
cgcgcggtgg gcggcgaggc cggcgccctt cacggcggcg cagtacgagg agctggagca    1020
gcaggcgctc atctacaagt acctcgtcgc cggcgtcccc gtcccgcagg acctcctcct    1080
ccccatccgc cgcggcttcg agaccctcgc ctcgcgcttc taccaccacc acgcccgtac    1140
gtaccccatc ccttcctcct cctacccgg ccaggagtag tacttgcttt tttgcattcg    1200
ccatgcgatt tgcccggttg tttattcgga tcgagcactt gcttttgcat tcgccatgcg    1260
atttgcccgg cttgttattt gggatcgaga gattcaggtg tgctcgaccc ccatcccatg    1320
attcccatct ctttgttaat tgctccggtc atttgttaat ccctcccggg atttggccga    1380
```

| | |
|---|---|
| gcaaaagtct cattattcta atccgagcaa gcctcgtgcc cctgttcaaa gatttgctcc | 1440 |
| taccatcacc acctaccacc atccagcaag catcccctgc ctcgccgggt cttttaattt | 1500 |
| acttgggatt tcattctcat gtcatgtcat gtgctatgat ttgattagat ggcgctagtc | 1560 |
| gagtcttggg ttagtttcca ttggtccttc cgtggcaagg gggttattcc tgtctggttg | 1620 |
| ttgggagcct cacccacgca ttcactcgct cgctcgctgg tcatgtcctg ccacggccga | 1680 |
| tctcaccgat ccatcctgca tcgcatcaca tggaccccg acgaaaaaga tcggcaatca | 1740 |
| accacgcaca gctcctcctt tccccggaaa ttatttcgca tacgtccttc cttccttcgt | 1800 |
| tccttccttc ttgcggggta aatgattggt ttggtgggt gggcacacag atagatccag | 1860 |
| gacgaggacg accgccttcg tccgtccctc cggccggccg gcgtcatgat tgattgctac | 1920 |
| ctgctacggc cttggactgg acgcgtctcc gttcttccga tctcgcgtct cctcctgagt | 1980 |
| tgatttcttg gtccctccgg | 2000 |

<210> SEQ ID NO 198
<211> LENGTH: 2000
<212> TYPE: DNA
<213> ORGANISM: Sorghum bicolor

<400> SEQUENCE: 198

| | |
|---|---|
| taaatattgt ttattataga ctaactaggc ttaaaaaatt cgtctcacaa attacaattg | 60 |
| aactgtctaa ttagtttata tttttgtcta tatttaatgc ttcatgcata agtataaaga | 120 |
| tttgacgtga cagagaatct aaaaaatttt acaaaattgt ttggaactaa acaaggccct | 180 |
| agaatacaag gctaaggcct tgtttagatg cacccaaaaa tccaaaactt tacaagattc | 240 |
| tccgtcacat cgaatcttac agcacatgca tgaagtatta aatatagata aaaataaaaa | 300 |
| ctaattcac agtttatctg taaatcgcga gacaaatctt ttaagcctag ttactccatg | 360 |
| attggacaat gtttgtcaaa taaaaacgaa agtgctacag tgtcaaaatc caaaagtttt | 420 |
| ttgcatctaa acaagcccta aatataaggc ctcgtttagt tcaccccaaa aatcaaaaac | 480 |
| ttttcaagat tctccgtcac atcgaatctt gcggcacatg cataaagcac taaataaaga | 540 |
| tgaaaataaa aactaattgt acagtttacg tgtaaatgaa tcttttaagc ctaattactc | 600 |
| catgattaga taatatttat caaataaaaa cgaaagtttt acggtttgga aaccaaaaa | 660 |
| gttttcggaa ctagccctgt ttaaattgaa gttaaaattt ttttagatgt cacgttgtat | 720 |
| gtgtcggaag gatatcggga ggggttttaa gaaactaata aaagaacaaa ttacatagct | 780 |
| cgtctagaaa ctgcaagaca aatctattaa tcataattaa tatatcatta gcacatatga | 840 |
| gttattatag aacttaaggc taatcataga ctaactaggc ttaaagatt catctcgcaa | 900 |
| ttctaaaccaa aactgtgtaa ttagtttatt ttttattac atttagtgat caatgtatgt | 960 |
| gtccaaagat ttgatatgat gaatctaaac acaaatctag gccttgttta gtttcaaaat | 1020 |
| attttgcaaa atggacacgg tagctctttc gtttgtattt gacaaatatt gtccaatcat | 1080 |
| ggactaaata ggctcaaaag atttatctcg tcaattccga ccaaactgtg caattagttt | 1140 |
| ttatttttgt ctatatttag taattcatgc atgtgtctaa agattcgata tgacgtggaa | 1200 |
| tctgaaaaat tttgtaaaat tttttgggaa ctaaacaaga ccctaaccat caacaaatga | 1260 |
| ccggatgtac agtactagtt tccagtcggc tgtccaaacg ccccgctgc tcgctcgccg | 1320 |
| cctcgccggg agtctcgaca cgcctgacgc tccagcgcga ggcagacagc gacgcagaga | 1380 |
| gagacaaagg gggcaataaa ggcagcgcgc gcgagcacca gcgagggagc gaagcaaagc | 1440 |
| acatcacgag cccggaagct cattaagagc aactccagca ttagacccta aaactaaacc | 1500 |

```
cctactttta atttgggtgc tcttcctact tcgtggggct caattttttt gcttcaactc    1560
caacagtagc acccaaattt aggcccccaa acttattcca gagagaatga cacaagggac    1620
ccactcgtca gtgtccttt cttcttcctc tttcttcttc ctttggacat ggacacaatt    1680
agagcatcga gccggttacc gtagggtgtc atgcacatac aagggtagag agagaaggag    1740
catgagctga ggctaggaca cgcgatggag gatgggggct gccctgttgg gccaacagga    1800
atggggtcta ggagagaaat atgggtgccc agccaaatat ggggtctgga gtagggaccg    1860
tgctggagta atgttttag tctgagcacc catatttagc tattggggct tgagtagaag    1920
ctctgctgga gttgctctaa agaggggtgc cgtccggccg ccgcgggga gcaagcagcg    1980 cgcgcgagag acaggttgag                                                2000

<210> SEQ ID NO 199
<211> LENGTH: 2000
<212> TYPE: DNA
<213> ORGANISM: Glycine max

<400> SEQUENCE: 199
acatacactc tttctctcca aaataaata aattaatata cactagtttg gcttttaatt      60
cccaaattac accattttt tgtgacattg agatgtaggg atttgacaac ccgacttctc     120
agtgattttt attttttttt aatttaaatt ttattttat tctaaattta tgttttagtt     180
taaattatta tacacaaaag ttaagaagtt aaaaagttgg gattcatccc tattttttat    240
ctatggtttt actccaattt actctaatca agaattaaga gaatctaact tacttgaatg    300
ttataaatcc ttcatacctt atttaattct tacctataaa aaatcccaat caagaaaaaa    360
atcccaatta agagaatcta acttacttta attataaccg aaacaaagct acgtaacttg    420
attacaaaat gtacgagaaa ccaaaattag tgatggtgaa aaaaatcacc gacaaaagta    480
agaatctaca cgtgatctga gatcagagac atactttaag aagcaacaat caacagccga    540
aaaccaaaat taaaggtata tattccttaa attgctttgt ccctttgact tttgccatcg    600
tgatgattaa ttaaaggttt agcaaacccc ttcgaacttc atacaattga ctgaattgag    660
aattttattt tcacattcga ggaagcgatg ctacaacatc acttttttg ttctgtattg    720 tgcttttta ctgcctttt tcttcttctt tttttgcctc cctaacaaag acatgtaaaa    780
gtaattgtaa taatattcgt ttcttatgga atgcaatcag ttgattgatg taactataaa    840
ctattatctc cttaatatcg aaagacaagt gaagccaaac acaaacaaga tagggcctag    900
ggagaggtgt ggtccatgaa tgatgaggta tgggtgacca acaatgaat gaataattga    960 agcatccttg accgttgctt gagtttgtgt catcctcaat aatatactag tcccttggct   1020
acagaaaccg ataagcctaa aactggaatt gcacacattt acgttttga ttttgatttt   1080 gttttggca atctcgcccc acatcaaatg tcacccgcat tccggcaagt agtggatggt   1140
ttcctctagc ggtgctttgc ctttgggcca ctgggcccgc aattactcca gcccatcatg   1200
ccttgttgct gtccgttaaa gggtagcata ataaataaa agtagatcaa caaaatgaga   1260
gcaagtattt caaaaaaaa aaacatagt aaaaaacac ttcctctatt tatattatca    1320
agatttattt atcttaaaac attcattatc tcaaaaatac ctatattact taatagtatt   1380
tcatgaattt aaatctaagt ttactatcaa actcaccttt taaaacaatt attcacaaac    1440
aagttataat tgaatgtcat aaaaaaaatt gattattgtg ctaacacgtg aaaaaaattt   1500
atatttaatt ttttatgta taatttgttt ggaccaatga tagagattaa ttgtgatcta   1560
```

```
atgagttata agaaatacgt ggcacatgat cctagacaaa aataaataag aattgtaaaa    1620
taatgtattt tatagctttt ctgaaagatt ttttttttta atttcttctc atgcccatac    1680
atgaatacat gaatgagaat tttttatttt atttttttgt ctgaaataaa gttaaaaatt    1740
gggagcagtg aatgttaagg atgacttttg acttgaatgc aacaagaagt aaagttcact    1800
ttaagttgga ggcttggagc atcgccatcc ataacacaac acaatcgaca atcctaatgg    1860
ttccgacaaa gctcgacctg agtgtgatct catgatgttt ctgctctaac tatgtttgat    1920
ttggataccc aacaacaaaa agagtgttgt cgtgttgttg tagttaatag aataggact    1980 aagtaagagt agtggaaaac                                                2000
```

<210> SEQ ID NO 200
<211> LENGTH: 2000
<212> TYPE: DNA
<213> ORGANISM: Brassica napus

<400> SEQUENCE: 200

```
cataccttca ggatgtgtga agcattccta ttgaattttg tcgataaaat agaaattgca      60
agttgaacaa attgcaatat atatggaaag atgctagcta gtgccaataa tatattaacg     120
gaacaattca tatttcattt tatattatat aatgattatt ttagttttta gttaatacta     180
ataaataata agaaatataa ctacatagtt taaaatgata gtgtgttcta aatttgttaa     240
atggatatct aaatcagttt aggtggcttt taaatgttat tttatgttca tgtaaattaa     300
ttattgtttt acatttaaca ttgtattact ttttatcata ttagttaatt aatgacactc     360
gttttcattc taaaatcaaa atatcagaca tattcatctt tataacaata tgaaaattaa     420 tttttcagtat taatctaaaa aatctattta aattttgatg cgtctgactt ataaaaacac     480
acacacatat atatatatat atatgtatat atttattaat tagtaaaatt tattttaaga     540
aaaattgaaa ctaattaaat tttgggaaag tagtgattat ataatagttt tgttattta     600 tatgctaaaa tttattaagt acttttttt ttaatttgag acttaccaaa ttacggatcc     660
taaatatatt gatcttgaat tatgatatat taattaaatt ttaaagttat cataaatttg     720
ttgtgaattc agtttaggta attgtctatt aaattagaaa aaagataaat aatgataaag     780
ttatgttagt tattagttta atagtattga ggtgtaaata aattaaagtt gtaatggtta     840
atttataagt gtatttgtgt tttaattata ttagatttca attgattcca cagataattc     900
aacatgttcc atgtaattaa tgttacagca gaaatctaga taaattttt ttttaacact     960 ggataatgcg attataaacg ataagacgat tctatatgcg acatgtctta taatgattca    1020
tgtctgaata catcatttga accgttttat aagatctacg tttggtggta ttttttgtgc    1080
tatgctgcag atttttata agtatttatt tcattaattc gcataatttt attttttttc    1140
taaagatcga aactccgatt ttatggtgtt gaacatctag atagagatct atggataaaa    1200
caaatataga ggaagctaca caattttaaag ggtcaaaata gaaacacaga actgaaaagt    1260
atactcagtg ccatatgatt aatagtatg aatttaactt gaacttaatg tcgtttggtt     1320
tgtcatcaaa tgcaactgca aatcatatcg aagtaacgcc cgtgtcataa tatatctgat    1380
taaggactat tattttctgt ttgacaaaaa aaaaaggact attattttct cactaatcag    1440
gctattgttt ttttctcaat aaactaattt aaagaaatac agattattca agtgctattt    1500
ccaaggcaga tgcaggttac tatctctcga tcttcatctc ggagtgtggt tctttatgtg    1560
ttttctgact tgctttatta tactaatatt attaatagat taatgaagat taatagttta    1620
atagattaat gaagacataa actataattt aataatcata gattaatgaa gatttgtgaa    1680
```

```
ccccattaat aaagtttaat agttgttgtt cttatagtct tttaccgtat agttttctcc      1740
ccccatctgt ctcgtctcac tgtcttttcc tctcaagttt caagtgccct aaataaaaac      1800
ctctttcccc ttctctctct ctgcagaaga aggtcagata cagaaactga ctgcaaagaa      1860
caaagctgca aggtgcagct attccttagt aaaaagcttt gttctctttc ttcttttgct      1920
cttcacatcc cccccaacag agacttttct gctatttaaa accagaccct ggaaaaagta      1980
gccaacactc tctctttccc                                                  2000

<210> SEQ ID NO 201
<211> LENGTH: 2000
<212> TYPE: DNA
<213> ORGANISM: Lycopersicon esculentum

<400> SEQUENCE: 201
catttaatta gttaaatcaa atacatacat atataattgt tattaatttt taggtatgat       60
gtaccattaa gactaagaag atcagtgatg acgcaacgta tttcaatttt tttgtgggtt      120
aagtatatgt cttaaactta acatagattt aaaattattt aaattgttaa tacctaaagt      180
ttatttttat tttcattttt gaaagaacaa taattcaagt gggtaattga caaattattt      240
tgaatataaa aaaatgaaa aacagagaaa aaaaacatta gtaaaatcat taaattacac       300
caaacaaatt tggagaattg aaaaagaaca tttataacaa ctctaatata aataaaaaga      360
aaattaaatt acaaaagttt ttttttaaaaa aaataaaggg ttagtttagt catttaggaa     420
tcttatccga ggtttaacaa attttgaatt agttatccct ccatttcgaa gggataagat      480
aatactagat atgatggata agcaatccat gagttaaatt aaatgaagta accaaaacaa      540
tgtattagtt gaattaaatt ttaatccata aattattcta cctaatattg tctatcaaac      600
gggtccttag tattagttaa ctggtgacga ggatcatata atttaaagag ttgggtccag      660
ttttaaagcg tgattatagc gaatgaaat gtttcttatc ccaccaaaaa tttgattata       720
aaacgaaaat gactctcgtt gagaaaagaa aatttacaaa tgatattcat cctcccgtaa      780
ttctcatata atttgttttt gatgtacatg aatatttttt aaaatagttt ttttagtttt      840
tacaaaaata tataatctca ctcaacacaa actcgttagg aattaaatta aacttttgtg      900
ttgatcaaca taagtcgcat aacttatgag ttttgatatc gaactttgtc ggactggata      960
taaattagaa aacagagtca tgaaatactt aatataagtc acataattta tgaatttttga    1020 tattagactt tgtcttgctc gaaacaagtt ttgaataaaa aaaattatgc aatacgacat      1080
aactaatgag attaatcaca tttgcattat tcaagactca taaatacaaa atttctaaat     1140
tgagtaatct catctatgtc atctgttcac atacaaaact aaaaactatc tatgccacca     1200
cacttcttga tgatgtgttg gagcttattt ctcaagatat ttcacattct tgctcaaaca     1260
aaaagcacaa agtttcaaaa agtaaaaaaa aaagagaga aaacaatca tatatatata       1320 tatatatcaa actagaataa gatcttttgt aggtcatctt aattattgtt gaaccttaaa     1380
ggacaaagtt tacatcttta gggtcatgat acattcacat gactaaattt tgaaagatat     1440
aaaaagaggt gttacatcat ttggaccaca ataagacatt atccattcta ccccactcca    1500
taaggtcccc cttctttcaa tccccttttc tcccccccat gccccaatgc ttccttaaac    1560
ccttcattat ctttcacaaa acttatacta taatgtcatc attcatattg ttattgtcat    1620
ttattcttct caccataaag ttcaatgtaa gttgttaat tttgtcttgt acattaataa     1680
gtactagtgt tatgaatgtt tcttgatttc actctaatta aatctcactc tctttcttca    1740
```

```
gcttttatct ctctgctctt tcttccatgc ttgtccaaac cctagatctg tcccctctt    1800 aggtaacctc aacaaacttt gctctctata actcacacac aacacacaaa aacacattct    1860
ttttctcttt ctctgtgtat atgtttgtat attaactgat attgtgttga tttctaggtg    1920 cagcttttg agtgaagtga aaaagggaa agggggtgg gtaaaatttg gaaagattag      1980
ttttttagtg aagggagaag                                                2000
```

<210> SEQ ID NO 202
<211> LENGTH: 12
<212> TYPE: DNA
<213> ORGANISM: Artificial Sequence
<220> FEATURE:
<223> OTHER INFORMATION: synthesized - Fig 3g sequence

<400> SEQUENCE: 202

```
ggcggcggcg gc                                                          12
```

<210> SEQ ID NO 203
<211> LENGTH: 12
<212> TYPE: DNA
<213> ORGANISM: Artificial Sequence
<220> FEATURE:
<223> OTHER INFORMATION: synthesized - fig 3g sequence

<400> SEQUENCE: 203

```
cggcggcggc gg                                                          12
```

<210> SEQ ID NO 204
<211> LENGTH: 394
<212> TYPE: PRT
<213> ORGANISM: Oryza sativa

<400> SEQUENCE: 204

```
Met Ala Met Pro Tyr Ala Ser Leu Ser Pro Ala Val Ala Asp His Arg
1               5                   10                  15

Ser Ser Pro Ala Ala Thr Ala Ser Leu Leu Pro Phe Cys Arg Ser
            20                  25                  30

Thr Pro Leu Ser Ala Gly Gly Gly Val Ala Met Gly Glu Asp Ala
        35                  40                  45

Pro Met Thr Ala Arg Trp Pro Pro Ala Ala Ala Arg Leu Pro Pro
    50                  55                  60

Phe Thr Ala Ala Gln Tyr Glu Glu Leu Glu Gln Gln Ala Leu Ile Tyr
65                  70                  75                  80

Lys Tyr Leu Val Ala Gly Val Pro Val Pro Pro Asp Leu Val Leu Pro
                85                  90                  95

Ile Arg Arg Gly Leu Asp Ser Leu Ala Ala Arg Phe Tyr Asn His Pro
            100                 105                 110

Ala Leu Gly Tyr Gly Pro Tyr Phe Gly Lys Lys Leu Asp Pro Glu Pro
        115                 120                 125

Gly Arg Cys Arg Arg Thr Asp Gly Lys Lys Trp Arg Cys Ser Lys Glu
    130                 135                 140

Ala Ala Pro Asp Ser Lys Tyr Cys Glu Arg His Met His Arg Gly Arg
145                 150                 155                 160

Asn Arg Ser Arg Lys Pro Val Glu Thr Gln Leu Val Ala Gln Ser Gln
                165                 170                 175

Pro Pro Ser Ser Val Val Gly Ser Ala Ala Pro Leu Ala Ala Ala
            180                 185                 190

Ser Asn Gly Ser Ser Phe Gln Asn His Ser Leu Tyr Pro Ala Ile Ala
```

```
                195                 200                 205
Gly Ser Asn Gly Gly Gly Gly Arg Asn Met Pro Ser Ser Phe Gly
210                 215                 220

Ser Ala Leu Gly Ser Gln Leu His Met Asp Asn Ala Ala Pro Tyr Ala
225                 230                 235                 240

Ala Val Gly Gly Gly Thr Gly Lys Asp Leu Arg Tyr Thr Ala Tyr Gly
                245                 250                 255

Thr Arg Ser Leu Ala Asp Glu Gln Ser Gln Leu Ile Thr Glu Ala Ile
            260                 265                 270

Asn Thr Ser Ile Glu Asn Pro Trp Arg Leu Leu Pro Ser Gln Asn Ser
        275                 280                 285

Pro Phe Pro Leu Ser Ser Tyr Ser Gln Leu Gly Ala Leu Ser Asp Leu
    290                 295                 300

Gly Gln Asn Thr Pro Ser Ser Leu Ser Lys Val Gln Arg Gln Pro Leu
305                 310                 315                 320

Ser Phe Phe Gly Asn Asp Tyr Ala Ala Val Asp Ser Val Lys Gln Glu
                325                 330                 335

Asn Gln Thr Leu Arg Pro Phe Phe Asp Glu Trp Pro Lys Gly Arg Asp
            340                 345                 350

Ser Trp Ser Asp Leu Ala Asp Glu Asn Ala Asn Leu Ser Ser Phe Ser
        355                 360                 365

Gly Thr Gln Leu Ser Ile Ser Ile Pro Met Ala Ser Ser Asp Phe Ser
    370                 375                 380

Ala Ala Ser Ser Arg Ser Thr Asn Gly Asp
385                 390

<210> SEQ ID NO 205
<211> LENGTH: 207
<212> TYPE: PRT
<213> ORGANISM: Oryza sativa

<400> SEQUENCE: 205

Met Ala Met Pro Tyr Ala Ser Leu Ser Pro Ala Gly Arg Trp Trp Arg
1               5                   10                  15

Arg Asp Gly Gly Arg Ala Asp Asp Arg Glu Val Ala Ala Gly Gly
            20                  25                  30

Gly Gly Glu Ala Ala Ala Val His Arg Gly Ala Val Arg Gly Ala Gly
                35                  40                  45

Ala Ala Gly Ala His Ile Gln Val Pro Gly Gly Arg Arg Ala Arg Pro
    50                  55                  60

Ala Gly Ser Arg Ala Pro His Pro Pro Thr Arg Leu Pro Arg Arg Pro
65                  70                  75                  80

Leu Leu Gln Pro Ser Arg Pro Trp Ile Trp Ser Val Leu Arg Gln Glu
                85                  90                  95

Ala Gly Pro Arg Ala Arg Ala Val Pro Ala Tyr Gly Arg Gln Glu Met
            100                 105                 110

Ala Val Leu Glu Gly Gly Arg Ala Gly Phe Gln Val Leu Arg Ala Pro
        115                 120                 125

His Ala Pro Arg Pro Gln Pro Phe Lys Lys Ala Cys Gly Asn Ala Ala
    130                 135                 140

Gly Arg Pro Val Pro Thr Ala Leu Ile Cys Cys Arg Phe Cys Gly Gly
145                 150                 155                 160

Ala Pro Cys Cys Cys Leu Gln Trp Gln Gln Leu Pro Lys Pro Leu Ser
                165                 170                 175
```

-continued

```
Leu Pro Cys Tyr Cys Arg Gln Gln Trp Arg Gly Arg Gly Glu His
                180                 185                 190

Ala Gln Leu Ile Trp Leu Gly Val Gly Phe Ser Ala Ala His Gly
        195                 200                 205

<210> SEQ ID NO 206
<211> LENGTH: 394
<212> TYPE: PRT
<213> ORGANISM: Oryza sativa

<400> SEQUENCE: 206

Met Ala Met Pro Tyr Ala Ser Leu Ser Pro Ala Val Ala Asp His Arg
1               5                   10                  15

Ser Ser Pro Ala Ala Ala Thr Ala Ser Leu Leu Pro Phe Cys Arg Ser
            20                  25                  30

Thr Pro Leu Ser Ala Gly Gly Gly Val Ala Met Gly Glu Asp Ala
            35                  40                  45

Pro Met Thr Ala Arg Trp Pro Pro Ala Ala Ala Arg Leu Pro Pro
    50                  55                  60

Phe Thr Ala Ala Gln Tyr Glu Glu Leu Glu Gln Gln Ala Leu Ile Tyr
65                  70                  75                  80

Lys Tyr Leu Val Ala Gly Val Pro Val Pro Pro Asp Leu Val Leu Pro
                85                  90                  95

Ile Arg Arg Gly Leu Asp Ser Leu Ala Ala Arg Phe Tyr Asn His Pro
            100                 105                 110

Ala Leu Gly Tyr Gly Pro Tyr Phe Gly Lys Lys Leu Asp Pro Glu Pro
        115                 120                 125

Gly Arg Cys Arg Arg Thr Asp Gly Lys Lys Trp Arg Cys Ser Lys Glu
    130                 135                 140

Ala Ala Pro Asp Ser Lys Tyr Cys Glu Arg His Met His Arg Gly Arg
145                 150                 155                 160

Asn Arg Ser Arg Lys Pro Val Glu Thr Gln Leu Val Ala Gln Ser Gln
                165                 170                 175

Pro Pro Ser Ser Val Val Gly Ser Ala Ala Pro Leu Ala Ala Ala
            180                 185                 190

Ser Asn Gly Ser Ser Phe Gln Asn His Ser Leu Tyr Pro Ala Ile Ala
        195                 200                 205

Gly Ser Asn Gly Gly Gly Gly Arg Asn Met Pro Ser Ser Phe Gly
    210                 215                 220

Ser Ala Leu Gly Ser Gln Leu His Met Asp Asn Ala Ala Pro Tyr Ala
225                 230                 235                 240

Ala Val Gly Gly Gly Thr Gly Lys Asp Leu Arg Tyr Thr Ala Tyr Gly
                245                 250                 255

Thr Arg Ser Leu Ala Asp Glu Gln Ser Gln Leu Ile Thr Glu Ala Ile
            260                 265                 270

Asn Thr Ser Ile Glu Asn Pro Trp Arg Leu Leu Pro Ser Gln Asn Ser
        275                 280                 285

Pro Phe Pro Leu Ser Ser Tyr Ser Gln Leu Gly Ala Leu Ser Asp Leu
    290                 295                 300

Gly Gln Asn Thr Pro Ser Ser Leu Ser Lys Val Gln Arg Gln Pro Leu
305                 310                 315                 320

Ser Phe Phe Gly Asn Asp Tyr Ala Ala Val Asp Ser Val Lys Gln Glu
                325                 330                 335

Asn Gln Thr Leu Arg Pro Phe Phe Asp Glu Trp Pro Lys Gly Arg Asp
            340                 345                 350
```

```
Ser Trp Ser Asp Leu Ala Asp Glu Asn Ala Asn Leu Ser Ser Phe Ser
            355                 360                 365

Gly Thr Gln Leu Ser Ile Ser Ile Pro Met Ala Ser Ser Asp Phe Ser
        370                 375                 380

Ala Ala Ser Ser Arg Ser Thr Asn Gly Asp
385                 390

<210> SEQ ID NO 207
<211> LENGTH: 208
<212> TYPE: PRT
<213> ORGANISM: Oryza sativa

<400> SEQUENCE: 207

Met Ala Met Pro Tyr Ala Ser Leu Ser Pro Ala Gly Arg Trp Trp Arg
1               5                   10                  15

Arg Asp Gly Gly Arg Ala Asp Asp Arg Glu Val Ala Ala Gly Gly
            20                  25                  30

Gly Gly Glu Ala Ala Val His Arg Gly Ala Val Arg Gly Ala Gly
        35                  40                  45

Ala Ala Gly Ala His Ile Gln Val Pro Gly Gly Arg Arg Ala Arg Pro
    50                  55                  60

Ala Gly Ser Arg Ala Pro His Pro Pro Arg Thr Arg Leu Pro Arg Arg
65                  70                  75                  80

Pro Leu Leu Gln Pro Ser Arg Pro Trp Ile Trp Ser Val Leu Arg Gln
                85                  90                  95

Glu Ala Gly Pro Arg Ala Arg Ala Val Pro Ala Tyr Gly Arg Gln Glu
            100                 105                 110

Met Ala Val Leu Glu Gly Gly Arg Ala Gly Phe Gln Val Leu Arg Ala
            115                 120                 125

Pro His Ala Pro Arg Pro Gln Pro Phe Lys Lys Ala Cys Gly Asn Ala
    130                 135                 140

Ala Gly Arg Pro Val Pro Thr Ala Leu Ile Cys Cys Arg Phe Cys Gly
145                 150                 155                 160

Gly Ala Pro Cys Cys Cys Leu Gln Trp Gln Gln Leu Pro Lys Pro Leu
                165                 170                 175

Ser Leu Pro Cys Tyr Cys Arg Gln Gln Trp Arg Gly Arg Gly Glu Glu
            180                 185                 190

His Ala Gln Leu Ile Trp Leu Gly Val Gly Phe Ser Ala Ala His Gly
        195                 200                 205
```